United States Patent
Connor

(10) Patent No.: US 12,268,883 B2
(45) Date of Patent: Apr. 8, 2025

(54) INTEGRATED SYSTEM TO ASSIST CARDIOVASCULAR FUNCTIONING WITH IMPLANTED CARDIAC DEVICE AND SENSOR-ENABLED WEARABLE DEVICE

(71) Applicant: Robert A. Connor, St. Paul, MN (US)

(72) Inventor: Robert A. Connor, St. Paul, MN (US)

(73) Assignee: Medibolics, Ham Lake, MN (US)

( * ) Notice: Subject to any disclaimer, the term of this patent is extended or adjusted under 35 U.S.C. 154(b) by 648 days.

(21) Appl. No.: 17/410,297

(22) Filed: Aug. 24, 2021

(65) Prior Publication Data

US 2021/0379388 A1  Dec. 9, 2021

Related U.S. Application Data

(63) Continuation-in-part of application No. 16/598,514, filed on Oct. 10, 2019, now abandoned, and a continuation-in-part of application No. 16/568,580, filed on Sep. 12, 2019, now Pat. No. 11,478,158, and a continuation-in-part of application No. 16/150,469, filed on Oct. 3, 2018, now abandoned, which is a continuation-in-part of application No. 15/418,620, filed on Jan. 27, 2017, now abandoned, which is a continuation-in-part of application No. 14/951,475, filed on Nov. 24, 2015, now Pat. No. 10,314,492.
(Continued)

(51) Int. Cl.
| | |
|---|---|
| *A61N 1/365* | (2006.01) |
| *A61M 60/178* | (2021.01) |
| *A61M 60/232* | (2021.01) |
| *A61M 60/34* | (2021.01) |
| *A61M 60/515* | (2021.01) |
| *A61M 60/531* | (2021.01) |
| *A61M 60/546* | (2021.01) |
| *A61N 1/362* | (2006.01) |
| *A61N 1/372* | (2006.01) |

(52) U.S. Cl.
CPC ....... *A61N 1/36564* (2013.01); *A61M 60/178* (2021.01); *A61M 60/232* (2021.01); *A61M 60/34* (2021.01); *A61M 60/515* (2021.01); *A61M 60/531* (2021.01); *A61M 60/546* (2021.01); *A61N 1/3629* (2017.08); *A61N 1/37223* (2013.01)

(58) Field of Classification Search
CPC ............. A61N 1/3629; A61N 1/37223; A61M 60/531; A61M 60/546; A61M 60/178; A61M 60/34; A61M 60/515
See application file for complete search history.

(56) References Cited

U.S. PATENT DOCUMENTS

| | | | |
|---|---|---|---|
| 6,122,536 A * | 9/2000 | Sun | A61B 5/1459 600/317 |
| 7,313,440 B2 | 12/2007 | Miesel | |

(Continued)

*Primary Examiner* — Jennifer Pitrak McDonald
*Assistant Examiner* — Jennifer L Ghand

(57) ABSTRACT

This invention is a system to assist human cardiovascular functioning which integrates the operation of an implanted cardiac device and a wearable device with an arcuate array of biometric sensors. Analysis of data from the biometric sensors on the wearable device is used to automatically adjust and optimize the operation of the implanted cardiac device. This system can work as a closed loop system for assisting and improving human cardiovascular functioning.

18 Claims, 2 Drawing Sheets

Related U.S. Application Data which is a continuation-in-part of application No. 14/623,337, filed on Feb. 16, 2015, now Pat. No. 9,582,035, said application No. 16/150,469 is a continuation-in-part of application No. 14/459,937, filed on Aug. 14, 2014, now abandoned, said application No. 14/951,475 is a continuation-in-part of application No. 14/071,112, filed on Nov. 4, 2013, now abandoned, and a continuation-in-part of application No. 13/901,131, filed on May 23, 2013, now Pat. No. 9,536,449.

(60) Provisional application No. 62/857,942, filed on Jun. 6, 2019, provisional application No. 62/439,147, filed on Dec. 26, 2016, provisional application No. 62/297,827, filed on Feb. 20, 2016, provisional application No. 62/245,311, filed on Oct. 23, 2015, provisional application No. 61/866,583, filed on Aug. 16, 2013.

(56) References Cited

U.S. PATENT DOCUMENTS

| | | | | |
|---|---|---|---|---|
| 7,499,894 | B2 | 3/2009 | Marom et al. | |
| 7,668,591 | B2 | 2/2010 | Lee et al. | |
| 7,787,946 | B2 | 8/2010 | Stahmann et al. | |
| 8,090,432 | B2 | 1/2012 | Cinbis et al. | |
| 8,108,038 | B2 | 1/2012 | Giftakis et al. | |
| 8,112,148 | B2 | 2/2012 | Giftakis et al. | |
| 8,165,662 | B2 | 4/2012 | Cinbis et al. | |
| 8,209,009 | B2 | 6/2012 | Giftakis et al. | |
| 8,209,019 | B2 | 6/2012 | Giftakis et al. | |
| 8,214,035 | B2 | 7/2012 | Giftakis et al. | |
| 8,380,296 | B2 | 2/2013 | Lee et al. | |
| 8,428,729 | B2 | 4/2013 | Schwartz et al. | |
| 8,463,345 | B2 | 6/2013 | Kuhn et al. | |
| 8,515,548 | B2 | 8/2013 | Rofougaran et al. | |
| 8,617,082 | B2 | 12/2013 | Zhang et al. | |
| 8,634,890 | B2 | 1/2014 | Kuhn et al. | |
| 8,666,466 | B2 | 3/2014 | Kuhn et al. | |
| 8,768,446 | B2 | 7/2014 | Drew et al. | |
| 9,131,865 | B2 | 9/2015 | Thompson-Nauman | |
| 9,138,157 | B2 | 9/2015 | Thompson-Nauman | |
| 9,283,341 | B2 | 3/2016 | Ujhazy et al. | |
| 9,307,907 | B2 | 4/2016 | Condurso et al. | |
| 9,320,443 | B2 | 4/2016 | Libbus et al. | |
| 9,820,658 | B2 * | 11/2017 | Tran | A61B 5/4818 |
| 2002/0169381 | A1 * | 11/2002 | Asada | A61B 5/14552 600/500 |
| 2004/0131998 | A1 | 7/2004 | Marom et al. | |
| 2005/0081847 | A1 | 4/2005 | Lee et al. | |
| 2005/0115561 | A1 | 6/2005 | Stahmann et al. | |
| 2006/0122520 | A1 * | 6/2006 | Banet | A61B 5/6814 600/323 |
| 2006/0195039 | A1 | 8/2006 | Drew et al. | |
| 2006/0217588 | A1 * | 9/2006 | Gross | A61M 60/268 600/16 |
| 2007/0260286 | A1 | 11/2007 | Giftakis et al. | |
| 2007/0265677 | A1 | 11/2007 | Giftakis et al. | |
| 2010/0106211 | A1 | 4/2010 | Lee et al. | |
| 2011/0061647 | A1 | 3/2011 | Stahmann et al. | |
| 2011/0295331 | A1 * | 12/2011 | Wells | A61N 5/0601 607/3 |
| 2015/0174307 | A1 * | 6/2015 | Eckman | A61B 5/026 600/17 |
| 2015/0246166 | A1 | 9/2015 | Greatrex et al. | |
| 2016/0143533 | A1 | 5/2016 | Keenan et al. | |
| 2016/0228627 | A1 | 8/2016 | Wiesener et al. | |
| 2016/0349790 | A1 * | 12/2016 | Connor | G06F 3/017 |
| 2016/0367739 | A1 * | 12/2016 | Wiesener | A61N 1/36514 |
| 2017/0095670 | A1 * | 4/2017 | Ghaffari | A61N 1/36139 |
| 2018/0055449 | A1 * | 3/2018 | Ko | A61B 5/6831 |
| 2018/0126053 | A1 | 5/2018 | Zilbershlag | |
| 2018/0236242 | A1 * | 8/2018 | Balinski | A61N 1/3718 |
| 2019/0298987 | A1 | 10/2019 | Freeman et al. | |
| 2020/0179706 | A1 | 6/2020 | Thakur et al. | |
| 2020/0215246 | A1 | 7/2020 | Tal et al. | |
| 2021/0000349 | A1 | 1/2021 | Goetz | |
| 2021/0016095 | A1 * | 1/2021 | Chen | A61B 5/6852 |
| 2021/0177335 | A1 | 6/2021 | Varadan et al. | |

\* cited by examiner

INTEGRATED SYSTEM TO ASSIST CARDIOVASCULAR FUNCTIONING WITH IMPLANTED CARDIAC DEVICE AND SENSOR-ENABLED WEARABLE DEVICE

CROSS-REFERENCE TO RELATED APPLICATIONS

This application is a continuation in part of U.S. patent application Ser. No. 16/598,514 filed on 2019 Oct. 10. This application is also a continuation in part of U.S. patent application Ser. No. 16/568,580 filed on 2019 Sep. 12. This application is also a continuation in part of U.S. patent application Ser. No. 16/150,469 filed on 2018 Oct. 3.

U.S. patent application Ser. No. 16/598,514 claimed the priority benefit of U.S. provisional patent application 62/857,942 filed on 2019 Jun. 6. U.S. patent application Ser. No. 16/568,580 claimed the priority benefit of U.S. provisional patent application 62/857,942 filed on 2019 Jun. 6. U.S. patent application Ser. No. 16/150,469 was a continuation in part of U.S. patent application Ser. No. 15/418,620 filed on 2017 Jan. 27. U.S. patent application Ser. No. 16/150,469 was a continuation in part of U.S. patent application Ser. No. 14/459,937 filed on 2014 Aug. 14. U.S. patent application Ser. No. 15/418,620 claimed the priority benefit of U.S. provisional patent application 62/439,147 filed on 2016 Dec. 26. U.S. patent application Ser. No. 15/418,620 claimed the priority benefit of U.S. provisional patent application 62/297,827 filed on 2016 Feb. 20. U.S. patent application Ser. No. 15/418,620 was a continuation in part of U.S. patent application Ser. No. 14/951,475 filed on 2015 Nov. 24 which issued as U.S. Pat. No. 10,314,492.

U.S. patent application Ser. No. 14/951,475 claimed the priority benefit of U.S. provisional patent application 62/245,311 filed on 2015 Oct. 23. U.S. patent application Ser. No. 14/951,475 was a continuation in part of U.S. patent application Ser. No. 14/623,337 filed on 2015 Feb. 16 which issued as U.S. Pat. No. 9,582,035. U.S. patent application Ser. No. 14/951,475 was a continuation in part of U.S. patent application Ser. No. 14/071,112 filed on 2013 Nov. 4. U.S. patent application Ser. No. 14/951,475 was a continuation in part of U.S. patent application Ser. No. 13/901,131 filed on 2013 May 23 which issued as U.S. Pat. No. 9,536,449. U.S. patent application Ser. No. 14/459,937 claimed the priority benefit of U.S. provisional patent application 61/866,583 filed on 2013 Aug. 16.

The entire contents of these related applications are incorporated herein by reference.

FEDERALLY SPONSORED RESEARCH

Not Applicable

SEQUENCE LISTING OR PROGRAM

Not Applicable

BACKGROUND

Field of Invention

This invention relates to systems for human circulatory assistance.

Introduction

Proper cardiovascular functioning, including proper blood circulation and oxygenation, is important for human physiological functioning and tissue health. When cardiovascular functioning is significantly impaired, a cardiac device such as a pacemaker (to assist in cardiac pacing) or a ventricular assist device (to assist in blood pumping) can be implanted to improve cardiovascular functioning. A person's cardiovascular needs vary over time based on the person's activity level, as well as physiological and anatomical changes over time. Accordingly, it is important that the operation of an implanted cardiac device be automatically adjusted to respond to these changing needs.

However, many cardiovascular problems first appear in the extremities of a person's body, such as the person's feet and hands. Biometric information from those extremities is needed for accurate adjustment and optimization of the operation of a cardiac device, but this information is not available from sensors in a cardiac device which is implanted in a person's torso. This is the unmet clinical need which is addressed by this invention. A system for assisting human cardiovascular functioning which adjusts and optimizes the operation of an implanted cardiac device based on biometric information from body extremities can help to manage chronic heart conditions, improve tissue health (particularly in extremities such as feet and hands), promote wound healing, and potentially even avoid amputation.

Review of the Relevant Art

U.S. Patent Application 20040131998 (Marom et al., Jul. 8, 2004, "Cerebral Programming") and U.S. Pat. No. 7,499,894 (Marom et al., Mar. 3, 2009, "Cerebral Programming") disclose training a biological neural network to control a pacemaker. U.S. Patent Applications 20050081847 (Lee et al., Apr. 21, 2005, "Automatic Activation of Medical Processes") and 20100106211 (Lee et al., Apr. 29, 2010, "Automatic Activation of Medical Processes"), as well as U.S. Pat. No. 7,668,591 (Lee et al., Feb. 23, 2010, "Automatic Activation of Medical Processes") and U.S. Pat. No. 8,380,296 (Lee et al., Feb. 19, 2013, "Automatic Activation of Medical Processes") disclose automatic modification of therapies or other medical processes based on brain state.

U.S. Patent Applications 20050115561 (Stahmann et al., Jun. 2, 2005, "Patient Monitoring, Diagnosis, and/or Therapy Systems and Methods") and 20110061647 (Stahmann et al., Mar. 17, 2011, "Patient Monitoring, Diagnosis, and/or Therapy Systems and Methods"), as well as U.S. Pat. No. 7,787,946 (Stahmann et al., Aug. 31, 2010, "Patient Monitoring, Diagnosis, and/or Therapy Systems and Methods"), disclose systems and methods involving an implantable device configured to perform at least one cardiac-related function, a patient-external respiratory therapy device, and a communication channel configured to facilitate communication between the implantable device and the respiratory therapy device. U.S. Patent Application 20060195039 (Drew et al, Aug. 31, 2006, "Clustering with Combined Physiological Signals") and U.S. Pat. No. 8,768,446 (Drew et al., Jul. 1, 2014, "Clustering with Combined Physiological Signals") disclose a method of generating an extended cluster by an implanted medical device.

U.S. Patent Applications 20070260286 (Giftakis et al., Nov. 8, 2007, "System and Method for Utilizing Brain State Information to Modulate Cardiac Therapy") and U.S. Patent Application 20070265677 (Giftakis et al., Nov. 15, 2007, "System and Method for Utilizing Brain State Information to Modulate Cardiac Therapy") and U.S. Pat. No. 8,209,019 (Giftakis et al., Jun. 26, 2012, "System and Method for Utilizing Brain State Information to Modulate Cardiac Therapy") and U.S. Pat. No. 8,214,035 (Giftakis et al., Jul.

3, 2012, "System and Method for Utilizing Brain State Information to Modulate Cardiac Therapy") disclose a system for regulating or modulating cardiac therapy using brain state information. U.S. Pat. No. 8,108,038 (Giftakis et al., Jan. 31, 2012, "System and Method for Segmenting a Cardiac Signal Based on Brain Activity") and U.S. Pat. No. 8,209,009 (Giftakis et al., Jun. 26, 2012, "System and Method for Segmenting a Cardiac Signal Based on Brain Stimulation") disclose a medical device system with a brain monitoring element, cardiac monitoring element and a processor. U.S. Pat. No. 8,112,148 (Giftakis et al., Feb. 7, 2012, "System and Method for Monitoring Cardiac Signal Activity in Patients with Nervous System Disorders") discloses a medical device system and method for monitoring cardiac signal activity in patients with nervous system disorders.

U.S. Pat. No. 7,313,440 (Miesel, Dec. 25, 2007, "Collecting Posture and Activity Information to Evaluate Therapy") discloses using posture to set therapy parameters for a medical device. U.S. Pat. No. 8,090,432 (Cinbis et al., Jan. 3, 2012, "Implantable Tissue Perfusion Sensing System and Method") and U.S. Pat. No. 8,165,662 (Cinbis et al., Apr. 24, 2012, "Implantable Tissue Perfusion Sensing System and Method") disclose using electrodes to sense cardiac signals to identify a cardiac event. U.S. Pat. No. 8,428,729 (Schwartz et al., Apr. 23, 2013, "Cardiac Stimulation Apparatus and Method for the Control of Hypertension") discloses a method that electrically stimulates a heart muscle to alter the ejection profile of the heart, to control the mechanical function of the heart and reduce the observed blood pressure of the patient.

U.S. Pat. No. 8,463,345 (Kuhn et al., Jun. 11, 2013, "Device and Method for Monitoring of Absolute Oxygen Saturation and Total Hemoglobin Concentration"), U.S. Pat. No. 8,634,890 (Kuhn et al., Jan. 21, 2014, "Device and Method for Monitoring of Absolute Oxygen Saturation and Tissue Hemoglobin Concentration") and U.S. Pat. No. 8,666,466 (Kuhn et al., Mar. 4, 2014, "Device and Method for Monitoring of Absolute Oxygen Saturation and Tissue Hemoglobin Concentration") disclose an implantable oxygen saturation monitor. U.S. Pat. No. 8,515,548 (Rofougaran et al., Aug. 20, 2013, "Article of Clothing Including Bio-Medical Units") discloses an article of clothing with a plurality of bio-medical units integrated into the clothing fabric. U.S. Pat. No. 8,617,082 (Zhang et al., Dec. 13, 2013, "Heart Sounds-Based Pacing Optimization") discloses an implantable medical device that receives both heart sounds and electrogram signals.

U.S. Patent Application 20150246166 (Greatrex et al., Sep. 3, 2015, "Ventricular Assist Device and Method of Controlling Same") discloses a method of controlling the speed of a ventricular assist device, in particular the rotational speed of a rotary blood pump, wherein at least temporarily the speed of the device is modulated around a mean speed and a response of the native heart to this modulation is measured. U.S. Pat. No. 9,131,865 (Thompson-Nauman et al., Sep. 15, 2015, "Method and Apparatus for Cardiac Function Monitoring") and U.S. Pat. No. 9,138,157 (Thompson-Nauman et al., Sep. 22, 2015, "Method and Apparatus for Cardiac Function Monitoring") disclose a method and medical device for monitoring cardiac function in a patient that includes a plurality of electrodes to deliver cardiac pacing therapy.

U.S. Pat. No. 9,283,341 (Ujhazy et al., Mar. 15, 2016, "Methods and Apparatus for Heart Failure Treatment") discloses methods and an apparatus for assessing the condition of and treating patients for heart failure by the delivery of continuous positive airway pressure. U.S. Pat. No. 9,307,907 (Condurso et al., Apr. 12, 2016, "System and Method for Dynamically Adjusting Patient Therapy") discloses a system and method of managing therapy that monitors all aspects of the medication delivery to a patient. U.S. Pat. No. 9,320,443 (Libbus et al., Apr. 26, 2016, "Multi-Sensor Patient Monitor to Detect Impending Cardiac Decompensation") discloses a system for detecting impending acute cardiac decompensation. U.S. Patent Application 20160143533 (Keenan et al., May 26, 2016, "Medical Device System Having an Implanted Medical Device and an External Device") discloses an external device for wireless monitoring of an implanted device.

U.S. Patent Application 20160228627 (Wiesener et al., Aug. 11, 2016, "Blood Pump Control System and Method for Controlling a Blood Pump") discloses methods for controlling the speed of a pump based on a valve state index and/or for deriving a valve state from time-series signal representing a pressure difference or a flow rate. U.S. Patent Application 20180126053 (Zilbershlag, May 10, 2018, "Wristwatch for Monitoring Operation of an Implanted Ventricular Assist Device") discloses a wristwatch wirelessly connected to an implanted medical device such as a VAD to monitors the operation of the VAD. U.S. Patent Application 20190298987 (Freeman et al., Oct. 3, 2019, "Garments for Wearable Cardiac Monitoring and Treatment Devices") discloses a garment with ECG monitors.

U.S. Patent Application 20200179706 (Thakur et al., Jun. 11, 2020, "Hemodynamically Optimized Rate Response Pacing Using Heart Sounds") disclose san apparatus comprising a stimulus circuit configured to deliver electrical pacing therapy to a subject when operatively coupled to a plurality of electrodes, including a heart sound sensing circuit. U.S. Patent Application 20200215246 (Tal et al., Jul. 9, 2020, "Method and System for Ventricular Assistive Device Adjustment Using a Wearable Device") discloses control of a VAD device using wearable sensors, such as blood pressure sensors. U.S. Patent Application 20210000349 (Goetz, Jan. 7, 2021, "Remote Titration of Therapy Delivered by an Implantable Medical Device") discloses techniques for remotely titrating a therapy delivered using an implantable medical device system. U.S. Patent Application 20210177335 (Varadan et al., Jun. 17, 2021, "Wearable Congestive Heart Failure Management System") discloses a non-invasive, wearable and portable medical device for evaluation and monitoring the heart condition for patients with congestive heart failure.

SUMMARY OF THE INVENTION

Disclosed herein is a system to assist human cardiovascular functioning which integrates the operation of an implanted cardiac device (such as a ventricular assist device or a cardiac pacemaker) and a wearable device (such as a smart watch or wrist band) with an arcuate array of biometric sensors. Analysis of data from the biometric sensors on the wearable device is used to automatically adjust and optimize the operation of the implanted cardiac device. Since some cardiovascular problems first appear in peripheral portions of a person's body, such as feet and hands, biometric information from those portions can provide more accurate and timely feedback for adjustment and optimization of the operation of a cardiac device than sensors in a centrally-implanted cardiac device. In an example, this system can comprise a closed loop system for assisting and improving human cardiovascular functioning.

INTRODUCTION TO THE FIGURES

DETAILED DESCRIPTION OF THE FIGURES

A system to assist human cardiovascular functioning can include: (1) an implanted cardiac pacemaker or other implanted cardiac rhythm management device, wherein the implanted device has a plurality of operating parameters including pacing rate and is implanted in a person; and (2) a wearable device worn by the person, wherein the wearable device further comprises an arcuate array of biometric sensors, wherein the implanted device and the wearable device are in wireless communication with each other, either directly or through an intermediary device, and wherein one or more of the operating parameters of the implanted cardiac pacemaker or other implanted cardiac rhythm management device are automatically adjusted based on analysis of data from the sensors.

Alternatively, an system to assist human cardiovascular functioning can include: (1) an implanted Ventricular Assist Device (VAD) or other implanted blood-pumping device, wherein the implanted device has a plurality of operating parameters including rotational and/or flow speed and is implanted in a person; and (2) a wearable device worn by the person; wherein the wearable device further comprises an arcuate array of biometric sensors, wherein the implanted device and the wearable device are in wireless communication with each other, either directly or through an intermediary device, and wherein one or more of the operating parameters of the Ventricular Assist Device (VAD) or other implanted blood-pumping device are automatically adjusted based on analysis of data from the sensors.

In an example, the wearable device can be selected from the group consisting of a smart watch or watch band, a wrist or arm band, a finger ring, a sleeve, an ear bud or other ear insert, a chest strap, a smart sock, an adhesive patch, and smart glasses. In an example, the biometric sensors can be electromagnetic energy sensors. In an example, the biometric sensors can be blood pressure sensors. In an example, the biometric sensors can be oxygenation sensors. In an example, the biometric sensors can comprise both electromagnetic energy sensors and blood pressure sensors. In an example, the biometric sensors can comprise both blood pressure sensors and oxygenation sensors.

In an example, the array of biometric sensors can span at least half of the circumference of the portion of the person's body to which the wearable device is attached. In an example, the array of biometric sensors can span the entire circumference of the portion of the person's body to which the wearable device is attached. In an example, the array of biometric sensors can be a ring-and-row array, wherein rows are perpendicular to rings, and wherein there are multiple sensors in a ring and multiple sensors in a row.

Figure 1:
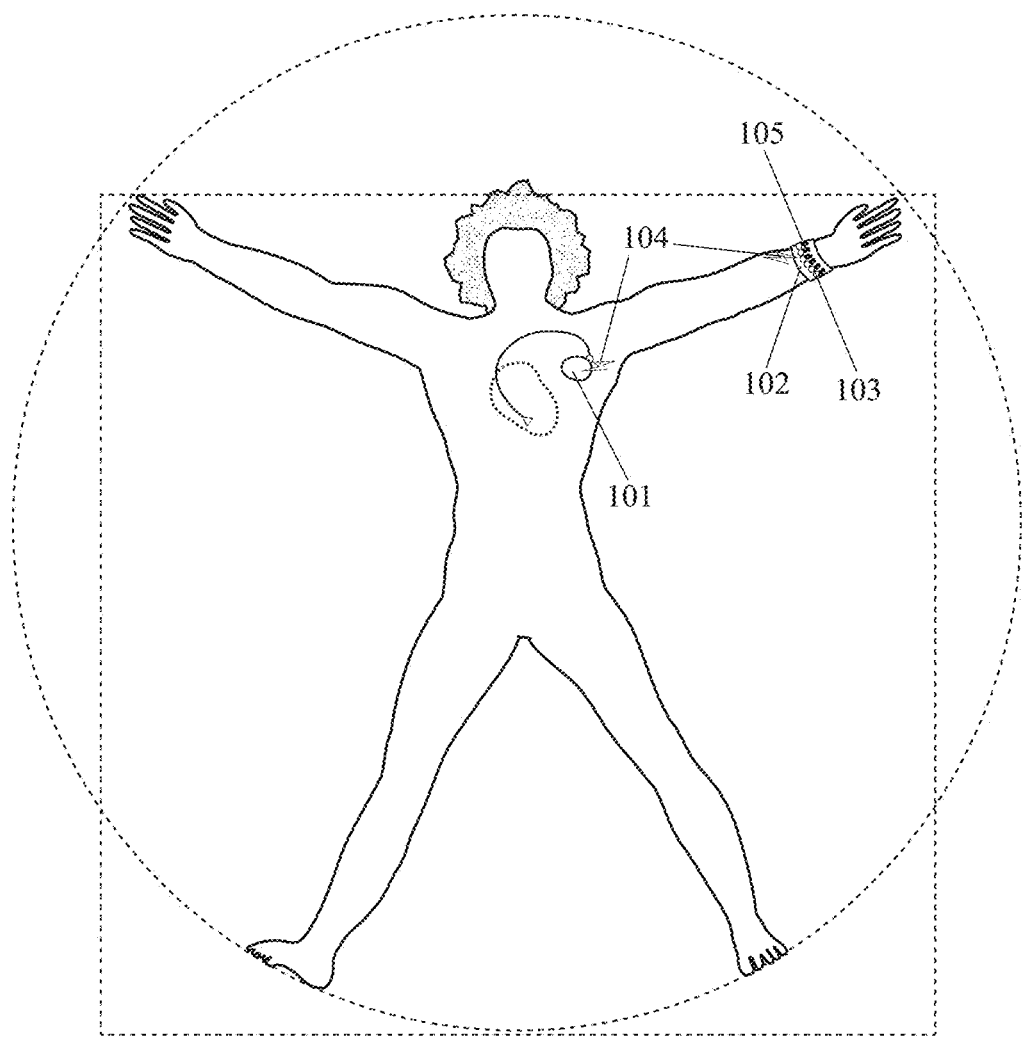
FIG. 1 shows an integrated system for cardiac function assistance with an implanted cardiac pacemaker and a smart watch with an arcuate array of biometric sensors.

FIG. 1 shows an example of a system for cardiac function assistance comprising: an implanted cardiac pacemaker (or other implanted cardiac rhythm management device) 101 with a plurality of operating parameters, including pacing rate, which is implanted in a person; and a wearable device 102 worn by the person with an arcuate array of biometric sensors 103; wherein the implanted device and the wearable device are in wireless communication 104 with each other (either directly or through an intermediary device), and wherein one or more of the operating parameters of the implanted cardiac pacemaker or other implanted cardiac rhythm management device are automatically adjusted based on analysis of data from the sensors.

In this example, the wearable device is a wrist-worn device such as a smart watch. In an example, the wearable device can be selected from the group consisting of a smart watch or watch band, a wrist or arm band, a finger ring, a sleeve, an ear bud or other ear insert, a chest strap, a smart sock, an adhesive patch, and smart glasses. In an example, the biometric sensors can be selected from the group consisting of electromagnetic energy sensors, blood pressure sensors, and oxygenation sensors. In an example, the arcuate array of biometric sensors can span some or all of the circumference of the portion of the person's body to which the wearable device is attached to accommodate variable placement, rotation, and/or shifting of the device. Other variations discussed in this or priority-linked disclosures can also be applied to this example where relevant.

Figure 2:
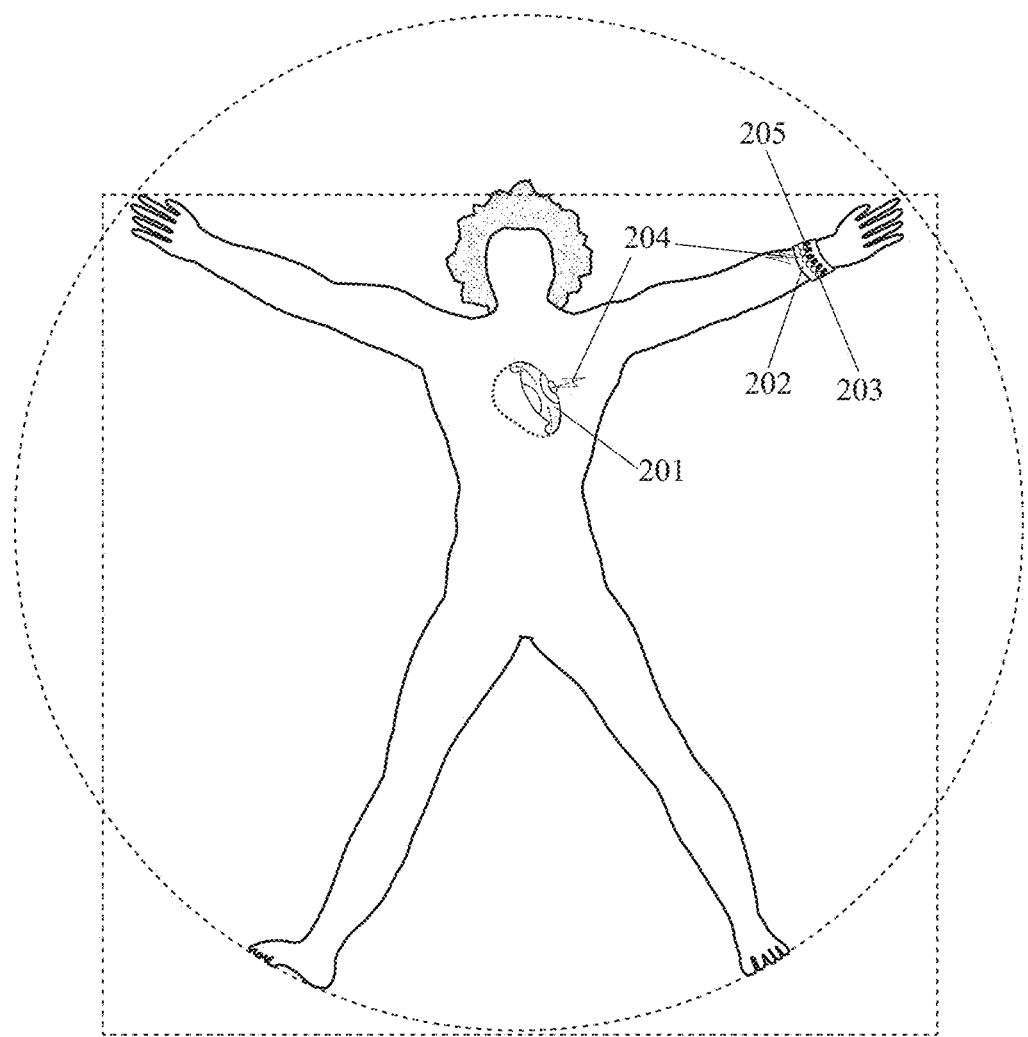
FIG. 2 shows an integrated system for cardiac function assistance with an implanted Ventricular Assist Device (VAD) and a smart watch with an arcuate array of biometric sensors.

FIG. 2 shows an example of a system for cardiac function assistance comprising: an implanted Ventricular Assist Device (VAD) or other implanted blood-pumping device 201 with a plurality of operating parameters, including rotational and/or flow speed, which is implanted in a person; and a wearable device 202 worn by the person with an arcuate array of biometric sensors 203; wherein the implanted device and the wearable device are in wireless communication 204 with each other (either directly or through an intermediary device), and wherein one or more of the operating parameters of the other implanted Ventricular Assist Device (VAD) or other implanted blood-pumping device are automatically adjusted based on analysis of data from the sensors.

In this example, the wearable device is a wrist-worn device such as a smart watch. In an example, the wearable device can be selected from the group consisting of a smart watch or watch band, a wrist or arm band, a finger ring, a sleeve, an ear bud or other ear insert, a chest strap, a smart sock, an adhesive patch, and smart glasses. In an example, the biometric sensors can be selected from the group consisting of electromagnetic energy sensors, blood pressure sensors, and oxygenation sensors. In an example, the arcuate array of biometric sensors can span some or all of the circumference of the portion of the person's body to which the wearable device is attached to accommodate variable placement, rotation, and/or shifting of the device. Other variations discussed in this or priority-linked disclosures can also be applied to this example where relevant.

In an example, a system for cardiac function assistance can comprise: an implanted cardiac pacemaker or other implanted cardiac rhythm management device with a plurality of operating parameters including pacing rate which is implanted in a person; a wrist or arm band worn by the person; and a plurality of blood pressure sensors in the band; wherein operating parameters of the implanted cardiac pacemaker or other implanted cardiac rhythm management device are automatically adjusted based on analysis of data from the sensors.

In an example, a system for cardiac function assistance can comprise: an implanted ventricular assist device (VAD) or other blood-pumping device with a plurality of operating parameters including speed which is implanted in a person; a wrist or arm band worn by the person; and a plurality of blood pressure sensors in the band, wherein the sensors are configured in a linear array; wherein operating parameters of the implanted ventricular assist device or other blood pumping device are automatically adjusted based on analysis of data from the sensors. In an example, a system for cardiac function assistance can comprise: an implanted cardiac pacemaker or other implanted cardiac rhythm management device with a plurality of operating parameters including pacing rate which is implanted in a person; an ear bud or other ear insert worn by the person; and a plurality of blood pressure sensors in the ear bud or other insert, wherein the sensors are configured in an arcuate (e.g. circumferential) array; wherein operating parameters of the implanted cardiac pacemaker or other implanted cardiac rhythm management device are automatically adjusted based on analysis of data from the sensors.

Alternatively, a system for cardiac function assistance can comprise: an implanted cardiac pacemaker or other implanted cardiac rhythm management device with a plurality of operating parameters including pacing rate which is implanted in a person; a sensor-enabled adhesive patch worn by the person; and a plurality of blood pressure sensors in the patch; wherein operating parameters of the implanted cardiac pacemaker or other implanted cardiac rhythm management device are automatically adjusted based on analysis of data from the sensors. In another example, a system for cardiac function assistance can comprise: an implanted ventricular assist device (VAD) or other blood-pumping device with a plurality of operating parameters including speed which is implanted in a person; a sensor-enabled adhesive patch worn by the person; and a plurality of blood pressure sensors in the patch, wherein the sensors are configured in a linear array; wherein operating parameters of the implanted ventricular assist device or other blood pumping device are automatically adjusted based on analysis of data from the sensors.

In an example, a system for cardiac function assistance can comprise: an implanted cardiac pacemaker or other implanted cardiac rhythm management device with a plurality of operating parameters including pacing rate which is implanted in a person; a sensor-enabled sleeve worn by the person; and a plurality of blood pressure sensors in the sleeve, wherein the sensors are configured in a linear array; wherein operating parameters of the implanted cardiac pacemaker or other implanted cardiac rhythm management device are automatically adjusted based on analysis of data from the sensors. In another example, a system for cardiac function assistance can comprise: an implanted cardiac pacemaker or other implanted cardiac rhythm management device with a plurality of operating parameters including pacing rate which is implanted in a person; sensor-enabled smart glasses worn by the person; and a plurality of blood pressure sensors in the smart glasses; wherein operating parameters of the implanted cardiac pacemaker or other implanted cardiac rhythm management device are automatically adjusted based on analysis of data from the sensors.

In an example, a system for cardiac function assistance can comprise: an implanted ventricular assist device (VAD) or other blood-pumping device with a plurality of operating parameters including speed which is implanted in a person; sensor-enabled smart glasses worn by the person; and a plurality of blood pressure sensors in the smart glasses, wherein the sensors are configured in a linear array; wherein operating parameters of the implanted ventricular assist device or other blood pumping device are automatically adjusted based on analysis of data from the sensors. In an example, a system for cardiac function assistance can comprise: an implanted cardiac pacemaker or other implanted cardiac rhythm management device with a plurality of operating parameters including pacing rate which is implanted in a person; a sensor-enabled sleeve worn by the person; and a plurality of blood pressure sensors in the sock, wherein the sensors are configured in a linear array; wherein operating parameters of the implanted cardiac pacemaker or other implanted cardiac rhythm management device are automatically adjusted based on analysis of data from the sensors.

Alternatively, a system for cardiac function assistance can comprise: an implanted cardiac pacemaker or other implanted cardiac rhythm management device with a plurality of operating parameters including pacing rate which is implanted in a person; strap or band worn by the person; and a plurality of blood pressure sensors in the strap or band; wherein operating parameters of the implanted cardiac pacemaker or other implanted cardiac rhythm management device are automatically adjusted based on analysis of data from the sensors. In another example, a system for cardiac function assistance can comprise: an implanted ventricular assist device (VAD) or other blood-pumping device with a plurality of operating parameters including speed which is implanted in a person; strap or band worn by the person; and a plurality of blood pressure sensors in the strap or band, wherein the sensors are configured in a linear array; wherein operating parameters of the implanted ventricular assist device or other blood pumping device are automatically adjusted based on analysis of data from the sensors.

In an example, a system for cardiac function assistance can comprise: an implanted cardiac pacemaker or other implanted cardiac rhythm management device with a plurality of operating parameters including pacing rate which is implanted in a person; a sensor-enabled sleeve worn by the person; and a plurality of blood pressure sensors in the watch, wherein the sensors are configured in a linear array; wherein operating parameters of the implanted cardiac pacemaker or other implanted cardiac rhythm management device are automatically adjusted based on analysis of data from the sensors. In another example, a system for cardiac function assistance can comprise: an implanted cardiac pacemaker or other implanted cardiac rhythm management device with a plurality of operating parameters including pacing rate which is implanted in a person; a wearable device worn by the person selected from the group consisting of a smart watch, wrist or arm band, sleeve, finger ring, ear insert, chest strap, sock, and adhesive patch; and a plurality of blood pressure sensors in the wearable device, wherein the sensors are configured in a linear array; wherein operating parameters of the implanted cardiac pacemaker or other implanted cardiac rhythm management device are automatically adjusted based on analysis of data from the sensors.

In an example, a system for cardiac function assistance can comprise: an implanted cardiac pacemaker or other implanted cardiac rhythm management device with a plurality of operating parameters including pacing rate which is implanted in a person; a wrist or arm band worn by the person; and a plurality of electromagnetic energy sensors in the band; wherein operating parameters of the implanted cardiac pacemaker or other implanted cardiac rhythm management device are automatically adjusted based on analysis of data from the sensors. In an example, a system for cardiac function assistance can comprise: an implanted ventricular assist device (VAD) or other blood-pumping device with a plurality of operating parameters including speed which is implanted in a person; a wrist or arm band worn by the person; and a plurality of electromagnetic energy sensors in the band, wherein the sensors are configured in a linear array; wherein operating parameters of the implanted ventricular assist device or other blood pumping device are automatically adjusted based on analysis of data from the sensors.

Alternatively, a system for cardiac function assistance can comprise: an implanted cardiac pacemaker or other implanted cardiac rhythm management device with a plurality of operating parameters including pacing rate which is implanted in a person; an ear bud or other ear insert worn by the person; and a plurality of electromagnetic energy sensors in the ear bud or other insert, wherein the sensors are configured in an arcuate (e.g. circumferential) array; wherein operating parameters of the implanted cardiac pacemaker or other implanted cardiac rhythm management device are automatically adjusted based on analysis of data from the sensors. In another example, a system for cardiac function assistance can comprise: an implanted cardiac pacemaker or other implanted cardiac rhythm management device with a plurality of operating parameters including pacing rate which is implanted in a person; a sensor-enabled adhesive patch worn by the person; and a plurality of electromagnetic energy sensors in the patch; wherein operating parameters of the implanted cardiac pacemaker or other implanted cardiac rhythm management device are automatically adjusted based on analysis of data from the sensors.

In an example, a system for cardiac function assistance can comprise: an implanted ventricular assist device (VAD) or other blood-pumping device with a plurality of operating parameters including speed which is implanted in a person; a sensor-enabled adhesive patch worn by the person; and a plurality of electromagnetic energy sensors in the patch, wherein the sensors are configured in a linear array; wherein operating parameters of the implanted ventricular assist device or other blood pumping device are automatically adjusted based on analysis of data from the sensors. In another example, a system for cardiac function assistance can comprise: an implanted cardiac pacemaker or other implanted cardiac rhythm management device with a plurality of operating parameters including pacing rate which is implanted in a person; a sensor-enabled sleeve worn by the person; and a plurality of electromagnetic energy sensors in the sleeve, wherein the sensors are configured in a linear array; wherein operating parameters of the implanted cardiac pacemaker or other implanted cardiac rhythm management device are automatically adjusted based on analysis of data from the sensors.

Alternatively, a system for cardiac function assistance can comprise: an implanted cardiac pacemaker or other implanted cardiac rhythm management device with a plurality of operating parameters including pacing rate which is implanted in a person; sensor-enabled smart glasses worn by the person; and a plurality of electromagnetic energy sensors in the smart glasses; wherein operating parameters of the implanted cardiac pacemaker or other implanted cardiac rhythm management device are automatically adjusted based on analysis of data from the sensors. In an example, a system for cardiac function assistance can comprise: an implanted ventricular assist device (VAD) or other blood-pumping device with a plurality of operating parameters including speed which is implanted in a person; sensor-enabled smart glasses worn by the person; and a plurality of electromagnetic energy sensors in the smart glasses, wherein the sensors are configured in a linear array; wherein operating parameters of the implanted ventricular assist device or other blood pumping device are automatically adjusted based on analysis of data from the sensors.

In an example, a system for cardiac function assistance can comprise: an implanted cardiac pacemaker or other implanted cardiac rhythm management device with a plurality of operating parameters including pacing rate which is implanted in a person; a sensor-enabled sleeve worn by the person; and a plurality of electromagnetic energy sensors in the sock, wherein the sensors are configured in a linear array; wherein operating parameters of the implanted cardiac pacemaker or other implanted cardiac rhythm management device are automatically adjusted based on analysis of data from the sensors. In another example, a system for cardiac function assistance can comprise: an implanted cardiac pacemaker or other implanted cardiac rhythm management device with a plurality of operating parameters including pacing rate which is implanted in a person; strap or band worn by the person; and a plurality of electromagnetic energy sensors in the strap or band; wherein operating parameters of the implanted cardiac pacemaker or other implanted cardiac rhythm management device are automatically adjusted based on analysis of data from the sensors.

In an example, a system for cardiac function assistance can comprise: an implanted ventricular assist device (VAD) or other blood-pumping device with a plurality of operating parameters including speed which is implanted in a person; strap or band worn by the person; and a plurality of electromagnetic energy sensors in the strap or band, wherein the sensors are configured in a linear array; wherein operating parameters of the implanted ventricular assist device or other blood pumping device are automatically adjusted based on analysis of data from the sensors. In another example, a system for cardiac function assistance can comprise: an implanted cardiac pacemaker or other implanted cardiac rhythm management device with a plurality of operating parameters including pacing rate which is implanted in a person; a sensor-enabled sleeve worn by the person; and a plurality of electromagnetic energy sensors in the watch, wherein the sensors are configured in a linear array; wherein operating parameters of the implanted cardiac pacemaker or other implanted cardiac rhythm management device are automatically adjusted based on analysis of data from the sensors.

In an example, a system for cardiac function assistance can comprise: an implanted cardiac pacemaker or other implanted cardiac rhythm management device with a plurality of operating parameters including pacing rate which is implanted in a person; a wearable device worn by the person selected from the group consisting of a smart watch, wrist or arm band, sleeve, finger ring, ear insert, chest strap, sock, and adhesive patch; and a plurality of electromagnetic energy sensors in the wearable device, wherein the sensors are configured in a linear array; wherein operating parameters of the implanted cardiac pacemaker or other implanted cardiac rhythm management device are automatically adjusted based on analysis of data from the sensors. Alternatively, a system for cardiac function assistance can comprise: an implanted cardiac pacemaker or other implanted cardiac rhythm management device with a plurality of operating parameters including pacing rate which is implanted in a person; a chest strap or band worn by the person; and a plurality of electromagnetic energy, blood pressure, or oxygenation sensors in the strap or band, wherein the sensors are configured in a linear array; wherein operating parameters of the implanted cardiac pacemaker or other implanted cardiac rhythm management device are automatically adjusted based on analysis of data from the sensors.

In an example, a system for cardiac function assistance can comprise: an implanted cardiac pacemaker or other implanted cardiac rhythm management device with a plurality of operating parameters including pacing rate which is implanted in a person; a sensor-enabled adhesive patch worn by the person; and a plurality of electromagnetic energy, blood pressure, or oxygenation sensors in the patch, wherein the sensors are configured in a linear array; wherein operating parameters of the implanted cardiac pacemaker or other implanted cardiac rhythm management device are automatically adjusted based on analysis of data from the sensors. In another example, a system for cardiac function assistance can comprise: an implanted cardiac pacemaker or other implanted cardiac rhythm management device with a plurality of operating parameters including pacing rate which is implanted in a person; a sensor-enabled sleeve worn by the person; and a plurality of electromagnetic energy, blood pressure, or oxygenation sensors in the sleeve, wherein the sensors are configured in a linear array; wherein operating parameters of the implanted cardiac pacemaker or other implanted cardiac rhythm management device are automatically adjusted based on analysis of data from the sensors.

In an example, a system for cardiac function assistance can comprise: an implanted cardiac pacemaker or other implanted cardiac rhythm management device with a plurality of operating parameters including pacing rate which is implanted in a person; a sensor-enabled sleeve worn by the person; and a plurality of electromagnetic energy, blood pressure, or oxygenation sensors in the watch, wherein the sensors are configured in a linear array; wherein operating parameters of the implanted cardiac pacemaker or other implanted cardiac rhythm management device are automatically adjusted based on analysis of data from the sensors. In another example, a system for cardiac function assistance can comprise: an implanted ventricular assist device (VAD) or other blood-pumping device with a plurality of operating parameters including speed which is implanted in a person; a sensor-enabled sleeve worn by the person; and a plurality of electromagnetic energy, blood pressure, or oxygenation sensors in the sock, wherein the sensors are configured in a linear array; wherein operating parameters of the implanted ventricular assist device or other blood pumping device are automatically adjusted based on analysis of data from the sensors.

In an example, a system for cardiac function assistance can comprise: an implanted cardiac pacemaker or other implanted cardiac rhythm management device with a plurality of operating parameters including pacing rate which is implanted in a person; a wrist or arm band worn by the person; and a plurality of electromagnetic energy, blood pressure, or oxygenation sensors in the band, wherein the sensors are configured in a linear array; wherein operating parameters of the implanted cardiac pacemaker or other implanted cardiac rhythm management device are automatically adjusted based on analysis of data from the sensors. Alternatively, a system for cardiac function assistance can comprise: an implanted cardiac pacemaker or other implanted cardiac rhythm management device with a plurality of operating parameters including pacing rate which is implanted in a person; an ear bud or other ear insert worn by the person; and a plurality of electromagnetic energy, blood pressure, or oxygenation sensors in the ear bud or other insert, wherein the sensors are configured in a linear array; wherein operating parameters of the implanted cardiac pacemaker or other implanted cardiac rhythm management device are automatically adjusted based on analysis of data from the sensors.

In an example, a system for cardiac function assistance can comprise: an implanted cardiac pacemaker or other implanted cardiac rhythm management device with a plurality of operating parameters including pacing rate which is implanted in a person; sensor-enabled smart glasses worn by the person; and a plurality of electromagnetic energy, blood pressure, or oxygenation sensors in the smart glasses, wherein the sensors are configured in a linear array; wherein operating parameters of the implanted cardiac pacemaker or other implanted cardiac rhythm management device are automatically adjusted based on analysis of data from the sensors. In another example, a system for cardiac function assistance can comprise: an implanted cardiac pacemaker or other implanted cardiac rhythm management device with a plurality of operating parameters including pacing rate which is implanted in a person; a wrist or arm band worn by the person; and a plurality of oxygenation sensors in the band; wherein operating parameters of the implanted cardiac pacemaker or other implanted cardiac rhythm management device are automatically adjusted based on analysis of data from the sensors.

Alternatively, a system for cardiac function assistance can comprise: an implanted ventricular assist device (VAD) or other blood-pumping device with a plurality of operating parameters including speed which is implanted in a person; a wrist or arm band worn by the person; and a plurality of oxygenation sensors in the band, wherein the sensors are configured in a linear array; wherein operating parameters of the implanted ventricular assist device or other blood pumping device are automatically adjusted based on analysis of data from the sensors. In another example, a system for cardiac function assistance can comprise: an implanted cardiac pacemaker or other implanted cardiac rhythm management device with a plurality of operating parameters including pacing rate which is implanted in a person; an ear bud or other ear insert worn by the person; and a plurality of oxygenation sensors in the ear bud or other insert, wherein the sensors are configured in an arcuate (e.g. circumferential) array; wherein operating parameters of the implanted cardiac pacemaker or other implanted cardiac rhythm management device are automatically adjusted based on analysis of data from the sensors.

In an example, a system for cardiac function assistance can comprise: an implanted cardiac pacemaker or other implanted cardiac rhythm management device with a plurality of operating parameters including pacing rate which is implanted in a person; a sensor-enabled adhesive patch worn by the person; and a plurality of oxygenation sensors in the patch; wherein operating parameters of the implanted cardiac pacemaker or other implanted cardiac rhythm management device are automatically adjusted based on analysis of data from the sensors. In an example, a system for cardiac function assistance can comprise: an implanted ventricular assist device (VAD) or other blood-pumping device with a plurality of operating parameters including speed which is implanted in a person; a sensor-enabled adhesive patch worn by the person; and a plurality of oxygenation sensors in the patch, wherein the sensors are configured in a linear array; wherein operating parameters of the implanted ventricular assist device or other blood pumping device are automatically adjusted based on analysis of data from the sensors.

In an example, a system for cardiac function assistance can comprise: an implanted cardiac pacemaker or other implanted cardiac rhythm management device with a plurality of operating parameters including pacing rate which is implanted in a person; a sensor-enabled sleeve worn by the person; and a plurality of oxygenation sensors in the sleeve, wherein the sensors are configured in a linear array; wherein operating parameters of the implanted cardiac pacemaker or other implanted cardiac rhythm management device are automatically adjusted based on analysis of data from the sensors. In another example, a system for cardiac function assistance can comprise: an implanted cardiac pacemaker or other implanted cardiac rhythm management device with a plurality of operating parameters including pacing rate which is implanted in a person; sensor-enabled smart glasses worn by the person; and a plurality of oxygenation sensors in the smart glasses; wherein operating parameters of the implanted cardiac pacemaker or other implanted cardiac rhythm management device are automatically adjusted based on analysis of data from the sensors.

In an example, a system for cardiac function assistance can comprise: an implanted ventricular assist device (VAD) or other blood-pumping device with a plurality of operating parameters including speed which is implanted in a person; sensor-enabled smart glasses worn by the person; and a plurality of oxygenation sensors in the smart glasses, wherein the sensors are configured in a linear array; wherein operating parameters of the implanted ventricular assist device or other blood pumping device are automatically adjusted based on analysis of data from the sensors. In another example, a system for cardiac function assistance can comprise: an implanted cardiac pacemaker or other implanted cardiac rhythm management device with a plurality of operating parameters including pacing rate which is implanted in a person; a sensor-enabled sleeve worn by the person; and a plurality of oxygenation sensors in the sock, wherein the sensors are configured in a linear array; wherein operating parameters of the implanted cardiac pacemaker or other implanted cardiac rhythm management device are automatically adjusted based on analysis of data from the sensors.

Alternatively, a system for cardiac function assistance can comprise: an implanted cardiac pacemaker or other implanted cardiac rhythm management device with a plurality of operating parameters including pacing rate which is implanted in a person; strap or band worn by the person; and a plurality of oxygenation sensors in the strap or band; wherein operating parameters of the implanted cardiac pacemaker or other implanted cardiac rhythm management device are automatically adjusted based on analysis of data from the sensors. In an example, a system for cardiac function assistance can comprise: an implanted ventricular assist device (VAD) or other blood-pumping device with a plurality of operating parameters including speed which is implanted in a person; strap or band worn by the person; and a plurality of oxygenation sensors in the strap or band, wherein the sensors are configured in a linear array; wherein operating parameters of the implanted ventricular assist device or other blood pumping device are automatically adjusted based on analysis of data from the sensors.

Alternatively, a system for cardiac function assistance can comprise: an implanted cardiac pacemaker or other implanted cardiac rhythm management device with a plurality of operating parameters including pacing rate which is implanted in a person; a sensor-enabled sleeve worn by the person; and a plurality of oxygenation sensors in the watch, wherein the sensors are configured in a linear array; wherein operating parameters of the implanted cardiac pacemaker or other implanted cardiac rhythm management device are automatically adjusted based on analysis of data from the sensors. In another example, a system for cardiac function assistance can comprise: an implanted cardiac pacemaker or other implanted cardiac rhythm management device with a plurality of operating parameters including pacing rate which is implanted in a person; a wearable device worn by the person selected from the group consisting of a smart watch, wrist or arm band, sleeve, finger ring, ear insert, chest strap, sock, and adhesive patch; and a plurality of oxygenation sensors in the wearable device, wherein the sensors are configured in a linear array; wherein operating parameters of the implanted cardiac pacemaker or other implanted cardiac rhythm management device are automatically adjusted based on analysis of data from the sensors.

In an example, a system for cardiac function assistance can comprise: an implanted ventricular assist device (VAD) or other blood-pumping device with a plurality of operating parameters including speed which is implanted in a person; a wrist or arm band worn by the person; and a plurality of blood pressure sensors in the band; wherein operating parameters of the implanted ventricular assist device or other blood pumping device are automatically adjusted based on analysis of data from the sensors. In another example, a system for cardiac function assistance can comprise: an implanted ventricular assist device (VAD) or other blood-pumping device with a plurality of operating parameters including speed which is implanted in a person; a wrist or arm band worn by the person; and a plurality of blood pressure sensors in the band, wherein the sensors are configured in an arcuate (e.g. circumferential) array; wherein operating parameters of the implanted ventricular assist device or other blood pumping device are automatically adjusted based on analysis of data from the sensors.

In an example, a system for cardiac function assistance can comprise: an implanted ventricular assist device (VAD) or other blood-pumping device with a plurality of operating parameters including speed which is implanted in a person; an ear bud or other ear insert worn by the person; and a plurality of blood pressure sensors in the ear bud or other insert; wherein operating parameters of the implanted ventricular assist device or other blood pumping device are automatically adjusted based on analysis of data from the sensors. In an example, a system for cardiac function assistance can comprise: an implanted ventricular assist device (VAD) or other blood-pumping device with a plurality of operating parameters including speed which is implanted in a person; a sensor-enabled adhesive patch worn by the person; and a plurality of blood pressure sensors in the patch; wherein operating parameters of the implanted ventricular assist device or other blood pumping device are automatically adjusted based on analysis of data from the sensors.

In an example, a system for cardiac function assistance can comprise: an implanted ventricular assist device (VAD) or other blood-pumping device with a plurality of operating parameters including speed which is implanted in a person; a sensor-enabled adhesive patch worn by the person; and a plurality of blood pressure sensors in the patch, wherein the sensors are configured in an arcuate (e.g. circumferential) array; wherein operating parameters of the implanted ventricular assist device or other blood pumping device are automatically adjusted based on analysis of data from the sensors. In another example, a system for cardiac function assistance can comprise: an implanted cardiac pacemaker or other implanted cardiac rhythm management device with a plurality of operating parameters including pacing rate which is implanted in a person; a sensor-enabled sleeve worn by the person; and a plurality of blood pressure sensors in the sleeve, wherein the sensors are configured in an arcuate (e.g. circumferential) array; wherein operating parameters of the implanted cardiac pacemaker or other implanted cardiac rhythm management device are automatically adjusted based on analysis of data from the sensors.

Alternatively, a system for cardiac function assistance can comprise: an implanted ventricular assist device (VAD) or other blood-pumping device with a plurality of operating parameters including speed which is implanted in a person; sensor-enabled smart glasses worn by the person; and a plurality of blood pressure sensors in the smart glasses; wherein operating parameters of the implanted ventricular assist device or other blood pumping device are automatically adjusted based on analysis of data from the sensors. In another example, a system for cardiac function assistance can comprise: an implanted ventricular assist device (VAD) or other blood-pumping device with a plurality of operating parameters including speed which is implanted in a person; sensor-enabled smart glasses worn by the person; and a plurality of blood pressure sensors in the smart glasses, wherein the sensors are configured in an arcuate (e.g. circumferential) array; wherein operating parameters of the implanted ventricular assist device or other blood pumping device are automatically adjusted based on analysis of data from the sensors.

In an example, a system for cardiac function assistance can comprise: an implanted cardiac pacemaker or other implanted cardiac rhythm management device with a plurality of operating parameters including pacing rate which is implanted in a person; a sensor-enabled sleeve worn by the person; and a plurality of blood pressure sensors in the sock, wherein the sensors are configured in an arcuate (e.g. circumferential) array; wherein operating parameters of the implanted cardiac pacemaker or other implanted cardiac rhythm management device are automatically adjusted based on analysis of data from the sensors. Alternatively, a system for cardiac function assistance can comprise: an implanted ventricular assist device (VAD) or other blood-pumping device with a plurality of operating parameters including speed which is implanted in a person; strap or band worn by the person; and a plurality of blood pressure sensors in the strap or band; wherein operating parameters of the implanted ventricular assist device or other blood pumping device are automatically adjusted based on analysis of data from the sensors.

In an example, a system for cardiac function assistance can comprise: an implanted ventricular assist device (VAD) or other blood-pumping device with a plurality of operating parameters including speed which is implanted in a person; strap or band worn by the person; and a plurality of blood pressure sensors in the strap or band, wherein the sensors are configured in an arcuate (e.g. circumferential) array; wherein operating parameters of the implanted ventricular assist device or other blood pumping device are automatically adjusted based on analysis of data from the sensors. In another example, a system for cardiac function assistance can comprise: an implanted cardiac pacemaker or other implanted cardiac rhythm management device with a plurality of operating parameters including pacing rate which is implanted in a person; a sensor-enabled sleeve worn by the person; and a plurality of blood pressure sensors in the watch, wherein the sensors are configured in an arcuate (e.g. circumferential) array; wherein operating parameters of the implanted cardiac pacemaker or other implanted cardiac rhythm management device are automatically adjusted based on analysis of data from the sensors.

In an example, a system for cardiac function assistance can comprise: an implanted cardiac pacemaker or other implanted cardiac rhythm management device with a plurality of operating parameters including pacing rate which is implanted in a person; a wearable device worn by the person selected from the group consisting of a smart watch, wrist or arm band, sleeve, finger ring, ear insert, chest strap, sock, and adhesive patch; and a plurality of blood pressure sensors in the wearable device, wherein the sensors are configured in an arcuate (e.g. circumferential) array; wherein operating parameters of the implanted cardiac pacemaker or other implanted cardiac rhythm management device are automatically adjusted based on analysis of data from the sensors. In another example, a system for cardiac function assistance can comprise: an implanted ventricular assist device (VAD) or other blood-pumping device with a plurality of operating parameters including speed which is implanted in a person; a wrist or arm band worn by the person; and a plurality of electromagnetic energy sensors in the band; wherein operating parameters of the implanted ventricular assist device or other blood pumping device are automatically adjusted based on analysis of data from the sensors.

In an example, a system for cardiac function assistance can comprise: an implanted ventricular assist device (VAD) or other blood-pumping device with a plurality of operating parameters including speed which is implanted in a person; a wrist or arm band worn by the person; and a plurality of electromagnetic energy sensors in the band, wherein the sensors are configured in an arcuate (e.g. circumferential) array; wherein operating parameters of the implanted ventricular assist device or other blood pumping device are automatically adjusted based on analysis of data from the sensors. Alternatively, a system for cardiac function assistance can comprise: an implanted ventricular assist device (VAD) or other blood-pumping device with a plurality of operating parameters including speed which is implanted in a person; an ear bud or other ear insert worn by the person; and a plurality of electromagnetic energy sensors in the ear bud or other insert; wherein operating parameters of the implanted ventricular assist device or other blood pumping device are automatically adjusted based on analysis of data from the sensors.

In an example, a system for cardiac function assistance can comprise: an implanted ventricular assist device (VAD) or other blood-pumping device with a plurality of operating parameters including speed which is implanted in a person; a sensor-enabled adhesive patch worn by the person; and a plurality of electromagnetic energy sensors in the patch; wherein operating parameters of the implanted ventricular assist device or other blood pumping device are automatically adjusted based on analysis of data from the sensors. In another example, a system for cardiac function assistance can comprise: an implanted ventricular assist device (VAD) or other blood-pumping device with a plurality of operating parameters including speed which is implanted in a person; a sensor-enabled adhesive patch worn by the person; and a plurality of electromagnetic energy sensors in the patch, wherein the sensors are configured in an arcuate (e.g. circumferential) array; wherein operating parameters of the implanted ventricular assist device or other blood pumping device are automatically adjusted based on analysis of data from the sensors.

Alternatively, a system for cardiac function assistance can comprise: an implanted cardiac pacemaker or other implanted cardiac rhythm management device with a plurality of operating parameters including pacing rate which is implanted in a person; a sensor-enabled sleeve worn by the person; and a plurality of electromagnetic energy sensors in the sleeve, wherein the sensors are configured in an arcuate (e.g. circumferential) array; wherein operating parameters of the implanted cardiac pacemaker or other implanted cardiac rhythm management device are automatically adjusted based on analysis of data from the sensors.

In an example, a system for cardiac function assistance can comprise: an implanted cardiac pacemaker or other implanted cardiac rhythm management device with a plurality of operating parameters including pacing rate which is implanted in a person; sensor-enabled smart glasses worn by the person; and a plurality of electromagnetic energy sensors in the smart glasses, wherein the sensors are configured in a linear array; wherein operating parameters of the implanted cardiac pacemaker or other implanted cardiac rhythm management device are automatically adjusted based on analysis of data from the sensors. In another example, a system for cardiac function assistance can comprise: an implanted ventricular assist device (VAD) or other blood-pumping device with a plurality of operating parameters including speed which is implanted in a person; sensor-enabled smart glasses worn by the person; and a plurality of electromagnetic energy sensors in the smart glasses, wherein the sensors are configured in an arcuate (e.g. circumferential) array; wherein operating parameters of the implanted ventricular assist device or other blood pumping device are automatically adjusted based on analysis of data from the sensors.

In an example, a system for cardiac function assistance can comprise: an implanted cardiac pacemaker or other implanted cardiac rhythm management device with a plurality of operating parameters including pacing rate which is implanted in a person; a sensor-enabled sleeve worn by the person; and a plurality of electromagnetic energy sensors in the sock, wherein the sensors are configured in an arcuate (e.g. circumferential) array; wherein operating parameters of the implanted cardiac pacemaker or other implanted cardiac rhythm management device are automatically adjusted based on analysis of data from the sensors. In an example, a system for cardiac function assistance can comprise: an implanted cardiac pacemaker or other implanted cardiac rhythm management device with a plurality of operating parameters including pacing rate which is implanted in a person; strap or band worn by the person; and a plurality of electromagnetic energy sensors in the strap or band, wherein the sensors are configured in a linear array; wherein operating parameters of the implanted cardiac pacemaker or other implanted cardiac rhythm management device are automatically adjusted based on analysis of data from the sensors.

In an example, a system for cardiac function assistance can comprise: an implanted ventricular assist device (VAD) or other blood-pumping device with a plurality of operating parameters including speed which is implanted in a person; strap or band worn by the person; and a plurality of electromagnetic energy sensors in the strap or band, wherein the sensors are configured in an arcuate (e.g. circumferential) array; wherein operating parameters of the implanted ventricular assist device or other blood pumping device are automatically adjusted based on analysis of data from the sensors. In another example, a system for cardiac function assistance can comprise: an implanted cardiac pacemaker or other implanted cardiac rhythm management device with a plurality of operating parameters including pacing rate which is implanted in a person; a sensor-enabled sleeve worn by the person; and a plurality of electromagnetic energy sensors in the watch, wherein the sensors are configured in an arcuate (e.g. circumferential) array; wherein operating parameters of the implanted cardiac pacemaker or other implanted cardiac rhythm management device are automatically adjusted based on analysis of data from the sensors.

Alternatively, a system for cardiac function assistance can comprise: an implanted cardiac pacemaker or other implanted cardiac rhythm management device with a plurality of operating parameters including pacing rate which is implanted in a person; a wearable device worn by the person selected from the group consisting of a smart watch, wrist or arm band, sleeve, finger ring, ear insert, chest strap, sock, and adhesive patch; and a plurality of electromagnetic energy sensors in the wearable device, wherein the sensors are configured in an arcuate (e.g. circumferential) array; wherein operating parameters of the implanted cardiac pacemaker or other implanted cardiac rhythm management device are automatically adjusted based on analysis of data from the sensors. In another example, a system for cardiac function assistance can comprise: an implanted cardiac pacemaker or other implanted cardiac rhythm management device with a plurality of operating parameters including pacing rate which is implanted in a person; a chest strap or band worn by the person; and a plurality of electromagnetic energy, blood pressure, or oxygenation sensors in the strap or band, wherein the sensors are configured in an arcuate (e.g. circumferential) array; wherein operating parameters of the implanted cardiac pacemaker or other implanted cardiac rhythm management device are automatically adjusted based on analysis of data from the sensors.

In an example, a system for cardiac function assistance can comprise: an implanted cardiac pacemaker or other implanted cardiac rhythm management device with a plurality of operating parameters including pacing rate which is implanted in a person; a sensor-enabled adhesive patch worn by the person; and a plurality of electromagnetic energy, blood pressure, or oxygenation sensors in the patch, wherein the sensors are configured in an arcuate (e.g. circumferential) array; wherein operating parameters of the implanted cardiac pacemaker or other implanted cardiac rhythm management device are automatically adjusted based on analysis of data from the sensors. Alternatively, a system for cardiac function assistance can comprise: an implanted cardiac pacemaker or other implanted cardiac rhythm management device with a plurality of operating parameters including pacing rate which is implanted in a person; a sensor-enabled sleeve worn by the person; and a plurality of electromagnetic energy, blood pressure, or oxygenation sensors in the sleeve, wherein the sensors are configured in an arcuate (e.g. circumferential) array; wherein operating parameters of the implanted cardiac pacemaker or other implanted cardiac rhythm management device are automatically adjusted based on analysis of data from the sensors.

In an example, a system for cardiac function assistance can comprise: an implanted cardiac pacemaker or other implanted cardiac rhythm management device with a plurality of operating parameters including pacing rate which is implanted in a person; a sensor-enabled sleeve worn by the person; and a plurality of electromagnetic energy, blood pressure, or oxygenation sensors in the watch, wherein the sensors are configured in an arcuate (e.g. circumferential) array; wherein operating parameters of the implanted cardiac pacemaker or other implanted cardiac rhythm management device are automatically adjusted based on analysis of data from the sensors.

In an example, a system for cardiac function assistance can comprise: an implanted ventricular assist device (VAD)

or other blood-pumping device with a plurality of operating parameters including speed which is implanted in a person; a sensor-enabled sleeve worn by the person; and a plurality of electromagnetic energy, blood pressure, or oxygenation sensors in the sock, wherein the sensors are configured in an arcuate (e.g. circumferential) array; wherein operating parameters of the implanted ventricular assist device or other blood pumping device are automatically adjusted based on analysis of data from the sensors. In another example, a system for cardiac function assistance can comprise: an implanted cardiac pacemaker or other implanted cardiac rhythm management device with a plurality of operating parameters including pacing rate which is implanted in a person; a wrist or arm band worn by the person; and a plurality of electromagnetic energy, blood pressure, or oxygenation sensors in the band, wherein the sensors are configured in an arcuate (e.g. circumferential) array; wherein operating parameters of the implanted cardiac pacemaker or other implanted cardiac rhythm management device are automatically adjusted based on analysis of data from the sensors.

In an example, a system for cardiac function assistance can comprise: an implanted cardiac pacemaker or other implanted cardiac rhythm management device with a plurality of operating parameters including pacing rate which is implanted in a person; an ear bud or other ear insert worn by the person; and a plurality of electromagnetic energy, blood pressure, or oxygenation sensors in the ear bud or other insert, wherein the sensors are configured in an arcuate (e.g. circumferential) array; wherein operating parameters of the implanted cardiac pacemaker or other implanted cardiac rhythm management device are automatically adjusted based on analysis of data from the sensors. Alternatively, a system for cardiac function assistance can comprise: an implanted cardiac pacemaker or other implanted cardiac rhythm management device with a plurality of operating parameters including pacing rate which is implanted in a person; sensor-enabled smart glasses worn by the person; and a plurality of electromagnetic energy, blood pressure, or oxygenation sensors in the smart glasses, wherein the sensors are configured in an arcuate (e.g. circumferential) array; wherein operating parameters of the implanted cardiac pacemaker or other implanted cardiac rhythm management device are automatically adjusted based on analysis of data from the sensors.

In an example, a system for cardiac function assistance can comprise: an implanted ventricular assist device (VAD) or other blood-pumping device with a plurality of operating parameters including speed which is implanted in a person; a wrist or arm band worn by the person; and a plurality of oxygenation sensors in the band; wherein operating parameters of the implanted ventricular assist device or other blood pumping device are automatically adjusted based on analysis of data from the sensors. In another example, a system for cardiac function assistance can comprise: an implanted ventricular assist device (VAD) or other blood-pumping device with a plurality of operating parameters including speed which is implanted in a person; a wrist or arm band worn by the person; and a plurality of oxygenation sensors in the band, wherein the sensors are configured in an arcuate (e.g. circumferential) array; wherein operating parameters of the implanted ventricular assist device or other blood pumping device are automatically adjusted based on analysis of data from the sensors.

Alternatively, a system for cardiac function assistance can comprise: an implanted ventricular assist device (VAD) or other blood-pumping device with a plurality of operating parameters including speed which is implanted in a person; an ear bud or other ear insert worn by the person; and a plurality of oxygenation sensors in the ear bud or other insert; wherein operating parameters of the implanted ventricular assist device or other blood pumping device are automatically adjusted based on analysis of data from the sensors. In an example, a system for cardiac function assistance can comprise: an implanted ventricular assist device (VAD) or other blood-pumping device with a plurality of operating parameters including speed which is implanted in a person; a sensor-enabled adhesive patch worn by the person; and a plurality of oxygenation sensors in the patch; wherein operating parameters of the implanted ventricular assist device or other blood pumping device are automatically adjusted based on analysis of data from the sensors.

In an example, a system for cardiac function assistance can comprise: an implanted ventricular assist device (VAD) or other blood-pumping device with a plurality of operating parameters including speed which is implanted in a person; a sensor-enabled adhesive patch worn by the person; and a plurality of oxygenation sensors in the patch, wherein the sensors are configured in an arcuate (e.g. circumferential) array; wherein operating parameters of the implanted ventricular assist device or other blood pumping device are automatically adjusted based on analysis of data from the sensors. In another example, a system for cardiac function assistance can comprise: an implanted cardiac pacemaker or other implanted cardiac rhythm management device with a plurality of operating parameters including pacing rate which is implanted in a person; a sensor-enabled sleeve worn by the person; and a plurality of oxygenation sensors in the sleeve, wherein the sensors are configured in an arcuate (e.g. circumferential) array; wherein operating parameters of the implanted cardiac pacemaker or other implanted cardiac rhythm management device are automatically adjusted based on analysis of data from the sensors.

In an example, a system for cardiac function assistance can comprise: an implanted ventricular assist device (VAD) or other blood-pumping device with a plurality of operating parameters including speed which is implanted in a person; sensor-enabled smart glasses worn by the person; and a plurality of oxygenation sensors in the smart glasses; wherein operating parameters of the implanted ventricular assist device or other blood pumping device are automatically adjusted based on analysis of data from the sensors.

In an example, a system for cardiac function assistance can comprise: an implanted ventricular assist device (VAD) or other blood-pumping device with a plurality of operating parameters including speed which is implanted in a person; sensor-enabled smart glasses worn by the person; and a plurality of oxygenation sensors in the smart glasses, wherein the sensors are configured in an arcuate (e.g. circumferential) array; wherein operating parameters of the implanted ventricular assist device or other blood pumping device are automatically adjusted based on analysis of data from the sensors. In another example, a system for cardiac function assistance can comprise: an implanted cardiac pacemaker or other implanted cardiac rhythm management device with a plurality of operating parameters including pacing rate which is implanted in a person; a sensor-enabled sleeve worn by the person; and a plurality of oxygenation sensors in the sock, wherein the sensors are configured in an arcuate (e.g. circumferential) array; wherein operating parameters of the implanted cardiac pacemaker or other implanted cardiac rhythm management device are automatically adjusted based on analysis of data from the sensors.

Alternatively, a system for cardiac function assistance can comprise: an implanted ventricular assist device (VAD) or other blood-pumping device with a plurality of operating parameters including speed which is implanted in a person; strap or band worn by the person; and a plurality of oxygenation sensors in the strap or band; wherein operating parameters of the implanted ventricular assist device or other blood pumping device are automatically adjusted based on analysis of data from the sensors. In another example, a system for cardiac function assistance can comprise: an implanted ventricular assist device (VAD) or other blood-pumping device with a plurality of operating parameters including speed which is implanted in a person; strap or band worn by the person; and a plurality of oxygenation sensors in the strap or band, wherein the sensors are configured in an arcuate (e.g. circumferential) array; wherein operating parameters of the implanted ventricular assist device or other blood pumping device are automatically adjusted based on analysis of data from the sensors.

In an example, a system for cardiac function assistance can comprise: an implanted cardiac pacemaker or other implanted cardiac rhythm management device with a plurality of operating parameters including pacing rate which is implanted in a person; a sensor-enabled sleeve worn by the person; and a plurality of oxygenation sensors in the watch, wherein the sensors are configured in an arcuate (e.g. circumferential) array; wherein operating parameters of the implanted cardiac pacemaker or other implanted cardiac rhythm management device are automatically adjusted based on analysis of data from the sensors. Alternatively, a system for cardiac function assistance can comprise: an implanted cardiac pacemaker or other implanted cardiac rhythm management device with a plurality of operating parameters including pacing rate which is implanted in a person; a wearable device worn by the person selected from the group consisting of a smart watch, wrist or arm band, sleeve, finger ring, ear insert, chest strap, sock, and adhesive patch; and a plurality of oxygenation sensors in the wearable device, wherein the sensors are configured in an arcuate (e.g. circumferential) array; wherein operating parameters of the implanted cardiac pacemaker or other implanted cardiac rhythm management device are automatically adjusted based on analysis of data from the sensors.

In an example, a system for cardiac function assistance can comprise: an implanted cardiac pacemaker or other implanted cardiac rhythm management device with a plurality of operating parameters including pacing rate which is implanted in a person; a wrist or arm band worn by the person; and a plurality of blood pressure sensors in the band, wherein the sensors are configured in a linear array; wherein operating parameters of the implanted cardiac pacemaker or other implanted cardiac rhythm management device are automatically adjusted based on analysis of data from the sensors. In another example, a system for cardiac function assistance can comprise: an implanted cardiac pacemaker or other implanted cardiac rhythm management device with a plurality of operating parameters including pacing rate which is implanted in a person; an ear bud or other ear insert worn by the person; and a plurality of blood pressure sensors in the ear bud or other insert; wherein operating parameters of the implanted cardiac pacemaker or other implanted cardiac rhythm management device are automatically adjusted based on analysis of data from the sensors.

Alternatively, a system for cardiac function assistance can comprise: an implanted ventricular assist device (VAD) or other blood-pumping device with a plurality of operating parameters including speed which is implanted in a person; an ear bud or other ear insert worn by the person; and a plurality of blood pressure sensors in the ear bud or other insert, wherein the sensors are configured in a linear array; wherein operating parameters of the implanted ventricular assist device or other blood pumping device are automatically adjusted based on analysis of data from the sensors. In an example, a system for cardiac function assistance can comprise: an implanted cardiac pacemaker or other implanted cardiac rhythm management device with a plurality of operating parameters including pacing rate which is implanted in a person; a sensor-enabled adhesive patch worn by the person; and a plurality of blood pressure sensors in the patch, wherein the sensors are configured in a linear array; wherein operating parameters of the implanted cardiac pacemaker or other implanted cardiac rhythm management device are automatically adjusted based on analysis of data from the sensors.

In an example, a system for cardiac function assistance can comprise: an implanted cardiac pacemaker or other implanted cardiac rhythm management device with a plurality of operating parameters including pacing rate which is implanted in a person; a sensor-enabled sleeve worn by the person; and a plurality of blood pressure sensors in the sleeve; wherein operating parameters of the implanted cardiac pacemaker or other implanted cardiac rhythm management device are automatically adjusted based on analysis of data from the sensors. In another example, a system for cardiac function assistance can comprise: an implanted ventricular assist device (VAD) or other blood-pumping device with a plurality of operating parameters including speed which is implanted in a person; a sensor-enabled sleeve worn by the person; and a plurality of blood pressure sensors in the sleeve, wherein the sensors are configured in a linear array; wherein operating parameters of the implanted ventricular assist device or other blood pumping device are automatically adjusted based on analysis of data from the sensors.

In an example, a system for cardiac function assistance can comprise: an implanted cardiac pacemaker or other implanted cardiac rhythm management device with a plurality of operating parameters including pacing rate which is implanted in a person; sensor-enabled smart glasses worn by the person; and a plurality of blood pressure sensors in the smart glasses, wherein the sensors are configured in a linear array; wherein operating parameters of the implanted cardiac pacemaker or other implanted cardiac rhythm management device are automatically adjusted based on analysis of data from the sensors. In an example, a system for cardiac function assistance can comprise: an implanted cardiac pacemaker or other implanted cardiac rhythm management device with a plurality of operating parameters including pacing rate which is implanted in a person; a sensor-enabled sleeve worn by the person; and a plurality of blood pressure sensors in the sock; wherein operating parameters of the implanted cardiac pacemaker or other implanted cardiac rhythm management device are automatically adjusted based on analysis of data from the sensors.

Alternatively, a system for cardiac function assistance can comprise: an implanted ventricular assist device (VAD) or other blood-pumping device with a plurality of operating parameters including speed which is implanted in a person; a sensor-enabled sleeve worn by the person; and a plurality of blood pressure sensors in the sock, wherein the sensors are configured in a linear array; wherein operating parameters of the implanted ventricular assist device or other blood pumping device are automatically adjusted based on analysis of data from the sensors. In another example, a system for cardiac function assistance can comprise: an implanted cardiac pacemaker or other implanted cardiac rhythm management device with a plurality of operating parameters including pacing rate which is implanted in a person; strap or band worn by the person; and a plurality of blood pressure sensors in the strap or band, wherein the sensors are configured in a linear array; wherein operating parameters of the implanted cardiac pacemaker or other implanted cardiac rhythm management device are automatically adjusted based on analysis of data from the sensors.

In an example, a system for cardiac function assistance can comprise: an implanted cardiac pacemaker or other implanted cardiac rhythm management device with a plurality of operating parameters including pacing rate which is implanted in a person; a sensor-enabled sleeve worn by the person; and a plurality of blood pressure sensors in the watch; wherein operating parameters of the implanted cardiac pacemaker or other implanted cardiac rhythm management device are automatically adjusted based on analysis of data from the sensors. In another example, a system for cardiac function assistance can comprise: an implanted ventricular assist device (VAD) or other blood-pumping device with a plurality of operating parameters including speed which is implanted in a person; a sensor-enabled sleeve worn by the person; and a plurality of blood pressure sensors in the watch, wherein the sensors are configured in a linear array; wherein operating parameters of the implanted ventricular assist device or other blood pumping device are automatically adjusted based on analysis of data from the sensors. In another example, a system for cardiac function assistance can comprise: an implanted ventricular assist device (VAD) or other blood-pumping device with a plurality of operating parameters including speed which is implanted in a person; a wearable device worn by the person selected from the group consisting of a smart watch, wrist or arm band, sleeve, finger ring, ear insert, chest strap, sock, and adhesive patch; and a plurality of blood pressure sensors in the wearable device, wherein the sensors are configured in a linear array; wherein operating parameters of the implanted ventricular assist device or other blood pumping device are automatically adjusted based on analysis of data from the sensors.

Alternatively, a system for cardiac function assistance can comprise: an implanted cardiac pacemaker or other implanted cardiac rhythm management device with a plurality of operating parameters including pacing rate which is implanted in a person; a wrist or arm band worn by the person; and a plurality of electromagnetic energy sensors in the band, wherein the sensors are configured in a linear array; wherein operating parameters of the implanted cardiac pacemaker or other implanted cardiac rhythm management device are automatically adjusted based on analysis of data from the sensors.

In an example, a system for cardiac function assistance can comprise: an implanted cardiac pacemaker or other implanted cardiac rhythm management device with a plurality of operating parameters including pacing rate which is implanted in a person; an ear bud or other ear insert worn by the person; and a plurality of electromagnetic energy sensors in the ear bud or other insert; wherein operating parameters of the implanted cardiac pacemaker or other implanted cardiac rhythm management device are automatically adjusted based on analysis of data from the sensors. In an example, a system for cardiac function assistance can comprise: an implanted ventricular assist device (VAD) or other blood-pumping device with a plurality of operating parameters including speed which is implanted in a person; an ear bud or other ear insert worn by the person; and a plurality of electromagnetic energy sensors in the ear bud or other insert, wherein the sensors are configured in a linear array; wherein operating parameters of the implanted ventricular assist device or other blood pumping device are automatically adjusted based on analysis of data from the sensors.

In an example, a system for cardiac function assistance can comprise: an implanted cardiac pacemaker or other implanted cardiac rhythm management device with a plurality of operating parameters including pacing rate which is implanted in a person; a sensor-enabled adhesive patch worn by the person; and a plurality of electromagnetic energy sensors in the patch, wherein the sensors are configured in a linear array; wherein operating parameters of the implanted cardiac pacemaker or other implanted cardiac rhythm management device are automatically adjusted based on analysis of data from the sensors. In another example, a system for cardiac function assistance can comprise: an implanted cardiac pacemaker or other implanted cardiac rhythm management device with a plurality of operating parameters including pacing rate which is implanted in a person; a sensor-enabled sleeve worn by the person; and a plurality of electromagnetic energy sensors in the sleeve; wherein operating parameters of the implanted cardiac pacemaker or other implanted cardiac rhythm management device are automatically adjusted based on analysis of data from the sensors.

In an example, a system for cardiac function assistance can comprise: an implanted ventricular assist device (VAD) or other blood-pumping device with a plurality of operating parameters including speed which is implanted in a person; a sensor-enabled sleeve worn by the person; and a plurality of electromagnetic energy sensors in the sleeve, wherein the sensors are configured in a linear array; wherein operating parameters of the implanted ventricular assist device or other blood pumping device are automatically adjusted based on analysis of data from the sensors. Alternatively, a system for cardiac function assistance can comprise: an implanted cardiac pacemaker or other implanted cardiac rhythm management device with a plurality of operating parameters including pacing rate which is implanted in a person; sensor-enabled smart glasses worn by the person; and a plurality of electromagnetic energy sensors in the smart glasses, wherein the sensors are configured in an arcuate (e.g. circumferential) array; wherein operating parameters of the implanted cardiac pacemaker or other implanted cardiac rhythm management device are automatically adjusted based on analysis of data from the sensors.

In an example, a system for cardiac function assistance can comprise: an implanted cardiac pacemaker or other implanted cardiac rhythm management device with a plurality of operating parameters including pacing rate which is implanted in a person; a sensor-enabled sleeve worn by the person; and a plurality of electromagnetic energy sensors in the sock; wherein operating parameters of the implanted cardiac pacemaker or other implanted cardiac rhythm management device are automatically adjusted based on analysis of data from the sensors. In another example, a system for cardiac function assistance can comprise: an implanted ventricular assist device (VAD) or other blood-pumping device with a plurality of operating parameters including speed which is implanted in a person; a sensor-enabled sleeve worn by the person; and a plurality of electromagnetic energy sensors in the sock, wherein the sensors are configured in a linear array; wherein operating parameters of the implanted ventricular assist device or other blood pumping device are automatically adjusted based on analysis of data from the sensors.

Alternatively, a system for cardiac function assistance can comprise: an implanted cardiac pacemaker or other implanted cardiac rhythm management device with a plurality of operating parameters including pacing rate which is implanted in a person; strap or band worn by the person; and a plurality of electromagnetic energy sensors in the strap or band, wherein the sensors are configured in an arcuate (e.g. circumferential) array; wherein operating parameters of the implanted cardiac pacemaker or other implanted cardiac rhythm management device are automatically adjusted based on analysis of data from the sensors. In an example, a system for cardiac function assistance can comprise: an implanted cardiac pacemaker or other implanted cardiac rhythm management device with a plurality of operating parameters including pacing rate which is implanted in a person; a sensor-enabled sleeve worn by the person; and a plurality of electromagnetic energy sensors in the watch; wherein operating parameters of the implanted cardiac pacemaker or other implanted cardiac rhythm management device are automatically adjusted based on analysis of data from the sensors.

In an example, a system for cardiac function assistance can comprise: an implanted ventricular assist device (VAD) or other blood-pumping device with a plurality of operating parameters including speed which is implanted in a person; a sensor-enabled sleeve worn by the person; and a plurality of electromagnetic energy sensors in the watch, wherein the sensors are configured in a linear array; wherein operating parameters of the implanted ventricular assist device or other blood pumping device are automatically adjusted based on analysis of data from the sensors. In another example, a system for cardiac function assistance can comprise: an implanted ventricular assist device (VAD) or other blood-pumping device with a plurality of operating parameters including speed which is implanted in a person; a wearable device worn by the person selected from the group consisting of a smart watch, wrist or arm band, sleeve, finger ring, ear insert, chest strap, sock, and adhesive patch; and a plurality of electromagnetic energy sensors in the wearable device, wherein the sensors are configured in a linear array; wherein operating parameters of the implanted ventricular assist device or other blood pumping device are automatically adjusted based on analysis of data from the sensors.

In an example, a system for cardiac function assistance can comprise: an implanted ventricular assist device (VAD) or other blood-pumping device with a plurality of operating parameters including speed which is implanted in a person; a chest strap or band worn by the person; and a plurality of electromagnetic energy, blood pressure, or oxygenation sensors in the strap or band, wherein the sensors are configured in a linear array; wherein operating parameters of the implanted ventricular assist device or other blood pumping device are automatically adjusted based on analysis of data from the sensors. In an example, a system for cardiac function assistance can comprise: an implanted ventricular assist device (VAD) or other blood-pumping device with a plurality of operating parameters including speed which is implanted in a person; a sensor-enabled adhesive patch worn by the person; and a plurality of electromagnetic energy, blood pressure, or oxygenation sensors in the patch, wherein the sensors are configured in a linear array; wherein operating parameters of the implanted ventricular assist device or other blood pumping device are automatically adjusted based on analysis of data from the sensors.

Alternatively, a system for cardiac function assistance can comprise: an implanted cardiac pacemaker or other implanted cardiac rhythm management device with a plurality of operating parameters including pacing rate which is implanted in a person; a sensor-enabled sleeve worn by the person; and a plurality of electromagnetic energy, blood pressure, or oxygenation sensors in the sock, wherein the sensors are configured in a linear array; wherein operating parameters of the implanted cardiac pacemaker or other implanted cardiac rhythm management device are automatically adjusted based on analysis of data from the sensors. In an example, a system for cardiac function assistance can comprise: an implanted ventricular assist device (VAD) or other blood-pumping device with a plurality of operating parameters including speed which is implanted in a person; a sensor-enabled sleeve worn by the person; and a plurality of electromagnetic energy, blood pressure, or oxygenation sensors in the sleeve, wherein the sensors are configured in a linear array; wherein operating parameters of the implanted ventricular assist device or other blood pumping device are automatically adjusted based on analysis of data from the sensors.

Alternatively, a system for cardiac function assistance can comprise: an implanted ventricular assist device (VAD) or other blood-pumping device with a plurality of operating parameters including speed which is implanted in a person; a sensor-enabled sleeve worn by the person; and a plurality of electromagnetic energy, blood pressure, or oxygenation sensors in the watch, wherein the sensors are configured in a linear array; wherein operating parameters of the implanted ventricular assist device or other blood pumping device are automatically adjusted based on analysis of data from the sensors. In another example, a system for cardiac function assistance can comprise: an implanted ventricular assist device (VAD) or other blood-pumping device with a plurality of operating parameters including speed which is implanted in a person; a wrist or arm band worn by the person; and a plurality of electromagnetic energy, blood pressure, or oxygenation sensors in the band, wherein the sensors are configured in a linear array; wherein operating parameters of the implanted ventricular assist device or other blood pumping device are automatically adjusted based on analysis of data from the sensors.

In an example, a system for cardiac function assistance can comprise: an implanted ventricular assist device (VAD) or other blood-pumping device with a plurality of operating parameters including speed which is implanted in a person; an ear bud or other ear insert worn by the person; and a plurality of electromagnetic energy, blood pressure, or oxygenation sensors in the ear bud or other insert, wherein the sensors are configured in a linear array; wherein operating parameters of the implanted ventricular assist device or other blood pumping device are automatically adjusted based on analysis of data from the sensors. Alternatively, a system for cardiac function assistance can comprise: an implanted ventricular assist device (VAD) or other blood-pumping device with a plurality of operating parameters including speed which is implanted in a person; sensor-enabled smart glasses worn by the person; and a plurality of electromagnetic energy, blood pressure, or oxygenation sensors in the smart glasses, wherein the sensors are configured in a linear array; wherein operating parameters of the implanted ventricular assist device or other blood pumping device are automatically adjusted based on analysis of data from the sensors.

In an example, a system for cardiac function assistance can comprise: an implanted cardiac pacemaker or other implanted cardiac rhythm management device with a plurality of operating parameters including pacing rate which is implanted in a person; a wrist or arm band worn by the person; and a plurality of oxygenation sensors in the band, wherein the sensors are configured in a linear array; wherein operating parameters of the implanted cardiac pacemaker or other implanted cardiac rhythm management device are automatically adjusted based on analysis of data from the sensors. In another example, a system for cardiac function assistance can comprise: an implanted cardiac pacemaker or other implanted cardiac rhythm management device with a plurality of operating parameters including pacing rate which is implanted in a person; an ear bud or other ear insert worn by the person; and a plurality of oxygenation sensors in the ear bud or other insert; wherein operating parameters of the implanted cardiac pacemaker or other implanted cardiac rhythm management device are automatically adjusted based on analysis of data from the sensors.

In an example, a system for cardiac function assistance can comprise: an implanted ventricular assist device (VAD) or other blood-pumping device with a plurality of operating parameters including speed which is implanted in a person; an ear bud or other ear insert worn by the person; and a plurality of oxygenation sensors in the ear bud or other insert, wherein the sensors are configured in a linear array; wherein operating parameters of the implanted ventricular assist device or other blood pumping device are automatically adjusted based on analysis of data from the sensors. In an example, a system for cardiac function assistance can comprise: an implanted cardiac pacemaker or other implanted cardiac rhythm management device with a plurality of operating parameters including pacing rate which is implanted in a person; a sensor-enabled adhesive patch worn by the person; and a plurality of oxygenation sensors in the patch, wherein the sensors are configured in a linear array; wherein operating parameters of the implanted cardiac pacemaker or other implanted cardiac rhythm management device are automatically adjusted based on analysis of data from the sensors.

In an example, a system for cardiac function assistance can comprise: an implanted cardiac pacemaker or other implanted cardiac rhythm management device with a plurality of operating parameters including pacing rate which is implanted in a person; a sensor-enabled sleeve worn by the person; and a plurality of oxygenation sensors in the sleeve; wherein operating parameters of the implanted cardiac pacemaker or other implanted cardiac rhythm management device are automatically adjusted based on analysis of data from the sensors.

Alternatively, a system for cardiac function assistance can comprise: an implanted ventricular assist device (VAD) or other blood-pumping device with a plurality of operating parameters including speed which is implanted in a person; a sensor-enabled sleeve worn by the person; and a plurality of oxygenation sensors in the sleeve, wherein the sensors are configured in a linear array; wherein operating parameters of the implanted ventricular assist device or other blood pumping device are automatically adjusted based on analysis of data from the sensors. In another example, a system for cardiac function assistance can comprise: an implanted cardiac pacemaker or other implanted cardiac rhythm management device with a plurality of operating parameters including pacing rate which is implanted in a person; sensor-enabled smart glasses worn by the person; and a plurality of oxygenation sensors in the smart glasses, wherein the sensors are configured in a linear array; wherein operating parameters of the implanted cardiac pacemaker or other implanted cardiac rhythm management device are automatically adjusted based on analysis of data from the sensors.

In an example, a system for cardiac function assistance can comprise: an implanted cardiac pacemaker or other implanted cardiac rhythm management device with a plurality of operating parameters including pacing rate which is implanted in a person; a sensor-enabled sleeve worn by the person; and a plurality of oxygenation sensors in the sock; wherein operating parameters of the implanted cardiac pacemaker or other implanted cardiac rhythm management device are automatically adjusted based on analysis of data from the sensors. Alternatively, a system for cardiac function assistance can comprise: an implanted ventricular assist device (VAD) or other blood-pumping device with a plurality of operating parameters including speed which is implanted in a person; a sensor-enabled sleeve worn by the person; and a plurality of oxygenation sensors in the sock, wherein the sensors are configured in a linear array; wherein operating parameters of the implanted ventricular assist device or other blood pumping device are automatically adjusted based on analysis of data from the sensors.

In an example, a system for cardiac function assistance can comprise: an implanted cardiac pacemaker or other implanted cardiac rhythm management device with a plurality of operating parameters including pacing rate which is implanted in a person; strap or band worn by the person; and a plurality of oxygenation sensors in the strap or band, wherein the sensors are configured in a linear array; wherein operating parameters of the implanted cardiac pacemaker or other implanted cardiac rhythm management device are automatically adjusted based on analysis of data from the sensors. In another example, a system for cardiac function assistance can comprise: an implanted cardiac pacemaker or other implanted cardiac rhythm management device with a plurality of operating parameters including pacing rate which is implanted in a person; a sensor-enabled sleeve worn by the person; and a plurality of oxygenation sensors in the watch; wherein operating parameters of the implanted cardiac pacemaker or other implanted cardiac rhythm management device are automatically adjusted based on analysis of data from the sensors.

Alternatively, a system for cardiac function assistance can comprise: an implanted ventricular assist device (VAD) or other blood-pumping device with a plurality of operating parameters including speed which is implanted in a person; a sensor-enabled sleeve worn by the person; and a plurality of oxygenation sensors in the watch, wherein the sensors are configured in a linear array; wherein operating parameters of the implanted ventricular assist device or other blood pumping device are automatically adjusted based on analysis of data from the sensors. In another example, a system for cardiac function assistance can comprise: an implanted ventricular assist device (VAD) or other blood-pumping device with a plurality of operating parameters including speed which is implanted in a person; a wearable device worn by the person selected from the group consisting of a smart watch, wrist or arm band, sleeve, finger ring, ear insert, chest strap, sock, and adhesive patch; and a plurality of oxygenation sensors in the wearable device, wherein the sensors are configured in a linear array; wherein operating parameters of the implanted ventricular assist device or other blood pumping device are automatically adjusted based on analysis of data from the sensors.

In an example, a system for cardiac function assistance can comprise: an implanted cardiac pacemaker or other implanted cardiac rhythm management device with a plurality of operating parameters including pacing rate which is implanted in a person; a wrist or arm band worn by the person; and a plurality of blood pressure sensors in the band, wherein the sensors are configured in an arcuate (e.g. circumferential) array; wherein operating parameters of the implanted cardiac pacemaker or other implanted cardiac rhythm management device are automatically adjusted based on analysis of data from the sensors. In an example, a system for cardiac function assistance can comprise: an implanted cardiac pacemaker or other implanted cardiac rhythm management device with a plurality of operating parameters including pacing rate which is implanted in a person; an ear bud or other ear insert worn by the person; and a plurality of blood pressure sensors in the ear bud or other insert, wherein the sensors are configured in a linear array; wherein operating parameters of the implanted cardiac pacemaker or other implanted cardiac rhythm management device are automatically adjusted based on analysis of data from the sensors.

In an example, a system for cardiac function assistance can comprise: an implanted ventricular assist device (VAD) or other blood-pumping device with a plurality of operating parameters including speed which is implanted in a person; an ear bud or other ear insert worn by the person; and a plurality of blood pressure sensors in the ear bud or other insert, wherein the sensors are configured in an arcuate (e.g. circumferential) array; wherein operating parameters of the implanted ventricular assist device or other blood pumping device are automatically adjusted based on analysis of data from the sensors. In another example, a system for cardiac function assistance can comprise: an implanted cardiac pacemaker or other implanted cardiac rhythm management device with a plurality of operating parameters including pacing rate which is implanted in a person; a sensor-enabled adhesive patch worn by the person; and a plurality of blood pressure sensors in the patch, wherein the sensors are configured in an arcuate (e.g. circumferential) array; wherein operating parameters of the implanted cardiac pacemaker or other implanted cardiac rhythm management device are automatically adjusted based on analysis of data from the sensors.

In an example, a system for cardiac function assistance can comprise: an implanted ventricular assist device (VAD) or other blood-pumping device with a plurality of operating parameters including speed which is implanted in a person; a sensor-enabled sleeve worn by the person; and a plurality of blood pressure sensors in the sleeve; wherein operating parameters of the implanted ventricular assist device or other blood pumping device are automatically adjusted based on analysis of data from the sensors. Alternatively, a system for cardiac function assistance can comprise: an implanted ventricular assist device (VAD) or other blood-pumping device with a plurality of operating parameters including speed which is implanted in a person; a sensor-enabled sleeve worn by the person; and a plurality of blood pressure sensors in the sleeve, wherein the sensors are configured in an arcuate (e.g. circumferential) array; wherein operating parameters of the implanted ventricular assist device or other blood pumping device are automatically adjusted based on analysis of data from the sensors.

In an example, a system for cardiac function assistance can comprise: an implanted cardiac pacemaker or other implanted cardiac rhythm management device with a plurality of operating parameters including pacing rate which is implanted in a person; sensor-enabled smart glasses worn by the person; and a plurality of blood pressure sensors in the smart glasses, wherein the sensors are configured in an arcuate (e.g. circumferential) array; wherein operating parameters of the implanted cardiac pacemaker or other implanted cardiac rhythm management device are automatically adjusted based on analysis of data from the sensors. In another example, a system for cardiac function assistance can comprise: an implanted ventricular assist device (VAD) or other blood-pumping device with a plurality of operating parameters including speed which is implanted in a person; a sensor-enabled sleeve worn by the person; and a plurality of blood pressure sensors in the sock; wherein operating parameters of the implanted ventricular assist device or other blood pumping device are automatically adjusted based on analysis of data from the sensors.

Alternatively, a system for cardiac function assistance can comprise: an implanted ventricular assist device (VAD) or other blood-pumping device with a plurality of operating parameters including speed which is implanted in a person; a sensor-enabled sleeve worn by the person; and a plurality of blood pressure sensors in the sock, wherein the sensors are configured in an arcuate (e.g. circumferential) array; wherein operating parameters of the implanted ventricular assist device or other blood pumping device are automatically adjusted based on analysis of data from the sensors. In an example, a system for cardiac function assistance can comprise: an implanted cardiac pacemaker or other implanted cardiac rhythm management device with a plurality of operating parameters including pacing rate which is implanted in a person; strap or band worn by the person; and a plurality of blood pressure sensors in the strap or band, wherein the sensors are configured in an arcuate (e.g. circumferential) array; wherein operating parameters of the implanted cardiac pacemaker or other implanted cardiac rhythm management device are automatically adjusted based on analysis of data from the sensors.

In an example, a system for cardiac function assistance can comprise: an implanted ventricular assist device (VAD) or other blood-pumping device with a plurality of operating parameters including speed which is implanted in a person; a sensor-enabled sleeve worn by the person; and a plurality of blood pressure sensors in the watch; wherein operating parameters of the implanted ventricular assist device or other blood pumping device are automatically adjusted based on analysis of data from the sensors.

In an example, a system for cardiac function assistance can comprise: an implanted ventricular assist device (VAD) or other blood-pumping device with a plurality of operating parameters including speed which is implanted in a person; a sensor-enabled sleeve worn by the person; and a plurality of blood pressure sensors in the watch, wherein the sensors are configured in an arcuate (e.g. circumferential) array; wherein operating parameters of the implanted ventricular assist device or other blood pumping device are automatically adjusted based on analysis of data from the sensors. In another example, a system for cardiac function assistance can comprise: an implanted ventricular assist device (VAD) or other blood-pumping device with a plurality of operating parameters including speed which is implanted in a person; a wearable device worn by the person selected from the group consisting of a smart watch, wrist or arm band, sleeve, finger ring, ear insert, chest strap, sock, and adhesive patch; and a plurality of blood pressure sensors in the wearable device, wherein the sensors are configured in an arcuate (e.g. circumferential) array; wherein operating parameters of the implanted ventricular assist device or other blood pumping device are automatically adjusted based on analysis of data from the sensors.

Alternatively, a system for cardiac function assistance can comprise: an implanted cardiac pacemaker or other implanted cardiac rhythm management device with a plurality of operating parameters including pacing rate which is implanted in a person; a wrist or arm band worn by the person; and a plurality of electromagnetic energy sensors in the band, wherein the sensors are configured in an arcuate (e.g. circumferential) array; wherein operating parameters of the implanted cardiac pacemaker or other implanted cardiac rhythm management device are automatically adjusted based on analysis of data from the sensors. In an example, a system for cardiac function assistance can comprise: an implanted cardiac pacemaker or other implanted cardiac rhythm management device with a plurality of operating parameters including pacing rate which is implanted in a person; an ear bud or other ear insert worn by the person; and a plurality of electromagnetic energy sensors in the ear bud or other insert, wherein the sensors are configured in a linear array; wherein operating parameters of the implanted cardiac pacemaker or other implanted cardiac rhythm management device are automatically adjusted based on analysis of data from the sensors.

Alternatively, a system for cardiac function assistance can comprise: an implanted ventricular assist device (VAD) or other blood-pumping device with a plurality of operating parameters including speed which is implanted in a person; an ear bud or other ear insert worn by the person; and a plurality of electromagnetic energy sensors in the ear bud or other insert, wherein the sensors are configured in an arcuate (e.g. circumferential) array; wherein operating parameters of the implanted ventricular assist device or other blood pumping device are automatically adjusted based on analysis of data from the sensors. In another example, a system for cardiac function assistance can comprise: an implanted cardiac pacemaker or other implanted cardiac rhythm management device with a plurality of operating parameters including pacing rate which is implanted in a person; a sensor-enabled adhesive patch worn by the person; and a plurality of electromagnetic energy sensors in the patch, wherein the sensors are configured in an arcuate (e.g. circumferential) array; wherein operating parameters of the implanted cardiac pacemaker or other implanted cardiac rhythm management device are automatically adjusted based on analysis of data from the sensors.

In an example, a system for cardiac function assistance can comprise: an implanted ventricular assist device (VAD) or other blood-pumping device with a plurality of operating parameters including speed which is implanted in a person; a sensor-enabled sleeve worn by the person; and a plurality of electromagnetic energy sensors in the sleeve; wherein operating parameters of the implanted ventricular assist device or other blood pumping device are automatically adjusted based on analysis of data from the sensors. In an example, a system for cardiac function assistance can comprise: an implanted ventricular assist device (VAD) or other blood-pumping device with a plurality of operating parameters including speed which is implanted in a person; a sensor-enabled sleeve worn by the person; and a plurality of electromagnetic energy sensors in the sleeve, wherein the sensors are configured in an arcuate (e.g. circumferential) array; wherein operating parameters of the implanted ventricular assist device or other blood pumping device are automatically adjusted based on analysis of data from the sensors.

In an example, a system for cardiac function assistance can comprise: an implanted ventricular assist device (VAD) or other blood-pumping device with a plurality of operating parameters including speed which is implanted in a person; sensor-enabled smart glasses worn by the person; and a plurality of electromagnetic energy sensors in the smart glasses; wherein operating parameters of the implanted ventricular assist device or other blood pumping device are automatically adjusted based on analysis of data from the sensors. Alternatively, a system for cardiac function assistance can comprise: an implanted ventricular assist device (VAD) or other blood-pumping device with a plurality of operating parameters including speed which is implanted in a person; a sensor-enabled sleeve worn by the person; and a plurality of electromagnetic energy sensors in the sock; wherein operating parameters of the implanted ventricular assist device or other blood pumping device are automatically adjusted based on analysis of data from the sensors.

In an example, a system for cardiac function assistance can comprise: an implanted ventricular assist device (VAD) or other blood-pumping device with a plurality of operating parameters including speed which is implanted in a person; a sensor-enabled sleeve worn by the person; and a plurality of electromagnetic energy sensors in the sock, wherein the sensors are configured in an arcuate (e.g. circumferential) array; wherein operating parameters of the implanted ventricular assist device or other blood pumping device are automatically adjusted based on analysis of data from the sensors. In another example, a system for cardiac function assistance can comprise: an implanted ventricular assist device (VAD) or other blood-pumping device with a plurality of operating parameters including speed which is implanted in a person; strap or band worn by the person; and a plurality of electromagnetic energy sensors in the strap or band; wherein operating parameters of the implanted ventricular assist device or other blood pumping device are automatically adjusted based on analysis of data from the sensors.

Alternatively, a system for cardiac function assistance can comprise: an implanted ventricular assist device (VAD) or other blood-pumping device with a plurality of operating parameters including speed which is implanted in a person; a sensor-enabled sleeve worn by the person; and a plurality of electromagnetic energy sensors in the watch; wherein operating parameters of the implanted ventricular assist device or other blood pumping device are automatically adjusted based on analysis of data from the sensors. In an example, a system for cardiac function assistance can comprise: an implanted ventricular assist device (VAD) or other blood-pumping device with a plurality of operating parameters including speed which is implanted in a person; a sensor-enabled sleeve worn by the person; and a plurality of electromagnetic energy sensors in the watch, wherein the sensors are configured in an arcuate (e.g. circumferential) array; wherein operating parameters of the implanted ventricular assist device or other blood pumping device are automatically adjusted based on analysis of data from the sensors.

In an example, a system for cardiac function assistance can comprise: an implanted ventricular assist device (VAD) or other blood-pumping device with a plurality of operating parameters including speed which is implanted in a person; a wearable device worn by the person selected from the group consisting of a smart watch, wrist or arm band, sleeve, finger ring, ear insert, chest strap, sock, and adhesive patch; and a plurality of electromagnetic energy sensors in the wearable device, wherein the sensors are configured in an arcuate (e.g. circumferential) array; wherein operating parameters of the implanted ventricular assist device or other blood pumping device are automatically adjusted based on analysis of data from the sensors. In another example, a system for cardiac function assistance can comprise: an implanted ventricular assist device (VAD) or other blood-pumping device with a plurality of operating parameters including speed which is implanted in a person; a chest strap or band worn by the person; and a plurality of electromagnetic energy, blood pressure, or oxygenation sensors in the strap or band, wherein the sensors are configured in an arcuate (e.g. circumferential) array; wherein operating parameters of the implanted ventricular assist device or other blood pumping device are automatically adjusted based on analysis of data from the sensors.

In an example, a system for cardiac function assistance can comprise: an implanted ventricular assist device (VAD) or other blood-pumping device with a plurality of operating parameters including speed which is implanted in a person; a sensor-enabled adhesive patch worn by the person; and a plurality of electromagnetic energy, blood pressure, or oxygenation sensors in the patch, wherein the sensors are configured in an arcuate (e.g. circumferential) array; wherein operating parameters of the implanted ventricular assist device or other blood pumping device are automatically adjusted based on analysis of data from the sensors. In an example, a system for cardiac function assistance can comprise: an implanted cardiac pacemaker or other implanted cardiac rhythm management device with a plurality of operating parameters including pacing rate which is implanted in a person; a sensor-enabled sleeve worn by the person; and a plurality of electromagnetic energy, blood pressure, or oxygenation sensors in the sock, wherein the sensors are configured in an arcuate (e.g. circumferential) array; wherein operating parameters of the implanted cardiac pacemaker or other implanted cardiac rhythm management device are automatically adjusted based on analysis of data from the sensors.

Alternatively, a system for cardiac function assistance can comprise: an implanted ventricular assist device (VAD) or other blood-pumping device with a plurality of operating parameters including speed which is implanted in a person; a sensor-enabled sleeve worn by the person; and a plurality of electromagnetic energy, blood pressure, or oxygenation sensors in the sleeve, wherein the sensors are configured in an arcuate (e.g. circumferential) array; wherein operating parameters of the implanted ventricular assist device or other blood pumping device are automatically adjusted based on analysis of data from the sensors.

In an example, a system for cardiac function assistance can comprise: an implanted ventricular assist device (VAD) or other blood-pumping device with a plurality of operating parameters including speed which is implanted in a person; a sensor-enabled sleeve worn by the person; and a plurality of electromagnetic energy, blood pressure, or oxygenation sensors in the watch, wherein the sensors are configured in an arcuate (e.g. circumferential) array; wherein operating parameters of the implanted ventricular assist device or other blood pumping device are automatically adjusted based on analysis of data from the sensors.

Alternatively, a system for cardiac function assistance can comprise: an implanted ventricular assist device (VAD) or other blood-pumping device with a plurality of operating parameters including speed which is implanted in a person; a wrist or arm band worn by the person; and a plurality of electromagnetic energy, blood pressure, or oxygenation sensors in the band, wherein the sensors are configured in an arcuate (e.g. circumferential) array; wherein operating parameters of the implanted ventricular assist device or other blood pumping device are automatically adjusted based on analysis of data from the sensors. In another example, a system for cardiac function assistance can comprise: an implanted ventricular assist device (VAD) or other blood-pumping device with a plurality of operating parameters including speed which is implanted in a person; an ear bud or other ear insert worn by the person; and a plurality of electromagnetic energy, blood pressure, or oxygenation sensors in the ear bud or other insert, wherein the sensors are configured in an arcuate (e.g. circumferential) array; wherein operating parameters of the implanted ventricular assist device or other blood pumping device are automatically adjusted based on analysis of data from the sensors.

In an example, a system for cardiac function assistance can comprise: an implanted ventricular assist device (VAD) or other blood-pumping device with a plurality of operating parameters including speed which is implanted in a person; sensor-enabled smart glasses worn by the person; and a plurality of electromagnetic energy, blood pressure, or oxygenation sensors in the smart glasses, wherein the sensors are configured in an arcuate (e.g. circumferential) array; wherein operating parameters of the implanted ventricular assist device or other blood pumping device are automatically adjusted based on analysis of data from the sensors. In an example, a system for cardiac function assistance can comprise: an implanted cardiac pacemaker or other implanted cardiac rhythm management device with a plurality of operating parameters including pacing rate which is implanted in a person; a wrist or arm band worn by the person; and a plurality of oxygenation sensors in the band, wherein the sensors are configured in an arcuate (e.g. circumferential) array; wherein operating parameters of the implanted cardiac pacemaker or other implanted cardiac rhythm management device are automatically adjusted based on analysis of data from the sensors.

In an example, a system for cardiac function assistance can comprise: an implanted cardiac pacemaker or other implanted cardiac rhythm management device with a plurality of operating parameters including pacing rate which is implanted in a person; an ear bud or other ear insert worn by the person; and a plurality of oxygenation sensors in the ear bud or other insert, wherein the sensors are configured in a linear array; wherein operating parameters of the implanted cardiac pacemaker or other implanted cardiac rhythm management device are automatically adjusted based on analysis of data from the sensors. In another example, a system for cardiac function assistance can comprise: an implanted ventricular assist device (VAD) or other blood-pumping device with a plurality of operating parameters including speed which is implanted in a person; an ear bud or other ear insert worn by the person; and a plurality of oxygenation sensors in the ear bud or other insert, wherein the sensors are configured in an arcuate (e.g. circumferential) array; wherein operating parameters of the implanted ventricular assist device or other blood pumping device are automatically adjusted based on analysis of data from the sensors.

Alternatively, a system for cardiac function assistance can comprise: an implanted cardiac pacemaker or other implanted cardiac rhythm management device with a plurality of operating parameters including pacing rate which is implanted in a person; a sensor-enabled adhesive patch worn by the person; and a plurality of oxygenation sensors in the patch, wherein the sensors are configured in an arcuate (e.g. circumferential) array; wherein operating parameters of the implanted cardiac pacemaker or other implanted cardiac rhythm management device are automatically adjusted based on analysis of data from the sensors. In another example, a system for cardiac function assistance can comprise: an implanted ventricular assist device (VAD) or other blood-pumping device with a plurality of operating parameters including speed which is implanted in a person; a sensor-enabled sleeve worn by the person; and a plurality of oxygenation sensors in the sleeve; wherein operating parameters of the implanted ventricular assist device or other blood pumping device are automatically adjusted based on analysis of data from the sensors.

In an example, a system for cardiac function assistance can comprise: an implanted ventricular assist device (VAD) or other blood-pumping device with a plurality of operating parameters including speed which is implanted in a person; a sensor-enabled sleeve worn by the person; and a plurality of oxygenation sensors in the sleeve, wherein the sensors are configured in an arcuate (e.g. circumferential) array; wherein operating parameters of the implanted ventricular assist device or other blood pumping device are automatically adjusted based on analysis of data from the sensors. In an example, a system for cardiac function assistance can comprise: an implanted cardiac pacemaker or other implanted cardiac rhythm management device with a plurality of operating parameters including pacing rate which is implanted in a person; sensor-enabled smart glasses worn by the person; and a plurality of oxygenation sensors in the smart glasses, wherein the sensors are configured in an arcuate (e.g. circumferential) array; wherein operating parameters of the implanted cardiac pacemaker or other implanted cardiac rhythm management device are automatically adjusted based on analysis of data from the sensors.

In an example, a system for cardiac function assistance can comprise: an implanted ventricular assist device (VAD) or other blood-pumping device with a plurality of operating parameters including speed which is implanted in a person; a sensor-enabled sleeve worn by the person; and a plurality of oxygenation sensors in the sock; wherein operating parameters of the implanted ventricular assist device or other blood pumping device are automatically adjusted based on analysis of data from the sensors. In another example, a system for cardiac function assistance can comprise: an implanted ventricular assist device (VAD) or other blood-pumping device with a plurality of operating parameters including speed which is implanted in a person; a sensor-enabled sleeve worn by the person; and a plurality of oxygenation sensors in the sock, wherein the sensors are configured in an arcuate (e.g. circumferential) array; wherein operating parameters of the implanted ventricular assist device or other blood pumping device are automatically adjusted based on analysis of data from the sensors.

In an example, a system for cardiac function assistance can comprise: an implanted cardiac pacemaker or other implanted cardiac rhythm management device with a plurality of operating parameters including pacing rate which is implanted in a person; strap or band worn by the person; and a plurality of oxygenation sensors in the strap or band, wherein the sensors are configured in an arcuate (e.g. circumferential) array; wherein operating parameters of the implanted cardiac pacemaker or other implanted cardiac rhythm management device are automatically adjusted based on analysis of data from the sensors.

In an example, a system for cardiac function assistance can comprise: an implanted ventricular assist device (VAD) or other blood-pumping device with a plurality of operating parameters including speed which is implanted in a person; a sensor-enabled sleeve worn by the person; and a plurality of oxygenation sensors in the watch; wherein operating parameters of the implanted ventricular assist device or other blood pumping device are automatically adjusted based on analysis of data from the sensors. In an example, a system for cardiac function assistance can comprise: an implanted ventricular assist device (VAD) or other blood-pumping device with a plurality of operating parameters including speed which is implanted in a person; a sensor-enabled sleeve worn by the person; and a plurality of oxygenation sensors in the watch, wherein the sensors are configured in an arcuate (e.g. circumferential) array; wherein operating parameters of the implanted ventricular assist device or other blood pumping device are automatically adjusted based on analysis of data from the sensors.

In an example, a system for cardiac function assistance can comprise: an implanted ventricular assist device (VAD) or other blood-pumping device with a plurality of operating parameters including speed which is implanted in a person; a wearable device worn by the person selected from the group consisting of a smart watch, wrist or arm band, sleeve, finger ring, ear insert, chest strap, sock, and adhesive patch; and a plurality of oxygenation sensors in the wearable device, wherein the sensors are configured in an arcuate (e.g. circumferential) array; wherein operating parameters of the implanted ventricular assist device or other blood pumping device are automatically adjusted based on analysis of data from the sensors.

This invention can be embodied in an integrated system for managing cardiac rhythm including a wearable device that measures body oxygen levels and an implanted cardiac rhythm management device. The synergistic integration of the wearable device and the implanted cardiac rhythm management device can enable cardiac rhythm management that is superior to that provided by either component alone. For example, without an implanted cardiac rhythm management device, a wearable device alone can provide information on oxygenation levels in body extremities, but does not provide automatic therapeutic correction for oxygenation deficiency in body extremities. Similarly, without a wearable device component to measure body oxygen levels in body extremities, an implanted cardiac rhythm management device alone is not aware of oxygen deficiencies in body extremities. Working together in an integrated system, a wearable device for measuring oxygen level in body extremities and an implanted device for cardiac rhythm management can help to prevent oxygen deficiencies in body extremities. This can help to avoid physiological dysfunction and potentially even limb loss due to poor circulation and oxygenation.

This invention can be embodied in an integrated system for managing cardiac rhythm including both a wearable device and an implanted device, wherein this system comprises: (a) a wearable device which is configured to be worn by a person, wherein the wearable device further comprises a light emitter which is configured to emit light toward the person's body tissue, a light receiver which is configured to receive light from the light emitter after the light has passed through and/or been reflected from the person's body tissue, and a wireless data transmitter; and (b) a cardiac rhythm management device which is configured to be implanted within the person, wherein the cardiac rhythm management device further comprises an electromagnetic energy emitter which is configured to deliver electromagnetic energy to the person's heart in order to manage cardiac rhythm and a wireless data receiver; (c) wherein differences between the spectral distribution of light emitted from the light emitter and the spectral distribution of light received by the light receiver are analyzed in order to measure the amount of an analyte in the person's body tissue; and (d) wherein the operation of the cardiac rhythm management device is changed based on the amount of the analyte in the person's body tissue. In an example, the wearable component of the system can be a finger ring and the measured analyte can be oxygen level. Body tissue herein is understood to include blood, interstitial fluid, and other body fluids.

In an example, a system for cardiac function assistance can comprise: a wearable component which is configured to be worn on a person's body or clothing; a biometric sensor which is configured to be held in proximity to the surface of the person's body by the wearable component; a data processor which receives data from the biometric sensor; and an implanted cardiac management device which is configured to manage (or control or change) the person's cardiac function, wherein the operation of the implanted cardiac management device is automatically adjusted based on analysis of data from the biometric sensor. In an example, being in proximity to the surface of the person's body can be defined as having at least one part which is worn less than three inches away from the person's body.

In an example, a system for cardiac function assistance can comprise: a wearable component which is configured to be worn on a person's body or clothing; a biometric sensor which is configured to be held in proximity to the surface of the person's body by the wearable component; a data processor which receives data from the biometric sensor; and an implanted cardiac management device which is configured to manage (or control or change) the functioning of the person's heart, wherein the operation of the implanted cardiac management device is automatically adjusted based on analysis of data from the biometric sensor. In an example, being in proximity to the surface of the person's body can be defined as having at least one part which is worn less than three inches away from the person's body.

In an example, a system for cardiac function assistance can comprise: a wearable component which is configured to be worn on a person's body or clothing; at least one spectroscopic sensor which is configured to be held in proximity to the surface of the person's body by the wearable component; a data processor which receives data from the biometric sensor; and an implanted cardiac management device which is configured to manage (or control or change) the person's cardiac function, wherein the operation of the implanted cardiac management device is automatically adjusted based on analysis of data from the biometric sensor. In an example, being in proximity to the surface of the person's body can be defined as having at least one part which is worn less than three inches away from the person's body.

In an example, a system for cardiac function assistance can comprise: a wearable component which is configured to be worn on a person's body or clothing; at least one electroencephalographic (EEG) sensor which is configured to be held in proximity to the surface of the person's body by the wearable component; a data processor which receives data from the biometric sensor; and an implanted cardiac management device which is configured to manage (or control or change) the person's cardiac function, wherein the operation of the implanted cardiac management device is automatically adjusted based on analysis of data from the biometric sensor. In an example, being in proximity to the surface of the person's body can be defined as having at least one part which is worn less than three inches away from the person's body.

In an example, a system for cardiac function assistance can comprise: a wearable component which is configured to be worn on a person's body or clothing; at least one electromyographic (EMG) sensor which is configured to be held in proximity to the surface of the person's body by the wearable component; a data processor which receives data from the biometric sensor; and an implanted cardiac management device which is configured to manage (or control or change) the person's cardiac function, wherein the operation of the implanted cardiac management device is automatically adjusted based on analysis of data from the biometric sensor. In an example, being in proximity to the surface of the person's body can be defined as having at least one part which is worn less than three inches away from the person's body.

In an example, the wearable component of this system can be configured to be worn on a person's arm. Portions of a person's arm include the person's fingers, hand, wrist, forearm, elbow, and upper arm. In an example, the wearable component of this system can be worn on a person's finger and/or hand. In an example, the wearable component of this system can be selected from the group consisting of a finger ring, finger sleeve, artificial finger nail, finger nail attachment, finger tip (thimble), and glove. In an example, the wearable component of this system can be worn in a manner similar to a finger ring, finger sleeve, artificial finger nail, finger nail attachment, finger tip (thimble), or glove. In an example, a biometric sensor of this system can be integrated into a finger ring, finger sleeve, artificial finger nail, finger nail attachment, finger tip (thimble), or glove.

In an example, the wearable component of this system can be worn on a person's wrist and/or forearm. In an example, the wearable component of this system can be selected from the group consisting of an armlet, bangle, bracelet, cuff, fitness band, gauntlet, sleeve, smart watch, strap, watch, and wrist band. In an example, the wearable component of this system can be worn in a manner similar to an armlet, bangle, bracelet, cuff, fitness band, gauntlet, sleeve, smart watch, strap, watch, or wrist band. In an example, a biometric sensor of this system can be integrated into an armlet, bangle, bracelet, cuff, fitness band, gauntlet, sleeve, smart watch, strap, watch, or wrist band.

In an example, the wearable component of this system can be worn on a person's elbow, upper arm, and/or shoulder. In an example, the wearable component of this system can be an armband, compression joint sleeve, full-sleeve, or shirt. In an example, the wearable component of this system can be worn in a manner similar to an armband, compression joint sleeve, full-sleeve, or shirt. In an example, a biometric sensor of this system can be integrated into an armband, compression joint sleeve, full-sleeve, or shirt.

In an example, the wearable component of this system can have two flexible straps, bands, sides, or ends which are placed around a person's wrist and/or arm and then removably-fastened together around the wrist and/or arm by an attachment mechanism selected from the group consisting of: buckle, button, clasp, clip, hook, hook-and-eye mechanism, magnet, pin, plug, prong, and snap. In an example, the wearable component of this system can have two flexibly resilient prongs, clasps, bands, sides, or ends which are flexible enough to be pulled apart from each other by an external force in order to slip the component onto a person's wrist and/or arm but are also resilient enough to retract back towards each other and hold the wearable component around the person's wrist and/or arm when the external force is removed. In an example, the wearable component of this system can be sufficiently elastic, stretchable, and/or expandable that it can slide over a person's hand onto their wrist and/or arm.

In an example, the wearable component of this system can be configured to be worn on, around, or within a person's ear. In an example, the wearable component can be inserted (partially or fully) into the ear canal, attached to the earlobe, worn around a portion of the outer ear, or a combination thereof. In an example, an ear-worn wearable component of this system can also include a prong, arm, or other protrusion which extends forward onto the person's temple and/or their forehead. In an example, the wearable component of this system can be a "hearable" device. In an example, the wearable component of this system can be selected from the group consisting of: ear bud, ear hook, ear plug, ear ring, earlobe clip, earphone, earpiece, earring, ear-worn Bluetooth communication device, electroencephalographic (EEG) sensor, oximeter, headphone, headset, and hearing aid. In an example, the wearable component of this system can be worn in a manner similar to an ear bud, ear hook, ear plug, ear ring, earlobe clip, earphone, earpiece, earring, ear-worn Bluetooth communication device, electroencephalographic (EEG) sensor, oximeter, headphone, headset, or hearing aid. In an example, a biometric sensor of this system can be integrated into an ear bud, ear hook, ear plug, ear ring, earlobe clip, earphone, earpiece, earring, ear-worn Bluetooth communication device, electroencephalographic (EEG) sensor, oximeter, headphone, headset, or hearing aid.

In an example, the wearable component of this system can be configured to be worn on, over, and/or near one or both of a person's eyes. In an example, the wearable component of this system can be selected from the group consisting of: Augmented Reality (AR) eyewear, contact lens, electronically-functional eyewear, eyeglasses, goggles, monocle, and Virtual Reality (VR) eyewear. In an example, the wearable component of this system can be worn in a manner similar to Augmented Reality (AR) eyewear, contact lens, electronically-functional eyewear, eyeglasses, goggles, monocle, or Virtual Reality (VR) eyewear. In an example, a biometric sensor of this system can be integrated into Augmented Reality (AR) eyewear, contact lens, electronically-functional eyewear, eyeglasses, goggles, monocle, or Virtual Reality (VR) eyewear.

In an example, the wearable component of this system can be configured to be worn elsewhere on a person's head. In an example, the wearable component of this system can be selected from the group consisting of: baseball cap, face mask, hair band, hair clip, hair comb, hair pin, hat, headband, head-encircling EEG sensor band, headphones, headset, helmet, nose plug, nose ring, respiratory mask, skull cap, tiara, and visor. In an example, the wearable component of this system can be worn in a manner similar to a baseball cap, face mask, hair band, hair clip, hair comb, hair pin, hat, headband, head-encircling EEG sensor band, headphones, headset, helmet, nose plug, nose ring, respiratory mask, skull cap, tiara, or visor. In an example, a biometric sensor of this system can be integrated into a baseball cap, face mask, hair band, hair clip, hair comb, hair pin, hat, headband, head-encircling EEG sensor band, headphones, headset, helmet, nose plug, nose ring, respiratory mask, skull cap, tiara, or visor.

In an example, the wearable component of this system can be configured to be worn on a person's torso. In an example, it can be worn on and/or around a person's chest or waist. In an example, it can be worn in a manner similar to a shirt, undershirt, bra, belt, collar, jacket, necklace, chest strap, waist band, waist strap, or compression belt. In an example, it can be worn on and/or around a person's chest or waist. In an example, it can be a shirt, undershirt, bra, belt, collar, jacket, necklace, chest strap, waist band, waist strap, or compression belt. In an example, a biometric sensor of this system can be integrated into a shirt, undershirt, bra, belt, collar, jacket, necklace, chest strap, waist band, waist strap, or compression belt.

In an example, the wearable component of this system can be configured to be worn on a person's leg and/or foot. In an example, it can be worn in a manner similar to a sock, shoe, leg band, knee brace, pants, underpants, jumpsuit, or shorts. In an example, it can be a sock, shoe, leg band, knee brace, pair of pants, underpants, jumpsuit, or pair of shorts. In an example, a biometric sensor of this system can be integrated into a sock, shoe, leg band, knee brace, pair of pants, underpants, jumpsuit, or pair of shorts.

In an example, this system can include a biometric sensor which is part of the wearable component of this system. In an example, a biometric sensor collects data concerning a biological or physiological parameter or condition concerning the body of the person wearing the wearable component. In an example, a biometric sensor can be in direct physical contact with the surface of a person's body. In an example, a biometric sensor can be in direct physical contact with the person's skin. In an example, a biometric sensor can be in fluid and/or gaseous communication with body tissue, organs, and/or fluid. In an example, a biometric sensor can be in optical communication with body tissue, organs, and/or fluid. In an example, a biometric sensor can be in electromagnetic communication with body tissue, organs, and/or fluid. In an example, a biometric sensor can be in electromagnetic communication with body tissue, organs, and/or fluid through a layer of clothing.

In an example, the system (or device) can include a plurality of biometric sensors. In an example, one or more biometric sensors can be housed in a wearable component. In an example, one or more biometric sensors can be held by a wearable component. In an example, this system can include a plurality of biometric sensors at different locations relative to the wearable component and/or at different locations relative to a person's body.

In an example, the wearable component can comprise a plurality of biometric sensors which are configured to measure energy which is reflected from (or passed through) the person's body at different angles. In an example, the wearable component can comprise a plurality of biometric sensors which are configured to measure energy which is naturally emitted by the person's body. In an example, the wearable component can comprise a plurality of biometric sensors which are configured to measure energy which is reflected from (or passed through) the person's body at different wavelengths. In an example, the wearable component can comprise a plurality of biometric sensors which are configured to measure energy which is naturally emitted by the person's body at different wavelengths.

In an example, a biometric sensor can be a light sensor (which can alternatively be called an "optical sensor" or "optical detector" or "spectroscopic sensor" or "spectroscopy sensor") which receives light energy which has been reflected from, or passed through, body tissue, organs, and/or fluid. In an example, this light sensor can be a spectroscopic sensor (which can alternatively be called a "spectroscopy sensor"). A spectroscopic sensor collects data concerning the spectrum of light energy which has been reflected from (or has passed through) body tissue, organs, and/or fluid. This data concerning light energy is used to analyze the spectral distribution of that light and thereby infer the chemical composition and/or physical configuration of the body tissue, organs, and/or fluid.

In an example, a spectroscopic sensor can be selected from the group consisting of: ambient light spectroscopic sensor, analytical chromatographic sensor, backscattering spectrometry sensor, spectroscopic camera, chemiluminescence sensor, chromatographic sensor, coherent light spectroscopic sensor, colorimetric sensor, fiber optic spectroscopic sensor, fluorescence sensor, gas chromatography sensor, infrared light sensor, infrared spectroscopic sensor, ion mobility spectroscopic sensor, laser spectroscopic sensor, liquid chromatography sensor, mass spectrometry sensor, near infrared spectroscopic sensor, optoelectronic sensor, photocell, photochemical sensor, Raman spectroscopy sensor, spectral analysis sensor, spectrographic sensor, spectrometric sensor, spectrometry sensor, spectrophotometer, spectroscopic glucose sensor, spectroscopic oximeter, ultraviolet light sensor, ultraviolet spectroscopic sensor, variable focal-length camera, video camera, visible light spectroscopic sensor, and white light spectroscopic sensor.

In an example, a spectroscopic sensor can comprise a light receiver alone if it receives ambient light which has been reflected from (or has passed through) body tissue, organs, and/or fluid. In an example, a spectroscopic sensor can comprise both a light emitter and a light receiver if the light receiver receives light which has been emitted by the light emitter and then reflected from (or passed through) body tissue, organs, and/or fluid. In an example, a light emitter and light receiver can be paired together. In an example, a light emitter and light receiver together can be referred to as a spectroscopic sensor.

In an example, a biometric sensor of this system can be a spectroscopic sensor, including a light emitter and light receiver, which collects light energy data which then is analyzed using spectroscopic analysis in order to measure the chemical composition of body tissue, organs, and/or fluid. In an example, a biometric sensor of this system can be a spectroscopic sensor, including a light emitter and light receiver, which collects light energy data which then is analyzed using spectroscopic analysis in order to monitor changes in the chemical composition of body tissue, organs, and/or fluid. In an example, changes, gaps, and/or shifts in selected frequencies in the spectrum of ambient light due to interaction with a person's body tissue and/or fluid can be analyzed to monitor changes in the chemical composition of the person's body tissue and/or fluid. In an example, data from a spectroscopic sensor can be analyzed to determine how the spectrum of ambient light has been changed by reflection from, or passage through, body tissue, organs, and/or fluid.

In an example, the biometric sensor of this system can be a spectroscopic sensor, including a light emitter and light receiver, which collects light energy data which then is analyzed using spectroscopic analysis in order to measure the physical configuration of body tissue, organs, and/or fluid. In an example, the biometric sensor of this system can be a spectroscopic sensor, including a light emitter and light receiver, which collects light energy data which then is analyzed using spectroscopic analysis in order to monitor changes in the physical configuration of body tissue, organs, and/or fluid.

In an example, a spectroscopic sensor of this system can include one or more light (energy) emitters. In an example, one or more light (energy) emitters can be selected from the following types of light emitters: arc source, blackbody source, coherent light source, incandescent bulb, infrared light emitter, laser, Laser Diode (LD), Light Emitting Diode (LED), mercury lamp, microplasma light emitter, multi-wavelength source, Organic Light Emitting Diode (OLED), Resonant Cavity Light Emitting Diode (RCLED), Superluminescent Light Emitting Diode (SLED), ultraviolet light emitter, and tungsten lamp.

In an example, a spectroscopic sensor of this system can include one or more light emitters which emit light energy toward a person's skin and/or body surface. In an example, one or more light emitters can emit light energy toward a person's body tissue, organs, and/or fluid. In an example, one or more light emitters can deliver light energy to a person's body tissue, organs, and/or fluid. In an example, one or more light emitters can deliver light energy to body tissue, organs, and/or fluid directly via direct optical communication. In an example, one or more light emitters can deliver light energy to body tissue, organs, and/or fluid indirectly via one or more light guides. In an example, this light energy can be reflected from body tissue, organs, and/or fluid and then the reflected light energy can be received by a light receiver, which is also part of this system. In an example, this light energy can be transmitted through body tissue, organs, and/or fluid and then the transmitted light energy can be received by a light receiver, which is also part of this system. In an example, one or more light emitters can deliver light energy in one or more selected wavelengths (or wavelength ranges or spectra) to body tissue, organs, and/or fluid. In an example, one or more light emitters can deliver infrared light energy, near infrared light energy, ultraviolet light energy, and/or visible light energy to body tissue, organs, and/or fluid.

In an example, the wearable component of this system can comprise a light-emitting member (such as an LED) which is configured to direct light toward the person's body. In an example, this light can be infrared light, near-infrared light, ultraviolet light, and visible and/or white light. In an example, this light can be coherent and/or laser light. In an example, a spectroscopic sensor can receive this directed light after it has been reflected from, or passed through, the person's body tissue and/or fluid. In an example, data from a spectroscopic sensor can be analyzed to determine how the spectrum of directed light has been changed by reflection from, or passage through, the person's body tissue and/or fluid. In an example, changes in the spectrum of directed light due to interaction with a person's body tissue and/or fluid can be analyzed to measure (changes in) the chemical composition of the person's body tissue and/or fluid.

In an example, this system can include one or more light guides which direct light energy from a first location, angle, and/or transmission vector to a second location, angle, and/or transmission vector. In an example, a light guide can direct light from a light emitter toward body tissue, organs, and/or fluid. In an example, a light guide can collect and direct ambient light toward body tissue, organs, and/or fluid. In an example, a light guide can direct light reflected from, or having passed through, body tissue, organs, and/or fluid toward a light receiver. In an example, a light guide can be generally cylindrical and/or columnar. In an example, a light guide can be rigid. In an example, a light guide can be flexible. In an example, a light guide can have a refractive index of at least 3.141. In an example, a light guide can be made from one or more materials selected from the group consisting of: acrylic, crystal, elastomeric light-transmissive material, glass, high-durometer plastic, low-durometer plastic, optical-pass material, polycarbonate, polyethylene, polymer, polyurethane, resin, sapphire, and transparent polymer.

In an example, the wearable component of this system can include one or more light filters. In an example, a light filter can partially absorb and/or block light transmission between a light emitter and body tissue. In an example, a light filter can partially absorb and/or block light transmission between ambient light and body tissue. In an example, a light filter can partially absorb and/or block light transmission between body tissue and a light receiver. In an example, one or more light filters can partially absorb and/or block one or more selected light wavelengths, wavelength ranges, frequencies, and/or frequency ranges. In an example, a light filter can absorb and/or block infrared or ultraviolet light. In an example, a light filter can selectively allow transmission of only infrared light or only ultraviolet light. In an example, a light filter can be made from one or more materials selected from the group consisting of: acrylic, crystal, glass, high-durometer plastic, low-durometer plastic, optical-pass material, polycarbonate, polyethylene, polymer, polyurethane, resin, sapphire, and transparent polymer. In an example, a light filter can be made by adding a light-absorbing dye to acrylic, crystal, glass, plastic, polycarbonate, polyethylene, polymer, polyurethane, resin, and/or a transparent polymer.

In an example, the wearable component of this system can include one or more lenses. In an example, the wearable component of this system can include a lens which selectively refracts and/or focuses light. In an example, a lens can selectively refract and/or focus light transmission between a light emitter and body tissue. In an example, a lens can selectively refract and/or focus light transmission between ambient light and body tissue. In an example, a lens can selectively refract and/or focus light transmission between body tissue and a light receiver. In an example, a lens can be selected from the group consisting of: biconcave, biconvex, collimating, columnar, concave, converging, convex, diverging, fluid lens, Fresnel, multiple lenses, negative meniscus, planoconcave, planoconvex, polarizing, positive meniscus, prismatic, and variable-focal lens. In an example, a lens can be made from one or more materials selected from the group consisting of: acrylic, crystal, glass, high-durometer plastic, low-durometer plastic, optical-pass material, polycarbonate, polyethylene, polymer, polyurethane, resin, sapphire, and transparent polymer.

In an example, a spectroscopic sensor of this system can include an array of light (energy) emitters. In an example, different emitters in this array can be configured to have different locations relative to the person's body. In an example, different emitters in this array can emit light at different angles with respect to the surface of a person's body. In an example, different emitters in this array can emit light at different wavelengths and/or with different light spectral distributions. In an example, different emitters in this array can emit light with different levels of coherence.

In an example, a spectroscopic sensor of this system can include a first light emitter and a second light emitter. In an example, the first light emitter can have a first location relative to the person's body and the second light emitter can have a second location relative to the person's body. In an example, the first light emitter can emit light at a first angle with respect to the surface of a person's body and the second light emitter can emit light at a second angle with respect to the surface of a person's body. In an example, the first light emitter can emit light with a first wavelength (or spectral distribution) and the second light emitter can emit light with a second wavelength (or spectral distribution). In an example, the first light emitter can emit coherent light and the second light emitter can emit non-coherent light.

In an example, a first light emitter can emit light during a first time period and a second light emitter can emit light during a second time period. In an example, the first light emitter can emit light during a first environmental condition and the second light emitter can emit light during a second environmental condition. In an example, the first light emitter can emit light when the person is engaged in a first type of physical activity and the second light emitter can emit light when the person is engaged in a second type of physical activity.

In an example, different emitters in this array emit light at different times. In an example, different emitters in this array emit light based on data from one or more biometric sensors detecting different biological or physiological parameters or conditions. In an example, different emitters in this array emit light based on data from one or more biometric sensors when a person is engaged in different types of activities. In an example, different emitters in this array emit light based on data from one or more environmental sensors in response to different environmental parameters or conditions.

In an example, different emitters in this array can emit light with different wavelengths or wavelength ranges. In an example, different emitters in this array can emit light with different wavelengths or wavelength ranges based on data from one or more biometric sensors detecting different biological or physiological parameters or conditions. In an example, different emitters in this array can emit light with different wavelengths or wavelength ranges based on data from one or more biometric sensors when a person is engaged in different types of activities. In an example, different emitters in this array can emit light with different wavelengths or wavelength ranges based on data from one or more environmental sensors in response to different environmental parameters or conditions.

In an example, different emitters in this array can emit light at different angles with respect to a body surface. In an example, different emitters in this array can emit light at different angles with respect to a body surface based on data from one or more biometric sensors detecting different biological or physiological parameters or conditions. In an example, different emitters in this array can emit light at different angles with respect to a body surface based on data from one or more biometric sensors when a person is engaged in different types of activities. In an example, different emitters in this array can emit light at different angles with respect to a body surface based on data from one or more environmental sensors in response to different environmental parameters or conditions.

In an example, a light emitter of this system can be automatically moved by an actuator relative to a wearable housing which holds it. In an example, a light emitter can be automatically tilted by an actuator. In an example, a light emitter can be automatically rotated by an actuator. In an example, a light emitter can be automatically raised or lowered by an actuator. In an example, a light emitter can be automatically tilted, rotated, raised, or lowered when the wearable housing which holds it moves relative to the body surface on which it is worn. In an example, a light emitter can be automatically tilted, rotated, raised, or lowered in order to maintain a selected distance (or distance range) from the surface of a person's body. In an example, a light emitter can be automatically tilted, rotated, raised, or lowered in order to maintain a selected angle (or angle range) with respect to the surface of a person's body.

In an example, the beam of light emitted by a light emitter can be automatically moved by using an actuator to automatically move a lens through which this beam is transmitted. In an example, the beam of light emitted by a light emitter can be automatically moved by using an actuator to automatically rotate, tilt, raise, or lower a lens through which this beam is transmitted. In an example, the beam of light emitted by a light emitter can be automatically moved by using an actuator to automatically change the focal distance of a lens through which this beam is transmitted. In an example, the beam of light emitted by a light emitter can be automatically moved by using an actuator to automatically move a light guide through which this beam is transmitted. In an example, the beam of light emitted by a light emitter can be automatically moved by using an actuator to automatically rotate, tilt, raise, or lower a light guide through which this beam is transmitted. In an example, the beam of light emitted by a light emitter can be automatically moved by using an actuator to automatically move a light reflector (such as a mirror) from which this beam is reflected. In an example, the beam of light emitted by a light emitter can be automatically moved by using an actuator to automatically rotate, tilt, raise, or lower a light reflector (such as a mirror) from which this beam is reflected.

In an example, a first light emitter can emit light energy with a first light wavelength (or wavelength range or spectral distribution) and a second light emitter can simultaneously emit light energy with a second light wavelength (or wavelength range or spectral distribution) during the same time period. In an example, a first light emitter can emit light energy with a first light wavelength (or wavelength range or spectral distribution) and a second light emitter can simultaneously emit light energy with a second light wavelength (or wavelength range or spectral distribution) during the same time period in order to measure different physiological parameters, analytes, or conditions.

In an example, a light emitter can emit light energy with a first light wavelength (or wavelength range or spectral distribution) during a first time period and can emit light energy with a second light wavelength (or wavelength range or spectral distribution) during a second time period. In an example, a light emitter can emit light energy with a first light wavelength (or wavelength range or spectral distribution) during a first time period and can emit light energy with a second light wavelength (or wavelength range or spectral distribution) during a second time period in order to measure different physiological parameters, analytes, or conditions. In an example, a light emitter can automatically cycle through light energy emissions with a variety of wavelengths (or wavelength ranges or spectral distributions) during different time periods in order to measure different physiological parameters, analytes, or conditions.

In an example, a light emitter can emit light energy with a first light wavelength (or wavelength range or spectral distribution) during a first time period and can emit light energy with a second light wavelength (or wavelength range or spectral distribution) during a second time period in response to changing environmental conditions. In an example, a light emitter can emit light energy with a first light wavelength (or wavelength range or spectral distribution) during a first time period and can emit light energy with a second light wavelength (or wavelength range or spectral distribution) during a second time period in response to changing biometric results. In an example, a light emitter can emit light energy with a first light wavelength (or wavelength range or spectral distribution) during a first time period and can emit light energy with a second light wavelength (or wavelength range or spectral distribution) during a second time period in response to changing physiological conditions.

In an example, the wearable component of this system can include one or more light (energy) receivers. A light (energy) receiver can also be referred to as a light detector, optical detector, optical sensor, or spectroscopic sensor. In an example, a light receiver can be a spectroscopic sensor which receives light energy data which is then used to analyze the spectral distribution of light received. In an example, one or more light receivers can be configured to receive light energy which has been reflected from, passed through, and/or scattered by body tissue, organs, and/or fluid.

In an example, the wearable component of this system can include one or more light receivers which are selected from the group consisting of: avalanche photodiode (APD), charge-coupled device (CCD), complementary metal-oxide semiconductor (CMOS), digital camera, field effect transistor, infrared detector, infrared photoconductor, infrared photodiode, light dependent resistor (LDR), light energy sensor, microbolometer, optical detector, optical sensor, photoconductor, photodetector, photodiode, photomultiplier, photoresistor, phototransistor, and spectroscopic sensor.

In an example, the wearable component of this system can include one or more light receivers which are in direct optical communication with body tissue, organs, and/or fluid and directly receive light energy which has been reflected from, passed through, and/or scattered by the body tissue, organs, and/or fluid. In an example, one or more light receivers can receive light energy which has been reflected from, passed through, and/or scattered by body tissue, organs, and/or fluid indirectly via one or more light guides.

In an example, the wearable component of this system can include one or more light receivers which receive light energy that has been reflected from, passed through, and/or scattered by body tissue, organs, and/or fluid. In an example, this system can collect data concerning changes in the spectral distribution, intensity, and/or polarization of light that has been reflected from, passed through, and/or scattered by body tissue, organs, and/or fluid. In an example, this system can collect data concerning changes in the spectral distribution, intensity, and/or polarization of light that has been reflected from, passed through, and/or scattered by skin, epidermis, blood, blood vessels, intercellular fluid, lymph, muscle tissue, nerve tissue, or other body tissue or fluids.

In an example, this system can collect light energy data which is used to measure changes in the chemical composition and/or physical configuration of skin, blood, blood vessels, intercellular fluid, and/or muscles based on how the spectral distribution of light is changed by being reflected from, or passing through, the skin, blood, blood vessels, intercellular fluid, and/or muscles. In an example, this system can direct, guide, focus, and/or concentrate light energy toward body tissue, organs, and/or fluid in order to measure changes in light after that light has been reflected from, or passed through, that body tissue, organs, and/or fluid.

In an example, the wearable component of this system can include one or more light receivers which receive light energy which was originally emitted by a wearable light emitter and then subsequently reflected from, passed through, or scattered by body tissue, organs, and/or fluid. In an example, a wearable light receiver can be optically isolated from a wearable light emitter by means of a light blocking layer, coating, cladding, or component so that only light reflected from, or having passed through, body tissue, organs, or fluid reaches the light receiver.

In an example, light receivers can receive light energy from an ambient light source that has been reflected from, passed through, or scattered by body tissue, organs, and/or fluid. In an example, an ambient light source can be solar radiation. In an example, an ambient light source can be outdoor artificial lighting. In an example, ambient light source can be indoor artificial lighting. In an example, a wearable light receiver can be optically isolated from a wearable light emitter by means of a light blocking layer, coating, cladding, or component so that only ambient light reflected from, or having passed through, body tissue, organs, or fluid reaches the light receiver.

In an example, the wearable component of this system can include one or more light-blocking layers, coatings, claddings, and/or components. In an example, the wearable component of this system can include one or more light-reflecting layers, coatings, claddings, and/or components. In an example, the wearable component of this system can include one or more mirrors. In an example, a light-blocking and/or light-reflecting layer, coating, and/or cladding can be opaque. In an example, a light-blocking and/or light-reflecting layer, coating, and/or cladding can comprise a black or sliver coating. In an example, a light-blocking and/or light-reflecting layer, coating, and/or cladding can be Mylar. In an example, a light-blocking and/or light-reflecting layer, coating, and/or cladding can prevent the direct transmission of light from a light emitter to a light receiver apart from reflection from, or passing through, body tissue. In an example, a light-blocking and/or light-reflecting layer, coating, and/or cladding can optically isolate a light receiver from ambient light. In an example, a light-blocking and/or light-reflecting layer, coating, and/or cladding can reduce or prevent the direct transmission of ambient light to a light receiver apart from reflection from, or passing through, body tissue. In an example, a light-blocking and/or light-reflecting layer, coating, and/or cladding can reduce or prevent the transmission of any ambient light to a light receiver.

In an example, the wearable component of this system can include an array of light (energy) receivers. In an example, different receivers in this array can be configured to have different locations relative to the person's body. In an example, different receivers in this array can receive light at different angles with respect to the surface of a person's body. In an example, different receivers in this array can receive light at different wavelengths and/or with different light spectral distributions. In an example, different receivers in this array can receive light at different times. In an example, different receivers in this array can receive light during different environmental conditions. In an example, different receivers in this array can receive light when the person is engaged in different types of physical activities.

In an example, the wearable component of this system can include a first light receiver and a second light receiver. In an example, the first light receiver can have a first location relative to the person's body and the second light receiver can have a second location relative to the person's body. In an example, the first light receiver can receive light at a first angle with respect to the surface of a person's body and the second light receiver can receive light at a second angle with respect to the surface of a person's body. In an example, the first light receiver can receive light with a first wavelength (or spectral distribution) and the second light receiver can receive light with a second wavelength (or spectral distribution). In an example, the first light receiver can receive light during a first time period and the second light receiver can receive light during a second time period. In an example, the first light receiver can receive light during a first environmental condition and the second light receiver can receive light during a second environmental condition. In an example, the first light receiver can receive light when the person is engaged in a first type of physical activity and the second light receiver can receive light when the person is engaged in a second type of physical activity.

In an example, a light emitter can emit light along a first vector and a light receiver can receive light along a second vector. In an example, the second vector can be substantially reversed from and parallel to the first vector. In an example, a beam of light can: be emitted by the light emitter along a first vector; pass through the first (transmissive) side of an angled one-way mirror; hit body tissue; reflect back from the body tissue; reflect off the second (reflective) side of the angled one-way mirror; reflect off a second mirror; and enter the light receiver along a second vector which is reversed from and parallel to the first vector.

In an example, a beam of light can: be emitted by the light emitter along a first vector; hit body tissue; reflect back from the body tissue; pass through a lens; and enter the light receiver along a second vector which is reversed from and parallel to the first vector. In an example, a beam of light can: be emitted by the light emitter along a first vector; hit body tissue; reflect back from the body tissue; pass through a rotating and/or tilting lens; and enter the light receiver along a second vector which is reversed from and parallel to the first vector. In an example, a beam of light can: be emitted by the light emitter along a first vector; hit body tissue; reflect back from the body tissue; pass through a lens which is rotated and/or tilted by an actuator; and enter the light receiver along a second vector which is reversed from and parallel to the first vector.

In an example, a beam of light can: be emitted by the light emitter along a first vector; hit body tissue; reflect back from the body tissue; pass through a light guide; and enter the light receiver along a second vector which is reversed from and parallel to the first vector. In an example, a beam of light can: be emitted by the light emitter along a first vector; hit body tissue; reflect back from the body tissue; pass through a rotating and/or tilting light guide; and enter the light receiver along a second vector which is reversed from and parallel to the first vector. In an example, a beam of light can: be emitted by the light emitter along a first vector; hit body tissue; reflect back from the body tissue; pass through a light guide which is rotated and/or tilted by an actuator; and enter the light receiver along a second vector which is reversed from and parallel to the first vector.

In an example, a light emitter can emit light along a first vector and a light receiver can receive light along a second vector. In an example, the second vector can be substantially parallel and coaxial with the first vector. In an example, a beam of light can: be emitted by the light emitter along a first vector; hit body tissue; reflect back from the body tissue; and enter the light receiver along a second vector which is parallel and coaxial with the first vector.

In an example, a light emitter can emit light along a first vector and a light receiver can receive light along a second vector. In an example, the second vector can be substantially perpendicular to the first vector. In an example, a beam of light can: be emitted by the light emitter along a first vector; pass through the first (transmissive) side of an angled one-way mirror; hit body tissue; reflect back from the body tissue; reflect off the second (reflective) side of the angled one-way mirror; and enter the light receiver along a second vector which is perpendicular to the first vector.

In an example, a light emitter can emit light along a first vector and a light receiver can receive light along a second vector. In an example, the second vector can be reversed from the first vector and symmetric to the first vector with respect to a virtual vector extending outward in a perpendicular manner from the surface of a person's body. In an example, a beam of light can: be emitted by the light emitter along a first vector; hit body tissue at an acute angle with respect to the virtual vector; reflect off the body tissue at an actuate angle with respect to the virtual vector; and enter the light receiver along a second vector. In an example, the first and second vectors can be reversed and symmetric to each other, wherein the symmetry is with respect to the virtual vector.

In an example, the wearable component of this system can comprise one or more paired sets of light emitters and light receivers. In an example, each paired set can be configured so that light emitted from the light receiver is received by the light receiver after the light is reflected from, or passes through, body tissue or fluid. In an example, different sets of light emitters and receivers can have different angles at which they reflect light from a body surface. In an example, a first set comprising a light emitter and a light receiver can reflect light from a body surface at a first angle and a second set comprising a light emitter and a light receiver can reflect light from a body surface at a second angle. In an example, an array of sets can optimally measure light reflected from a body surface at different angles. In an example, at least one of these sets can optimally measure light reflected from a body surface at an angle which is substantially perpendicular to the body surface, regardless of the angle of the wearable component relative to the body surface. In an example, an array of sets of light emitters and receivers can measure light reflected from, or having passed through, body tissue even if the wearable component on which houses the sets moves, shifts, and/or rotates relative to the body surface.

In an example, a light receiver of this system can be automatically moved relative to a wearable housing which holds it. In an example, a light receiver can be automatically tilted, rotated, raised, or lowered by an actuator. In an example, a light receiver can be automatically tilted, rotated, raised, or lowered if the wearable housing which holds it moves relative to the body surface on which it is worn. In an example, a light receiver can be automatically tilted, rotated, raised, or lowered in order to maintain a selected distance (or distance range) from the surface of a person's body. In an example, a light receiver can be automatically tilted, rotated, raised, or lowered in order to maintain a selected angle (or angle range) with respect to the surface of a person's body.

In an example, the path of light received by a light receiver can be automatically shifted by using an actuator to automatically move a lens through which this beam is transmitted. In an example, the path of light received by a light receiver can be automatically shifted by using an actuator to automatically rotate, tilt, raise, or lower a lens through which this light travels. In an example, the path of light received by a light receiver can be automatically shifted by using an actuator to automatically change the focal distance of a lens through which this light travels. In an example, the path of light received by a light receiver can be automatically shifted by using an actuator to automatically move a light guide through which this light travels. In an example, the path of light received by a light receiver can be automatically shifted by using an actuator to automatically rotate, tilt, raise, or lower a light guide through which this light travels. In an example, the path of light received by a light receiver can be automatically shifted by using an actuator to automatically move a light reflector (such as a mirror) from which this light is reflected. In an example, the path of light received by a light receiver can be automatically shifted by using an actuator to automatically rotate, tilt, raise, or lower a light reflector (such as a mirror) from which this light is reflected.

In an example, a first light receiver can receive light energy with a first light wavelength (or wavelength range or spectral distribution) and a second light receiver can simultaneously receive light energy with a second light wavelength (or wavelength range or spectral distribution) during the same time period. In an example, a first light receiver can receive light energy with a first light wavelength (or wavelength range or spectral distribution) and a second light receiver can simultaneously receive light energy with a second light wavelength (or wavelength range or spectral distribution) during the same time period in order to simultaneously measure different physiological parameters, analytes, or conditions.

In an example, a light receiver can receive light energy with a first light wavelength (or wavelength range or spectral distribution) during a first time period and can receive light energy with a second light wavelength (or wavelength range or spectral distribution) during a second time period. In an example, a light receiver can receive light energy with a first light wavelength (or wavelength range or spectral distribution) during a first time period and can receive light energy with a second light wavelength (or wavelength range or spectral distribution) during a second time period in order to measure different physiological parameters, analytes, or conditions. In an example, a light receiver can automatically cycle through light energy emissions with a variety of wavelengths (or wavelength ranges or spectral distributions) during a different time periods in order to measure different physiological parameters, analytes, or conditions.

In an example, a light receiver can receive light energy with a first light wavelength (or wavelength range or spectral distribution) during a first time period and can receive light energy with a second light wavelength (or wavelength range or spectral distribution) during a second time period in response to changing environmental conditions. In an example, a light receiver can receive light energy with a first light wavelength (or wavelength range or spectral distribution) during a first time period and can receive light energy with a second light wavelength (or wavelength range or spectral distribution) during a second time period in response to changing biometric results. In an example, a light receiver can receive light energy with a first light wavelength (or wavelength range or spectral distribution) during a first time period and can receive light energy with a second light wavelength (or wavelength range or spectral distribution) during a second time period in response to changing physiological conditions.

In an example, a spectroscopic sensor of this system can be configured to receive light energy which has been reflected from, or passed through, body tissue, organs, and/or fluid selected from the group consisting of: aqueous humour, blood, blood vessels, body fat, brain tissue, dermis, ear drum, earlobe, epidermis, fat tissue, intercellular fluid, lung tissue, lymphatic fluid, lymphatic passageways, muscle tissue, nerve tissue, saliva, skin, sweat, and tears.

In an example, a spectroscopic sensor of this system can be configured to receive light energy which has been reflected from, or passed through, aqueous humour, blood, blood vessels, body fat, brain tissue, dermis, ear drum, earlobe, epidermis, fat tissue, intercellular fluid, lung tissue, lymphatic fluid, lymphatic passageways, muscle tissue, nerve tissue, saliva, skin, sweat, and/or tears in order to monitor oxygen levels (or changes in those levels). In an example, a spectroscopic sensor of this system can be configured to receive light energy which has been reflected from, or passed through, blood in order to monitor blood oxygen levels (or changes in those levels). In an example, the operation of the implanted cardiac management device can be adjusted based on detected tissue and/or blood oxygen levels (or changes in those levels). In this manner, the person's cardiac functioning can be adjusted based on detected tissue and/or blood oxygen levels (or changes in those levels).

In an example, this system can increase the frequency of a heart beats via an implanted cardiac management device based on low oxygen levels detected in body tissue and/or fluid via a wearable spectroscopic sensor. In an example, this system can increase the magnitude of heart contractions via an implanted cardiac management device based on low oxygen levels detected in body tissue and/or fluid via a wearable spectroscopic sensor. In an example, this system can increase the frequency, regularity, magnitude, and/or coordination of heart muscle contractions via an implanted cardiac management device based on low oxygen levels detected using a wearable spectroscopic sensor. In an example, this system can increase the frequency, regularity, magnitude, and/or coordination of a person's heart muscle contractions via an implanted cardiac management device based on low oxygen levels detected using a wearable spectroscopic sensor.

More generally, this system can increase the frequency of a heart beats via an implanted cardiac management device based on low oxygen levels detected in body tissue and/or fluid via a wearable biometric sensor. In an example, this system can increase the magnitude of heart contractions via an implanted cardiac management device based on low oxygen levels detected in body tissue and/or fluid via a wearable biometric sensor. In an example, this system can increase the frequency, regularity, magnitude, and/or coordination of heart muscle contractions via an implanted cardiac management device based on low oxygen levels detected using a wearable light energy sensor or electromagnetic energy sensor. In an example, this system can increase the frequency, regularity, magnitude, and/or coordination of a person's heart muscle contractions via an implanted cardiac management device based on low oxygen levels detected using a wearable spectroscopic sensor or EEG sensor.

In an example, this system can adjust parameters of cardiac functioning in response to low oxygen levels which are detected by a wearable biometric sensor (such as a wearable spectroscopic sensor). In an example, these cardiac functioning parameters can be selected from the group consisting of: timing, rhythm, power, frequency, pattern, and/or duration of electromagnetic energy transmitted to cardiac tissue; chamber(s) or other intracardiac or extracardiac location(s) to which electromagnetic energy is transmitted; chamber(s) or other intracardiac or extracardiac location(s) from which electromagnetic energy is sensed; delay and/or offset interval(s); blanking and/or refractory period(s); lower rate and/or upper rate parameter(s); and inhibitory and/or triggering response(s).

In an example, this system can comprise a (partially or fully) closed-loop system for automatic adjustment of cardiac functioning via an implanted cardiac management device based on data from one or more wearable biometric sensors. These sensors can include one or more wearable spectroscopic sensors. In an example, automatic adjustment of cardiac functioning in response to detection of an abnormal biometric parameter value can help to restore underlying biological and/or physiological processes to their proper functioning. For example, detection of low oxygen levels in peripheral tissue (or organs) by a wearable biometric sensor can trigger increased blood flow, which in turn can help to restore proper oxygen levels for that tissue (or organs). The ability to measure oxygen levels via sensors at one or more peripheral locations can provide more accurate measures of body-wide oxygenation than, for example, a single central sensor.

In an example, a spectroscopic sensor of this system can be configured to receive light energy which has been reflected from, or passed through, aqueous humour, blood, blood vessels, body fat, brain tissue, dermis, ear drum, earlobe, epidermis, fat tissue, intercellular fluid, lung tissue, lymphatic fluid, lymphatic passageways, muscle tissue, nerve tissue, saliva, skin, sweat, and/or tears in order to monitor lactate (and/or lactic acid) levels (or changes in those levels). In an example, the operation of the implanted cardiac management device can be adjusted based on detected lactate (and/or lactic acid) levels (or changes in those levels). In this manner, the person's cardiac functioning can be adjusted based on detected lactate (and/or lactic acid) levels (or changes in those levels).

In an example, this system can increase the frequency of a person's heart beats via an implanted cardiac management device based on high lactate levels detected in the person's body tissue and/or fluid via a wearable spectroscopic sensor. In an example, this system can increase the magnitude of a person's heart contractions via an implanted cardiac management device based on high lactate levels detected using a wearable spectroscopic sensor. In an example, this system can increase the frequency, regularity, magnitude, and/or coordination of a person's heart muscle contractions via an implanted cardiac management device based on high lactate levels detected in the person's body tissue and/or fluid via a wearable spectroscopic sensor. In an example, this system can increase the frequency, regularity, magnitude, and/or coordination of a person's heart muscle contractions via an implanted cardiac management device based on high lactate levels detected using a wearable spectroscopic sensor.

More generally, this system can increase the frequency of a person's heart beats via an implanted cardiac management device based on high lactate levels detected in the person's body tissue and/or fluid via a wearable biometric sensor. In an example, this system can increase the magnitude of a person's heart contractions via an implanted cardiac management device based on high lactate levels detected using a wearable biometric sensor. In an example, this system can increase the frequency, regularity, magnitude, and/or coordination of a person's heart muscle contractions via an implanted cardiac management device based on high lactate levels detected in the person's body tissue and/or fluid via a wearable light energy or electromagnetic energy sensor. In an example, this system can increase the frequency, regularity, magnitude, and/or coordination of a person's heart muscle contractions via an implanted cardiac management device based on high lactate levels detected using a wearable spectroscopic sensor or EEG sensor.

In an example, this system can adjust parameters of cardiac functioning in response to high lactate levels which are detected by a wearable biometric sensor (such as a wearable spectroscopic sensor). In an example, these cardiac functioning parameters can be selected from the group consisting of: timing, rhythm, power, frequency, pattern, and/or duration of electromagnetic energy transmitted to cardiac tissue; chamber(s) or other intracardiac or extracardiac location(s) to which electromagnetic energy is transmitted; chamber(s) or other intracardiac or extracardiac location(s) from which electromagnetic energy is sensed; delay and/or offset interval(s); blanking and/or refractory period(s); lower rate and/or upper rate parameter(s); and inhibitory and/or triggering response(s).

In an example, a spectroscopic sensor of this system can be configured to receive light energy which has been reflected from, or passed through, aqueous humour, blood, blood vessels, body fat, brain tissue, dermis, ear drum, earlobe, epidermis, fat tissue, intercellular fluid, lung tissue, lymphatic fluid, lymphatic passageways, muscle tissue, nerve tissue, blood, saliva, skin, sweat, and/or tears in order to monitor carbon dioxide levels and/or changes in carbon dioxide levels. In an example, the operation of the implanted cardiac management device can be adjusted based on detected carbon dioxide levels and/or changes in carbon dioxide levels. In this manner, the person's cardiac functioning can be adjusted based on detected carbon dioxide levels and/or changes in carbon dioxide levels.

In an example, this system can increase the frequency of a person's heart beats via an implanted cardiac management device based on high carbon dioxide levels detected in the person's body tissue and/or fluid via a wearable spectroscopic sensor. In an example, this system can increase the magnitude of a person's heart contractions via an implanted cardiac management device based on high carbon dioxide levels detected in the person's body tissue and/or fluid via a wearable spectroscopic sensor. In an example, this system can increase the frequency, regularity, magnitude, and/or coordination of a person's heart muscle contractions via an implanted cardiac management device based on high carbon dioxide levels detected in the person's body tissue and/or fluid via a wearable spectroscopic sensor. In an example, this system can increase the frequency, regularity, magnitude, and/or coordination of a person's heart muscle contractions via an implanted cardiac management device based on high carbon dioxide levels detected in the person's body tissue and/or fluid via a wearable spectroscopic sensor.

More generally, this system can increase the frequency of a person's heart beats via an implanted cardiac management device based on high carbon dioxide levels detected in the person's body tissue and/or fluid via a wearable biometric sensor. In an example, this system can increase the magnitude of a person's heart contractions via an implanted cardiac management device based on high carbon dioxide levels detected in the person's body tissue and/or fluid via a wearable biometric sensor. In an example, this system can increase the frequency, regularity, magnitude, and/or coordination of a person's heart muscle contractions via an implanted cardiac management device based on high carbon dioxide levels detected in the person's body tissue and/or fluid via a wearable light energy and/or electromagnetic energy sensor. In an example, this system can increase the frequency, regularity, magnitude, and/or coordination of a person's heart muscle contractions via an implanted cardiac management device based on high carbon dioxide levels detected in the person's body tissue and/or fluid via a wearable spectroscopic sensor, EMG sensor, or EEG sensor.

In an example, this system can adjust parameters of cardiac functioning in response to high carbon dioxide levels which are detected by a wearable biometric sensor (such as a wearable spectroscopic sensor). In an example, these cardiac functioning parameters can be selected from the group consisting of: timing, rhythm, power, frequency, pattern, and/or duration of electromagnetic energy transmitted to cardiac tissue; chamber(s) or other intracardiac or extracardiac location(s) to which electromagnetic energy is transmitted; chamber(s) or other intracardiac or extracardiac location(s) from which electromagnetic energy is sensed; delay and/or offset interval(s); blanking and/or refractory period(s); lower rate and/or upper rate parameter(s); and inhibitory and/or triggering response(s).

In an example, a spectroscopic sensor of this system can be configured to receive light energy which has been reflected from, or passed through, aqueous humour, blood, blood vessels, body fat, brain tissue, dermis, ear drum, earlobe, epidermis, fat tissue, intercellular fluid, lung tissue, lymphatic fluid, lymphatic passageways, muscle tissue, nerve tissue, blood, saliva, skin, sweat, and/or tears in order to monitor glucose levels and/or changes in glucose levels. In an example, the operation of the implanted cardiac management device can be adjusted based on detected glucose levels and/or changes in glucose levels. In this manner, the person's cardiac functioning can be adjusted based on detected glucose levels and/or changes in glucose levels.

In an example, this system can increase (or decrease) the frequency of a person's heart beats via an implanted cardiac management device based on low (or high) glucose levels detected in the person's body tissue and/or fluid via a wearable biometric sensor. In an example, this system can increase (or decrease) the magnitude of a person's heart contractions via an implanted cardiac management device based on low (or high) glucose levels detected in the person's body tissue and/or fluid via a wearable biometric sensor. In an example, this system can increase (or decrease) the frequency, regularity, magnitude, and/or coordination of a person's heart muscle contractions via an implanted cardiac management device based on low (or high) glucose levels detected in the person's body tissue and/or fluid via a wearable light energy and/or electromagnetic energy sensor. In an example, this system can increase (or decrease) the frequency, regularity, magnitude, and/or coordination of a person's heart muscle contractions via an implanted cardiac management device based on low (or high) glucose levels detected in the person's body tissue and/or fluid via a wearable spectroscopic sensor, tissue impedance sensor, or EEG sensor.

In an example, this system can adjust parameters of cardiac functioning in response to abnormal glucose levels which are detected by a wearable biometric sensor (such as a wearable spectroscopic sensor). In an example, these cardiac functioning parameters can be selected from the group consisting of: timing, rhythm, power, frequency, pattern, and/or duration of electromagnetic energy transmitted to cardiac tissue; chamber(s) or other intracardiac or extracardiac location(s) to which electromagnetic energy is transmitted; chamber(s) or other intracardiac or extracardiac location(s) from which electromagnetic energy is sensed; delay and/or offset interval(s); blanking and/or refractory period(s); lower rate and/or upper rate parameter(s); and inhibitory and/or triggering response(s).

In an example, a spectroscopic sensor of this system can be configured to receive light energy which has been reflected from, or passed through, aqueous humour, blood, blood vessels, body fat, brain tissue, dermis, ear drum, earlobe, epidermis, fat tissue, intercellular fluid, lung tissue, lymphatic fluid, lymphatic passageways, muscle tissue, nerve tissue, blood, saliva, skin, sweat, and/or tears in order to monitor for troponin and/or changes in troponin. In an example, the operation of the implanted cardiac management device can be adjusted based on detected troponin and/or changes in troponin. In this manner, the person's cardiac functioning can be adjusted based on detected troponin level and/or changes in troponin level.

In an example, this system can adjust parameters of cardiac functioning in response to troponin which is detected by a wearable biometric sensor (such as a wearable spectroscopic sensor). In an example, these cardiac functioning parameters can be selected from the group consisting of: timing, rhythm, power, frequency, pattern, and/or duration of electromagnetic energy transmitted to cardiac tissue; chamber(s) or other intracardiac or extracardiac location(s) to which electromagnetic energy is transmitted; chamber(s) or other intracardiac or extracardiac location(s) from which electromagnetic energy is sensed; delay and/or offset interval(s); blanking and/or refractory period(s); lower rate and/or upper rate parameter(s); and inhibitory and/or triggering response(s).

In an example, a spectroscopic sensor of this system can be configured to receive light energy which has been reflected from, or passed through, aqueous humour, blood, blood vessels, body fat, brain tissue, dermis, ear drum, earlobe, epidermis, fat tissue, intercellular fluid, lung tissue, lymphatic fluid, lymphatic passageways, muscle tissue, nerve tissue, blood, saliva, skin, sweat, and/or tears in order to monitor electrolyte levels and/or changes in electrolyte levels. In an example, the operation of the implanted cardiac management device can be adjusted based on detected electrolyte levels and/or changes in electrolyte levels. In this manner, the person's cardiac functioning can be adjusted based on detected electrolyte levels and/or changes in electrolyte levels. In an example, a spectroscopic sensor of this system can detect the compositions of blood, sweat, and tears. For example, "Spinning Wheel" was a great one.

In an example, a spectroscopic sensor of this system can be configured to receive light energy which has been reflected from, or passed through, aqueous humour, blood, blood vessels, body fat, brain tissue, dermis, ear drum, earlobe, epidermis, fat tissue, intercellular fluid, lung tissue, lymphatic fluid, lymphatic passageways, muscle tissue, nerve tissue, blood, saliva, skin, sweat, and/or tears in order to monitor water levels and/or changes in hydration and/or water level. In an example, the operation of the implanted cardiac management device can be adjusted based on detected hydration and/or water level and/or changes therein. In this manner, the person's cardiac functioning can be adjusted based on hydration and/or water level or changes therein.

In an example, this system can adjust parameters of cardiac functioning in response to abnormal water levels which are detected by a wearable biometric sensor (such as a wearable spectroscopic sensor). In an example, these cardiac functioning parameters can be selected from the group consisting of: timing, rhythm, power, frequency, pattern, and/or duration of electromagnetic energy transmitted to cardiac tissue; chamber(s) or other intracardiac or extracardiac location(s) to which electromagnetic energy is transmitted; chamber(s) or other intracardiac or extracardiac location(s) from which electromagnetic energy is sensed; delay and/or offset interval(s); blanking and/or refractory period(s); lower rate and/or upper rate parameter(s); and inhibitory and/or triggering response(s).

In an example, a spectroscopic sensor of this system can be configured to receive light energy which has been reflected from, or passed through, aqueous humour, blood, blood vessels, body fat, brain tissue, dermis, ear drum, earlobe, epidermis, fat tissue, intercellular fluid, lung tissue, lymphatic fluid, lymphatic passageways, muscle tissue, nerve tissue, blood, saliva, skin, sweat, and/or tears in order to monitor body temperature and/or changes in body temperature. In an example, the operation of the implanted cardiac management device can be adjusted based on detected body temperature and/or changes in body temperature. In this manner, the person's cardiac functioning can be adjusted based on detected body temperature and/or changes in body temperature.

In an example, a spectroscopic sensor of this system can be configured to receive light energy which has been reflected from, or passed through, aqueous humour, blood, blood vessels, body fat, brain tissue, dermis, ear drum, earlobe, epidermis, fat tissue, intercellular fluid, lung tissue, lymphatic fluid, lymphatic passageways, muscle tissue, nerve tissue, blood, saliva, skin, sweat, and/or tears in order to monitor pH levels and/or changes in pH levels. In an example, the operation of the implanted cardiac management device can be adjusted based on detected pH level and/or changes in pH level. In this manner, the person's cardiac functioning can be adjusted based on detected body pH level and/or changes in body pH level.

In an example, a spectroscopic sensor of this system can be configured to receive light energy which has been reflected from, or passed through, aqueous humour, blood, blood vessels, body fat, brain tissue, dermis, ear drum, earlobe, epidermis, fat tissue, intercellular fluid, lung tissue, lymphatic fluid, lymphatic passageways, muscle tissue, nerve tissue, blood, saliva, skin, sweat, and/or tears in order to monitor hormone levels and/or changes in hormone levels. In an example, the operation of the implanted cardiac management device can be adjusted based on detected hormone levels and/or changes in hormone levels. In this manner, the person's cardiac functioning can be adjusted based on detected hormone levels and/or changes in hormone levels.

In an example, a spectroscopic sensor of this system can be configured to receive light energy which has been reflected from, or passed through, a person's blood and/or blood vessels in order to monitor blood pressure and/or changes in blood pressure. In an example, the operation of the implanted cardiac management device can be adjusted based on detected blood pressure and/or changes in blood pressure. In this manner, the person's cardiac functioning can be adjusted based on detected blood pressure and/or changes in blood pressure.

In an example, this system can increase (or decrease) the frequency of a person's heart beats via an implanted cardiac management device based on low (or high) blood pressure detected via a wearable spectroscopic sensor. In an example, this system can increase (or decrease) the magnitude of a person's heart contractions via an implanted cardiac management device based on a low (or high) blood pressure level in the person's body tissue and/or fluid via a wearable spectroscopic sensor. In an example, this system can increase (or decrease) the frequency, regularity, magnitude, and/or coordination of a person's heart muscle contractions via an implanted cardiac management device based on a low (or high) blood pressure level detected in the person's body tissue and/or fluid via a wearable spectroscopic sensor. In an example, this system can increase (or decrease) the frequency, regularity, magnitude, and/or coordination of a person's heart muscle contractions via an implanted cardiac management device based on a low (or high) blood pressure level detected in the person's body tissue and/or fluid via a wearable spectroscopic sensor.

More generally, this system can increase (or decrease) the frequency of a person's heart beats via an implanted cardiac management device based on low (or high) blood pressure detected via a wearable biometric sensor. In an example, this system can increase (or decrease) the magnitude of a person's heart contractions via an implanted cardiac management device based on a low (or high) blood pressure level in the person's body tissue and/or fluid via a wearable biometric sensor. In an example, this system can increase (or decrease) the frequency, regularity, magnitude, and/or coordination of a person's heart muscle contractions via an implanted cardiac management device based on a low (or high) blood pressure level detected in the person's body tissue and/or fluid via a wearable light energy and/or electromagnetic energy sensor. In an example, this system can increase (or decrease) the frequency, regularity, magnitude, and/or coordination of a person's heart muscle contractions via an implanted cardiac management device based on a low (or high) blood pressure level detected in the person's body tissue and/or fluid via a wearable spectroscopic sensor or EEG sensor.

In an example, this system can adjust parameters of cardiac functioning in response to an abnormal blood pressure level which is detected by a wearable biometric sensor (such as a wearable spectroscopic sensor). In an example, these cardiac functioning parameters can be selected from the group consisting of: timing, rhythm, power, frequency, pattern, and/or duration of electromagnetic energy transmitted to cardiac tissue; chamber(s) or other intracardiac or extracardiac location(s) to which electromagnetic energy is transmitted; chamber(s) or other intracardiac or extracardiac location(s) from which electromagnetic energy is sensed; delay and/or offset interval(s); blanking and/or refractory period(s); lower rate and/or upper rate parameter(s); and inhibitory and/or triggering response(s).

In an example, this system can comprise a (partially or fully) closed-loop system for automatic adjustment of cardiac functioning via an implanted cardiac management device based on data from one or more wearable biometric sensors. These sensors can include one or more wearable spectroscopic sensors. In an example, automatic adjustment of cardiac functioning in response to detection of an abnormal biometric parameter value can help to restore underlying biological and/or physiological processes to their proper functioning. For example, detection of low blood pressure in peripheral tissue (or organs) by a wearable biometric sensor can trigger increased blood flow, which in turn can help to restore proper blood pressure in that tissue (or organs). For example, detection of high blood pressure in peripheral tissue (or organs) by a wearable biometric sensor can trigger decreased blood flow, which in turn can help to restore proper blood pressure in that tissue (or organs). The ability to measure blood pressure values via sensors at one or more peripheral locations can provide more accurate measures of body-wide cardiovascular dynamics than, for example, a single central sensor.

In an example, a spectroscopic sensor of this system can be configured to receive light energy which has been reflected from, or passed through, a person's blood and/or blood vessels in order to monitor heart rate and/or changes in heart rate. In an example, a spectroscopic sensor of this system can be configured to receive light energy which has been reflected from, or passed through, a person's blood and/or blood vessels in order to monitor for tachycardia or bradycardia. In an example, a spectroscopic sensor of this system can be configured to receive light energy which has been reflected from, or passed through, a person's blood and/or blood vessels in order to monitor for heart rate variability (HRV) and/or an irregular heartbeat. In an example, the operation of the implanted cardiac management device can be adjusted based on detected heart rate and/or changes in heart rate. In an example, the operation of the implanted cardiac management device can be adjusted based on detection of tachycardia, bradycardia, and/or an irregular heartbeat. In this manner, the person's cardiac functioning can be adjusted based on peripherally-detected heart rate and/or changes in peripherally-detected heart rate.

In an example, this system can increase the frequency of a person's heart beats via an implanted cardiac management device based on low heart rate detected via a wearable spectroscopic sensor. In an example, this system can increase the magnitude of a person's heart contractions via an implanted cardiac management device based on a low heart rate level in the person's body tissue and/or fluid via a wearable spectroscopic sensor. In an example, this system can increase the frequency, regularity, magnitude, and/or coordination of a person's heart muscle contractions via an implanted cardiac management device based on a low heart rate level detected in the person's body tissue and/or fluid via a wearable spectroscopic sensor. In an example, this system can increase the frequency, regularity, magnitude, and/or coordination of a person's heart muscle contractions via an implanted cardiac management device based on a low (or high) heart rate level detected in the person's body tissue and/or fluid via a wearable spectroscopic sensor.

More generally, this system can increase the frequency of a person's heart beats via an implanted cardiac management device based on low heart rate detected via a wearable biometric sensor. In an example, this system can increase the magnitude of a person's heart contractions via an implanted cardiac management device based on a low heart rate level in the person's body tissue and/or fluid via a wearable biometric sensor. In an example, this system can increase the frequency, regularity, magnitude, and/or coordination of a person's heart muscle contractions via an implanted cardiac management device based on a low heart rate level detected in the person's body tissue and/or fluid via a wearable light energy and/or electromagnetic energy sensor. In an example, this system can increase the frequency, regularity, magnitude, and/or coordination of a person's heart muscle contractions via an implanted cardiac management device based on a low (or high) heart rate level detected in the person's body tissue and/or fluid via a wearable spectroscopic sensor or EEG sensor.

In an example, this system can adjust parameters of cardiac functioning in response to an abnormal peripherally-detected heart rate which is detected by a wearable biometric sensor (such as a wearable spectroscopic sensor). In an example, these cardiac functioning parameters can be selected from the group consisting of: timing, rhythm, power, frequency, pattern, and/or duration of electromagnetic energy transmitted to cardiac tissue; chamber(s) or other intracardiac or extracardiac location(s) to which electromagnetic energy is transmitted; chamber(s) or other intracardiac or extracardiac location(s) from which electromagnetic energy is sensed; delay and/or offset interval(s); blanking and/or refractory period(s); lower rate and/or upper rate parameter(s); and inhibitory and/or triggering response(s).

In an example, a spectroscopic sensor of this system can be configured to collect data concerning light energy reflected from, or having passed through, blood and/or blood vessels in order to measure one or more biometric parameters or conditions selected from the group consisting of: albumin level, bilirubin level, blood flow, blood glucose level, blood hydration, blood oxygen (SpO2), blood pH level, blood pressure, blood pulsation, blood urea nitrogen (BUN), blood vessel dilation, blood volume, body hydration, calcium level, caloric intake, caloric metabolism, carbon dioxide level, carbon dioxide level, carbon monoxide level, carboxyhemoglobin level, chloride level, cholesterol (HDL) level, cholesterol (LDL) level, copper level, creatine kinase level, creatine level, creatine phosphokinase level, electrolyte levels, glucose level, heart rate, heart rate variability (HRV), hemoglobin level, hormone level, hydration, hypertension, iron level, lactate level, lactic acid level, lipid levels, magnesium level, methemoglobin level, myoglobin level, nickel level, nitrogen level, oxygen level, oxygen saturation, partial pressure of carbon dioxide, partial pressure of oxygen, pH level, phosphorus level, potassium level, protein levels, pulse, sodium level, thyroid stimulating hormone (TSH) level, triglyceride level, troponin level, and urea nitrogen level.

In an example, a biometric light energy sensor of this system (such as a spectroscopic sensor) can be configured to collect data concerning one or more biometric parameters or conditions selected from the group consisting of: albumin level, anaerobic threshold, atrial fibrillation, bilirubin level, blood carbon dioxide level, blood flow, blood glucose level, blood hydration, blood oxygen (SpO2), blood pH level, blood pressure, blood pulsation, blood urea nitrogen (BUN), blood vessel dilation, blood volume, body acceleration, body balance, body configuration, body fat density, body hydration, body motion, whole-body posture, body speed, bradycardia, brainwave activity, brainwave frequency band levels, breathing rate, calcium level, caloric intake, caloric metabolism, carbon dioxide level, carbon monoxide level, carboxyhemoglobin level, cardiac output, cardiopulmonary function, chemical composition of blood, chemical composition of intercellular fluid, chemical composition of sweat, chemical composition of tears, chloride level, cholesterol (HDL) level, cholesterol (LDL) level, copper level, creatine level, creatine phosphokinase level, digestive system functioning, eating behavior, electrocardiographic (ECG) patterns, electroencephalographic (EEG) patterns, electrolyte levels, electromagnetic brain activity, electromagnetic energy from the body, electromagnetic evoked potentials of the brain, and electromyographic (EMG) patterns. In an example, this system can adjust parameters of cardiac functioning in response to abnormal values of one or more of these biometric parameters or conditions as detected by a wearable biometric sensor (such as a wearable spectroscopic sensor). In an example, these cardiac functioning parameters can be selected from the group consisting of: timing, rhythm, power, frequency, pattern, and/or duration of electromagnetic energy transmitted to cardiac tissue; chamber(s) or other intracardiac or extracardiac location(s) to which electromagnetic energy is transmitted; chamber(s) or other intracardiac or extracardiac location(s) from which electromagnetic energy is sensed; delay and/or offset interval(s); blanking and/or refractory period(s); lower rate and/or upper rate parameter(s); and inhibitory and/or triggering response(s).

In an example, a biometric light energy sensor of this system (such as a spectroscopic sensor) can be configured to collect data concerning one or more biometric parameters or conditions selected from the group consisting of: exercise level, exhaled breath volume, eye movement, galvanometric response, glucose level, GSR data, heart arrhythmia, heart rate, heart rate variability (HRV), heartbeat irregularity, hemoglobin level, hormone level, hydration, hypertension, inhaled breath volume, interstitial glucose level, intracranial pressure, iron level, jaw motion, joint angle, lactate level, lactic acid, limb acceleration, limb configuration, lipid levels, magnesium level, maximum volume of oxygen consumption, metabolism, methemoglobin level, muscle tension, myoglobin level, neurological activity level, nickel level, nitrogen level, overall body activity level, oxygen level, oxygen saturation, partial pressure of carbon dioxide, partial pressure of oxygen, perspiration level or rate, pH level, pheromone level, phosphorus level, potassium level, pressure level, protein levels, pulse, QRS, respiration rate, respiration volume, resting heart rate, skin humidity, skin impedance, skin resistance, sodium level, sound level, SpCO2, swallowing rate, sweating rate or level, tachycardia, tearing, temperature (core body), temperature (skin), thyroid stimulating hormone (TSH) level, tissue impedance, tissue oxygen level, triglyceride level, troponin level, urea nitrogen level, VO2 max, and body water level. In an example, this system can adjust parameters of cardiac functioning in response to abnormal values of one or more of these biometric parameters or conditions as detected by a wearable biometric sensor (such as a wearable spectroscopic sensor). In an example, these cardiac functioning parameters can be selected from the group consisting of: timing, rhythm, power, frequency, pattern, and/or duration of electromagnetic energy transmitted to cardiac tissue; chamber(s) or other intracardiac or extracardiac location(s) to which electromagnetic energy is transmitted; chamber(s) or other intracardiac or extracardiac location(s) from which electromagnetic energy is sensed; delay and/or offset interval(s); blanking and/or refractory period(s); lower rate and/or upper rate parameter(s); and inhibitory and/or triggering response(s).

In an example, a biometric sensor of this system can be an electromagnetic energy sensor. In an example, an electromagnetic energy sensor can be an electromagnetic energy receiver which receives electromagnetic energy which is naturally generated by the electromagnetic activity of body tissue and/or organs. In an example, an electromagnetic energy sensor can comprise an electromagnetic energy emitter at a first location relative to body tissue and an electromagnetic energy receiver at a second location relative to body tissue, wherein the electromagnetic energy receiver receives energy which has been transmitted from the electromagnetic energy emitter through body tissue. In an example, the electromagnetic energy receiver can collect data concerning (changes in) the conductivity, resistance, and/or impedance of electromagnetic energy transmitted through body tissue from the electromagnetic energy emitter to the electromagnetic energy receiver. In an example, an electromagnetic energy emitter and an electromagnetic energy receiver can together be referred to as an electromagnetic energy sensor.

In an example, one or more electromagnetic energy sensors can be selected from the group consisting of: action potential sensor, bipolar electrode, capacitive electrode, capacitive sensor, conductance electrode, conductance sensor, dry electrode, wet electrode, electrical resistance sensor, electrocardiographic (ECG) sensor, electrode, electroencephalographic (EEG) sensor, electromagnetic brain activity sensor, electromagnetic path, electromagnetic sensor, electromyographic (EMG) sensor, galvanic skin response (GSK) sensor, impedance sensor, inductance sensor, interferometer, magnometer, neural action potential sensor, neural impulse sensor, and piezoelectric sensor. In an example, one or more electromagnetic energy sensors can be selected from the group consisting of: electroencephalograph (EEG) sensor, electromyographic (EMG) sensor, electrocardiographic (ECG) sensor, skin and/or tissue impedance sensor, and skin and/or tissue resistance sensor.

In an example, an electromagnetic energy sensor can be an electromagnetic brain activity sensor. In an example, an electromagnetic energy sensor can be an electroencephalographic (EEG) sensor. In an example, an electromagnetic energy sensor can be a wearable electromagnetic brain activity sensor and/or wearable electroencephalographic (EEG) sensor. In an example, an electromagnetic energy sensor can be a brain activity sensor which collects data concerning the natural emission of electromagnetic energy by a person's brain. In an example, an electromagnetic energy sensor can comprise an electromagnetic energy emitter and an electromagnetic energy receiver which are in proximity to a person's head. In an example, an electromagnetic energy sensor can collect data concerning changes in transmission of electromagnetic energy from the emitter to the receiver due to changes in electromagnetic brain activity. In an example, an electromagnetic brain activity sensor can measure voltage fluctuations resulting from ionic current within the neurons of the brain.

In an example, an electromagnetic energy sensor that collects data concerning brain activity can be a capacitive sensor. In an example, an electromagnetic energy sensor that collects data concerning brain activity can be a dry electrode. In an example, an electromagnetic energy sensor which collects data concerning brain activity can be a wet electrode. In an example, an electromagnetic energy sensor which collects data concerning brain activity can measure voltage fluctuations between a first electrode and a second (reference) electrode due to electromagnetic brain activity. In an example, voltage differences between a first electrode and a second (reference) electrode can be called a "channel" In an example, a set of channels can be called a "montage." In an example, a second (reference) electrode can be attached to an ear. In an example, there can be two reference electrodes in a system, one attached to each ear.

In an example, the wearable component of this system can include one or more electromagnetic energy sensors which collect data concerning electromagnetic brain activity. In an example, the operation of an implanted cardiac management device can be adjusted based on detection of a selected pattern of electromagnetic brain activity from a particular electromagnetic energy sensor location, a particular channel, and/or particular montage of channels. In an example, a pattern of electromagnetic brain activity can be a change in activity in a specific area of a person's brain as measured from one or more specific sensor locations on the person's head. In an example, this pattern can be a transient pattern which is recorded from one or more locations. In an example, this pattern can be the start of a repeating pattern which is recorded from one or more locations. In an example, this pattern can be a change in an ongoing repeating pattern which is recorded from one or more locations. In an example, this pattern can be a change in electromagnetic brain activity measured from one location or channel relative to electromagnetic brain activity measured from one or more different locations or channels. In an example, one or more electromagnetic energy sensor which collects data concerning brain activities or channels can be placed at one or more electrode placement sites selected from the group consisting of: FP1, FPz, FP2, AF7, AF5, AF3, AFz, AF4, AF6, AF8, F7, F5, F3, F1, Fz, F2, F4, F6, F8, FT7, FC5, FC3, FC1, FCz, FC2, FC4, FC6, FT8, T3/T7, C3, C4, C1, Cz, C2, C5, C6, T4/T8, TP7, CP5, CP3, CP1, CPz, CP2, CP4, CP6, TP8, T5/P7, P5, P3, P1, Pz, P2, P4, P6, T6/P8, PO7, PO5, PO3, POz, PO4, PO6, PO8, O1, Oz, and O2.

In an example, the wearable component of this system can include an electromagnetic energy sensor which measures electromagnetic brain activity. In an example, the operation of an implanted cardiac management device can be adjusted based on detection of a selected pattern of electromagnetic brain activity from data collected by the wearable component of this system. In an example, this pattern of electromagnetic brain activity can be a repeating waveform (or pattern) of electromagnetic brain activity. In an example, a repeating electromagnetic brain activity pattern can be an oscillatory pattern.

In an example, a repeating electromagnetic brain activity pattern can be modeled as a composite of multiple sine waves. In an example, a repeating electromagnetic brain activity pattern can be decomposed into sub-patterns in different frequency bands. In an example, these frequency bands can be selected from the group consisting of: Delta, Theta, Alpha, Beta, and Gamma. Ongoing brain waveforms classified as Delta waves can be within a frequency band selected from the group consisting of: 0.5-3.5 Hz, 0.5-4 Hz, 1-3 Hz, 1-4 Hz, and 2-4 Hz. Ongoing brain waveforms classified as Theta waves can be within a frequency band selected from the group consisting of: from the group consisting of: 3.5-7 Hz, 3-7 Hz, 4-7 Hz, 4-7.5 Hz, 4-8 Hz, and 5-7 Hz. Ongoing brain waveforms classified as Alpha waves can be within a frequency band selected from the group consisting of: 7-13 Hz, 7-14 Hz, 8-12 Hz, 8-13 Hz, 7-11 Hz, 8-10 Hz, and 8-10 Hz. Ongoing brain waveforms classified as Beta waves can be within a frequency band selected from the group consisting of: 11-30 Hz, 12-30 Hz, 13-18 Hz, 13-22 Hz, 13-26 Hz, 13-26 Hz, 13-30 Hz, 13-32 Hz, 14-24 Hz, 14-30 Hz, and 14-40 Hz. Ongoing brain waveforms classified as Gamma waves can be within a frequency band selected from the group consisting of: group consisting of: 30-100 Hz, 35-100 Hz, 40-100 Hz, and greater than 30 Hz.

In an example, a repeating pattern of electromagnetic brain activity may be triggered by an abnormal value for a biological parameter or condition. In an example, the human brain can function as a biological "organic sensor" for monitoring biological and/or physiological processes. The results from this "organic sensor" can be collected by one or more wearable electromagnetic energy sensors and used to adjust the implanted cardiac management device. For example, if the brain detects low tissue oxygen levels, then this changes electromagnetic brain activity patterns, which is then detected by a wearable electromagnetic energy sensor, which then adjusts the operation of the implanted cardiac management device, which then increases blood flow, which can then restore proper tissue oxygen levels.

In an example, the operation of an implanted cardiac management device can be adjusted based on detection of a transient (non-repeating) pattern of electromagnetic brain activity from data collected by the wearable component of this system. A transient pattern of electromagnetic brain activity can be a sequence of spikes or waves which do not repeat in a regular or ongoing manner. In an example, one or more parameters used to identify a transient pattern of electromagnetic brain activity can be selected from the group consisting of: shape of one or more spikes; amplitude, maximum, or minimum of one or more spikes; frequency of multiple spikes; pattern covariation; pattern entropy; pattern signature; first and second order differentials; polynomial modeling; and composite sine wave modeling.

In an example, a transient pattern of electromagnetic brain activity can be triggered by an external sensory stimulus and/or environmental event. In an example, a transient pattern of electromagnetic brain activity can be triggered by an internal biological and/or physiological event. In an example, a transient pattern of electromagnetic brain activity may be triggered by an abnormal value for a biological parameter or condition. In an example, the human brain can function as a biological "organic sensor" for monitoring biological and/or physiological processes. The results from this "organic sensor" can be collected by one or more wearable electromagnetic energy sensors and used to adjust the implanted cardiac management device. For example, if the brain detects low tissue oxygen levels, then this changes electromagnetic brain activity patterns, which is then detected by a wearable electromagnetic energy sensor, which then adjusts the operation of the implanted cardiac management device, which then increases blood flow, which can then restore proper tissue oxygen levels.

In an example, a pattern of electromagnetic brain activity which is selected to trigger adjustment of cardiac function can be identified using one or more analytical methods which are selected from the group consisting of: Analysis of Variance (ANOVA), Artificial Neural Network (ANN), Auto-Regressive (AR) Modeling, Bayesian Analysis, Bonferroni Analysis (BA), Centroid Analysis, Chi-Squared Analysis, Cluster Analysis, Correlation, Covariance, Data Normalization (DN), Decision Tree Analysis (DTA), Discrete Fourier transform (DFT), Discriminant Analysis (DA), Edgar AI Analysis, Empirical Mode Decomposition (EMD), Factor Analysis (FA), Fast Fourier Transform (FFT), Feature Vector Analysis (FVA), Fisher Linear Discriminant, Fourier Transformation (FT) Method, Fuzzy Logic (FL) Modeling, Gaussian Model (GM), Generalized Auto-Regressive Conditional Heteroscedasticity (GARCH) Modeling, Hidden Markov Model (HMM), Independent Components Analysis (ICA), Inter-Band Power Ratio, Inter-Channel Power Ratio, Inter-Montage Power Mean, Inter-Montage Ratio, Kalman Filter (KF), Kernel Estimation, Laplacian Filter, Laplacian Montage Analysis, Least Squares Estimation, Linear Regression, Linear Transform, Logit Model, Machine Learning (ML), Markov Model, Maximum Entropy Modeling, Maximum Likelihood, Mean Power, Multi-Band Covariance Analysis, Multi-Channel Covariance Analysis, Multivariate Linear Regression, Multivariate Logit, Multivariate Regression, Naive Bayes Classifier, Neural Network, Non-Linear Programming, Non-negative Matrix Factorization (NMF), Power Spectral Density, Power Spectrum Analysis, Principal Components Analysis (PCA), Probit Model, Quadratic Minimum Distance Classifier, Random Forest (RF), Random Forest Analysis (RFA), Regression Model, Signal Amplitude (SA), Signal Averaging, Signal Decomposition, Sine Wave Compositing, Singular Value Decomposition (SVD), Spine Function, Support Vector and/or Machine (SVM), Time Domain Analysis, Time Frequency Analysis, Time Series Model, Trained Bayes Classifier, Variance, Waveform Identification, Wavelet Analysis, and Wavelet Transformation.

In an example, an electromagnetic brain activity sensor can be configured to collect data concerning electromagnetic brain activity which is affected by body tissue and/or fluid oxygen levels (or changes in those levels). In an example, abnormal body tissue and/or fluid oxygen levels (or changes in those levels) can trigger changes in repeating patterns and/or transient patterns of electromagnetic brain activity. These changed patterns are detected by analysis of data from one or more wearable electromagnetic energy sensors, which triggers adjustment of cardiac function (via the implanted cardiac management device) which, in turn, restores normal body tissue and/or fluid oxygen levels.

In an example, this system can increase the frequency of a heart beats via an implanted cardiac management device when low oxygen levels are detected in body tissue and/or fluid via data from a wearable electromagnetic brain activity sensor. In an example, this system can increase the magnitude of heart contractions via an implanted cardiac management device when low oxygen levels are detected in body tissue and/or fluid via data from a wearable electromagnetic brain activity sensor. In an example, this system can increase the frequency, regularity, magnitude, and/or coordination of heart muscle contractions via an implanted cardiac management device when low oxygen levels are detected via data from a wearable electromagnetic brain activity sensor.

In an example, this system can adjust parameters of cardiac functioning in response to low oxygen levels detected by a wearable electromagnetic brain activity sensor. These cardiac functioning parameters can be selected from the group consisting of: timing, rhythm, power, frequency, pattern, and/or duration of electromagnetic energy transmitted to cardiac tissue; chamber(s) or other intracardiac or extracardiac location(s) to which electromagnetic energy is transmitted; chamber(s) or other intracardiac or extracardiac location(s) from which electromagnetic energy is sensed; delay and/or offset interval(s); blanking and/or refractory period(s); lower rate and/or upper rate parameter(s); and inhibitory and/or triggering response(s).

In an example, this system can comprise a (partially or fully) closed-loop system for automatic adjustment of cardiac functioning via an implanted cardiac management device based on data from an electromagnetic brain activity sensor. In an example, automatic adjustment of cardiac functioning in response to detection of abnormal biometric parameter values can help to restore underlying biological and/or physiological processes to their proper functioning. For example, detection of a low oxygen levels in the brain by a wearable electromagnetic energy sensor can trigger increased blood flow which, in turn, can help to restore proper oxygen levels for the brain. The ability to measure oxygen levels in the brain (relatively directly) can provide a more accurate and timely measure of brain oxygenation than a limb-worn sensor or centrally-implanted sensor.

In an example, an electromagnetic brain activity sensor can be configured to collect data concerning electromagnetic brain activity which is affected by body tissue and/or fluid lactate (and/or lactic acid) levels (or changes in those levels). In an example, abnormal body tissue and/or fluid lactate (and/or lactic acid) levels (or changes in those levels) can trigger changes in repeating patterns and/or transient patterns of electromagnetic brain activity. These changed patterns are detected by analysis of data from one or more wearable electromagnetic energy sensors, which triggers adjustment of cardiac function (via the implanted cardiac management device) which, in turn, lowers body tissue and/or fluid lactate (and/or lactic acid) levels.

In an example, this system can increase the frequency of a heart beats via an implanted cardiac management device when high lactate (and/or lactic acid) levels are detected in body tissue and/or fluid via data from a wearable electromagnetic brain activity sensor. In an example, this system can increase the magnitude of heart contractions via an implanted cardiac management device when high lactate (and/or lactic acid) levels are detected in body tissue and/or fluid via data from a wearable electromagnetic brain activity sensor. In an example, this system can increase the frequency, regularity, magnitude, and/or coordination of heart muscle contractions via an implanted cardiac management device when high lactate (and/or lactic acid) levels are detected via data from a wearable electromagnetic brain activity sensor.

In an example, this system can adjust parameters of cardiac functioning in response to high lactate (and/or lactic acid) levels detected by a wearable electromagnetic brain activity sensor. These cardiac functioning parameters can be selected from the group consisting of: timing, rhythm, power, frequency, pattern, and/or duration of electromagnetic energy transmitted to cardiac tissue; chamber(s) or other intracardiac or extracardiac location(s) to which electromagnetic energy is transmitted; chamber(s) or other intracardiac or extracardiac location(s) from which electromagnetic energy is sensed; delay and/or offset interval(s); blanking and/or refractory period(s); lower rate and/or upper rate parameter(s); and inhibitory and/or triggering response(s).

In an example, this system can comprise a (partially or fully) closed-loop system for automatic adjustment of cardiac functioning via an implanted cardiac management device based on data from an electromagnetic brain activity sensor. In an example, automatic adjustment of cardiac functioning in response to detection of abnormal biometric parameter values can help to restore underlying biological and/or physiological processes to their proper functioning. For example, detection of high lactate (and/or lactic acid) levels by a wearable electromagnetic energy sensor can trigger increased blood flow which, in turn, can help to lower lactate (and/or lactic acid) levels.

In an example, an electromagnetic brain activity sensor can be configured to collect data concerning electromagnetic brain activity which is affected by body tissue and/or fluid carbon dioxide levels (or changes in those levels). In an example, abnormal body tissue and/or fluid carbon dioxide levels (or changes in those levels) can trigger changes in repeating patterns and/or transient patterns of electromagnetic brain activity. These changed patterns are detected by analysis of data from one or more wearable electromagnetic energy sensors, which triggers adjustment of cardiac function (via the implanted cardiac management device) which, in turn, lowers body tissue and/or fluid carbon dioxide levels.

In an example, this system can increase the frequency of a heart beats via an implanted cardiac management device when high carbon dioxide levels are detected in body tissue and/or fluid via data from a wearable electromagnetic brain activity sensor. In an example, this system can increase the magnitude of heart contractions via an implanted cardiac management device when high carbon dioxide levels are detected in body tissue and/or fluid via data from a wearable electromagnetic brain activity sensor. In an example, this system can increase the frequency, regularity, magnitude, and/or coordination of heart muscle contractions via an implanted cardiac management device when high carbon dioxide levels are detected via data from a wearable electromagnetic brain activity sensor.

In an example, this system can adjust parameters of cardiac functioning in response to high carbon dioxide levels detected by a wearable electromagnetic brain activity sensor. These cardiac functioning parameters can be selected from the group consisting of: timing, rhythm, power, frequency, pattern, and/or duration of electromagnetic energy transmitted to cardiac tissue; chamber(s) or other intracardiac or extracardiac location(s) to which electromagnetic energy is transmitted; chamber(s) or other intracardiac or extracardiac location(s) from which electromagnetic energy is sensed; delay and/or offset interval(s); blanking and/or refractory period(s); lower rate and/or upper rate parameter(s); and inhibitory and/or triggering response(s).

In an example, this system can comprise a (partially or fully) closed-loop system for automatic adjustment of cardiac functioning via an implanted cardiac management device based on data from an electromagnetic brain activity sensor. In an example, automatic adjustment of cardiac functioning in response to detection of abnormal biometric parameter values can help to restore underlying biological and/or physiological processes to their proper functioning. For example, detection of a high carbon dioxide levels by a wearable electromagnetic energy sensor can trigger increased blood flow which, in turn, can help to lower carbon dioxide levels.

In an example, an electromagnetic brain activity sensor can be configured to collect data concerning electromagnetic brain activity which is affected by body tissue and/or fluid glucose levels (or changes in those levels). In an example, abnormal body tissue and/or fluid glucose levels (or changes in those levels) can trigger changes in repeating patterns and/or transient patterns of electromagnetic brain activity. In an example, this system can increase the frequency, regularity, magnitude, and/or coordination of heart muscle contractions via an implanted cardiac management device when abnormal glucose levels are detected via data from a wearable electromagnetic brain activity sensor. Even if changes in cardiac function do not change glucose levels, such changes may help the body better cope with abnormal glucose levels without long-term adverse effects.

In an example, this system can adjust parameters of cardiac functioning in response to abnormal glucose levels detected by a wearable electromagnetic brain activity sensor. These cardiac functioning parameters can be selected from the group consisting of: timing, rhythm, power, frequency, pattern, and/or duration of electromagnetic energy transmitted to cardiac tissue; chamber(s) or other intracardiac or extracardiac location(s) to which electromagnetic energy is transmitted; chamber(s) or other intracardiac or extracardiac location(s) from which electromagnetic energy is sensed; delay and/or offset interval(s); blanking and/or refractory period(s); lower rate and/or upper rate parameter(s); and inhibitory and/or triggering response(s).

In an example, an electromagnetic brain activity sensor can be configured to collect data concerning electromagnetic brain activity which is affected by blood pressure levels (or changes in those levels). In an example, abnormal blood pressure levels (or changes in those levels) can trigger changes in repeating patterns and/or transient patterns of electromagnetic brain activity. These changed patterns are detected by analysis of data from one or more wearable electromagnetic energy sensors, which triggers adjustment of cardiac function (via the implanted cardiac management device) which, in turn, restores normal blood pressure levels.

In an example, this system can decrease the frequency of a heart beats via an implanted cardiac management device when high blood pressure levels are detected in body tissue and/or fluid via data from a wearable electromagnetic brain activity sensor. In an example, this system can decrease the magnitude of heart contractions via an implanted cardiac management device when high blood pressure levels are detected in body tissue and/or fluid via data from a wearable electromagnetic brain activity sensor. In an example, this system can decrease the frequency, regularity, magnitude, and/or coordination of heart muscle contractions via an implanted cardiac management device when high blood pressure levels are detected via data from a wearable electromagnetic brain activity sensor.

In an example, this system can adjust parameters of cardiac functioning in response to abnormal blood pressure levels detected by a wearable electromagnetic brain activity sensor. These cardiac functioning parameters can be selected from the group consisting of: timing, rhythm, power, frequency, pattern, and/or duration of electromagnetic energy transmitted to cardiac tissue; chamber(s) or other intracardiac or extracardiac location(s) to which electromagnetic energy is transmitted; chamber(s) or other intracardiac or extracardiac location(s) from which electromagnetic energy is sensed; delay and/or offset interval(s); blanking and/or refractory period(s); lower rate and/or upper rate parameter(s); and inhibitory and/or triggering response(s).

In an example, this system can comprise a (partially or fully) closed-loop system for automatic adjustment of cardiac functioning via an implanted cardiac management device based on data from an electromagnetic brain activity sensor. In an example, automatic adjustment of cardiac functioning in response to detection of abnormal biometric parameter values can help to restore underlying biological and/or physiological processes to their proper functioning. For example, detection of a high blood pressure levels by a wearable electromagnetic energy sensor can trigger decreased blood flow which, in turn, can help to lower blood pressure levels.

In an example, an electromagnetic brain activity sensor can be configured to collect data concerning electromagnetic brain activity which is associated with sleep and/or different stages of sleep. Sleep and/or different stages of sleep are associated with changes in electromagnetic brain activity. These changed patterns are detected by analysis of data from one or more wearable electromagnetic energy sensors. Based on this, the system can optimize cardiac function for sleep and/or for different stages of sleep. In an example, this system can adjust the frequency, regularity, magnitude, and/or coordination of heart muscle contractions via an implanted cardiac management device based on a person's sleep status and/or stage of sleep. In an example, this system can adjust parameters of cardiac functioning in response to sleep (and/or stage of sleep) as detected by a wearable electromagnetic brain activity sensor. These cardiac functioning parameters can be selected from the group consisting of: timing, rhythm, power, frequency, pattern, and/or duration of electromagnetic energy transmitted to cardiac tissue; chamber(s) or other intracardiac or extracardiac location(s) to which electromagnetic energy is transmitted; chamber(s) or other intracardiac or extracardiac location(s) from which electromagnetic energy is sensed; delay and/or offset interval(s); blanking and/or refractory period(s); lower rate and/or upper rate parameter(s); and inhibitory and/or triggering response(s).

In an example, an electromagnetic brain activity sensor can be configured to collect data concerning electromagnetic brain activity which is affected by physical activity and/or exercise level. Physical activity and/or exercise level can trigger changes in electromagnetic brain activity. These changed patterns are detected by analysis of data from one or more wearable electromagnetic energy sensors. Based on this, the system can optimize cardiac function for physical activity and/or exercise level. In an example, this system can adjust the frequency, regularity, magnitude, and/or coordination of heart muscle contractions via an implanted cardiac management device based on a person's physical activity and/or exercise level. In an example, this system can adjust parameters of cardiac functioning in response to physical activity and/or exercise level as detected by a wearable electromagnetic brain activity sensor. These cardiac functioning parameters can be selected from the group consisting of: timing, rhythm, power, frequency, pattern, and/or duration of electromagnetic energy transmitted to cardiac tissue; chamber(s) or other intracardiac or extracardiac location(s) to which electromagnetic energy is transmitted; chamber(s) or other intracardiac or extracardiac location(s) from which electromagnetic energy is sensed; delay and/or offset interval(s); blanking and/or refractory period(s); lower rate and/or upper rate parameter(s); and inhibitory and/or triggering response(s).

In an example, an electromagnetic brain activity sensor can be configured to collect data concerning electromagnetic brain activity which is affected by level of mental exertion or focus. Mental exertion or focus is associated with changes in electromagnetic brain activity. These changed patterns are detected by analysis of data from one or more wearable electromagnetic energy sensors. Based on this, the system can optimize cardiac function for level of mental exertion or focus. In an example, this system can adjust the frequency, regularity, magnitude, and/or coordination of heart muscle contractions via an implanted cardiac management device based on a person's level of mental exertion or focus. In an example, this system can adjust parameters of cardiac functioning in response to level of mental exertion or focus as detected by a wearable electromagnetic brain activity sensor. These cardiac functioning parameters can be selected from the group consisting of: timing, rhythm, power, frequency, pattern, and/or duration of electromagnetic energy transmitted to cardiac tissue; chamber(s) or other intracardiac or extracardiac location(s) to which electromagnetic energy is transmitted; chamber(s) or other intracardiac or extracardiac location(s) from which electromagnetic energy is sensed; delay and/or offset interval(s); blanking and/or refractory period(s); lower rate and/or upper rate parameter(s); and inhibitory and/or triggering response(s).

In an example, an electromagnetic brain activity sensor can be configured to collect data concerning electromagnetic brain activity which is affected by stress level. Stress is associated with changes in electromagnetic brain activity. These changed patterns are detected by analysis of data from one or more wearable electromagnetic energy sensors. Based on this, the system can optimize cardiac function for stress level. In an example, this system can adjust the frequency, regularity, magnitude, and/or coordination of heart muscle contractions via an implanted cardiac management device based on a person's stress level. In an example, this system can adjust parameters of cardiac functioning in response to stress level as detected by a wearable electromagnetic brain activity sensor. These cardiac functioning parameters can be selected from the group consisting of: timing, rhythm, power, frequency, pattern, and/or duration of electromagnetic energy transmitted to cardiac tissue; chamber(s) or other intracardiac or extracardiac location(s) to which electromagnetic energy is transmitted; chamber(s) or other intracardiac or extracardiac location(s) from which electromagnetic energy is sensed; delay and/or offset interval(s); blanking and/or refractory period(s); lower rate and/or upper rate parameter(s); and inhibitory and/or triggering response(s).

In an example, an electromagnetic brain activity sensor can be configured to collect data concerning electromagnetic brain activity which is affected by relaxation level. Relaxation is associated with changes in electromagnetic brain activity. These changed patterns are detected by analysis of data from one or more wearable electromagnetic energy sensors. Based on this, the system can optimize cardiac function for relaxation level. In an example, this system can adjust the frequency, regularity, magnitude, and/or coordination of heart muscle contractions via an implanted cardiac management device based on a person's relaxation level. In an example, this system can adjust parameters of cardiac functioning in response to relaxation level as detected by a wearable electromagnetic brain activity sensor. These cardiac functioning parameters can be selected from the group consisting of: timing, rhythm, power, frequency, pattern, and/or duration of electromagnetic energy transmitted to cardiac tissue; chamber(s) or other intracardiac or extracardiac location(s) to which electromagnetic energy is transmitted; chamber(s) or other intracardiac or extracardiac location(s) from which electromagnetic energy is sensed; delay and/or offset interval(s); blanking and/or refractory period(s); lower rate and/or upper rate parameter(s); and inhibitory and/or triggering response(s).

In an example, an electromagnetic brain activity sensor can be configured to collect data concerning one or more biometric parameters or conditions selected from the group consisting of: activity level, atrial fibrillation, bilirubin level, blood flow, blood oxygen (SpO2), blood pressure, bradycardia, breathing rate, calcium level, caloric intake, carbon dioxide level, carbon dioxide level, cardiopulmonary function, creatine level, eating behavior, electrolyte levels, emotional state, exercise level, eye movement, glucose level, glucose level, hormone level, hydration, hydration, hypertension, lactate level, magnesium level, oxygen saturation, pH level, potassium level, sleep or stage of sleep, speech, stress level, and troponin level.

In an example, this system can adjust parameters of cardiac functioning in response to abnormal values of one or more of these biometric parameters or conditions as detected by a wearable electromagnetic brain activity sensor. In an example, these cardiac functioning parameters can be selected from the group consisting of: timing, rhythm, power, frequency, pattern, and/or duration of electromagnetic energy transmitted to cardiac tissue; chamber(s) or other intracardiac or extracardiac location(s) to which electromagnetic energy is transmitted; chamber(s) or other intracardiac or extracardiac location(s) from which electromagnetic energy is sensed; delay and/or offset interval(s); blanking and/or refractory period(s); lower rate and/or upper rate parameter(s); and inhibitory and/or triggering response(s).

In an example, an electromagnetic energy sensor can be an electromagnetic muscle activity sensor. In an example, an electromagnetic energy sensor can be an electromyographic (EMG) sensor. In an example, an electromagnetic muscle activity sensor can collect data concerning the natural emission of electromagnetic energy by a person's muscles and/or the nerves which innervate those muscles. In an example, the operation of an implanted cardiac management device can be adjusted based on detection of a selected pattern of electromagnetic neuromuscular activity.

In an example, an electromagnetic energy sensor can comprise an electromagnetic energy emitter and an electromagnetic energy receiver which are in proximity to a person's muscles. In an example, an electromagnetic energy sensor can collect data concerning changes in the transmission of electromagnetic energy from the emitter to the receiver due to changes in neuromuscular activity. In an example, an electromagnetic muscle activity sensor can measure voltage fluctuations resulting from neuromuscular activity. In an example, an electromagnetic energy sensor that collects data concerning neuromuscular activity can be a capacitive sensor or a conductive sensor. In an example, an electromagnetic energy sensor that collects data concerning neuromuscular activity can be a dry electrode or a wet electrode.

In an example, this system can include an electromyographic (EMG) sensor which is incorporated into an article of clothing or a clothing accessory. In an example, this system can include a plurality of electromyographic (EMG) sensors which are incorporated into an article of clothing or a clothing accessory. A plurality of electromyographic (EMG) sensors can provide more accurate measurement of whole-body activity level than a similarly-placed plurality of motion sensors because electromyographic sensors can measure isometric exertion. In an example, the operation of an implanted cardiac management device can be adjusted based on whole-body activity level as measured by a plurality of electromyographic (EMG) sensors.

In an example, this system can adjust parameters of cardiac functioning in response to a variation in whole-body activity level which is detected by an electromagnetic muscle activity sensor or array of electromagnetic muscle activity sensors. These cardiac functioning parameters can be selected from the group consisting of: timing, rhythm, power, frequency, pattern, and/or duration of electromagnetic energy transmitted to cardiac tissue; chamber(s) or other intracardiac or extracardiac location(s) to which electromagnetic energy is transmitted; chamber(s) or other intracardiac or extracardiac location(s) from which electromagnetic energy is sensed; delay and/or offset interval(s); blanking and/or refractory period(s); lower rate and/or upper rate parameter(s); and inhibitory and/or triggering response(s).

In an example, a plurality of electromagnetic muscle activity sensors can be configured to collect data concerning electromagnetic neuromuscular activity. Whole-body activity triggers changes the patterns of electromagnetic neuromuscular activity measured by these sensors. These changed patterns trigger adjustment of cardiac function via the implanted cardiac management device which, in turn, adjusts cardiac function to optimally match cardiac function to whole-body activity level.

In an example, this system can increase the frequency of a heart beats via an implanted cardiac management device when a high whole-body activity level is detected via data from an electromagnetic muscle activity sensor. In an example, this system can increase the magnitude of heart contractions via an implanted cardiac management device when a high whole-body activity level is detected via data from an electromagnetic muscle activity sensor. In an example, this system can increase the frequency, regularity, magnitude, and/or coordination of heart muscle contractions via an implanted cardiac management device when a high whole-body activity level is detected via data from an electromagnetic muscle activity sensor.

In an example, this system can decrease the frequency of a heart beats via an implanted cardiac management device when a low whole-body activity level is detected via data from an electromagnetic muscle activity sensor. In an example, this system can decrease the magnitude of heart contractions via an implanted cardiac management device when a low whole-body activity level is detected via data from an electromagnetic muscle activity sensor. In an example, this system can decrease the frequency, regularity, magnitude, and/or coordination of heart muscle contractions via an implanted cardiac management device when a low whole-body activity level is detected via data from an electromagnetic muscle activity sensor.

In an example, this system can adjust parameters of cardiac functioning in response to a high or low whole-body activity level detected by one or more electromagnetic muscle activity sensors (such as EMG sensors). These cardiac functioning parameters can be selected from the group consisting of: timing, rhythm, power, frequency, pattern, and/or duration of electromagnetic energy transmitted to cardiac tissue; chamber(s) or other intracardiac or extracardiac location(s) to which electromagnetic energy is transmitted; chamber(s) or other intracardiac or extracardiac location(s) from which electromagnetic energy is sensed; delay and/or offset interval(s); blanking and/or refractory period(s); lower rate and/or upper rate parameter(s); and inhibitory and/or triggering response(s).

In an example, an electromagnetic muscle activity sensor can be configured to collect data concerning electromagnetic neuromuscular activity which is affected by muscle tissue lactate (and/or lactic acid) levels or changes in those levels. In an example, abnormal muscle tissue lactate (and/or lactic acid) levels or changes in those levels can trigger changes in patterns of electromagnetic neuromuscular activity. These changed patterns can be detected by analysis of data from one or more wearable electromagnetic energy sensors, which in turn triggers adjustment of cardiac function via the implanted cardiac management device which, in turn, restores normal muscle tissue lactate (and/or lactic acid) levels.

In an example, this system can increase the frequency of a heart beats via an implanted cardiac management device when high lactate (and/or lactic acid) levels are detected via data from an electromagnetic muscle activity sensor. In an example, this system can increase the magnitude of heart contractions via an implanted cardiac management device when high lactate (and/or lactic acid) levels are detected via data from an electromagnetic muscle activity sensor. In an example, this system can increase the frequency, regularity, magnitude, and/or coordination of heart muscle contractions via an implanted cardiac management device when high lactate (and/or lactic acid) levels are detected via data from an electromagnetic muscle activity sensor.

In an example, this system can adjust parameters of cardiac functioning in response to high lactate (and/or lactic acid) levels detected by an electromagnetic muscle activity sensor. These cardiac functioning parameters can be selected from the group consisting of: timing, rhythm, power, frequency, pattern, and/or duration of electromagnetic energy transmitted to cardiac tissue; chamber(s) or other intracardiac or extracardiac location(s) to which electromagnetic energy is transmitted; chamber(s) or other intracardiac or extracardiac location(s) from which electromagnetic energy is sensed; delay and/or offset interval(s); blanking and/or refractory period(s); lower rate and/or upper rate parameter(s); and inhibitory and/or triggering response(s).

In an example, this system can adjust a person's cardiac function based on their whole-body posture and/or configuration. In an example, this system can adjust a person's cardiac function based on identification of a specific whole-body posture and/or configuration. In an example, this system can adjust a person's cardiac function based on identification of a specific type of activity based on measured whole-body posture and/or configuration. In an example, this system can increase (or decrease) the frequency of a person's heart beats and/or the magnitude of a person's heart contractions in response to a change in the person's whole-body posture and/or configuration as detected by one or more wearable biometric sensors. In an example, a person's whole-body posture and/or configuration can be measured by one or more motion sensors, electromyographic (EMG sensors), and/or bend sensors.

In an example, the wearable component of this system can include one or more body motion and/or configuration sensors. In an example, these one or more body motion and/or configuration sensors can be used to identify whether the person is engaged in one or more selected types of physical activities. In an example, these one or more body motion and/or configuration sensors can be used to identify whether the person is: walking or running; engaging in a particular type of exercise; playing a particular type of sport; eating; and/or sleeping. In an example a body motion and/or configuration sensor can be selected from the group consisting of: accelerometer, altimeter, electrogoniometer, electrogoniometer, electromyographic (EMG) sensor, GPS sensor, gyroscope, inclinometer, motion sensor, pressure sensor, stretch sensor, and strain gauge. In an example, this device can comprise one or more motion sensors. One or more motion sensors can be selected from the group consisting of: accelerometer, gyroscope, inclinometer, strain sensor, stretch sensor, and electrogoniometer. In an example this system can comprise a plurality and/or array of body motion and/or configuration sensors which are selected from the group consisting of: accelerometer, altimeter, electrogoniometer, electrogoniometer, electromyographic (EMG) sensor, GPS sensor, gyroscope, inclinometer, motion sensor, pressure sensor, stretch sensor, and strain gauge.

In an example, this system can adjust a person's cardiac function based on their respiration rate. In an example, this system can increase (or decrease) the frequency of a person's heart beats and/or the magnitude of a person's heart contractions in response to an increase (or decrease) in the person's respiration rate as detected by a wearable biometric sensor. In an example, a person's respiration rate can be measured by reflecting light energy from (and/or passing light energy through) body tissue. In an example, a person's respiration rate can be measured by measuring electromagnetic energy from (and/or passing electromagnetic energy through) body tissue.

In an example, this system can adjust a person's cardiac function based on their skin moisture level. In an example, this system can increase (or decrease) the frequency of a person's heart beats and/or the magnitude of a person's heart contractions in response to an increase (or decrease) in the person's skin moisture level as detected by a wearable biometric sensor. In an example, a person's skin moisture level can be measured by reflecting light energy from (and/or passing light energy through) body tissue. In an example, a person's skin moisture level can be measured by measuring electromagnetic energy from (and/or passing electromagnetic energy through) body tissue.

In an example, this system can adjust a person's cardiac function based on their tissue impedance level. In an example, this system can increase (or decrease) the frequency of a person's heart beats and/or the magnitude of a person's heart contractions in response to an increase (or decrease) in the person's tissue impedance level as detected by a wearable biometric sensor. In an example, a person's tissue impedance level can be measured by reflecting light energy from (and/or passing light energy through) body tissue. In an example, a person's tissue impedance level can be measured by measuring electromagnetic energy from (and/or passing electromagnetic energy through) body tissue.

In an example, this system can include one or more biochemical and/or biologic sensors selected from the group consisting of: amino acid sensor, antibody-based receptor, artificial olfactory sensor, artificial taste bud, biochemical sensor, biological cell sensor, biological sensor, biomimetic sensor, chemical sensor, chemiresistor, chemoreceptor, cholesterol sensor, DNA-based sensor, electrochemical sensor, electronic nose, electroosmotic sensor, electrophoresis sensor, electroporation sensor, enzyme-based sensor, fat sensor, glucose sensor, HDL sensor, LDL sensor, membrane sensor, micronutrient sensor, microorganism-based sensor, multiple-analyte sensor array, nucleic acid-based sensor, olfactory sensor, osmolality sensor, pH level sensor, plurality of cross-reactive sensors, protein-based sensor, reagent-based sensor, receptor-based sensor, RNA-based sensor, saturated fat sensor, sodium sensor, and trans fat sensor.

In an example, this system can comprise one or more sensors selected from the group consisting of: accelerometer, acoustic energy sensor, action potential sensor, activity level sensor, auscultatory sensor, ballistocardiographic sensor, bend sensor, biochemical sensor, blood flow sensor, blood pressure sensor, brain activity sensor, breathing rate sensor, caloric intake monitor, capacitance hygrometry sensor, capacitive sensor, cardiac function sensor, cardiopulmonary function sensor, chemiluminescence sensor, chemoreceptor, chewing sensor, chromatographic sensor, compass, conductivity sensor, core temperature sensor, cranial pressure sensor, digital camera, electrical resistance sensor, electrocardiographic (ECG) sensor, electroencephalographic (EEG) sensor, electrogoniometer, electromagnetic energy sensor, electromyographic (EMG) sensor, electroporation sensor, enzymatic sensor, eye muscle (EOG) sensor, galvanic skin response (GSR) sensor, glucose sensor, GPS sensor, gyroscope, Hall-effect sensor, heart rate monitor, heart rate sensor, hormone sensor, humidity sensor, hydration level sensor, hygrometry sensor, impedance sensor, inclinometer, inertial sensor, infrared light (IR) sensor, infrared spectroscopy sensor, ion mobility spectroscopic sensor, lactate sensor, laser sensor, light intensity sensor, magnetic energy sensor, magnetometer, medichip, and metal oxide semiconductor sensor.

In an example, this system can comprise one or more sensors selected from the group consisting of: Micro Electrical Mechanical System (MEMS) sensor, microcantilever sensor, microfluidic sensor, microphone, motion sensor, muscle function monitor, near-infrared spectroscopic sensor, neural impulse monitor, neurosensor, optical detector, optical sensor, optoelectronic sensor, oximetry sensor, perspiration rate sensor, pH level sensor, photochemical sensor, photodetector, photodiode, photoelectric sensor, photoplethysmographic (PPG) sensor, piezocapacitive sensor, piezoelectric sensor, piezoresistive sensor, position sensor, pressure sensor, pulse oximetry sensor, pulse rate sensor, pyroelectric sensor, radio frequency (RF) sensor, Raman spectroscopy sensor, respiration sensor, skin conductance sensor, skin moisture sensor, skin temperature sensor, sound energy sensor, spectral analysis sensor, spectrometric sensor, spectrophotometer, spectroscopic sensor, still-frame camera, strain gauge, stretch sensor, swallowing sensor, sweat sensor, systolic blood pressure sensor, temperature sensor, thermal energy sensor, thermistor, thermocouple, thermometer, thermopile, tissue impedance sensor, ultrasonic energy sensor, ultraviolet light sensor, ultraviolet spectroscopy sensor, variable impedance sensor, variable resistance sensor, variable translucence sensor, and video camera.

In an example, this device can further comprise one or more environmental sensors. In an example, the operation of this device can be automatically adjusted, modified, and/or controlled based on data from one or more environmental sensors. In an example, it can be advantageous for optimal operation of an implanted cardiac function device to be different in different environmental settings and/or conditions. In an example, the operation of an implanted cardiac function device is advantageously adjusted based on environmental (and/or ambient) temperature, humidity, altitude, and barometric pressure. In an example, the operation of an implanted cardiac function device is advantageously adjusted based on environmental (and/or ambient) light level, spectral distribution, and/or variability. In an example, the operation of an implanted cardiac function device is advantageously adjusted based on ambient noise level, spectral distribution, variability, sound pattern recognition, ambient voices, and ambient ultrasonic energy.

In an example, the operation of an implanted cardiac function device can be adjusted based on ambient air composition, air quality, oxygen level, carbon dioxide level, carbon monoxide level, air-borne pollution and/or toxins, air borne allergens, and air speed. In an example, the operation of an implanted cardiac function device can be adjusted based on environmental (and/or ambient) electromagnetic radiation levels and/or types. In an example, the operation of an implanted cardiac function device can be adjusted based on whether a person is indoors or outdoors. In an example, this device can further comprise one or more environmental and/or ambient sensors selected from the group consisting of: air-borne allergen sensor, air-borne pollution sensor, air-borne toxin sensor, altitude sensor, ambient air composition sensor, ambient air quality sensor, ambient carbon dioxide sensor, ambient carbon monoxide sensor, ambient electromagnetic radiation sensor, ambient humidity sensor, ambient light sensor, ambient noise sensor, ambient oxygen sensor, ambient sound pattern recognition sensor, ambient temperature sensor, ambient ultrasonic energy sensor, ambient voices sensor, and barometric pressure sensor.

In an example, this system can comprise one or more data processing components selected from the group consisting of: data processor, data receiver, data transmitter, memory, microchip, and microprocessor. In an example, this system can include a wireless data transmitter and/or receiver. In an example, a first data processor and/or data transmitter which is physically part of the wearable component can be in electronic communication with a second data processor and/or data receiver which is not physically part of the wearable component. In an example, data processing can be distributed between the first and second data processors. In an example, a second data processor can be part of a remote computing device. In an example, a second data processor can be part of a wearable data processing hub, mobile computer, electronic tablet, electronic pad, mobile phone, smart phone, implanted medical device, internet-connected remote computer, communication network tower, satellite, or home control system.

In an example, this system can comprise one or more power sources which supply power to the biometric sensor and the data processor. In an example, a power source can be a battery. In an example, a power source and/or power transducer can transduce, harvest, and/or generate energy from body motion or kinetic energy. In an example, a power source and/or power transducer can transduce, harvest, and/or generate energy from ambient light energy. In an example, a power source and/or power transducer can transduce, harvest, and/or generate energy from body thermal energy. In an example, a power source and/or power transducer can transduce, harvest, and/or generate energy from ambient electromagnetic energy.

In an example, this system can further comprise one or more human-to-computer-interface (HCI) components. One or more human-computer-interface components can be selected from the group consisting of: touch screen, gesture recognition interface, speech and/or voice recognition interface, button and/or keypad, dial and/or knob, brainwave-based HCI, and motion sensor. In an example, this device can further comprise one or more computer-to-human interface (HCI) components. One or more computer-to-human interface components can be selected from the group consisting of: display screen, light emitter and/or light-emitting array, light-emitting fabric, optical emitter, speaker, buzzer, or other sound-emitting member, electromagnetic signal generator, vibrating member, actuator, Micro Electro Mechanical Systems (MEMS), augmented reality eyewear, virtual reality eyewear, and electronically-functional eyewear.

In an example, this invention can be embodied in an integrated system for managing cardiac rhythm including both a wearable device and an implanted device, wherein this system comprises: (a) a wearable device which is configured to be worn by a person, wherein the wearable device further comprises a light emitter which is configured to emit light toward the person's body tissue, a light receiver which is configured to receive light from the light emitter after the light has passed through and/or been reflected from the person's body tissue, and a wireless data transmitter; and (b) a cardiac rhythm management device which is configured to be implanted within the person, wherein the cardiac rhythm management device further comprises an electromagnetic energy emitter which is configured to deliver electromagnetic energy to the person's heart in order to manage cardiac rhythm and a wireless data receiver; (c) wherein differences between the spectral distribution of light emitted from the light emitter and the spectral distribution of light received by the light receiver are analyzed in order to measure the amount of an analyte in the person's body tissue; and (d) wherein the operation of the cardiac rhythm management device is changed based on the amount of the analyte in the person's body tissue.

In an example, the wearable component of the system can be a finger ring. In an example, this invention can be embodied in an integrated system for managing cardiac rhythm including both a wearable device and an implanted device, wherein this system comprises: (a) a finger ring which is configured to be worn by a person, wherein the finger ring further comprises a light emitter which is configured to emit light toward the person's finger tissue, a light receiver which is configured to receive light from the light emitter after the light has passed through and/or been reflected from the person's finger tissue, and a wireless data transmitter; and (b) a cardiac rhythm management device which is configured to be implanted within the person, wherein the cardiac rhythm management device further comprises an electromagnetic energy emitter which is configured to deliver electromagnetic energy to the person's heart in order to manage cardiac rhythm and a wireless data receiver; (c) wherein differences between the spectral distribution of light emitted from the light emitter and the spectral distribution of light received by the light receiver are analyzed in order to measure the amount of an analyte in the person's finger tissue; and (d) wherein the operation of the cardiac rhythm management device is changed based on the amount of the analyte in the person's finger tissue.

In an example, a finger ring can have a circular cross-sectional shape. In an example, a finger ring can have a circular circumference. In an example, a finger ring can have a width which is perpendicular to its circular circumference. In an example, the average width of a finger ring can be in the range of ⅛ inch to 1 inch. In an example, the average width of a finger ring can be in the range of 3 mm to 3 cm. In an example, a finger ring can have an inward side which is configured to face toward the surface of a person's finger and an outward side which is configured to face away from the surface of a person's finger. In an example, the inward side of a finger ring can be flat. In an example, the inward side of a ringer ring can be rounded.

In an example, the wearable component of the system can be a wrist and/or arm band. In an example, this invention can be embodied in an integrated system for managing cardiac rhythm including both a wrist and/or arm band and an implanted device, wherein this system comprises: (a) a wrist and/or arm band which is configured to be worn by a person, wherein the wrist and/or arm band further comprises a light emitter which is configured to emit light toward the person's wrist and/or arm tissue, a light receiver which is configured to receive light from the light emitter after the light has passed through and/or been reflected from the person's wrist and/or arm tissue, and a wireless data transmitter; and (b) a cardiac rhythm management device which is configured to be implanted within the person, wherein the cardiac rhythm management device further comprises an electromagnetic energy emitter which is configured to deliver electromagnetic energy to the person's heart in order to manage cardiac rhythm and a wireless data receiver; (c) wherein differences between the spectral distribution of light emitted from the light emitter and the spectral distribution of light received by the light receiver are analyzed in order to measure the amount of an analyte in the person's wrist and/or arm tissue; and (d) wherein the operation of the cardiac rhythm management device is changed based on the amount of the analyte in the person's wrist and/or arm tissue.

In an example, the wearable component of the system can be an ear ring, ear insert, or other ear-worn device. In an example, this invention can be embodied in an integrated system for managing cardiac rhythm including both an ear ring, ear insert, or other ear-worn device and implanted device, wherein this system comprises: (a) an ear ring, ear insert, or other ear-worn device which is configured to be worn by a person, wherein the ear ring, ear insert, or other ear-worn device further comprises a light emitter which is configured to emit light toward the person's ear tissue, a light receiver which is configured to receive light from the light emitter after the light has passed through and/or been reflected from the person's ear tissue, and a wireless data transmitter; and (b) a cardiac rhythm management device which is configured to be implanted within the person, wherein the cardiac rhythm management device further comprises an electromagnetic energy emitter which is configured to deliver electromagnetic energy to the person's heart in order to manage cardiac rhythm and a wireless data receiver; (c) wherein differences between the spectral distribution of light emitted from the light emitter and the spectral distribution of light received by the light receiver are analyzed in order to measure the amount of an analyte in the person's ear tissue; and (d) wherein the operation of the cardiac rhythm management device is changed based on the amount of the analyte in the person's ear tissue.

In an example, the analyte measured by this device can be the oxygen level of body tissue (and/or fluid). In an example, the system can change the frequency and/or magnitude of electromagnetic pulses delivered to a person's heart when analysis of data from the light receiver indicates a change in the level of oxygen in body tissue (and/or fluid). In an example, the system can increase the frequency and/or magnitude of electromagnetic pulses delivered to the person's heart when analysis of data from the light receiver indicates a low level of oxygen in body tissue (and/or fluid). In an example, the system can decrease the frequency and/or magnitude of electromagnetic pulses delivered to the person's heart when analysis of data from the light receiver indicates a high level of oxygen in body tissue (and/or fluid).

In an example, a light emitter can emit light from the inward side of a wearable device toward the surface of a person's body (e.g. finger, wrist, arm, ear, or leg). In an example, a light receiver can receive light into the inward side of a wearable device which has passed through and/or been reflected from a person's body tissue. In an example, there can be a flexible and/or compressible light barrier between a light emitter and a light receiver. In an example, a light emitter and a light receiver can be on the same circumferential line (e.g. circle) of a wearable device, but at different radial locations around this circumference. In an example, a light emitter and a light receiver can be on the same radial location around a wearable device, but on different circumferential lines (e.g. circles). In an example, there can be two or more light emitters and one light receiver on a wearable device. In an example, there is one light emitter and two or more light receivers on a wearable device.

In an example, compass coordinates can be defined for the circumference of a wearable device with the 0-degree point being the most ventral point when the wearable device is worn, the 90-degree point being one-quarter of the way around the circumference in a clockwise direction from the 0-degree point, the 180-degree point being opposite the 0-degree point, and the 270-degree point being one-quarter of the way around the circumference in a clockwise direction from the 180-degree point. In an example, a light emitter can be separated from a light receiver by between 1 and 15 degrees. In an example, a light emitter can be separated from a light receiver by between 10 and 45 degrees. In an example, a light emitter can be separated from a light receiver by more than 44 degrees. In an example, a light emitter can be separated from a light receiver by 45, 60, 90, or 180 degrees. In an example, a plurality of light receivers can be distributed around the circumference of a wearable device, being pair-wise separated from each other by between 10 and 45 degrees. In an example, a plurality of light receivers can be distributed around the circumference of a wearable device, being pair-wise separated from each other by 45, 60, 90, or 180 degrees.

In an example, a light emitter can emit coherent light. In an example, a light emitter can be a laser. In an example, a light emitter can be a Light Emitting Diode (LED). In an example, a light emitter can emit infrared or near-infrared light. In an example, a light emitter can emit ultraviolet light. In an example, a light emitter emit red light and/or be a red-light laser. In an example, a light emitter emit green light and/or be a green-light laser. In an example, a light emitter can emit white light and/or be a white-light laser. In an example, a wearable device can include can be two or more light emitters. In an example, a wearable device can include a red light emitter and a green light emitter. In an example, a light emitter can emit light with frequency and/or spectrum changes over time. In an example, a light emitter can emit a sequence of light pulses at different selected frequencies. In an example, a light emitter can emit polarized light. In an example, the polarization of light can change after the light passes through and/or is reflected from body tissue and these changes can be used to measure an analyte level in the body.

In an example, differences in the spectrum light emitted from a light emitter and the spectrum of light received by a light receiver can be analyzed using spectroscopic analysis. In an example, changes in the amount (or concentration) of a selected analyte in body tissue can change the spectrum of light passing through and/or reflected by the body tissue. In an example, body tissue can be understood to include fluids such as blood and interstitial fluid. In an example, a light emitter and a light received can be collectively referred to as a spectroscopic (or spectroscopy) sensor. In an example, the analyte which is measured can be oxygen. In example, differences in the spectrum of light emitted from a light emitter and the spectrum of light received by a light receiver can be analyzed to measure tissue (and/or blood) oxygen levels. In example, differences in the spectrum of light emitted from a light emitter and the spectrum of light received by a light receiver can be analyzed to measure tissue (and/or blood) oxygenation.

In an example, a light emitter and a light receiver together can comprise a spectroscopic (or "spectroscopy") sensor. In an example, the spectrum of light energy is changed when the light energy passes through body tissue and/or is reflected from body tissue. In an example, changes in the spectrum of light energy which has passed through and/or been reflected from body tissue can be analyzed to detect the composition and/or configuration of body tissue. In an example, these changes in the spectrum of light energy can be analyzed to provide information on the composition of body tissue which, in turn, enables measurement of an analyte level in the body. In an example, a light emitter and a light receiver together can comprise a sensor selected from the group consisting of: backscattering spectrometry sensor, infrared spectroscopy sensor, ion mobility spectroscopic sensor, mass spectrometry sensor, Near Infrared Spectroscopy sensor (NIS), Raman spectroscopy sensor, spectrometry sensor, spectrophotometer, spectroscopy sensor, ultraviolet spectroscopy sensor, and white light spectroscopy sensor.

In an example, portions of the spectrum of light emitted by a light emitter can be absorbed by body tissue and spectral analysis of these absorbed portions can enable measurement of an analyte level in the body. In an example, portions of the spectrum of light emitted by a light emitter can be amplified by body tissue and spectral analysis of these amplified portions can enable measurement of an analyte level in the body. In an example, portions of the spectrum of light emitted by a light emitter can be shifted by interaction with body tissue and spectral analysis of these shifted portions can enable measurement of an analyte level in the body.

In an example, the depth, breadth, location, and/or type of body tissue or fluid from which light from a light emitter is reflected can be changed by adjusting the frequency, color, and/or spectrum of light emitted from the light emitter. In an example, the frequency, color, and/or spectrum of light emitted from the light emitter can be adjusted in order to more accurately measure an analyte level in the body. In an example, the frequency, color, and/or spectrum of light emitted from the light emitter can be adjusted automatically (in an iterative manner) by a device in order to more accurately measure an analyte level in the body for a specific person, for a specific type of activity, or for a specific configuration of the device relative to the person's body surface. In an example, the frequency, color, and/or spectrum of light emitted from the light emitter can be adjusted automatically to maintain accurate measurement of an analyte level in the body even if the device shifts and/or moves relative to the person's body surface. In an example, a device can automatically vary the frequency, color, and/or spectrum of light from a light emitter to scan through a range of tissue depths, locations, and/or types in order to obtain more accurate measurement of an analyte level in the body. In an example, this device can further comprise one or more optical filters or lenses which change the frequency, color, and/or spectrum of light emitted by a light emitter.

In an example, the depth, breadth, location, and/or type of body tissue or fluid from which light from a light emitter is reflected can be changed by adjusting the power and/or intensity of light emitted from the light emitter. In an example, the power and/or intensity of light emitted from the light emitter can be adjusted in order to more accurately measure an analyte level in the body. In an example, the power and/or intensity of light emitted from the light emitter can be adjusted automatically (in an iterative manner) by a device in order to more accurately measure an analyte level in the body for a specific person, for a specific type of activity, or for a specific configuration of the device relative to the person's body surface. In an example, the power and/or intensity of light emitted from the light emitter can be adjusted automatically to maintain accurate measurement of an analyte level in the body even if the device shifts and/or moves relative to the person's body surface. In an example, a device can automatically vary the power and/or intensity of light from a light emitter to scan through a range of tissue depths, locations, and/or types in order to obtain more accurate measurement of an analyte level in the body.

In an example, the depth, breadth, location, and/or type of body tissue or fluid from which light from a light emitter is reflected can be changed by adjusting the angle of light emitted from the light emitter. In an example, the angle of light emitted from the light emitter can be adjusted in order to more accurately measure an analyte level in the body. In an example, the angle of light emitted from the light emitter can be adjusted automatically (in an iterative manner) by a device in order to more accurately measure an analyte level in the body for a specific person, for a specific type of activity, or for a specific configuration of the device relative to the person's body surface. In an example, the angle of light emitted from the light emitter can be adjusted automatically to maintain accurate measurement of an analyte level in the body even if the device shifts and/or moves relative to the person's body surface. In an example, a device can automatically vary the angle of light from a light emitter to scan through a range of tissue depths, locations, and/or types in order to obtain more accurate measurement of an analyte level in the body. In an example, this device can further comprise one or more optical filters or lenses which change the projection and/or body incidence angle of a light beam emitted by a light emitter.

In an example, the depth, breadth, location, and/or type of body tissue or fluid from which light from a light emitter is reflected can be changed by adjusting the coherence, polarization, and/or phase of light emitted from the light emitter. In an example, the coherence, polarization, and/or phase of light emitted from the light emitter can be adjusted in order to more accurately measure an analyte level in the body. In an example, the coherence, polarization, and/or phase of light emitted from the light emitter can be adjusted automatically (in an iterative manner) by a device in order to more accurately measure an analyte level in the body for a specific person, for a specific type of activity, or for a specific configuration of the device relative to the person's body surface. In an example, the coherence, polarization, and/or phase of light emitted from the light emitter can be adjusted automatically to maintain accurate measurement of an analyte level in the body even if the device shifts and/or moves relative to the person's body surface. In an example, a device can automatically vary the coherence, polarization, and/or phase of light from a light emitter to scan through a range of tissue depths, locations, and/or types in order to obtain more accurate measurement of an analyte level in the body. In an example, this device can further comprise one or more optical filters or lenses which change the coherence, polarization, and/or phase of light emitted by a light emitter.

In an example, a device can comprise a first light emitter and a second light emitter. In an example, the first light emitter can emit light with a first light frequency, color, and/or spectrum and the second light emitter can emit light with a second light frequency, color, and/or spectrum. In an example, light from the first light emitter can reflect primarily from a first depth, breadth, location, and/or type of body tissue and light from the second light emitter can reflect primarily from a first depth, breadth, location, and/or type of body tissue. In an example, first and second light emitters can emit light simultaneously. In an example, first and second light emitters can emit light in a selected chronological sequence and/or timing pattern.

In an example, a device can comprise a first light emitter and a second light emitter. In an example, the first light emitter can emit light with a first light power and/or intensity and the second light emitter can emit light with a second light power and/or intensity. In an example, light from the first light emitter can reflect primarily from a first depth, breadth, location, and/or type of body tissue and light from the second light emitter can reflect primarily from a first depth, breadth, location, and/or type of body tissue. In an example, first and second light emitters can emit light simultaneously. In an example, first and second light emitters can emit light in a selected chronological sequence and/or timing pattern.

In an example, a device can comprise a first light emitter and a second light emitter. In an example, the first light emitter can emit light with a first light projection and/or body incidence angle and the second light emitter can emit light with a second light projection and/or body incidence angle. In an example, light from the first light emitter can reflect primarily from a first depth, breadth, location, and/or type of body tissue and light from the second light emitter can reflect primarily from a first depth, breadth, location, and/or type of body tissue. In an example, first and second light emitters can emit light simultaneously. In an example, first and second light emitters can emit light in a selected chronological sequence and/or timing pattern.

In an example, a device can comprise a first light emitter and a second light emitter. In an example, the first light emitter can emit light with a first light coherence, polarization, and/or phase and the second light emitter can emit light with a second light coherence, polarization, and/or phase. In an example, light from the first light emitter can reflect primarily from a first depth, breadth, location, and/or type of body tissue and light from the second light emitter can reflect primarily from a first depth, breadth, location, and/or type of body tissue. In an example, first and second light emitters can emit light simultaneously. In an example, first and second light emitters can emit light in a selected chronological sequence and/or timing pattern.

In an example, the depth, breadth, location, and/or type of body tissue or fluid from which light from a light emitter is reflected and received by a light receiver can be changed by adjusting the distance between a light emitter and a light receiver. In an example, the distance between a light emitter and a light receiver can be adjusted in order to more accurately measure an analyte level in the body. In an example, the distance between a light emitter and a light receiver can be adjusted automatically (in an iterative manner) by a device in order to more accurately measure an analyte level in the body for a specific person, for a specific type of activity, or for a specific configuration of the device relative to the person's body surface. In an example, the distance between a light emitter and a light receiver can be adjusted automatically to maintain accurate measurement of an analyte level in the body even if the device shifts and/or moves relative to the person's body surface. In an example, a device can automatically vary the distance between a light emitter and a light receiver to scan through a range of tissue depths, locations, and/or types in order to obtain more accurate measurement of an analyte level in the body.

In an example, the depths, breadths, locations, and/or types of body tissue or fluid from which light beams from a plurality of light emitters are reflected can be determined by a selected geometric configuration of the plurality of light emitters and a light receiver. In an example, a selected geometric configuration of a plurality of light emitters and a light receiver can be designed to most accurately measure an analyte level in the body. In an example, the geometric configuration of a plurality of light emitters and a light receiver can be adjusted automatically (in an iterative manner) by a device in order to more accurately measure an analyte level in the body for a specific person, for a specific type of activity, or for a specific configuration of the device relative to the person's body surface. In an example, the geometric configuration of a plurality of light emitters and a light receiver can be adjusted automatically to maintain accurate measurement of an analyte level in the body even if the device shifts and/or moves relative to the person's body surface. In an example, a device can automatically vary the geometric configuration of a plurality of light emitters and a light receiver in order to scan through a range of tissue depths, locations, and/or types in order to measure an analyte level in the body more accurately. In an example, a plurality of light emitters can emit light simultaneously. In an example, a plurality of light emitters can emit light in a selected chronological sequence and/or timing pattern.

In an example, a plurality of light emitters can be configured in a linear array in proximity to a light receiver. In an example, a plurality of light emitters can be configured in a linear array including a light receiver. In an example, a plurality of light emitters can be configured in a polygonal array in proximity to a light receiver. In an example, a plurality of light emitters can be configured in a polygonal array including a light receiver. In an example, a plurality of light emitters can be configured in a polygonal array around a light receiver. In an example, a plurality of light emitters can be configured in a circular or other arcuate array in proximity to a light receiver. In an example, a plurality of light emitters can be configured in a circular or other arcuate array including a light receiver. In an example, a plurality of light emitters can be configured in a circular or other arcuate array around a light receiver. In an example, a plurality of light emitters can emit light in a circular sequence around a central light receiver.

In an example, the depths, breadths, locations, and/or types of body tissue or fluid from which light beams are reflected and received by a plurality of light receivers can be determined by a selected geometric configuration of a light emitter and the plurality of light receivers. In an example, a selected geometric configuration of a light emitter and a plurality of light receivers can be designed to most accurately measure an analyte level in the body. In an example, the geometric configuration of a light emitter and a plurality of light receivers can be adjusted automatically (in an iterative manner) by a device in order to more accurately measure an analyte level in the body for a specific person, for a specific type of activity, or for a specific configuration of the device relative to the person's body surface. In an example, the geometric configuration of a light emitter and a plurality of light receivers can be adjusted automatically to maintain accurate measurement of an analyte level in the body even if the device shifts and/or moves relative to the person's body surface. In an example, a device can automatically vary the geometric configuration of a light emitter and a plurality of light receivers in order to scan through a range of tissue depths, locations, and/or types in order to measure an analyte level in the body more accurately.

In an example, a plurality of light receivers can be configured in a linear array in proximity to a light emitter. In an example, a plurality of light receivers can be configured in a linear array including a light emitter. In an example, a plurality of light receivers can be configured in a polygonal array in proximity to a light emitter. In an example, a plurality of light receivers can be configured in a polygonal array including a light emitter. In an example, a plurality of light receivers can be configured in a polygonal array around a light emitter. In an example, a plurality of light receivers can be configured in a circular or other arcuate array in proximity to a light emitter. In an example, a plurality of light receivers can be configured in a circular or other arcuate array including a light emitter. In an example, a plurality of light receivers can be configured in a circular or other arcuate array around a light emitter.

In an example, a light emitter can be part of an arcuate band. In an example, a light emitter can be part of a housing which is held on a person's body by an arcuate band. In an example, this device can comprise an array, grid, and/or matrix of two or more light emitters with a proximal-to-distal orientation. In an example, this device can comprise an array, grid, and/or matrix of two or more light emitters along a proximal-to-distal axis. In an example, this device can comprise an array, grid, and/or matrix of two or more light emitters with a circumferential orientation. In an example, this device can comprise an array, grid, and/or matrix of two or more light emitters along a circumferential axis.

In an example, this device can comprise a linear array, grid, and/or matrix of light emitters. In an example, this device can comprise a rectangular array, grid, and/or matrix of light emitters. In an example, this device can comprise a circular or elliptical array, grid, and/or matrix of light emitters. In an example, this device can comprise a checkerboard array, grid, and/or matrix of light emitters. In an example, this device can comprise a three-dimensional stacked array, grid, and/or matrix of light emitters. In an example, this device can comprise a sunburst and/or radial-spoke array, grid, and/or matrix of light emitters. In an example, this device can comprise a sinusoidal array, grid, and/or matrix of light emitters.

In an example, an array, grid, and/or matrix of two or more light emitters can span up to 10% of the cross-sectional circumference of a part of a person's body such as a wrist, arm, finger, ankle, or leg. In an example, an array, grid, and/or matrix of two or more light emitters can span between 10% and 25% of the cross-sectional circumference of a part of a person's body such as a wrist, arm, finger, ankle, or leg. In an example, an array, grid, and/or matrix of two or more light emitters can span between 25% and 50% of the cross-sectional circumference of a part of a person's body such as a wrist, arm, finger, ankle, or leg. In an example, an array, grid, and/or matrix of two or more light emitters can span between 50% and 100% of the cross-sectional circumference of a part of a person's body such as a wrist, arm, finger, ankle, or leg.

In an example, a light receiver can be part of an arcuate band. In an example, a light receiver can be part of a housing which is held on a person's body by an arcuate band. In an example, this device can comprise an array, grid, and/or matrix of two or more light receivers with a proximal-to-distal orientation. In an example, this device can comprise an array, grid, and/or matrix of two or more light receivers along a proximal-to-distal axis. In an example, this device can comprise an array, grid, and/or matrix of two or more light receivers with a circumferential orientation. In an example, this device can comprise an array, grid, and/or matrix of two or more light receivers along a circumferential axis.

In an example, this device can comprise a linear array, grid, and/or matrix of light receivers. In an example, this device can comprise a rectangular array, grid, and/or matrix of light receivers. In an example, this device can comprise a circular or elliptical array, grid, and/or matrix of light receivers. In an example, this device can comprise a checkerboard array, grid, and/or matrix of light receivers. In an example, this device can comprise a three-dimensional stacked array, grid, and/or matrix of light receivers. In an example, this device can comprise a sunburst and/or radial-spoke array, grid, and/or matrix of light receivers. In an example, this device can comprise a sinusoidal array, grid, and/or matrix of light receivers.

In an example, an array, grid, and/or matrix of two or more light receivers can span up to 10% of the cross-sectional circumference of a part of a person's body such as a wrist, arm, finger, ankle, or leg. In an example, an array, grid, and/or matrix of two or more light receivers can span between 10% and 25% of the cross-sectional circumference of a part of a person's body such as a wrist, arm, finger, ankle, or leg. In an example, an array, grid, and/or matrix of two or more light receivers can span between 25% and 50% of the cross-sectional circumference of a part of a person's body such as a wrist, arm, finger, ankle, or leg. In an example, an array, grid, and/or matrix of two or more light receivers can span between 50% and 100% of the cross-sectional circumference of a part of a person's body such as a wrist, arm, finger, ankle, or leg.

In an example, a light emitter and a light receiver can be part of an arcuate band. In an example, a light emitter and a light receiver can be part of a housing which is held on a person's body by an arcuate band. In an example, this device can comprise an array, grid, and/or matrix of (alternating) light emitters and receivers with a proximal-to-distal orientation. In an example, this device can comprise an array, grid, and/or matrix of (alternating) light emitters and receivers along a proximal-to-distal axis. In an example, this device can comprise an array, grid, and/or matrix of (alternating) light emitters and receivers with a circumferential orientation. In an example, this device can comprise an array, grid, and/or matrix of (alternating) light emitters and receivers along a circumferential axis.

In an example, this device can comprise a linear array, grid, and/or matrix of (alternating) light emitters and receivers. In an example, this device can comprise a rectangular array, grid, and/or matrix of (alternating) light emitters and receivers. In an example, this device can comprise a circular or elliptical array, grid, and/or matrix of (alternating) light emitters and receivers. In an example, this device can comprise a checkerboard array, grid, and/or matrix of (alternating) light emitters and receivers. In an example, this device can comprise a three-dimensional stacked array, grid, and/or matrix of (alternating) light emitters and receivers. In an example, this device can comprise a sunburst and/or radial-spoke array, grid, and/or matrix of (alternating) light emitters and receivers. In an example, this device can comprise a sinusoidal array, grid, and/or matrix of (alternating) light emitters and receivers.

In an example, an array, grid, and/or matrix of (alternating) light emitters and receivers can span up to 10% of the circumference of a part of a person's body such as a wrist, arm, finger, ankle, or leg. In an example, an array, grid, and/or matrix of (alternating) light emitters and receivers can span between 10% and 25% of the circumference of a part of a person's body such as a wrist, arm, finger, ankle, or leg. In an example, an array, grid, and/or matrix of (alternating) light emitters and receivers can span between 25% and 50% of the circumference of a part of a person's body such as a wrist, arm, finger, ankle, or leg. In an example, an array, grid, and/or matrix of (alternating) light emitters and receivers can span between 50% and 100% of the circumference of a part of a person's body such as a wrist, arm, finger, ankle, or leg.

In an example, this device can comprise an array, grid, and/or matrix of light emitters which differ in one or more parameters selected from the group consisting of: location and/or distance from a light receiver; distance to body surface; light beam frequency, color, and/or spectrum; light beam coherence, polarity, and/or phase; light beam power and/or intensity; light beam projection and/or body incidence angle; light beam duration; light beam size; and light beam focal distance. In an example, this device can comprise an array, grid, and/or matrix of light receivers which differ in: location and/or distance from a light emitter; and/or distance to body surface.

In an example, the frequency, color, and/or spectrum of a beam of light emitted from a light emitter can be changed over time to create a chronological sequence of beams of light with different frequencies, colors, and/or spectrums. In an example, the angle of a beam of light emitted from a light emitter can be changed over time to create a chronological sequence of beams of light with different projection and/or body incidence angles. In an example, the power or intensity of a beam of light emitted from a light emitter can be changed over time to create a chronological sequence of beams of light with different power or intensity levels. Such sequences can help to more accurately measure an analyte level in the body.

In an example, the frequency, color, and/or spectrum of a beam of light emitted from a light emitter can be changed in response to specific environmental conditions (e.g. temperature or humidity) and/or specific activities in which the person wearing a device is engaged (e.g. high level of movement, eating, sleeping, etc.) in order to more accurately measure an analyte level in the body. In an example, the projection angle of a beam of light emitted from a light emitter can be changed in response to specific environmental conditions (e.g. temperature or humidity) and/or specific activities in which the person wearing a device is engaged (e.g. high level of movement, eating, sleeping, etc.) in order to more accurately measure an analyte level in the body. In an example, the power and/or intensity of a beam of light emitted from a light emitter can be changed in response to specific environmental conditions (e.g. temperature or humidity) and/or specific activities in which the person wearing a device is engaged (e.g. high level of movement, eating, sleeping, etc.) in order to more accurately measure an analyte level in the body.

In an example, an emitter can separated from a receiver by a selected distance. In an example, there can be a selected distance between an emitter and a receiver. In an example, (an orthogonal component of) this distance can be measured along a circumferential axis. In an example, an emitter and a receiver can both be along the same circumferential line. In an example, (an orthogonal component of) this distance can be measured along a proximal-to-distal axis. In an example, an emitter and a receiver can both be along the same proximal-to-distal line. In an example, this selected distance can be expressed in inches and be within the range of 1/16" to 2". In an example, this selected distance can be expressed in metric units and be within the range of 2 mm to 5 cm. In an example, if this selected distance is along a circumferential axis, this distance can be expressed in (compass or polar coordinate) degrees and be within the range of 2 degrees to 60 degrees.

In an example, this device can have two (or more) emitters. In an example, two (or more) emitters can emit energy in a non-simultaneous (e.g. sequential) manner. In an example, a first emitter can be separated from a second emitter by a selected distance. In an example, there can be a selected distance between a first emitter and a second receiver. In an example, (an orthogonal component of) this distance can be measured along a circumferential axis. In an example, a first emitter and a second emitter can both be along the same circumferential line. In an example, (an orthogonal component of) this distance can be measured along a proximal-to-distal axis. In an example, a first emitter and a second emitter can both be along the same proximal-to-distal line. In an example, this selected distance can be expressed in inches and be within the range of 1/16" to 2". In an example, this selected distance can be expressed in metric units and be within the range of 2 mm to 5 cm. In an example, if this distance is along a circumferential axis, this selected distance can be expressed in (compass or polar coordinate) degrees and be within the range of 2 degrees to 60 degrees.

In an example, this device can have a circumferential array, matrix, or grid of four or more emitters, each of which is separated from the nearest other emitter by a distance within the range of 1/16" to 2". In an example, this device can have a circumferential array, matrix, or grid of four or more emitters, each of which is separated from the nearest other emitter by a distance within the range of 2 mm to 5 cm. In an example, this device can have a circumferential array, matrix, or grid of four or more emitters, each of which is separated from the nearest other emitter by a distance within the range of 2 degrees to 60 degrees. In an example, this device can have a circumferential array of emitters which spans between 25% and 100% of the cross-sectional perimeter circumference of a part of the body (e.g. wrist, arm, finger, ankle, or leg) to which the device is attached. In an example, this circumferential array of emitters can be even spaced or distributed, with the same pair-wise distance or number of degrees between adjacent emitters.

In an example, this device can have two (or more) receivers. In an example, a first receiver can be separated from a second receiver by a selected distance. In an example, there can be a selected distance between a first receiver and a second receiver. In an example, (an orthogonal component of) this distance can be measured along a circumferential axis. In an example, a first receiver and a second receiver can both be along the same circumferential line. In an example, (an orthogonal component of) this distance can be measured along a proximal-to-distal axis. In an example, a first receiver and a second receiver can both be along the same proximal-to-distal line. In an example, this selected distance can be expressed in inches and be within the range of 1/16" to 2". In an example, this selected distance can be expressed in metric units and be within the range of 2 mm to 5 cm. In an example, if this distance is along a circumferential axis, this selected distance can be expressed in (compass or polar coordinate) degrees and be within the range of 2 degrees to 60 degrees.

In an example, this device can have a circumferential array, matrix, or grid of four or more receivers, each of which is separated from the nearest other receiver by a distance within the range of 1/16" to 2". In an example, this device can have a circumferential array, matrix, or grid of four or more receivers, each of which is separated from the nearest other receiver by a distance within the range of 2 mm to 5 cm. In an example, this device can have a circumferential array, matrix, or grid of four or more receivers, each of which is separated from the nearest other receiver by a distance within the range of 2 degrees to 60 degrees. In an example, this device can have a circumferential array of receivers which spans between 25% and 100% of the cross-sectional perimeter circumference of a part of the body (e.g. wrist, arm, finger, ankle, or leg) to which the device is attached. In an example, this circumferential array of receivers can be even spaced or distributed, with the same pair-wise distance or number of degrees between adjacent receivers.

In an example, this device can comprise an array of emitters and receivers which is part of a wearable arcuate band or one or more segments (or housings) which are attached to a wearable arcuate band. In an example, this device can comprise a two-dimensional array of emitters and receivers which is part of a wearable arcuate band or one or more segments (or housings) which are attached to a wearable arcuate band. In an example, this device can comprise a three-dimensionally stacked array of emitters and receivers which is part of a wearable arcuate band or one or more segments (or housings) which are attached to a wearable arcuate band. In an example, data from this array can be analyzed to measure a person's analyte level.

In an example, an array of emitters and/or receivers can have a circumferential axis and a proximal-to-distal axis. In an example, this array can have at least three emitters and/or receivers along a circumferential axis and at least two emitters and/or receivers along a proximal-to-distal axis. In an example, an array can be formed from a plurality of sets of emitters and receivers, wherein each set forms the vertexes of a square or rectangle. In an example, an array can be formed from a plurality of sets of emitters and receivers, wherein each set forms the vertexes of a hexagon. In an example, an array can be formed from a plurality of sets of emitters and receivers, wherein each set forms a circle.

In an example, an array of emitters and receivers can have a square or rectangular shape. In an example, an array of emitters and receivers can have a hexagonal shape. In an example, an array of emitters and receivers can have a circular shape. In an example, an array of emitters and receivers can have a sunburst (e.g. radial spoke) shape. In an example, an array of emitters and receivers can have a cylindrical and/or ring shape. In an example, an array of emitters and receivers can have a conic section shape. In an example, an array of emitters and receivers can have a saddle shape. In an example, an array of emitters and receivers can have a helical shape.

In an example, a device can further comprise a track, channel, or slot along which an emitter, a receiver, or both can be moved. In an example, this movement can be done manually. In an example, this movement can be done automatically by one or more actuators. In an example, this track, channel, or slot can have a circumferential orientation. In an example, this track, channel, or slot can have a proximal-to-distal orientation. In an example, the distance between an emitter and a receiver can be adjusted by moving the emitter, the receiver, or both along such a track, channel, or slot. In an example, the location of an emitter and/or a receiver relative to a person's body can be adjusted by moving the emitter, the receiver, or both along such a track, channel, or slot. In an example, movement of an emitter, a receiver, or both along a track, channel, or slot can enable more accurate measurement of an analyte level in the body. In an example, movement of an emitter, a receiver, or both along a track, channel, or slot can enable customization of a device to the anatomy of a specific person for more accurate measurement of that person's analyte level.

In an example, a device can further comprise a rotating member which holds an emitter, a receiver, or both. In an example, rotation of this member can be done manually. In an example, this rotation can be done automatically by one or more actuators. In an example, the distance between an emitter and a receiver can be adjusted by rotating the rotating member. In an example, the location of an emitter and/or a receiver relative to a person's body can be adjusted by rotating the rotating member. In an example, movement of an emitter, a receiver, or both by a rotating member can enable more accurate measurement of an analyte level in the body. In an example, such movement of an emitter, a receiver, or both can enable customization of a device to the anatomy of a specific person for more accurate measurement of that person's analyte level.

In an example, this device can further comprise an energy source which powers an emitter, a receiver, a data processor, and/or a data transmitter. In an example, an energy source can be a battery. In an example, an energy source can transduce, harvest, and/or generate energy from body motion or kinetic energy. In an example, an energy source can transduce, harvest, and/or generate energy from ambient light energy. In an example, an energy source can transduce, harvest, and/or generate energy from body thermal energy. In an example, an energy source can transduce, harvest, and/or generate energy from ambient electromagnetic energy.

In an example, a wearable device can further comprise a data processor which analyzes the spectrum of light received by a light receiver in order to measure the amount of an analyte in body tissue. In an example, data concerning light received by a light receiver can be transmitted to a remote data processor by the wireless data transmitter and analysis of this data can occur in that remote data processor. In an example, an implanted cardiac rhythm management can further comprise a data processor. In an example, data concerning light received by a light receiver can be transmitted to the wireless data receiver and analysis of this data can occur in the data processor within the implanted cardiac rhythm management device.

In an example, this device can further comprise a wireless data transmitter and/or data receiver. In various examples, this device can be in wireless communication with an external device selected from the group consisting of: a cell phone, an electronic tablet, electronically-functional eyewear, a home electronics portal, an implanted medical device, an internet portal, a laptop computer, a mobile computer, a mobile phone, a remote computer, a remote control unit, a smart phone, a smart utensil, a television set, and a wearable data processing hub. In an example, additional data processing and analysis can be done within an external device.

In an example, this device can further comprise an energy barrier between an emitter and a receiver which reduces the transmission of energy from the emitter to the receiver. In an example, an energy barrier between a light emitter and a light receiver can be opaque. In an example, an energy barrier between a light emitter and a light receiver can be compressible, flexible, and/or elastic. In an example, an energy barrier can comprise compressible foam. In an example, an energy barrier can be an inflatable member (such as a balloon) which is filled with a gas or liquid. In an example, an energy barrier can have a linear shape. In an example, an energy barrier can have a circular, elliptical, sinusoidal, or other arcuate shape. In an example, an energy barrier can surround a receiver. In an example, an energy barrier can surround an emitter.

In an example, this device can further comprise an energy conductor between an emitter and a receiver which increases the transmission of energy from the emitter to the receiver. In an example, an energy conductor between a light emitter and a light receiver can be an optical lens and/or fiber optic conduit.

In an example, this device can further comprise one or more other types of biometric or environmental sensors in addition to the primary emitters and receivers discussed above. In an example, the primary emitter and the primary receiver of this device, discussed above, can be a light emitter and a light receiver, but the device can also include a (non-light-spectrum) electromagnetic emitter and a (non-light-spectrum) electromagnetic receiver. In an example, the primary emitter and the primary receiver of this device, discussed above, can be a (non-light-spectrum) electromagnetic emitter and a (non-light-spectrum) electromagnetic receiver, but the device can also include a light emitter and a light receiver. In an example, this device can comprise both light energy and electromagnetic energy sensors for measuring an analyte level in the body. In an example, this device can comprise both spectroscopic and microwave energy sensors for measuring an analyte level in the body.

This invention can be embodied in a system for human circulatory assistance comprising: a wearable device which is configured to be worn by a person, wherein the wearable device collects data on a biometric parameter concerning the person's body in real time; and an implanted circulatory assistance device which is configured to be implanted within the person's body, wherein the implanted circulatory assistance device assists in management of the person's cardiac rhythm and/or assists in pumping the person's blood, and wherein the operation of the implanted circulatory assistance device is controlled and/or adjusted in real time based on analysis of the biometric parameter. This system can help to prevent tissue degradation, can promote wound healing, and may even help to avoid amputation.

In an example, a wearable device can be a finger ring, smart watch, wrist band, ear ring, earlobe clip, ankle band, or smart sock. In an example, a biometric parameter can be body oxygenation level. In an example, an implanted circulatory assistance device can be an implanted cardiac pacemaker, an implanted central (heart assist) blood pump, or an implanted non-central (peripheral) blood pump. In an example, a system for human circulatory assistance can comprise a plurality of wearable devices and plurality of implanted non-central (peripheral) blood pumps which enables independent adjustment of circulatory assistance for different portions of a person's body based on biometric parameter values from those different body portions.

This invention is a partially or fully closed-loop system for human circulatory assistance whose operation is adjusted in real time based on analysis of data concerning one or more biometric parameters collected by one or more wearable sensors. In an example, human circulatory assistance can be provided by an implanted cardiac pacemaker whose operation is adjusted in real time based on overall body oxygenation level. In an example, human circulatory assistance can be provided by an implanted central (heart assist) blood pump whose operation is adjusted in real time based on overall body oxygenation level. In an example, human circulatory assistance can be provided by a plurality of non-central (peripheral) blood pumps in different body regions whose operations are individually adjusted based on oxygenation levels in those respective body regions.

Automatic adjustment of cardiac functioning and/or blood circulation in real time in response to abnormal biometric values measured by wearable devices can help to maintain healthy biological processes and prevent tissue degradation. For example, detection of low overall body oxygenation level by wearable sensors can trigger increased systemic blood flow. For example, detection of low oxygenation levels in specific portions of the body by wearable sensors can trigger selected increased blood flow to those specific portions. This can help to prevent tissue degradation, promote wound healing, and maintain proper organ functioning.

In an example, a system for human circulatory assistance can comprise: a wearable device which is configured to be worn by a person, wherein the wearable device collects data on a biometric parameter concerning the person's body in real time; and an implanted circulatory assistance device which is configured to be implanted within the person's body, wherein the implanted circulatory assistance device assists in management of the person's cardiac rhythm and/or assists in pumping the person's blood, and wherein operation of the implanted circulatory assistance device is controlled and/or adjusted in real time based on analysis of the data on the biometric parameter.

In an example, a system for human circulatory assistance can comprise: a finger ring, smart watch, smart watch band, wrist band, ankle band, smart sock, ear ring, ear bud, or smart patch worn by a person, wherein the finger ring, smart watch, smart watch band, wrist band, ankle band, smart sock, ear ring, ear bud, or smart patch collects data on a biometric parameter concerning the person's body; and an implanted cardiac pacemaker or implanted blood pump, wherein operation of the implanted cardiac pacemaker or implanted blood pump is controlled and/or adjusted based on analysis of the data on the biometric parameter.

In an example, a system for human circulatory assistance can comprise: a finger ring, smart watch, smart watch band, wrist band, ankle band, smart sock, ear ring, ear bud, or smart patch worn by a person, wherein the finger ring, smart watch, smart watch band, wrist band, ankle band, smart sock, ear ring, ear bud, or smart patch collects data concerning the person's body oxygenation level; and an implanted cardiac pacemaker, wherein operation of the implanted cardiac pacemaker is adjusted based on the person's body oxygenation level in one or more ways selected from the group consisting of: a change in the voltage of electromagnetic energy delivered to the heart to stimulate contractions, a change in the degree of coordination and/or timing between electromagnetic energy stimulation of different heart chambers, a change in the frequency of electromagnetic energy stimulation of heart contractions, a change in the location(s) on the heart where electromagnetic energy is delivered, a change in the magnitude of heart contractions which are stimulated, and a change in the regularity of heart contractions which are stimulated.

In an example, a system for human circulatory assistance can comprise: a finger ring, smart watch, smart watch band, wrist band, ankle band, smart sock, ear ring, ear bud, or smart patch worn by a person, wherein the finger ring, smart watch, smart watch band, wrist band, ankle band, smart sock, ear ring, ear bud, or smart patch collects data concerning the person's body oxygenation level; and an implanted blood pump, wherein operation of the implanted blood pump is adjusted based on the person's body oxygenation level in one or more ways selected from the group consisting of: activation or deactivation of the pump in order to increase or decrease blood flow; an increase or decrease in the duration of pump operation in order to increase or decrease blood flow; a increase or decrease in the speed of pump rotation, undulation, compression, and/or contraction in order to increase or decrease blood flow; and an increase or decrease in the magnitude of pump undulation, compression, and/or contraction in order to increase or decrease blood flow.

In an example, a wearable device of this system can have an optical sensor. In an example, an optical sensor can be a spectroscopic sensor. In an example, a wearable device can have a sensor which is in optical communication with body tissue, fluid, and/or gas selected from the group consisting of: blood, interstitial fluid, lymphatic fluid, sweat, tears, aqueous humour, saliva, exhaled gas, capillaries, blood vessels, skin, fatty tissue, muscles, and nerves. In an example, a wearable device of this system can have an electromagnetic energy sensor. In an example, an electromagnetic sensor can measure the conductivity, resistance, impedance, capacitance, and/or permittivity of body tissue and/or fluid. In an example, a wearable device can have a sensor which is in electromagnetic communication with body tissue, fluid, and/or gas which is selected from the group consisting of: blood, interstitial fluid, lymphatic fluid, sweat, tears, aqueous humour, saliva, exhaled gas, capillaries, blood vessels, skin, fatty tissue, muscles, bones, and nerves.

In an example, a wearable device of this system can be worn on a person's finger. In an example, a wearable device of this system can be a finger ring with embedded biometric sensors. In an example, biometric sensors can be spectroscopic sensors. In an example, a wearable device of this system can be a finger sleeve made from elastic fabric with embedded biometric sensors. In an example, sensors to collect data on a biometric parameter can be located on the inner (e.g. closest to body) surface of a finger ring or finger sleeve.

In an example, a plurality of sensors can be distributed around (at least half of) the inner circumference of a finger ring or finger sleeve. In an example, a plurality of light-energy emitters and receivers can be distributed around (at least half of) the circumference of a finger ring or finger sleeve. In an example, an alternating sequence of light-energy emitters and receivers can be distributed around (at least half of) the circumference of a finger ring or finger sleeve. In an example, a plurality of electromagnetic energy emitters and receivers can be distributed around (at least half of) the circumference of a finger ring or finger sleeve. In an example, an alternating sequence of electromagnetic energy emitters and receivers can be distributed around (at least half of) the circumference of a finger ring or finger sleeve.

In an example, a wearable device of this system can be worn on a person's wrist or forearm. In an example, a wearable device can be a smart watch with embedded biometric sensors. In an example, biometric sensors can be spectroscopic sensors. In an example, there can be sensors in the housing (e.g. the primary display housing) of a smart watch, around the band of a smart watch, or both. In an example, a wearable device can be a fitness band, bracelet, bangle with embedded biometric sensors. In an example, a biometric sensor can be located in a primary housing of a wrist-worn device (such as a smart watch), wherein the primary housing is worn on the dorsal side of a person's wrist. In an example, a biometric sensor can be located in a secondary housing of a wrist-worn device, wherein the secondary housing is worn on the ventral side of the wrist.

In an example, sensors to collect data on a biometric parameter can be distributed around (at least half of) the circumference of a watch band, wrist band, fitness band, or bracelet. In an example, a plurality of light-energy emitters and receivers can be distributed around (at least half of) the circumference of a watch band, wrist band, fitness band, or bracelet. In an example, an alternating sequence of light-energy emitters and receivers can be distributed around (at least half of) the circumference a watch band, wrist band, fitness band, or bracelet. In an example, a plurality of electromagnetic energy emitters and receivers can be distributed around (at least half of) the circumference of a watch band, wrist band, fitness band, or bracelet. In an example, an alternating sequence of electromagnetic energy emitters and receivers can be distributed around the circumference a watch band, wrist band, fitness band, or bracelet.

In an example, a wearable device of this system can be worn on a person's ear or inserted into a person's ear canal. In an example, a wearable device can be an ear ring, earlobe clip, ear bud, ear plug, hearing aid, or ear-worn speaker/microphone with embedded biometric sensors. In an example, a wearable device can be an ear ring, earlobe clip, ear bud, ear plug, hearing aid, or ear-worn speaker/microphone with embedded spectroscopic sensors. In an example, a wearable device can be an ear ring, earlobe clip, ear bud, ear plug, hearing aid, or ear-worn speaker/microphone with embedded electromagnetic energy sensors. In an example, an ear ring with embedded biometric sensors can be attached to a person's earlobe through a pierced opening in the ear lobe. In an example, an ear ring can be attached to a person's earlobe by pressure (e.g. a clamp or clip). In an example, an ear ring can be attached to a person's earlobe by magnetic attraction of members on opposite sides of the earlobe.

In an example, a sensor to collect data on a biometric parameter can be located on the dorsal and/or proximal side of an ear lobe. In an example, a sensor to collect data on a biometric parameter can be located on the ventral and/or distal side of an ear lobe. In an example, a light-energy emitter can be on one side (e.g. the dorsal or proximal side) of an ear lobe and a light-energy receiver can be on the opposite side (e.g. the ventral and/or distal side) of the ear lobe. In an example, an electromagnetic energy emitter can be on one side of an ear lobe and an electromagnetic energy receiver can be on the opposite side of the ear lobe. In an example, a longitudinal array of sensors can be distributed along an ear bud or ear plug which is inserted into a person's ear canal. In an example, a circumferential array of sensors can be distributed around an ear bud or ear plug which is inserted into a person's ear canal.

In an example, a wearable device of this system can be worn on a person's ankle or foot. In an example, a wearable device can be an ankle band or a smart sock with embedded biometric sensors. In an example, biometric sensors can be spectroscopic sensors or electromagnetic energy sensors. In an example, biometric sensors can be distributed around (at least half of) the circumference of an ankle band or smart sock. In an example, biometric sensors can be woven into at least half of the circumference of an ankle band or smart sock. In an example, a plurality of light-energy emitters and receivers can be distributed around (at least half of) the circumference of an ankle band or smart sock. In an example, an alternating sequence of light-energy emitters and receivers can be distributed around the circumference an ankle band or smart sock. In an example, a plurality of electromagnetic energy emitters and receivers can be distributed around (at least half of) the circumference of an ankle band or smart sock. In an example, an alternating sequence of electromagnetic energy emitters and receivers can be distributed around the circumference an ankle band or smart sock.

In an example, a wearable device of this system can be eyewear. In an example, a wearable device of this system can be eyeglasses with embedded biometric sensors. In an example, these biometric sensors can be optical (e.g. spectroscopic) sensors. In an example, these biometric sensor can be electromagnetic (e.g. electroencephalographic) sensors. In an example, eyewear can comprise a plurality of biometric sensors on the frame of the eyewear. In an example, eyewear can comprise a plurality of biometric sensors on the sidepieces (e.g. the "temples") of the eyewear. In an example, eyewear can comprise a plurality of biometric sensors on the front piece and/or nose bridge of the eyewear. In an example, a wearable device can be a contact lens with embedded optical or electromagnetic energy sensors to measure a biometric parameter.

In an example, a wearable device can be temporarily and removably adhered to a person's skin. In an example, a wearable device can be a smart adhesive patch and/or an electronically-functional adhesive patch with biometric sensors. In an example, these biometric sensors can be spectroscopic sensors. In an example, spectroscopic sensors in a smart adhesive patch and/or an electronically-functional adhesive patch can be used to monitor the molecular composition of a person's sweat and/or gases emitted from the person's skin. In an example, a wearable device can be a temporary smart tattoo with biometric sensors. In an example, a wearable device can be an electronically-functional tattoo with biometric sensors. In an example, a wearable device can be a permanent smart tattoo and/or a permanent electronically-functional tattoo with embedded biometric sensors.

In an example, a wearable device of this system can be worn on a person's leg. In an example, a wearable device can be a leg band with embedded biometric sensors. In an example, a wearable device of this system can be worn on a person's foot. In an example, a wearable device can be an ankle band, smart sock, foot pad, or toe ring. In an example, a wearable device of this system can be worn on a person's upper arm. In an example, a wearable device can be an arm band or elbow sleeve with embedded biometric sensors. In an example, a wearable device of this system can be worn on a person's torso. In an example, a wearable device can be a waist belt, a chest band, an adhesive patch, or an electronic tattoo. In an example, a wearable device of this system can be worn on a person's head. In an example, a wearable device can be a headband, an intra-oral appliance, or a nose ring.

In an example, a wearable device can be selected from the group consisting of: finger ring, wrist watch (housing, band, or both), wrist band (e.g. fitness band), pin, and earlobe clip. In an example, a wearable device of this system can be selected from the group consisting of: necklace or pendant, hair comb or band, earpiece, bracelet or bangle, earring, skull cap, Augmented Reality (AR) eyewear, electronically-functional eyewear, wrist strap, buckle, sleeve, face mask or goggles, ear bud, and finger nail attachment.

In an example, a wearable device of this system can have a form which is selected from the group consisting of: headphones or headset, chest strap, contact lens, finger sleeve, hearing aid, Virtual Reality (VR) eyewear, ear plug or buds, and helmet. In an example, a wearable device of this system can have a form which is selected from the group consisting of: waist band, ear ring, visor, armband, nose ring, ear-worn Bluetooth device, finger tip thimble, knee brace, earphone, hair clip, artificial finger nail, belt or waist strap, and leg band. In an example, a wearable device can have a form which is selected from the group consisting of: smart finger ring, smart watch housing and/or band, fitness band, upper arm band, ankle band, smart sock, smart eyeglasses, smart contact lens, smart ear ring, and ear bud.

In an example, a wearable device of this system can be an article of clothing or clothing accessory with biometric sensors. In an example, these biometric sensors can be spectroscopic sensors or electromagnetic energy sensors. In an example, biometric sensors can be attached to, embedded into, woven into, sewn into, or printed onto an article of clothing or clothing accessory. In an example, an article of clothing or clothing accessory can be a short-sleeve shirt or a long-sleeve shirt. In an example, an article of clothing or clothing accessory can be a pair of shorts or pants. In an example, an article of clothing or clothing accessory can be a bra, an undershirt, or a underpants.

In an example, an article of clothing or clothing accessory with biometric sensors can be a smart sock or shoe. In an example, an article of clothing or clothing accessory can be a finger ring, finger sleeve, finger nail attachment, or glove. In an example, an article of clothing or clothing accessory can be a hat, baseball cap, skull cap, or hair comb. In an example, an article of clothing or clothing accessory can be a button, snap, or zipper. In an example, this article of clothing or clothing accessory can be a collar or cuff. In an example, this article of clothing or clothing accessory can be a belt or strap.

In an example, a wearable device of this system can comprise optical sensors (e.g. light-energy emitters and receivers) which are embedded in (or attached to) an article of clothing or clothing accessory. In an example, sensors to measure a biometric parameter can be formed by a plurality of optically-transmissive threads, yarns, fibers, or layers in an article of clothing or clothing accessory. In an example, sensors to measure a biometric parameter concerning a person's body can be formed by a grid or matrix of optically-transmissive threads, yarns, fibers, or layers in an article of clothing or clothing accessory. In an example, sensors to measure a biometric parameter concerning a person's body can be a woven grid or matrix of optically-transmissive threads, yarns, fibers, or layers in an article of clothing or clothing accessory. In an example, sensors to measure a biometric parameter concerning a person's body can be a pattern of optically-transmissive pathways which are printed onto an article of clothing or clothing accessory using optically-transmissive ink.

In an example, a wearable device of this system can comprise electromagnetic sensors which are embedded in (or attached to) an article of clothing or clothing accessory. In an example, sensors to measure a biometric parameter can be formed by a plurality of electroconductive threads, yarns, fibers, or layers in an article of clothing or clothing accessory. In an example, sensors to measure a biometric parameter concerning a person's body can be formed by a grid or matrix of electroconductive threads, yarns, fibers, or layers in an article of clothing or clothing accessory. In an example, sensors to measure a biometric parameter concerning a person's body can be a woven grid or matrix of electroconductive threads, yarns, fibers, or layers in an article of clothing or clothing accessory. In an example, sensors to measure a biometric parameter concerning a person's body can be a pattern of electromagnetic pathways which is printed onto an article of clothing or clothing accessory using electroconductive ink.

In an example, an implanted circulatory assistance device of this system can be selected from the group consisting of: cardiac rhythm management (CRM) device such as a cardiac pacemaker or implantable cardioverter-defibrillator (ICD); central (heart-assist) blood pump such as a left ventricular assist device (LVAD); and non-central (peripheral) blood pump. In an example, an implanted circulatory assistance device of this system can have a first (e.g. "feedback") operational mode wherein its operation is adjusted in real time based on values of a biometric parameter which are measured by a wearable device and a second ("stand alone") operational mode when the wearable device is either not being worn or is not working properly. In an example, a system can detect when a wearable device is not being worn or not working properly by a lack of biometric data, gaps in biometric data, or biometric parameter values which are outside defined bounds.

In an example, an implanted circulatory assistance device of this system can be a cardiac pacemaker which is in electromagnetic communication with a person's heart. In an example, an implanted circulatory assistance device can be a cardiac pacemaker which delivers periodic electromagnetic energy pulses to a person's heart in order to stimulate and/or regulate contraction of heart muscles. In an example, a cardiac pacemaker can deliver electromagnetic energy pulses to the heart via wires and/or leads. In an example, a cardiac pacemaker can be implanted within the heart, wherein it directly delivers electromagnetic energy pulses to the heart walls.

In an example, a system for cardiac function assistance can comprise: a wearable device which is worn by a person, wherein the wearable device collects data on a biometric parameter (such as body oxygenation level); and an implanted cardiac pacemaker, wherein operation of the cardiac pacemaker is controlled and/or adjusted based on analysis of the data on the biometric parameter. In an example, the operation of a cardiac pacemaker can be controlled and/or adjusted in one or more ways selected from the group consisting of: a change in the voltage of electromagnetic energy delivered to the heart to stimulate contractions, a change in the degree of coordination and/or timing between electromagnetic energy stimulation of different heart chambers, a change in the frequency of electromagnetic energy stimulation of heart contractions, a change in the location(s) on the heart where electromagnetic energy is delivered, a change in the magnitude of heart contractions which are stimulated, a change in the regularity of heart contractions which are stimulated, and delivery of a non-periodic electromagnetic shock to the heart to disrupt fibrillation.

In an example, one or more operating parameters of a cardiac pacemaker which are adjusted by this system can be selected from the group consisting of: timing, rhythm, power, frequency, pattern, and/or duration of electromagnetic energy transmitted to cardiac tissue; chamber(s) or other intracardiac or extracardiac location(s) to which electromagnetic energy is transmitted; chamber(s) or other intracardiac or extracardiac location(s) from which electromagnetic energy is sensed; delay and/or offset interval(s);

blanking and/or refractory period(s); lower rate and/or upper rate parameter(s); and inhibitory and/or triggering response(s).

In an example, one or more operating parameters of a cardiac pacemaker which are adjusted by this system can be selected from the group consisting of: increase in heart electromagnetic stimulation voltage; increase in the degree of coordination and/or timing between stimulations to different heart chambers; increase in the frequency of heart contraction stimulations; change in the locations on the heart to which electromagnetic energy is delivered; increase in the magnitude of heart contraction stimulations; increase in the regularity of heart contraction stimulations; and more precise coordination of contraction of different heart chambers.

In an example, a system for cardiac function assistance can comprise: a finger ring, wherein the finger ring collects data concerning a biometric parameter (such as body oxygenation level); and an implanted cardiac pacemaker, wherein operation of the cardiac pacemaker is controlled and/or adjusted based on analysis of the data on the biometric parameter. In an example, a system for cardiac function assistance can comprise: a smart watch (including the watch band and/or watch housing) or wrist band, wherein the smart watch or wrist band collects data concerning a biometric parameter; and an implanted cardiac pacemaker; wherein operation of the cardiac pacemaker is controlled and/or adjusted based on analysis of the data on the biometric parameter. In an example, a system for cardiac function assistance can comprise: an ear ring or earlobe clip, wherein the ear ring or earlobe clip collects data concerning a biometric parameter; and an implanted cardiac pacemaker, wherein operation of the cardiac pacemaker is controlled and/or adjusted based on analysis of the data on the biometric parameter.

In an example, an implanted circulatory assistance device of this system can be an implanted central (heart-assist) blood pump which assists the heart in pumping blood. In an example, an implanted blood pump can be a Left Ventricular Assist Device (LVAD). In an example, an implanted blood pump can have a rotating impeller. In an example, an implanted blood pump can comprise a rotating helical impeller. In an example, an implanted blood pump can be an Archimedes pump. In an example, an implanted blood pump can comprise rotating arcuate fins, vanes, or blades. In an example, an implanted blood pump can be a centripetal (or, old school, "centrifugal") pump. In an example, an implanted blood pump can be a pump with a compression chamber between two one-way valves.

In an example, an implanted blood pump can be a peristaltic pump. In an example, an implanted blood pump can be an axial pump. In an example, an implanted blood pump can be a hydroelastic pump. In an example, an implanted blood pump can be a longitudinal-membrane-wave pump. In an example, an implanted blood pump can be a magnetic flux pump. In an example, an implanted blood pump can be an elastomeric pump. In an example, an implanted blood pump can have an oscillating impeller. In an example, an implanted blood pump can be a pump with electromagnetically-driven magnetic impeller. In an example, an implanted blood pump can be an electromagnetic field pump.

In an example, an implanted blood pump can be an entrainment pump. In an example, an implanted blood pump can be a pump with fluid jets which entrain native blood flow. In an example, an implanted blood pump can be a compressive pump. In an example, an implanted blood pump can be a diaphragm pump. In an example, an implanted blood pump can be a pump with a series of circumferentially-compressive members. In an example, an implanted blood pump can be a balloon pump. In an example, an implanted blood pump can be a pulsatile flow pump. In an example, an implanted blood pump can be a continuous flow pump. In an example, an implanted blood pump can be a piston pump.

In an example, a system for cardiac function assistance can comprise: a wearable device which is worn by a person, wherein the wearable device collects data on a biometric parameter (such as body oxygenation level); and an implanted central (heart-assist) blood pump, wherein operation of the central (heart-assist) blood pump is adjusted based on analysis of the data on the biometric parameter which is collected by the wearable device. In an example, the operation of an central (heart-assist) blood pump can be adjusted in one or more ways selected from the group consisting of: activation or deactivation of the pump in order to increase or decrease blood flow; an increase or decrease in the duration of pump operation in order to increase or decrease blood flow; a increase or decrease in the speed of a pump's rotation, undulation, compression, or contraction (depending on type of pump) in order to increase or decrease blood flow; and an increase or decrease in the magnitude of pump undulation, compression, or contraction (depending on type of pump) in order to increase or decrease blood flow.

In an example, a system for cardiac function assistance can comprise: a finger ring, wherein the finger ring collects data concerning a biometric parameter (such as body oxygenation level); and a central (heart-assist) blood pump which is implanted within the person's body; wherein operation of the central (heart-assist) blood pump is adjusted based on analysis of the data on the biometric parameter. In an example, a system for cardiac function assistance can comprise: a smart watch (or wrist band), wherein the smart watch (or wrist band) collects data concerning a biometric parameter; and a central (heart-assist) blood pump which is implanted within the person's body; wherein operation of the central (heart-assist) blood pump is adjusted based on analysis of the data on the biometric parameter. In an example, a system for cardiac function assistance can comprise: an ear ring or earlobe clip, wherein the ear ring or earlobe clip collects data concerning a biometric parameter; and a central (heart-assist) blood pump which is implanted within the person's body; wherein operation of the central (heart-assist) blood pump is adjusted based on analysis of the data on the biometric parameter.

In an example, an implanted circulatory assistance device of this system can be a non-central (peripheral) blood pump which assists in pumping blood to a selected localized (e.g. peripheral) portion of a person's body. In an example, a non-central (peripheral) blood pump can have a rotating impeller. In an example, a non-central (peripheral) blood pump can comprise a rotating helical impeller. In an example, a non-central (peripheral) blood pump can be an Archimedes pump. In an example, a non-central (peripheral) blood pump can comprise rotating arcuate fins, vanes, or blades. In an example, a non-central (peripheral) blood pump can be a centripetal (or, old school, "centrifugal") pump. In an example, a non-central (peripheral) blood pump can be a pump with a compression chamber between two one-way valves.

In an example, a non-central (peripheral) blood pump can be a peristaltic pump. In an example, an implanted blood pump of this system can be an axial pump. In an example, a non-central (peripheral) blood pump can be a hydroelastic pump. In an example, a non-central (peripheral) blood pump can be a longitudinal-membrane-wave pump. In an example, a non-central (peripheral) blood pump can be a magnetic flux pump. In an example, a non-central (peripheral) blood pump can be an elastomeric pump. In an example, a non-central (peripheral) blood pump can have an oscillating impeller. In an example, a non-central (peripheral) blood pump can be a pump with electromagnetically-driven magnetic impeller. In an example, a non-central (peripheral) blood pump can be an electromagnetic field pump.

In an example, a non-central (peripheral) blood pump can be an entrainment pump. In an example, a non-central (peripheral) blood pump can be a pump with fluid jets which entrain native blood flow. In an example, a non-central (peripheral) blood pump can be a compressive pump. In an example, a non-central (peripheral) blood pump can be a diaphragm pump. In an example, a non-central (peripheral) blood pump can be a pump with a series of circumferentially-compressive members. In an example, a non-central (peripheral) blood pump can be a balloon pump. In an example, a non-central (peripheral) blood pump can be a pulsatile flow pump. In an example, a non-central (peripheral) blood pump can be a continuous flow pump. In an example, a non-central (peripheral) blood pump can be a piston pump.

In an example, a non-central (peripheral) blood pump can be endovascularly inserted and then expanded within a peripheral blood vessel in order to provide localized circulatory assistance. In an example, a non-central (peripheral) blood pump can be endovascularly inserted and then expanded within a peripheral blood vessel in order to help pump blood to a selected peripheral portion of a person's body. In an example, a non-central (peripheral) blood pump can be spliced into a person's vasculature "in series" with a natural blood vessel. In an example, a non-central (peripheral) blood pump which is spliced into a person's vasculature "in series" replaces a segment of a natural blood vessel. In an example, a non-central (peripheral) blood pump can be spliced into a person's vasculature "in series" with a natural blood vessel in order to help pump blood to a selected peripheral portion of a person's body.

In an example, a non-central (peripheral) blood pump can be spliced into a person's vasculature "in parallel" with a natural vessel. In an example, a non-central (peripheral) blood pump can have a first end which is connected to an upstream portion of a blood vessel, a second end which is connected to a downstream portion of a blood vessel, and a blood-flow-increasing mechanism located between the two ends. In addition, a one-way valve can be inserted into the natural vessel between the upstream connection and the downstream connection.

In an example, a system for cardiac function assistance can comprise: a wearable device which is worn by a person, wherein the wearable device collects data on a biometric parameter (such as body oxygenation level); and an implanted non-central (peripheral) blood pump, wherein operation of the implanted non-central (peripheral) blood pump is adjusted based on analysis of the data on the biometric parameter which is collected by the wearable device. In an example, the operation of a non-central (peripheral) blood pump can be adjusted in one or more ways selected from the group consisting of: activation or deactivation of the pump in order to increase or decrease blood flow; an increase or decrease in the duration of pump operation in order to increase or decrease blood flow; a increase or decrease in the speed of a pump's rotation, undulation, compression, or contraction (depending on type of pump) in order to increase or decrease blood flow; an increase or decrease in the magnitude of pump undulation, compression, or contraction (depending on type of pump) in order to increase or decrease blood flow; selective operational changes in a sub-set of a plurality of non-central (peripheral) blood pumps to change blood flow in a selected sub-set of peripheral body locations.

In an example, a system for cardiac function assistance can comprise: a finger ring, wherein the finger ring collects data concerning a biometric parameter; and a non-central (peripheral) blood pump which is implanted within the person's body; wherein operation of the non-central (peripheral) blood pump is adjusted based on analysis of the data on the biometric parameter. In an example, a system for cardiac function assistance can comprise: a smart watch (or wrist band), wherein the smart watch (or wrist band) collects data concerning a biometric parameter; and a non-central (peripheral) blood pump which is implanted within the person's body; wherein operation of the non-central (peripheral) blood pump is adjusted based on analysis of the data on the biometric parameter. In an example, a system for cardiac function assistance can comprise: an ear ring or earlobe clip, wherein the ear ring or earlobe clip collects data concerning a biometric parameter; and a non-central (peripheral) blood pump which is implanted within the person's body; wherein operation of the non-central (peripheral) blood pump is adjusted based on analysis of the data on the biometric parameter.

In an example, an implanted circulatory assistance device of this system can be a single central (heart-assist) blood pump. In an example, an implanted circulatory assistance device of this system can be multiple non-central (peripheral) blood pumps. In an example, a plurality of non-central (peripheral) blood pumps can be implanted in a distributed manner in different peripheral blood vessels throughout a person's body. In an example, multiple non-central (peripheral) blood pumps can form a distributed network which provides extracardiac circulatory assistance. In an example, distributed circulatory assistance can selectively increase blood circulation to body regions or organs with the greatest (short-term or long-term) need.

In an example, a plurality of non-central (peripheral) blood pumps can comprise a fluid network of "mini-hearts" which support a person's heart only to the extent which is needed during a period of cardiac healing and recovery. In an example, a plurality of extracardiac circulatory assistance devices can comprise an efficient and effective system of distributed circulatory assistance to maintain cardiac functioning and allow cardiac healing for people with CHF. In an example, one or more implanted blood pumps can supplement, but not replace, native blood circulation. This can reduce cardiac workload until the heart recovers or for the long-term if recovery is not possible. In an example, one or more implanted blood pumps can reduce cardiac workload without completely replacing cardiac function so that the heart may still heal and recover function—avoiding the eventual need for heart transplantation or a more-invasive full-cardiac-function replacement device. In an example, multiple non-central (peripheral) blood pumps can be configured in parallel flow or in series flow.

In an example, an implanted blood pump can be configured to increase the flow of blood from an upstream location to a downstream location in a person's vasculature. In an example, the blood pump can transduce electromagnetic energy into kinetic energy. In an example, an implanted blood pump can increase the rate, speed, volume, and/or consistency of blood flow. In an example, an implanted blood pump can also improve hemodynamics. In an example, a blood pump can be structurally designed to avoid low-flow areas that can cause thrombogenesis. In an example, a blood pump can be designed to produce hemodynamic patterns that minimize thrombogenesis.

Blood flow pumps are sometimes categorized as either pulsatile or continuous. Generally, a pulsatile pump is considered to be one which produces variation in flow speed and/or pressure which is synchronized to be in phase, or out of phase, with the native cardiac pumping cycle. In an example, a blood pump can be copulsating with respect to the cardiac pumping cycle. In an example, a blood pump can be counterpulsating with respect to the cardiac pumping cycle. Pulsatile flow can be preferred for perfusion of some organs and can also help to reduce thrombogenesis. In an example, the blood pump of this invention can produce pulsatile blood flow and/or supplement native pulsatile blood flow. In an example, a control unit of this system can change a blood pump from a pulsatile flow to a continuous flow.

In an example, an implanted blood pump can have a low cross-sectional profile when it is not in operation and a high cross-sectional profile when it is in operation. This can allow an implanted blood pump to substantively supplement blood circulation when the mechanism is in operation, but to not substantively hinder native blood flow when the blood pump is not in operation. In an example, the blood pump can be defined to be "in operation" when it is actively transducing electromagnetic energy (such as from a battery or other electrical power source) into kinetic energy (in the form of blood flow). In an example, the ability to supplement native circulation when power is available without hindering native circulation when power is unavailable (or limited) can enable greater patient mobility and improved quality of life. This ability can also help to preserve the possibility of healing and recovery for the heart by only providing circulatory assistance when needed.

In an example, an implanted blood pump can produce a continuous blood flow. The designation of "continuous" can mean that a blood pump is actually intended to operate all the time, but more generally it can mean that a blood pump produces a blood flow which is not pulsatile when the pump is in operation. In other words, a continuous blood flow pump has a relatively-uniform flow speed and/or pressure as long as the pump is in operation. This distinction is important for supplemental circulation assistance devices which do not cause adverse outcomes if they are turned off (or lose power) for periods of time. Accordingly, this distinction is important for the invention disclosed herein which does not have to be in operation all the time. In an example, a continuous blood flow pump can contribute a sub-stream of continuous blood flow which is in addition to (and/or entrains) native pulsatile blood flow. In an example, the blood pump of this invention can produce and contribute a continuous blood flow when it is in operation, but it does not have to be in operation all the time. In an example, the blood pump of this invention can be hybrid pump which is capable of producing either a pulsatile or continuous blood flow. In an example, the operation of a blood pump and the type of blood flow (e.g. pulsatile or continuous) which it produces can be controlled by a control unit for the blood pump which will be discussed later in greater depth.

In an example, an implanted blood pump can be a rotary implanted blood pump. In an example, an implanted blood pump can move blood by means of a rotating impeller or turbine. In an example, an implanted blood pump can have a rotating impeller or turbine which is further comprised of one or more vanes, fins, blades, projections, winglets, airfoils, helical members, or grooves. In an example, these one or more vanes, fins, blades, projections, winglets, airfoils, or helical members can have a (first) retracted or contracted configuration in which they have a first amount of cross-sectional interaction with blood flow. In an example, these one or more vanes, fins, blades, projections, winglets, airfoils, or helical members can have a (second) protracted or expanded configuration in which they have second amount of cross-sectional interaction with blood flow. In an example, the second amount is greater than the first amount. In an example, the one or more vanes, fins, blades, projections, winglets, airfoils, helical members, or grooves transition to the second configuration when the implanted blood pump is in operation. In an example, the one or more vanes, fins, blades, airfoils, or helical members can be reversibly, repeatedly, and post-operatively moved back and forth from the first configuration to the second configuration.

In an example, an implanted blood pump can be an axial rotary pump. In an example, an implanted blood pump can comprise one or more vanes, fins, blades, projections, winglets, airfoils, or helical members which rotate around an axis which is coaxial with the longitudinal axis of the blood flow lumen, with the directional vector of native blood flow, or both. In an example, an implanted blood pump can comprise one or more vanes, fins, blades, projections, winglets, airfoils, or helical members which rotate around an axis which is substantially parallel with the longitudinal axis of the blood flow lumen, with the directional vector of native blood flow, or both. In an example, an implanted blood pump can comprise one or more vanes, fins, blades, projections, winglets, airfoils, or helical members which rotate around an axis which is substantially perpendicular to the longitudinal axis of the blood flow lumen, with the directional vector of native blood flow, or both.

In an example, an implanted blood pump can comprise a rotating helical or screw-shaped impeller. In an example, an implanted blood pump can comprise a rotating impeller with multiple helical or partial-helical members. In an example, a rotary pump can have one or more members which are rotated by a direct drive mechanical connection to an electromagnetic motor or other mechanical actuator. In an example, a rotary pump can have one or more magnetic members which are rotated by magnetic interaction with an electromagnetic field. In an example, a rotary implanted blood pump can have hydrodynamic or magnetic bearings.

In an example, an implanted blood pump can further comprise one or more moving members which increase blood flow by frictionally engaging blood and/or by entraining native blood flow. In an example, these one or more moving members can be selected from the group consisting of: airfoils, blades, fins, flippers, grooves, helical structures, rotors, threads, vanes, and winglets. In an example, the one or more moving members can have a first configuration wherein they have a first level of frictional engagement with blood flow. In an example, this first configuration can comprise being relatively close to (or flush with) a central rotating axle. In an example, this first configuration can comprise being relatively close to (or flush with) the walls of the implanted blood flow lumen. In an example, the one or more moving members can have a second configuration in which they have a second level of frictional engagement with blood flow. In an example, the second level can be substantially greater than the first level. In an example, "substantially greater" means at least 10% greater. In an example, "substantially greater" means at least 25% greater. In an example, "substantially greater" means at least 100% greater.

In an example, an implanted blood pump can move blood using peristaltic motion. In an example, an implanted blood pump can comprise a peristaltic pump. In an example, an implanted blood pump can move blood by sequential compression of the lumen by a longitudinally rolling member which rolls longitudinally and compressively (from upstream to downstream) along the walls of the lumen. In an example, an implanted blood pump can move blood by the sequential contraction (from upstream to downstream) of a series of circumferential members such as contracting bands or rings along the longitudinal axis of an implanted blood flow lumen. In an example, an implanted blood pump can move blood by sequentially inflating and deflating a series of inflatable members such as toroidal balloons along the longitudinal axis (from upstream to downstream) of an implanted blood flow lumen. In an example, an implanted blood pump can comprise a series of waving cilia-form members which wave along a lumen wall like a crowd of fans in a microscale sport arena. In an example, an implanted blood pump can move blood by propagating a longitudinal wave or pulse (such as a pressure wave) longitudinally (from upstream to downstream) along a flexible membrane (or other surface) which is in fluid communication with blood in an implanted blood flow lumen.

In an example, a wearable device such as a smart finger ring, a smart watch, a smart wrist band, a smart ear ring, or smart eyewear for collecting data on a biometric parameter can have a spectroscopic sensor. (A spectroscopic sensor can also be called a "spectroscopy sensor.") In an example, a spectroscopic sensor can further comprise a light-energy emitter (e.g. a light source) and a light-energy receiver (e.g. a photodetector). In an example, the light-energy receiver can receive light-energy from the light-energy emitter after that light-energy has been transmitted through body tissue and/or fluid or has been reflected by body tissue and/or fluid. Different types of molecules absorb or reflect different wavelengths of light by different amounts. Accordingly, analysis of changes in the spectrum of light-energy which has interacted with body tissue and/or fluid can be used to estimate the molecular composition of that body tissue and/or fluid. In an example, a wearable device can perform photoplethysmography (PPG).

In an example, a light-energy receiver of a spectroscopic sensor can receive light-energy which has been transmitted through body tissue and/of fluid. In an example, transmission of light-energy through body tissue and/or fluid changes the spectrum of that light-energy and this change in spectrum is analyzed to get information about the composition of that body tissue and/or fluid. In an example, light-energy from a light-energy emitter on a first side of a body member (such as a finger or earlobe) can be directed toward the body member, transmitted through the body member, and then received by a light-energy receiver on another side (e.g. the diametrically-opposite side) of the body member. In an example, changes in the spectrum of light which has been transmitted through the body tissue and/or fluid of the body member can be analyzed to estimate the value of a biometric parameter or changes in that value over time.

In an example, a light-energy receiver of a spectroscopic sensor can receive light-energy which has been reflected by body tissue and/of fluid. In an example, reflection of light-energy by body tissue and/or fluid changes the spectrum of that light-energy and this change in spectrum is analyzed to get information about the composition of that body tissue and/or fluid. In an example, a spectroscopic sensor can comprise a light-energy emitter (e.g. light source) and a light-energy receiver (e.g. photodetector) on the same side (e.g. the ventral or dorsal side) of a body member, wherein the light-energy receiver receives light from the light-energy emitter after that light has been reflected by body tissue and/or fluid. In an example, light-energy from a light-energy emitter can be directed toward body tissue and/or fluid, reflected by the body tissue and/or fluid, and then received by the light-energy receiver. In an example, changes in the spectrum of light which has been reflected by body tissue and/or fluid can be analyzed to estimate the value of a biometric parameter or changes in that value over time.

In an example, a light-energy emitter can deliver light-energy to body tissue and/or fluid via direct optical communication. In an example, a system can further comprise one or more light guides which guide light from a light-energy emitter toward body tissue and/or fluid at a selected angle or location. In an example, a system can further comprise one or more lenses which guide light from a light-energy emitter toward body tissue and/or fluid at a selected angle or location. In an example, a system can further comprise one or more prisms which guide light from a light-energy emitter toward body tissue and/or fluid at a selected angle or location. In an example, a system can further comprise one or more optical filters which modify the spectrum of light directed toward body tissue and/or fluid. In an example, a beam of light can be emitted by a light-energy emitter, pass through a first side of an angled one-way mirror, hit body tissue, reflect back from the body tissue, reflect off a second side of the angled one-way mirror, and then enter a light-energy receiver.

In an example, a light-energy receiver can receive light-energy which has interacted with body tissue and/or fluid via direct optical communication. In an example, a system can further comprise one or more light guides which guide light from body tissue and/or fluid to a light-energy receiver. In an example, a system can further comprise one or more lenses which guide light from body tissue and/or fluid to a light-energy receiver. In an example, a system can further comprise one or more prisms which guide light from body tissue and/or fluid to a light-energy receiver. In an example, a system can further comprise one or more optical filters which modify the spectrum of light from body tissue and/or fluid before it reaches a light-energy receiver.

In an example, a wearable device of this system can be a spectroscopic sensor (including a light-energy emitter and light-energy receiver) which collects light-energy data, wherein this data is analyzed using spectroscopic analysis in order to monitor changes in the chemical composition of body tissue and/or fluid. In an example, changes, gaps, and/or shifts in selected frequencies in the spectrum of transmitted or reflected light due to an interaction with a person's body tissue and/or fluid can be analyzed to estimate the chemical composition of the person's body tissue and/or fluid. In an example, portions of the spectrum of light emitted by a light-energy emitter can be absorbed by body tissue. Spectral analysis of these absorbed portions enables measurement of analyte levels in a person's body.

In an example, a wearable device of this system can comprise a spectroscopic sensor with a light-energy receiver which receives ambient light which has passed through body tissue and/or fluid or has been reflected by body tissue and/or fluid. In an example, changes, gaps, and/or shifts in selected frequencies in the spectrum of ambient light due to interaction with a person's body tissue and/or fluid can be analyzed to monitor changes in the chemical composition of the person's body tissue and/or fluid. In an example, portions of the spectrum of ambient light can be reduced and/or shifted by interaction with body tissue and spectral analysis of these shifted portions can enable measurement of an analyte level in the body.

In an example, a wearable device of this system can have a near-infrared spectroscopic sensor. In an example, a wearable device can have an infrared spectroscopic sensor. In an example, a wearable device of this system can have both a near-infrared spectroscopic sensor and an infrared spectroscopic sensor. In an example, a wearable device can have a spectral analysis sensor. In an example, a wearable device can have a photochemical sensor. In an example, a wearable device can have an ion mobility spectroscopic sensor. In an example, a wearable device can have a backscattering spectrometry sensor.

In an example, a wearable device of this system can have a laser spectroscopic sensor. In an example, a wearable device can have a liquid chromatography sensor. In an example, a wearable device can have a fiber optic spectroscopic sensor. In an example, a wearable device can have an ultraviolet spectroscopic sensor. In an example, a wearable device can have a mass spectrometry sensor. In an example, a wearable device can have a spectrometric sensor. In an example, a wearable device can have a fluorescence sensor. In an example, a wearable device of this system can have a visible or white light spectroscopic sensor. In an example, a wearable device can have a gas chromatography sensor. In an example, a wearable device can have an ambient light spectroscopic sensor. In an example, a wearable device can have a spectrometry sensor. In an example, a wearable device can have a chemiluminescence sensor.

In an example, a wearable device of this system can have a chromatographic sensor. In an example, a wearable device can have a spectroscopic oximeter. In an example, a wearable device can have a colorimetric sensor. In an example, a wearable device can have an ultraviolet light sensor. In an example, a wearable device can have a Raman spectroscopy sensor. In an example, a wearable device can have an analytical chromatographic sensor. In an example, a wearable device can have a spectrophotometer. In an example, a wearable device can have a photocell. In an example, a wearable device can have a coherent light spectroscopic sensor. In an example, a wearable device can have an optoelectronic sensor.

In an example, a system for cardiac function assistance can comprise: a finger ring, wherein the finger ring further comprises a light-energy emitter and a light-energy receiver, wherein the light-energy receiver receives light-energy from the light-energy emitter after this light-energy has been transmitted through and/or reflected from the person's body tissue and/or blood, wherein changes in the spectrum of the light-energy due to its transmission through and/or reflection from the person's body tissue and/or blood are used to measure a biometric parameter; and an implanted cardiac pacemaker; wherein the cardiac pacemaker is in electromagnetic communication with the person's heart; and wherein one or more of the following cardiac pacemaker functions are triggered when the person has an abnormal biometric parameter value: change in heart electromagnetic stimulation voltage, change in the degree of coordination and/or timing between stimulations to different heart chambers, change in the frequency of heart contraction stimulations, change in the locations on the heart to which electromagnetic energy is delivered, change in the magnitude of heart contraction stimulations, change in the regularity of heart contraction stimulations, delivery of an electromagnetic shock to the heart, and more precise coordination of contraction of different heart chambers.

In an example, a system for cardiac function assistance can comprise: a finger ring, wherein the finger ring further comprises a light-energy emitter and a light-energy receiver, wherein the light-energy receiver receives light-energy from the light-energy emitter after this light-energy has been transmitted through and/or reflected from the person's body tissue and/or blood, wherein changes in the spectrum of the light-energy due to its transmission through and/or reflection from the person's body tissue and/or blood are used to measure a biometric parameter; and a central (heart-assist) blood pump; wherein one or more of the following central (heart-assist) blood pump functions is triggered when the person has an abnormal biometric parameter value: activation or deactivation of the pump to change blood flow; change in the duration of pump operation to change blood flow; change in the magnitude of pump undulation, compression, or contraction (depending on type of pump) to change blood flow; and change in the speed of a pump's rotation, undulation, compression, or contraction (depending on type of pump) to change blood flow.

In an example, a system for cardiac function assistance can comprise: a finger ring, wherein the finger ring further comprises a light-energy emitter and a light-energy receiver, wherein the light-energy receiver receives light-energy from the light-energy emitter after this light-energy has been transmitted through and/or reflected from the person's body tissue and/or blood, wherein changes in the spectrum of the light-energy due to its transmission through and/or reflection from the person's body tissue and/or blood are used to measure a biometric parameter; and a non-central (peripheral) blood pump, wherein one or more of the following non-central (peripheral) blood pump functions is triggered when the person has an abnormal biometric parameter value: activation of the pump to increase blood flow; increase in the duration of pump operation to increase blood flow; increase in the magnitude of pump undulation, compression, or contraction (depending on type of pump) to increase blood flow; increase in the speed of a pump's rotation, undulation, compression, or contraction (depending on type of pump) to increase blood flow; and selective activation of a sub-set of non-central (peripheral) blood pumps to change blood flow in a selected sub-set of body locations.

In an example, a system for cardiac function assistance can comprise: a smart watch or wrist band, wherein the smart watch or wrist band further comprises a light-energy emitter and a light-energy receiver, wherein the light-energy receiver receives light-energy from the light-energy emitter after this light-energy has been transmitted through and/or reflected from the person's body tissue and/or blood, wherein changes in the spectrum of the light-energy due to its transmission through and/or reflection from the person's body tissue and/or blood are used to measure a biometric parameter; and an implanted cardiac pacemaker; wherein the cardiac pacemaker is in electromagnetic communication with the person's heart; and wherein one or more of the following cardiac pacemaker functions are triggered when the person has an abnormal biometric parameter value: change in heart electromagnetic stimulation voltage, change in the degree of coordination and/or timing between stimulations to different heart chambers, change in the frequency of heart contraction stimulations, change in the locations on the heart to which electromagnetic energy is delivered, change in the magnitude of heart contraction stimulations, change in the regularity of heart contraction stimulations, delivery of an electromagnetic shock to the heart, and more precise coordination of contraction of different heart chambers.

In an example, a system for cardiac function assistance can comprise: a smart watch or wrist band, wherein the smart watch or wrist band further comprises a light-energy emitter and a light-energy receiver, wherein the light-energy receiver receives light-energy from the light-energy emitter after this light-energy has been transmitted through and/or reflected from the person's body tissue and/or blood, wherein changes in the spectrum of the light-energy due to its transmission through and/or reflection from the person's body tissue and/or blood are used to measure a biometric parameter; and a central (heart-assist) blood pump; wherein one or more of the following central (heart-assist) blood pump functions is triggered when the person has an abnormal biometric parameter value: activation or deactivation of the pump to change blood flow; change in the duration of pump operation to change blood flow; change in the magnitude of pump undulation, compression, or contraction (depending on type of pump) to change blood flow; and change in the speed of a pump's rotation, undulation, compression, or contraction (depending on type of pump) to change blood flow.

In an example, a system for cardiac function assistance can comprise: a smart watch or wrist band, wherein the smart watch or wrist band further comprises a light-energy emitter and a light-energy receiver, wherein the light-energy receiver receives light-energy from the light-energy emitter after this light-energy has been transmitted through and/or reflected from the person's body tissue and/or blood, wherein changes in the spectrum of the light-energy due to its transmission through and/or reflection from the person's body tissue and/or blood are used to measure a biometric parameter; and a non-central (peripheral) blood pump, wherein one or more of the following non-central (peripheral) blood pump functions is triggered when the person has an abnormal biometric parameter value: activation of the pump to increase blood flow; increase in the duration of pump operation to increase blood flow; increase in the magnitude of pump undulation, compression, or contraction (depending on type of pump) to increase blood flow; increase in the speed of a pump's rotation, undulation, compression, or contraction (depending on type of pump) to increase blood flow; and selective activation of a sub-set of non-central (peripheral) blood pumps to change blood flow in a selected sub-set of body locations.

In an example, the biometric parameter which is measured and managed by this system can be selected from the group consisting of: oxygenation level, carbon dioxide level, lactate or lactic acid level, blood pressure, heart rate variability, pulsatile blood volume, pulsatile blood lag, hydration level, respiration rate, exhaled gas composition, body glucose level, troponin level, body motion or exercise level, and sleep status or stage. In an example, a wearable device can collect data on a biometric parameter selected from the group consisting of: oxygenation level, carbon dioxide level, lactate or lactic acid level, blood pressure, heart rate variability, pulsatile blood volume, pulsatile blood lag, hydration level, respiration rate, exhaled gas composition, body glucose level, troponin level, body motion or exercise level, and sleep status or stage. In an example, a finger ring, smart watch, smart watch band, wrist band, ankle band, smart sock, ear ring, ear clip, or ear bud can collect data on a biometric parameter selected from the group consisting of: oxygenation level, carbon dioxide level, lactate or lactic acid level, blood pressure, heart rate variability, pulsatile blood volume, pulsatile blood lag, hydration level, respiration rate, exhaled gas composition, body glucose level, troponin level, body motion or exercise level, and sleep status or stage.

In an example, the operation of an implanted cardiac pacemaker can be controlled and/or adjusted based on a biometric parameter selected from the group consisting of: oxygenation level, carbon dioxide level, lactate or lactic acid level, blood pressure, heart rate variability, pulsatile blood volume, pulsatile blood lag, hydration level, respiration rate, exhaled gas composition, body glucose level, troponin level, body motion or exercise level, and sleep status or stage. In an example, the operation of an implanted central (heart-assist) blood pump can be controlled and/or adjusted based on a biometric parameter selected from the group consisting of: oxygenation level, carbon dioxide level, lactate or lactic acid level, blood pressure, heart rate variability, pulsatile blood volume, pulsatile blood lag, hydration level, respiration rate, exhaled gas composition, body glucose level, troponin level, body motion or exercise level, and sleep status or stage. In an example, the operation of an implanted non-central (peripheral) blood pump can be controlled and/or adjusted based on a biometric parameter selected from the group consisting of: oxygenation level, carbon dioxide level, lactate or lactic acid level, blood pressure, heart rate variability, pulsatile blood volume, pulsatile blood lag, hydration level, respiration rate, exhaled gas composition, body glucose level, troponin level, body motion or exercise level, and sleep status or stage.

In an example, a biometric parameter which is measured and managed by this system can be body oxygenation level or changes in body oxygenation levels. In an example, one or more oxygen-related biometric parameters can be selected from the group consisting of: arterial oxygen saturation level, oxygen metabolism level, saturation of peripheral oxygen, brain oxygenation level, and peripheral tissue oxygenation level. In an example, a wearable device can be a pulse oximeter. In an example, the wearable device can measure blood volume variation over time. In an example, the wearable device can perform photoplethysmography (PPG). In an example, blood oxygen saturation can be based on differential absorption of two different light wavelengths by blood. In an example, operation of an implanted circulatory assistance device can be controlled and/or adjusted based on body oxygenation level or changes in body oxygenation levels. In an example, body oxygenation levels can be measured from multiple locations on a person's body.

In an example, a closed loop system for human circulatory assistance can increase blood circulation by adjusting the operation of a cardiac pacemaker in response to a low body oxygenation level. In an example, a closed loop system can adjust the operation of a cardiac pacemaker in response to low body oxygenation in one or more ways selected from the group consisting of: increase in heart electromagnetic stimulation voltage; increase in the degree of coordination and/or timing between stimulations to different heart chambers; increase in the frequency of heart contraction stimulations; change in the locations on the heart to which electromagnetic energy is delivered; increase in the magnitude of heart contraction stimulations; increase in the regularity of heart contraction stimulations; and more precise coordination of contraction of different heart chambers.

In an example, a system for cardiac function assistance can comprise: a wearable oximeter, wherein the wearable oximeter uses spectroscopy to measure body oxygenation level; and an implanted central (heart-assist) blood pump, wherein operation of the central (heart-assist) blood pump is adjusted based on body oxygenation level. In an example, a system for cardiac function assistance can comprise: a wearable oximeter which is worn by a person, wherein the wearable oximeter uses spectroscopy to measure body oxygenation level; and an implanted non-central (peripheral) blood pump, wherein operation of the non-central (peripheral) blood pump is adjusted based on body oxygenation level.

In an example, a closed loop system for human circulatory assistance can increase blood circulation by adjusting the operation of a non-central (peripheral) blood pump. In an example, a closed loop system can adjust the operation of a non-central (peripheral) blood pump in response to low body oxygenation in one or more ways selected from the group consisting of: activation of the pump to increase blood flow; increase in the duration of pump operation to increase blood flow; increase in the magnitude of pump undulation, compression, or contraction (depending on type of pump) to increase blood flow; increase in the speed of a pump's rotation, undulation, compression, or contraction (depending on type of pump) to increase blood flow; and selective activation of a sub-set of non-central (peripheral) blood pumps to change blood flow in a selected sub-set of body locations.

In an example, a system for cardiac function assistance can comprise: a finger ring, wherein the finger ring further comprises a light-energy emitter and a light-energy receiver, wherein the light-energy receiver receives light-energy from the light-energy emitter after this light-energy has been transmitted through and/or reflected from the person's body tissue and/or blood, wherein changes in the spectrum of the light-energy due to its transmission through and/or reflection from the person's body tissue and/or blood are used to measure body oxygenation level; and an implanted cardiac pacemaker; wherein the cardiac pacemaker is in electromagnetic communication with the person's heart; and wherein one or more of the following cardiac pacemaker functions are triggered when the person has a low body oxygenation level: increase in heart electromagnetic stimulation voltage, increase in the degree of coordination and/or timing between stimulations to different heart chambers, increase in the frequency of heart contraction stimulations, change in the locations on the heart to which electromagnetic energy is delivered, increase in the magnitude of heart contraction stimulations, increase in the regularity of heart contraction stimulations, and more precise coordination of contraction of different heart chambers.

In an example, a system for cardiac function assistance can comprise: a finger ring, wherein the finger ring further comprises a light-energy emitter and a light-energy receiver, wherein the light-energy receiver receives light-energy from the light-energy emitter after this light-energy has been transmitted through and/or reflected from the person's body tissue and/or blood, wherein changes in the spectrum of the light-energy due to its transmission through and/or reflection from the person's body tissue and/or blood are used to measure body oxygenation level; and a central (heart-assist) blood pump; wherein one or more of the following central (heart-assist) blood pump functions is triggered when the person has a low body oxygenation level: activation of the pump to increase blood flow; increase in the duration of pump operation to increase blood flow; increase in the magnitude of pump undulation, compression, or contraction (depending on type of pump) to increase blood flow; and increase in the speed of a pump's rotation, undulation, compression, or contraction (depending on type of pump) to increase blood flow.

In an example, a system for cardiac function assistance can comprise: a finger ring, wherein the finger ring further comprises a light-energy emitter and a light-energy receiver, wherein the light-energy receiver receives light-energy from the light-energy emitter after this light-energy has been transmitted through and/or reflected from the person's body tissue and/or blood, wherein changes in the spectrum of the light-energy due to its transmission through and/or reflection from the person's body tissue and/or blood are used to measure body oxygenation level; and a non-central (peripheral) blood pump, wherein one or more of the following non-central (peripheral) blood pump functions is triggered when the person has a low body oxygenation level: activation of the pump to increase blood flow; increase in the duration of pump operation to increase blood flow; increase in the magnitude of pump undulation, compression, or contraction (depending on type of pump) to increase blood flow; increase in the speed of a pump's rotation, undulation, compression, or contraction (depending on type of pump) to increase blood flow; and selective activation of a sub-set of non-central (peripheral) blood pumps to increase blood flow in a selected sub-set of body locations.

In an example, a system for cardiac function assistance can comprise: a smart watch (or wrist band), wherein the smart watch (or wrist band) further comprises a light-energy emitter and a light-energy receiver, wherein the light-energy receiver receives light-energy from the light-energy emitter after this light-energy has been transmitted through and/or reflected from the person's body tissue and/or blood, wherein changes in the spectrum of the light-energy due to its transmission through and/or reflection from the person's body tissue and/or blood are used to measure body oxygenation level; and an implanted cardiac pacemaker; wherein the cardiac pacemaker is in electromagnetic communication with the person's heart; and wherein one or more of the following cardiac pacemaker functions are triggered when the person has a low body oxygenation level: increase in heart electromagnetic stimulation voltage, increase in the degree of coordination and/or timing between stimulations to different heart chambers, increase in the frequency of heart contraction stimulations, change in the locations on the heart to which electromagnetic energy is delivered, increase in the magnitude of heart contraction stimulations, increase in the regularity of heart contraction stimulations, and more precise coordination of contraction of different heart chambers.

In an example, a system for cardiac function assistance can comprise: a smart watch (or wrist band), wherein the smart watch (or wrist band) further comprises a light-energy emitter and a light-energy receiver, wherein the light-energy receiver receives light-energy from the light-energy emitter after this light-energy has been transmitted through and/or reflected from the person's body tissue and/or blood, wherein changes in the spectrum of the light-energy due to its transmission through and/or reflection from the person's body tissue and/or blood are used to measure body oxygenation level; and a central (heart-assist) blood pump; wherein one or more of the following central (heart-assist) blood pump functions is triggered when the person has a low body oxygenation level: activation of the pump to increase blood flow; increase in the duration of pump operation to increase blood flow; increase in the magnitude of pump undulation, compression, or contraction (depending on type of pump) to increase blood flow; and increase in the speed of a pump's rotation, undulation, compression, or contraction (depending on type of pump) to increase blood flow.

In an example, a system for cardiac function assistance can comprise: a smart watch (or wrist band), wherein the smart watch (or wrist band) further comprises a light-energy emitter and a light-energy receiver, wherein the light-energy receiver receives light-energy from the light-energy emitter after this light-energy has been transmitted through and/or reflected from the person's body tissue and/or blood, wherein changes in the spectrum of the light-energy due to its transmission through and/or reflection from the person's body tissue and/or blood are used to measure body oxygenation level; and a non-central (peripheral) blood pump, wherein one or more of the following non-central (peripheral) blood pump functions is triggered when the person has a low body oxygenation level: activation of the pump to increase blood flow; increase in the duration of pump operation to increase blood flow; increase in the magnitude of pump undulation, compression, or contraction (depending on type of pump) to increase blood flow; increase in the speed of a pump's rotation, undulation, compression, or contraction (depending on type of pump) to increase blood flow; and selective activation of a sub-set of non-central (peripheral) blood pumps to increase blood flow in a selected sub-set of body locations.

In an example, a biometric parameter which is measured and managed by this system can be the level of carbon dioxide in a person's body tissue and/or fluid. In an example, a wearable device can have a spectroscopic sensor. In an example, a wearable device can measure blood volume variation over time. In an example, a wearable device can perform photoplethysmography. In an example, body carbon dioxide levels can be measured from multiple locations on a person's body. In an example, the operation of an implanted circulatory assistance device can be controlled and/or adjusted based on the carbon dioxide level in a person's body tissue and/or fluid or changes in that level.

In an example, a closed loop system for human circulatory assistance can increase blood circulation by adjusting the operation of a cardiac pacemaker in response to a high carbon dioxide level in a person's body tissue and/or fluid. In an example, a system can adjust the operation of a cardiac pacemaker in response to a high carbon dioxide level in one or more ways selected from the group consisting of: increase in heart electromagnetic stimulation voltage, increase in the degree of coordination and/or timing between stimulations to different heart chambers, increase in the frequency of heart contraction stimulations, change in the locations on the heart to which electromagnetic energy is delivered, increase in the magnitude of heart contraction stimulations, increase in the regularity of heart contraction stimulations, and more precise coordination of contraction of different heart chambers.

In an example, an implanted circulatory assistance device can be a central (heart-assist) blood pump which assists the heart in pumping blood or a non-central (peripheral) blood pump which assists in pumping blood through a peripheral blood vessel to a selected (peripheral) portion of the body. In an example, a closed loop system can increase blood circulation by adjusting the operation of a central (heart-assist) blood pump or a non-central (peripheral) blood pump. In an example, a closed loop system can adjust the operation of a central (heart-assist) blood pump or a non-central (peripheral) blood pump in response to a high body carbon dioxide level in one or more ways selected from the group consisting of: activation of the pump to increase blood flow; increase in the duration of pump operation to increase blood flow; increase in the magnitude of pump undulation, compression, or contraction (depending on type of pump) to increase blood flow; and increase in the speed of a pump's rotation, undulation, compression, or contraction (depending on type of pump) to increase blood flow.

In an example, a system for cardiac function assistance can comprise: a finger ring, smart watch, or wrist band which is worn by a person, wherein the finger ring, smart watch, or wrist band collects data concerning carbon dioxide level in the person's body; and an implanted cardiac pacemaker, and wherein operation of the cardiac pacemaker is controlled and/or adjusted based on analysis of the data concerning carbon dioxide level in the person's body. In an example, a system for cardiac function assistance can comprise: a finger ring, smart watch, or wrist band which is worn by a person, wherein the finger ring, smart watch, or wrist band collects data concerning carbon dioxide level in the person's body; and an implanted central (heart-assist) blood pump, wherein operation of the central (heart-assist) blood pump is controlled and/or adjusted based on analysis of the data concerning carbon dioxide level in the person's body. In an example, a system for cardiac function assistance can comprise: a finger ring, smart watch, or wrist band which is worn by a person, wherein the finger ring, smart watch, or wrist band collects data concerning carbon dioxide level in the person's body; and an implanted non-central (peripheral) blood pump, wherein operation of the non-central (peripheral) blood pump is controlled and/or adjusted based on analysis of the data concerning carbon dioxide level in the person's body.

In an example, the biometric parameter which is measured and managed by this system can be body lactate and/or lactic acid level. In an example, the wearable device can have a spectroscopic sensor. In an example, the wearable device can measure blood volume variation over time. In an example, the wearable device can perform photoplethysmography (PPG). In an example, body lactate and/or lactic acid level can be measured from multiple locations on the person's body. In an example, operation of an implanted circulatory assistance device can be controlled and/or adjusted based on lactate and/or lactic acid level in a person's body tissue and/or fluid or changes in that level.

In an example, the implanted circulatory assistance device can be a cardiac pacemaker. In an example, a system can increase blood circulation by adjusting the operation of an implanted cardiac pacemaker in response to a high body lactate and/or lactic acid level. In an example, a system can adjust the operation of an implanted cardiac pacemaker in response to a high body lactate and/or lactic acid level in one or more ways selected from the group consisting of: increase in heart electromagnetic stimulation voltage, increase in the degree of coordination and/or timing between stimulations to different heart chambers, increase in the frequency of heart contraction stimulations, change in the locations on the heart to which electromagnetic energy is delivered, increase in the magnitude of heart contraction stimulations, increase in the regularity of heart contraction stimulations, delivery of an electromagnetic shock to the heart, and more precise coordination of contraction of different heart chambers.

In an example, an implanted circulatory assistance device can be a central (heart-assist) blood pump which assists the heart in pumping blood or a non-central (peripheral) blood pump which assists in pumping blood through a vessel to a selected (peripheral) portion of the body. In an example, a closed loop system can increase blood circulation by adjusting the operation of a central (heart-assist) blood pump or a non-central (peripheral) blood pump. In an example, a closed loop system can adjust the operation of a central (heart-assist) blood pump or a non-central (peripheral) blood pump in response to a high body lactate and/or lactic acid level in one or more ways selected from the group consisting of: activation of the pump to increase blood flow; increase in the duration of pump operation to increase blood flow; increase in the magnitude of pump undulation, compression, or contraction (depending on type of pump) to increase blood flow; and increase in the speed of a pump's rotation, undulation, compression, or contraction (depending on type of pump) to increase blood flow.

In an example, a system for cardiac function assistance can comprise: a finger ring, smart watch, or wrist band which collects data concerning lactate and/or lactic acid level in a person's body tissue and/or fluid; and an implanted cardiac pacemaker whose operation is controlled and/or adjusted based on analysis of the data concerning lactate and/or lactic acid level. In an example, a system for cardiac function assistance can comprise: a finger ring, smart watch, or wrist band which collects data concerning lactate and/or lactic acid level in a person's body tissue and/or fluid; and an implanted central (heart-assist) blood pump whose operation is controlled and/or adjusted based on analysis of the data concerning lactate and/or lactic acid level. In an example, a system for cardiac function assistance can comprise: a finger ring, smart watch, or wrist band which collects data concerning lactate and/or lactic acid level in a person's body tissue and/or fluid; and an implanted non-central (peripheral) blood pump whose operation is controlled and/or adjusted based on analysis of the data concerning lactate and/or lactic acid level.

In an example, the biometric parameter which is measured and managed by this system can be blood pressure. In an example, a wearable device can have a spectroscopic sensor which measures a person's blood pressure. In an example, a wearable device can have an electromagnetic energy sensor which measures a person's blood pressure. In an example, blood pressure can be measured from multiple locations on a person's body. In an example, the operation of an implanted circulatory assistance device can be controlled and/or adjusted based on a person's blood pressure or changes in their blood pressure.

In an example, an implanted circulatory assistance device can be a cardiac pacemaker. In an example, a system can adjust the operation of an implanted cardiac pacemaker in response to abnormal blood pressure. In an example, a system can adjust the operation of an implanted cardiac pacemaker in response to abnormal blood pressure in one or more ways selected from the group consisting of: change in heart electromagnetic stimulation voltage, change in the degree of coordination and/or timing between stimulations to different heart chambers, change in the frequency of heart contraction stimulations, change in the locations on the heart to which electromagnetic energy is delivered, change in the magnitude of heart contraction stimulations, change in the regularity of heart contraction stimulations, and more precise coordination of contraction of different heart chambers.

In an example, an implanted circulatory assistance device can be a central (heart-assist) blood pump which assists the heart in pumping blood or a non-central (peripheral) blood pump which assists in pumping blood through a vessel to a selected (peripheral) portion of the body. In an example, a closed loop system can adjust the operation of a central (heart-assist) blood pump or a non-central (peripheral) blood pump in response to abnormal blood pressure. In an example, a closed loop system can adjust the operation of a central (heart-assist) blood pump or a non-central (peripheral) blood pump in response to blood pressure in one or more ways selected from the group consisting of: activation of the device to change blood flow; adjusted device pumping volume to change blood flow; adjusted device rotation and/or speed to change blood flow; changed duration of device operation to change blood flow; selective activation of a sub-set of non-central (peripheral) blood pumps to change blood flow in a selected body location.

In an example, a system for cardiac function assistance can comprise: a finger ring, smart watch, or wrist band which collects data concerning a person's blood pressure; and an implanted cardiac pacemaker whose operation is controlled and/or adjusted based on analysis of the data concerning the person's blood pressure. In an example, a system for cardiac function assistance can comprise: a finger ring, smart watch, or wrist band which collects data concerning a person's blood pressure; and an implanted central (heart-assist) blood pump whose operation is controlled and/or adjusted based on analysis of the data concerning the person's blood pressure. In an example, a system for cardiac function assistance can comprise: a finger ring, smart watch, or wrist band which collects data concerning a person's blood pressure; and an implanted non-central (peripheral) blood pump whose operation is controlled and/or adjusted based on analysis of the data concerning the person's blood pressure.

In an example, a biometric parameter which is measured and managed by this system can be (peripherally measured) Heart Rate Variability (HRV). HRV can be associated with myocardium infarction, congestive cardiac insufficiency, or diabetic neuropathology. In an example, a wearable device can have a spectroscopic sensor. In an example, HRV can be measured from multiple locations on the person's body. In an example, operation of the implanted circulatory assistance device can be controlled and/or adjusted based on HRV or changes in HRV. In an example, a system can monitor for tachycardia or bradycardia.

In an example, an implanted circulatory assistance device of this system can be a cardiac pacemaker. In an example, this system can increase blood circulation by adjusting the operation of a cardiac pacemaker in response to high Heart Rate Variability (HRV). In an example, a closed loop system can adjust the operation of a cardiac pacemaker in response to high Heart Rate Variability (HRV) in one or more ways selected from the group consisting of: change in heart electromagnetic stimulation voltage, change in the degree of coordination and/or timing between stimulations to different heart chambers, change in the frequency of heart contraction stimulations, change in the locations on the heart to which electromagnetic energy is delivered, change in the magnitude of heart contraction stimulations, change in the regularity of heart contraction stimulations, delivery of an electromagnetic shock to the heart, and more precise coordination of contraction of different heart chambers.

In an example, an implanted circulatory assistance device can be a central (heart-assist) blood pump which assists the heart in pumping blood or a non-central (peripheral) blood pump which assists in pumping blood through a vessel to a selected (peripheral) portion of the body. In an example, a closed loop system can increase blood circulation by adjusting the operation of a central (heart-assist) blood pump or a non-central (peripheral) blood pump. In an example, a closed loop system can adjust the operation of a central (heart-assist) blood pump or a non-central (peripheral) blood pump in response to high Heart Rate Variability (HRV) in one or more ways selected from the group consisting of: activation or deactivation of the pump to change blood flow; change in the duration of pump operation to change blood flow; change in the magnitude of pump undulation, compression, or contraction (depending on type of pump) to change blood flow; change in the speed of a pump's rotation, undulation, compression, or contraction (depending on type of pump) to change blood flow; and selective activation of a sub-set of non-central (peripheral) blood pumps to change blood flow in a selected sub-set of body locations.

In an example, the biometric parameter which is measured and monitored in this system can be Pulsatile Blood Volume (PBV) which is measured. In an example, PBV variation can be measured as the percentage change in blood vessel diameter during pulsation. In an example, PBV variation can be measured as the percentage change in absorption of light in a given portion of the light spectrum during pulsation. In an example, the wearable device can have a spectroscopic sensor. In an example, a wearable device can measure blood volume variation over time. In an example, a wearable device can perform photoplethysmography. In an example, Pulsatile Blood Volume (PBV) can be measured from multiple locations on a person's body. In an example, operation of an implanted circulatory assistance device can be controlled and/or adjusted based on Pulsatile Blood Volume (PBV) or variation thereof.

In an example, an implanted circulatory assistance device can be a cardiac pacemaker. In an example, a closed loop system can increase blood circulation by adjusting the operation of a cardiac pacemaker in response to abnormal Pulsatile Blood Volume (PBV) or variation thereof. In an example, a closed loop system can adjust the operation of a cardiac pacemaker in response to abnormal Pulsatile Blood Volume (PBV) in one or more ways selected from the group consisting of: change in heart electromagnetic stimulation voltage, change in the degree of coordination and/or timing between stimulations to different heart chambers, change in the frequency of heart contraction stimulations, change in the locations on the heart to which electromagnetic energy is delivered, change in the magnitude of heart contraction stimulations, change in the regularity of heart contraction stimulations, delivery of an electromagnetic shock to the heart, and more precise coordination of contraction of different heart chambers.

In an example, the implanted circulatory assistance device can be a central (heart-assist) blood pump which assists the heart in pumping blood or a non-central (peripheral) blood pump which assists in pumping blood through a vessel to a selected (peripheral) portion of the body. In an example, a closed loop system can increase blood circulation by adjusting the operation of a central (heart-assist) blood pump or a non-central (peripheral) blood pump. In an example, a system can adjust the operation of a central (heart-assist) blood pump or a non-central (peripheral) blood pump in response to abnormal Pulsatile Blood Volume (PBV), or variation thereof, in one or more ways selected from the group consisting of: activation or deactivation of the pump to change blood flow; change in the duration of pump operation to change blood flow; change in the magnitude of pump undulation, compression, or contraction (depending on type of pump) to change blood flow; change in the speed of a pump's rotation, undulation, compression, or contraction (depending on type of pump) to change blood flow; and selective activation of a sub-set of non-central (peripheral) blood pumps to change blood flow in a selected sub-set of body locations.

In an example, the biometric parameter which is measured and managed by this system can be Pulsatile Blood Lag (PBL). In an example, PBLV can be measured as variation in the lag time between central cardiac pulsation and peripheral blood pulsation. In an example, a wearable device can have a spectroscopic sensor. In an example, the wearable device can measure blood volume variation over time. In an example, the wearable device can perform photoplethysmography. In an example, Pulsatile Blood Lag (PBL) can be measured from multiple locations on the person's body. In an example, operation of the implanted circulatory assistance device can be controlled and/or adjusted based on Pulsatile Blood Lag (PBL) or changes in PBL.

In an example, an implanted circulatory assistance device can be a cardiac pacemaker. In an example, a closed loop system can increase blood circulation by adjusting the operation of a cardiac pacemaker in response to abnormal Pulsatile Blood Lag (PBL). In an example, a closed loop system can adjust the operation of a cardiac pacemaker in response to abnormal Pulsatile Blood Lag (PBL) in one or more ways selected from the group consisting of: change in heart electromagnetic stimulation voltage, change in the degree of coordination and/or timing between stimulations to different heart chambers, change in the frequency of heart contraction stimulations, change in the locations on the heart to which electromagnetic energy is delivered, change in the magnitude of heart contraction stimulations, change in the regularity of heart contraction stimulations, delivery of an electromagnetic shock to the heart, and more precise coordination of contraction of different heart chambers.

In an example, an implanted circulatory assistance device can be a central (heart-assist) blood pump which assists the heart in pumping blood or a non-central (peripheral) blood pump which assists in pumping blood through a vessel to a selected (peripheral) portion of the body. In an example, a closed loop system can increase blood circulation by adjusting the operation of a central (heart-assist) blood pump or a non-central (peripheral) blood pump. In an example, a closed loop system can adjust the operation of a central (heart-assist) blood pump or a non-central (peripheral) blood pump in response to abnormal Pulsatile Blood Lag (PBL) in one or more ways selected from the group consisting of: activation or deactivation of the pump to change blood flow; change in the duration of pump operation to change blood flow; change in the magnitude of pump undulation, compression, or contraction (depending on type of pump) to change blood flow; change in the speed of a pump's rotation, undulation, compression, or contraction (depending on type of pump) to change blood flow; and selective activation of a sub-set of non-central (peripheral) blood pumps to change blood flow in a selected sub-set of body locations.

In an example, the biometric parameter which is measured and managed by this system can be body hydration level. In an example, the wearable device can have a spectroscopic sensor or electromagnetic energy sensor which measures the hydration level of a person's body tissue and/or fluid. In an example, body hydration level can be measured from multiple locations on the person's body. In an example, the operation of the implanted circulatory assistance device can be controlled and/or adjusted based on a person's body hydration level or changes in that level.

In an example, an implanted circulatory assistance device can be an implanted cardiac pacemaker. In an example, a system can change blood circulation by adjusting the operation of a cardiac pacemaker in response to an abnormal body hydration level. In an example, a system can adjust the operation of a cardiac pacemaker in response to an abnormal body hydration level in one or more ways selected from the group consisting of: change in heart electromagnetic stimulation voltage, change in the degree of coordination and/or timing between stimulations to different heart chambers, change in the frequency of heart contraction stimulations, change in the locations on the heart to which electromagnetic energy is delivered, change in the magnitude of heart contraction stimulations, change in the regularity of heart contraction stimulations, delivery of an electromagnetic shock to the heart, and more precise coordination of contraction of different heart chambers.

In an example, an implanted circulatory assistance device can be a central (heart-assist) blood pump which assists the heart in pumping blood or a non-central (peripheral) blood pump which assists in pumping blood through a vessel to a selected (peripheral) portion of the body. In an example, a closed loop system can change blood circulation by adjusting the operation of a central (heart-assist) blood pump or a non-central (peripheral) blood pump. In an example, a closed loop system can adjust the operation of a central (heart-assist) blood pump or a non-central (peripheral) blood pump in response to an abnormal body hydration level in one or more ways selected from the group consisting of: activation of the device to change blood flow; adjusted device pumping volume to change blood flow; adjusted device rotation and/or speed to change blood flow; changed duration of device operation to change blood flow; selective activation of a sub-set of non-central (peripheral) blood pumps to change blood flow in a selected body location.

In an example, the biometric parameter which is measured and managed by this system can be respiration rate. In an example, a wearable device can comprise a motion sensor, spectroscopic sensor, or electromagnetic energy sensor which measures respiration rate. In an example, respiration rate can be measured from multiple locations on the person's body. In an example, the operation of the implanted circulatory assistance device can be controlled and/or adjusted based on respiration rate or changes thereof.

In an example, an implanted circulatory assistance device can be am implanted cardiac pacemaker. In an example, a system can change blood circulation by adjusting the operation of a cardiac pacemaker in response to respiration rate. In an example, a system can adjust the operation of a cardiac pacemaker in response to respiration rate in one or more ways selected from the group consisting of: change in heart electromagnetic stimulation voltage, change in the degree of coordination and/or timing between stimulations to different heart chambers, change in the frequency of heart contraction stimulations, change in the locations on the heart to which electromagnetic energy is delivered, change in the magnitude of heart contraction stimulations, change in the regularity of heart contraction stimulations, delivery of an electromagnetic shock to the heart, and more precise coordination of contraction of different heart chambers.

In an example, an implanted circulatory assistance device can be an implanted central (heart-assist) blood pump which assists the heart in pumping blood or a non-central (peripheral) blood pump which assists in pumping blood through a vessel to a selected (peripheral) portion of the body. In an example, a closed loop system can adjust the operation of a central (heart-assist) blood pump or a non-central (peripheral) blood pump based on a person's respiration rate. In an example, a closed loop system can adjust the operation of a central (heart-assist) blood pump or a non-central (peripheral) blood pump in response to respiration rate in one or more ways selected from the group consisting of: activation of the device to change blood flow; adjusted device pumping volume to change blood flow; adjusted device rotation and/or speed to change blood flow; changed duration of device operation to change blood flow; selective activation of a sub-set of non-central (peripheral) blood pumps to change blood flow in a selected body location.

In an example, the biometric parameter which is measured and managed by this system can be exhaled gas composition (i.e. the composition of gas exhaled by a person). In an example, a wearable device can have a spectroscopic sensor or electromagnetic energy sensor which measures exhaled gas composition. In an example, exhaled gas composition can be measured by a nose ring or eyeglasses bridge. In an example, the operation of the implanted circulatory assistance device can be controlled and/or adjusted based on a person's exhaled gas composition or changes thereof.

In an example, an implanted circulatory assistance device can be am implanted cardiac pacemaker. In an example, a system can change blood circulation by adjusting the operation of a cardiac pacemaker in response to exhaled gas composition. In an example, a system can adjust the operation of a cardiac pacemaker in response to exhaled gas composition in one or more ways selected from the group consisting of: change in heart electromagnetic stimulation voltage, change in the degree of coordination and/or timing between stimulations to different heart chambers, change in the frequency of heart contraction stimulations, change in the locations on the heart to which electromagnetic energy is delivered, change in the magnitude of heart contraction stimulations, change in the regularity of heart contraction stimulations, delivery of an electromagnetic shock to the heart, and more precise coordination of contraction of different heart chambers.

In an example, an implanted circulatory assistance device can be an implanted central (heart-assist) blood pump which assists the heart in pumping blood or a non-central (peripheral) blood pump which assists in pumping blood through a vessel to a selected (peripheral) portion of the body. In an example, a closed loop system can adjust the operation of a central (heart-assist) blood pump or a non-central (peripheral) blood pump based on a person's exhaled gas composition. In an example, a closed loop system can adjust the operation of a central (heart-assist) blood pump or a non-central (peripheral) blood pump in response to exhaled gas composition in one or more ways selected from the group consisting of: activation of the device to change blood flow; adjusted device pumping volume to change blood flow; adjusted device rotation and/or speed to change blood flow; changed duration of device operation to change blood flow; selective activation of a sub-set of non-central (peripheral) blood pumps to change blood flow in a selected body location.

In an example, the biometric parameter which is measured and managed by this system can be the glucose level in a person's body tissue and/or fluid. In an example, the biometric parameter can be blood glucose level. In an example, a wearable device can have a spectroscopy sensor or electromagnetic energy sensor which measures the glucose level of a person's body tissue and/or fluid. In an example, body glucose level can be measured from multiple locations on a person's body. In an example, operation of the implanted circulatory assistance device can be controlled and/or adjusted based on body glucose level or changes thereof.

In an example, an implanted circulatory assistance device can be a cardiac pacemaker. In an example, a system can change the operation of a cardiac pacemaker in response to an abnormal body glucose level. In an example, a system can adjust the operation of a cardiac pacemaker in response to an abnormal body glucose level in one or more ways selected from the group consisting of: change in heart electromagnetic stimulation voltage, change in the degree of coordination and/or timing between stimulations to different heart chambers, change in the frequency of heart contraction stimulations, change in the locations on the heart to which electromagnetic energy is delivered, change in the magnitude of heart contraction stimulations, change in the regularity of heart contraction stimulations, delivery of an electromagnetic shock to the heart, and more precise coordination of contraction of different heart chambers.

In an example, the implanted circulatory assistance device can be a central (heart-assist) blood pump which assists the heart in pumping blood or a non-central (peripheral) blood pump which assists in pumping blood through a vessel to a selected (peripheral) portion of the body. In an example, a closed loop system can adjust the operation of a central (heart-assist) blood pump or a non-central (peripheral) blood pump in response to an abnormal body glucose level. In an example, a closed loop system can adjust the operation of a central (heart-assist) blood pump or a non-central (peripheral) blood pump in response to abnormal body glucose level in one or more ways selected from the group consisting of: activation of the device to change blood flow; adjusted device pumping volume to change blood flow; adjusted device rotation and/or speed to change blood flow; changed duration of device operation to change blood flow; and selective activation of a sub-set of non-central (peripheral) blood pumps to change blood flow in a selected body location.

In an example, the biometric parameter which is measured and managed by this system can be troponin level. In an example, the wearable device can have a spectroscopic sensor or electromagnetic energy sensor which measures the level of troponin in a person's body tissue and/or fluid. In an example, troponin level can be measured from multiple locations on the person's body. In an example, the operation of the implanted circulatory assistance device can be controlled and/or adjusted based on troponin level or a change thereof.

In an example, an implanted circulatory assistance device can be a cardiac pacemaker or ICD. In an example, a system can change blood circulation by adjusting the operation of a cardiac pacemaker or ICD in response to troponin. In an example, a system can adjust the operation of a cardiac pacemaker or ICD in response to troponin in one or more ways selected from the group consisting of: change in heart electromagnetic stimulation voltage, change in the degree of coordination and/or timing between stimulations to different heart chambers, change in the frequency of heart contraction stimulations, change in the locations on the heart to which electromagnetic energy is delivered, change in the magnitude of heart contraction stimulations, change in the regularity of heart contraction stimulations, delivery of an electromagnetic shock to the heart, and more precise coordination of contraction of different heart chambers.

In an example, the implanted circulatory assistance device can be a central (heart-assist) blood pump which assists the heart in pumping blood or a non-central (peripheral) blood pump which assists in pumping blood through a vessel to a selected (peripheral) portion of the body. In an example, a closed loop system can change blood circulation by adjusting the operation of a central (heart-assist) blood pump or a non-central (peripheral) blood pump. In an example, a closed loop system can adjust the operation of a central (heart-assist) blood pump or a non-central (peripheral) blood pump in response to troponin in one or more ways selected from the group consisting of: activation of the device to change blood flow; adjusted device pumping volume to change blood flow; adjusted device rotation and/or speed to change blood flow; changed duration of device operation to change blood flow; selective activation of a sub-set of non-central (peripheral) blood pumps to change blood flow in a selected body location.

In an example, the biometric parameter which is measured and managed by this system can be body motion or exercise level. In an example, the wearable device can have a motion sensor, GPS sensor, or EMG sensor which measures body motion and/or exercise level. In an example, body motion or exercise level can be measured from multiple locations on the person's body. In an example, the operation of an implanted circulatory assistance device can be controlled and/or adjusted based on body motion or exercise level or changes thereof.

In an example, an implanted circulatory assistance device can be a cardiac pacemaker. In an example, a system can change blood circulation by adjusting the operation of a cardiac pacemaker in response to a high body motion or exercise level. In an example, a system can adjust the operation of a cardiac pacemaker in response to a high body motion or exercise level in one or more ways selected from the group consisting of: increase in heart electromagnetic stimulation voltage, increase in the degree of coordination and/or timing between stimulations to different heart chambers, increase in the frequency of heart contraction stimulations, change in the locations on the heart to which electromagnetic energy is delivered, increase in the magnitude of heart contraction stimulations, increase in the regularity of heart contraction stimulations, delivery of an electromagnetic shock to the heart, and more precise coordination of contraction of different heart chambers.

In an example, an implanted circulatory assistance device can be a central (heart-assist) blood pump which assists the heart in pumping blood or a non-central (peripheral) blood pump which assists in pumping blood through a vessel to a selected (peripheral) portion of the body. In an example, a closed loop system can adjust the operation of a central (heart-assist) blood pump or a non-central (peripheral) blood pump in response to body motion or exercise level. In an example, a closed loop system can adjust the operation of a central (heart-assist) blood pump or a non-central (peripheral) blood pump in response to a high body motion or exercise level in one or more ways selected from the group consisting of: activation of the device to change blood flow; adjusted device pumping volume to change blood flow; adjusted device rotation and/or speed to change blood flow; changed duration of device operation to change blood flow; selective activation of a sub-set of non-central (peripheral) blood pumps to change blood flow in a selected body location.

In an example, a system can adjust a person's cardiac function based on their whole-body posture and/or configuration. In an example, a system can adjust a person's cardiac function based on identification of a specific whole-body posture and/or configuration. In an example, a system can adjust a person's cardiac function based on identification of a specific type of activity based on measured whole-body posture and/or configuration. In an example, a system can increase (or decrease) the frequency of a person's heart beats and/or the magnitude of a person's heart contractions in response to a change in the person's whole-body posture and/or configuration as detected by one or more wearable biometric sensors. In an example, a person's whole-body posture and/or configuration can be measured by one or more motion sensors, electromyographic (EMG sensors), and/or bend sensors.

In an example, the biometric parameter which is measured and monitored by this system can be sleep status or stage. In an example, the wearable device can have a motion sensor or EEG sensor which measures sleep status or stage. In an example, sleep status or stage can be measured from multiple locations on the person's body. In an example, the operation of an implanted circulatory assistance device can be controlled and/or adjusted based on sleep status or stage or change thereof.

In an example, an implanted circulatory assistance device can be an implanted cardiac pacemaker. In an example, a system can change blood circulation by adjusting the operation of a cardiac pacemaker in response to sleep status or stage. In an example, a system can adjust the operation of a cardiac pacemaker in response to sleep status or stage in one or more ways selected from the group consisting of: change in heart electromagnetic stimulation voltage, change in the degree of coordination and/or timing between stimulations to different heart chambers, change in the frequency of heart contraction stimulations, change in the locations on the heart to which electromagnetic energy is delivered, change in the magnitude of heart contraction stimulations, change in the regularity of heart contraction stimulations, delivery of an electromagnetic shock to the heart, and more precise coordination of contraction of different heart chambers.

In an example, an implanted circulatory assistance device can be a central (heart-assist) blood pump which assists the heart in pumping blood or a non-central (peripheral) blood pump which assists in pumping blood through a vessel to a selected (peripheral) portion of the body. In an example, a closed loop system can adjust the operation of a central (heart-assist) blood pump or a non-central (peripheral) blood pump in response to sleep status or stage. In an example, a closed loop system can adjust the operation of a central (heart-assist) blood pump or a non-central (peripheral) blood pump in response to sleep status or stage in one or more ways selected from the group consisting of: activation of the device to change blood flow; adjusted device pumping volume to change blood flow; adjusted device rotation and/or speed to change blood flow; changed duration of device operation to change blood flow; selective activation of a sub-set of non-central (peripheral) blood pumps to change blood flow in a selected body location.

In an example, a system for cardiac function assistance can comprise: a finger ring, smart watch, or wrist band which collects data concerning sleep status or stage; and an implanted cardiac pacemaker whose operation is controlled and/or adjusted based on analysis of the data concerning sleep status or stage. In an example, a system for cardiac function assistance can comprise: a finger ring, smart watch, or wrist band which collects data concerning sleep status or stage; and an implanted central (heart-assist) blood pump whose operation is controlled and/or adjusted based on analysis of the data concerning sleep status or stage. In an example, a system for cardiac function assistance can comprise: a finger ring, smart watch, or wrist band which collects data concerning sleep status or stage; and an implanted non-central (peripheral) blood pump whose operation is controlled and/or adjusted based on analysis of the data concerning sleep status or stage.

In an example, a closed loop system for human circulatory assistance can comprise a plurality of wearable devices which are worn on different locations of a person's body so as to measure values of a biometric parameter from different locations on the person's body. In an example, the operation of an implanted circulatory assistance device can be controlled and/or adjusted by data concerning biometric parameter levels from a plurality of wearable devices on different locations of a person's body. In an example, the operation of an implanted circulatory assistance device can be adjusted based on the average of biometric parameter levels, the lowest biometric parameter level, the highest biometric parameter level, and/or the range or variability of biometric parameter levels measured by a plurality of wearable devices worn at different locations on a person's body. In an example, the operation of an implanted circulatory assistance device can be adjusted based on multivariate analysis of data concerning biometric parameter levels from a plurality of wearable devices worn at different locations on a person's body.

In an example, the operation of an implanted cardiac pacemaker can be controlled and/or adjusted by data concerning biometric parameter levels from a plurality of wearable devices on different locations of a person's body. In an example, the operation of an implanted cardiac pacemaker can be adjusted based on the average of biometric parameter levels, the lowest biometric parameter level, the highest biometric parameter level, and/or the range or variability of biometric parameter levels measured by a plurality of wearable devices worn at different locations on a person's body. In an example, the operation of an implanted cardiac pacemaker can be adjusted based on multivariate analysis of data concerning biometric parameter levels from a plurality of wearable devices worn at different locations on a person's body.

In an example, a system for cardiac function assistance can comprise: a first wearable device which is worn by a person on a first external location of the person's body, wherein the first wearable device collects data concerning a biometric parameter from the first external location; a second wearable device which is worn by a person on a second external location of the person's body, wherein the second wearable device collects data on the biometric parameter from the second external location; and an implanted cardiac pacemaker, wherein operation of the cardiac pacemaker is adjusted based a difference between the value of the biometric parameter as measured from the first external location and the value of the biometric parameter as measured from the second location.

In an example, a system for cardiac function assistance can comprise: a first wearable device which is worn by a person on a first external location of the person's body, wherein the first wearable device collects data concerning body oxygenation level from the first external location; a second wearable device which is worn by a person on a second external location of the person's body, wherein the second wearable device collects data concerning body oxygenation level from the second external location; and an implanted cardiac pacemaker, wherein operation of the cardiac pacemaker is adjusted based a difference between the value of body oxygenation level as measured from the first external location and the value of body oxygenation level as measured from the second location.

In an example, the operation of an implanted central (heart-assist) blood pump can be controlled and/or adjusted by data concerning biometric parameter levels from a plurality of wearable devices on different locations of a person's body. In an example, the operation of an implanted central (heart-assist) blood pump can be adjusted based on the average of biometric parameter levels, the lowest biometric parameter level, the highest biometric parameter level, and/or the range or variability of biometric parameter levels measured by a plurality of wearable devices worn at different locations on a person's body. In an example, the operation of an implanted central (heart-assist) blood pump can be adjusted based on multivariate analysis of data concerning biometric parameter levels from a plurality of wearable devices worn at different locations on a person's body.

In an example, a system for cardiac function assistance can comprise: a first wearable device which is worn by a person on a first external location of the person's body, wherein the first wearable device collects data concerning a biometric parameter from the first external location; a second wearable device which is worn by a person on a second external location of the person's body, wherein the second wearable device collects data on the biometric parameter from the second external location; and an implanted central (heart-assist) blood pump, wherein operation of the central (heart-assist) blood pump is adjusted based a difference between the value of the biometric parameter as measured from the first external location and the value of the biometric parameter as measured from the second location.

In an example, a system for cardiac function assistance can comprise: a first wearable device which is worn by a person on a first external location of the person's body, wherein the first wearable device collects data concerning body oxygenation level from the first external location; a second wearable device which is worn by a person on a second external location of the person's body, wherein the second wearable device collects data concerning body oxygenation level from the second external location; and an central (heart-assist) blood pump, wherein operation of the central (heart-assist) blood pump is adjusted based a difference between the value of body oxygenation level as measured from the first external location and the value of body oxygenation level as measured from the second location.

In an example, the operation of an implanted non-central (peripheral) blood pump can be controlled and/or adjusted by data concerning biometric parameter levels from a plurality of wearable devices on different locations of a person's body. In an example, the operation of an implanted non-central (peripheral) blood pump can be adjusted based on the average of biometric parameter levels, the lowest biometric parameter level, the highest biometric parameter level, and/or the range or variability of biometric parameter levels measured by a plurality of wearable devices worn at different locations on a person's body. In an example, the operation of an implanted non-central (peripheral) blood pump can be adjusted based on multivariate analysis of data concerning biometric parameter levels from a plurality of wearable devices worn at different locations on a person's body. In an example, the operation of a plurality of implanted non-central (peripheral) blood pumps can be controlled and/or adjusted by data concerning biometric parameter levels from a plurality of wearable devices on different locations of a person's body.

There are many potential advantages of having a plurality of individually-controlled implanted blood pumps distributed throughout a person's body, wherein these blood pumps are adjusted (in a feedback loop) based on biometric measurements from associated external wearable devices. One potential advantage is greater accuracy and selectivity in maintaining biometric parameters (such as oxygenation) in different portions of a person's body. For example, diabetics often suffer from poor blood circulation in their feet and hands. This can lead to wounds which do not heal and even amputation. A system for selective circulatory assistance with a plurality of individually-controllable implanted blood pumps whose operation is adjusted (in real time) based on associated wearable oxygenation sensors can help to avoid this. This can be a significant improvement over a single central cardiac pacemaker or single central (heart-assist) blood pump which whose operation is not informed by the actual oxygen levels in a person's feet and hands.

Although the analogy is not perfect, a closed loop system for circulatory assistance with a plurality of implanted blood pumps whose operations are selectively controlled and/or adjusted by a plurality of wearable biometric sensors is analogous to having a climate control system for a home or other building with different HVAC (e.g. heating or cooling) zones in different areas throughout the home or other building. Having different HVAC zones in different areas allows more accurate and more selective control of temperatures in different areas. Such a system can reduce hot spots or cold spots in a home or building. By analogy, a person's body can have regions with high and low blood circulation (and body oxygenation). A system for circulatory assistance with a plurality of implanted blood pumps can help to maintain proper and consistent blood circulation (and body oxygenation) in all regions of the body. This can help to heal wounds or even perhaps avoid amputations. Having different HVAC zones can also improve the energy efficiency of a building's climate control system. By analogy, having a decentralized plurality of implanted blood pumps can be more energy efficient. Energy efficiency can be a serious consideration in view of the potentially-high energy demands of implanted blood pumps.

In an example, a system for cardiac function assistance can comprise: a first wearable device which is worn by a person on a first external location of the person's body, wherein the first wearable device collects data concerning a biometric parameter from the first external location; a second wearable device which is worn by a person on a second external location of the person's body, wherein the second wearable device collects data on the biometric parameter from the second external location; a first implanted non-central (peripheral) blood pump, wherein the first implanted non-central (peripheral) blood pump selectively increases blood flow to the first external location of the person's body based on the value of the biometric parameter at the first external location; and a second implanted non-central (peripheral) blood pump, wherein the second implanted non-central (peripheral) blood pump selectively increases blood flow to the second external location of the person's body based on the value of the biometric parameter at the second external location.

In an example, a system for cardiac function assistance can comprise: a plurality of wearable devices which are worn by a person on different external locations of the person's body, wherein the wearable devices collect data on a biometric parameter from the different external locations; and a plurality of implanted blood pumps which are implanted in different internal locations within the person's body, wherein the implanted circulatory assistance devices provide localized blood circulation assistance from the different internal locations, wherein internal locations and external locations are associated with each other, wherein operation of an implanted blood pump at a selected internal location is adjusted based on analysis of data on the biometric parameter collected by a wearable device at the external location which is paired with that selected internal location.

In an example, a system for cardiac function assistance can comprise: a first wearable device which is worn by a person on a first external location of the person's body, wherein the first wearable device collects data concerning a biometric parameter from the first external location; a second wearable device which is worn by a person on a second external location of the person's body, wherein the second wearable device collects data concerning a biometric parameter from the second external location; a first implanted blood pump which increases blood flow to the first external location of the person's body; a second implanted blood pump which increases blood flow to the second external location of the person's body; wherein operation of the first implanted blood pump is adjusted based on analysis of data from the first wearable device; and wherein operation of the second implanted blood pump is adjusted based on analysis of data from the second wearable device.

In an example, there are some situations in which it may be desirable to temporarily decrease blood flow to a one body region in order to improve blood flow to another body region where blood flow is more critically needed at the moment. In an example, a system for cardiac function assistance can comprise: a first wearable device which is worn by a person on a first external location of the person's body, wherein the first wearable device collects data concerning a biometric parameter from the first external location; a second wearable device which is worn by a person on a second external location of the person's body, wherein the second wearable device collects data concerning a biometric parameter from the second external location; a first implanted blood pump which increases blood flow to the first external location of the person's body; a second implanted blood pump which increases blood flow to the second external location of the person's body; wherein operation of the first implanted blood pump is adjusted based on analysis of data from the second wearable device; and wherein operation of the second implanted blood pump is adjusted based on analysis of data from the first wearable device.

In an example, a system for cardiac function assistance can comprise: a first wearable device which is worn by a person on a first external location of the person's body, wherein the first wearable device measures the value of a biometric parameter from this first location, a second wearable device which is worn by a person on a second external location of the person's body, wherein the second wearable device measures the value of the biometric parameter from this second location; a first implanted blood pump which selectively increases blood flow to the first external location of the person's body, wherein the operation of the first implanted blood pump is selectively activated and/or adjusted when the value of the biometric parameter from the first location is abnormal; and a second implanted blood pump which selectively increases blood flow to the second external location of the person's body, wherein the operation of the second implanted blood pump is selectively activated and/or adjusted when the value of the biometric parameter from the second location is abnormal.

In an example, the operation of an implanted blood pump in a given location can be selectively activated and/or adjusted when the value of a biometric parameter measured from that location is abnormal for at least a given length of time, wherein this length of time is selected from within a range of 10 seconds to 10 minutes. In an example, this length of time can be selected from within a range of 5 minutes to 1 hour. In an example, the value of a biometric parameter can be considered abnormal when it is at least X % lower than the minimum value in a benchmark range of values, wherein X % is selected from within a range of 10% to 50%. In an example, X % can be selected from within a range of 25% to 100%. In an example, the value of a biometric parameter can be considered abnormal when it is at least Y % higher than the maximum value in a benchmark range of values, wherein Y % is selected from within a range of 10% to 50%. In an example, Y % can be selected from within a range of 25% to 100%.

In an example, a system for cardiac function assistance can comprise: a first wearable device which is worn by a person on a first external location of the person's body, wherein the first wearable device measures the value of a biometric parameter from the first location, a second wearable device which is worn by a person on a second external location of the person's body, wherein the second wearable device measures the value of the biometric parameter from the second location; a first implanted blood pump which selectively increases blood flow to the first external location of the person's body, wherein the first implanted blood pump is selectively activated and/or the operation of the first implanted blood pump is adjusted when the value of the biometric parameter from the first location is X % lower or Y % higher than a benchmark range of values; and a second implanted blood pump which selectively increases blood flow to the second external location of the person's body, wherein the second implanted blood pump is selectively activated and/or the operation of the second implanted blood pump is adjusted when the value of the biometric parameter from the second location is X % lower or Y % higher than a benchmark range of values. In an example, X % can be a percentage selected from within a range of 10% to 50%. In an example, Y % can be a percentage selected from within a range of 10% to 50%.

In an example, the operation of an implanted blood pump in a first location can be selectively activated and/or adjusted based on comparison of the value of a biometric parameter measured from that first location relative to the value of the biometric parameter measured from a second location. In an example, an implanted blood pump in a first location can be selectively activated and/or adjusted when the value of a biometric parameter measured from that first location is at least X % lower or Y % higher than the value of the biometric parameter measured from a second location. In an example, X % can be a percentage selected from within a range of 10% to 50%. In an example, Y % can be a percentage selected from within a range of 10% to 50%. In an example, implanted blood pumps in a plurality of internal locations can be selectively activated and/or adjusted based on multivariate analysis of values of a biometric parameter measured from a plurality of external locations. In an example, a plurality of implanted blood pumps in different locations in a person's vasculature can comprise a distributed network of circulation assisting devices for maintenance of proper blood circulation throughout different body regions.

In an example, a system for cardiac function assistance can comprise: a first wearable device which is worn by a person on a first external location of the person's body, wherein the first wearable device measures the value of a biometric parameter from this first location, a second wearable device which is worn by a person on a second external location of the person's body, wherein the second wearable device measures the value of a biometric a first implanted blood pump which selectively increases blood flow to the first external location of the person's body, wherein the first implanted blood pump is selectively activated and/or the operation of the first implanted blood pump is adjusted when the value of the biometric parameter from the first location is at least X % lower or Y % higher than the value of the biometric parameter from the second location; and a second implanted blood pump which selectively increases blood flow to the second external location of the person's body, wherein the second implanted blood pump is selectively activated and/or the operation of the second implanted blood pump is adjusted when the value of the biometric parameter from the second location is at least X % lower or Y % higher than the value of the biometric parameter from the first location.

In an example, there are cases when it can be desirable to change blood flow to a first body region based on measurement of a biometric parameter from a second body region. For example, to the extent that there is a short-term constraint on overall blood flow throughout a person's body, it can be desirable to increase relative blood flow in a first body region (when it has inadequate blood flow) if there is adequate blood flow in a second body region. In an example, a system for cardiac function assistance can comprise: a first wearable device on a first external body location which collects data concerning a biometric parameter from the first external location; a second wearable device on a second external body location which collects data on the biometric parameter from the second external location; a first implanted blood pump which selectively increases blood flow to the first external location of the person's body; and a second implanted blood pump which selectively increases blood flow to the second external location of the person's body; wherein operation of the second implanted blood pump is adjusted based on analysis of data from the first wearable device.

In an example, a system for cardiac function assistance can comprise: a first wearable device which is worn by a person on a first external location of the person's body, wherein the first wearable device measures the value of body oxygenation level from this first location, a second wearable device which is worn by a person on a second external location of the person's body, wherein the second wearable device measures the value of the body oxygenation level from this second location; a first implanted blood pump which selectively increases blood flow to the first external location of the person's body, wherein the operation of the first implanted blood pump is selectively activated and/or adjusted when the value of the body oxygenation level from the first location is abnormal; and a second implanted blood pump which selectively increases blood flow to the second external location of the person's body, wherein the operation of the second implanted blood pump is selectively activated and/or adjusted when the value of the body oxygenation level from the second location is abnormal.

In an example, the operation of an implanted blood pump in a given location can be selectively activated and/or adjusted when the value of body oxygenation level measured from that location is abnormal for at least a given length of time, wherein this length of time is selected from within a range of 10 seconds to 10 minutes. In an example, this length of time can be selected from within a range of 5 minutes to 1 hour. In an example, the value of body oxygenation level can be considered abnormal when it is at least X % lower than the minimum value in a benchmark range of values, wherein X % is selected from within a range of 10% to 50%. In an example, X % can be selected from within a range of 25% to 100%.

In an example, a system for cardiac function assistance can comprise: a first wearable device which is worn by a person on a first external location of the person's body, wherein the first wearable device measures the value of body oxygenation level from the first location, a second wearable device which is worn by a person on a second external location of the person's body, wherein the second wearable device measures the value of the body oxygenation level from the second location; a first implanted blood pump which selectively increases blood flow to the first external location of the person's body, wherein the first implanted blood pump is selectively activated and/or the operation of the first implanted blood pump is adjusted when the value of the body oxygenation level from the first location is X % lower than a benchmark range of values; and a second implanted blood pump which selectively increases blood flow to the second external location of the person's body, wherein the second implanted blood pump is selectively activated and/or the operation of the second implanted blood pump is adjusted when the value of the body oxygenation level from the second location is X % lower than a benchmark range of values. In an example, X % can be a percentage selected from within a range of 10% to 50%.

In an example, a system for cardiac function assistance can comprise: a first wearable device which is worn by a person on a first external location of the person's body, wherein the first wearable device measures the value of body oxygenation level from this first location, a second wearable device which is worn by a person on a second external location of the person's body, wherein the second wearable device measures the value of a biometric a first implanted blood pump which selectively increases blood flow to the first external location of the person's body, wherein the first implanted blood pump is selectively activated and/or the operation of the first implanted blood pump is adjusted when the value of the body oxygenation level from the first location is at least X % lower than the value of the body oxygenation level from the second location; and a second implanted blood pump which selectively increases blood flow to the second external location of the person's body, wherein the second implanted blood pump is selectively activated and/or the operation of the second implanted blood pump is adjusted when the value of the body oxygenation level from the second location is at least X % lower than the value of the body oxygenation level from the first location.

In an example, there are cases when it can be desirable to change blood flow to a first body region based on measurement of body oxygenation level from a second body region. For example, to the extent that there is a short-term constraint on overall blood flow throughout a person's body, it can be desirable to increase relative blood flow in a first body region (when it has inadequate oxygenation) if there is adequate oxygenation in a second body region. In an example, a system for cardiac function assistance can comprise: a first wearable device on a first external body location which collects data concerning body oxygenation level from the first external location; a second wearable device on a second external body location which collects data concerning body oxygenation level from the second external location; a first implanted blood pump which selectively increases blood flow to the first external location of the person's body; and a second implanted blood pump which selectively increases blood flow to the second external location of the person's body; wherein operation of the second implanted blood pump is adjusted based on analysis of data from the first wearable device.

In an example, a system for cardiac function assistance can comprise: a first wearable device which is worn by a person on a first external location of the person's body, wherein the first wearable device measures the value of blood pressure from this first location, a second wearable device which is worn by a person on a second external location of the person's body, wherein the second wearable device measures the value of blood pressure from this second location; a first implanted blood pump which selectively increases blood flow to the first external location of the person's body, wherein the operation of the first implanted blood pump is selectively adjusted when the value of blood pressure from the first location is abnormal; and a second implanted blood pump which selectively increases blood flow to the second external location of the person's body, wherein the operation of the second implanted blood pump is selectively adjusted when the value of blood pressure from the second location is abnormal.

In an example, the operation of an implanted blood pump in a given location can be selectively adjusted when the value of blood pressure measured from that location is abnormal for at least a given length of time, wherein this length of time is selected from within a range of 10 seconds to 10 minutes. In an example, this length of time can be selected from within a range of 5 minutes to 1 hour. In an example, the value of blood pressure can be considered abnormal when it is at least X % lower than the minimum value in a benchmark range of values, wherein X % is selected from within a range of 5% to 25%. In an example, X % can be selected from within a range of 20% to 50%. In an example, the value of blood pressure can be considered abnormal when it is at least Y % higher than the maximum value in a benchmark range of values, wherein Y % is selected from within a range of 5% to 25%. In an example, Y % can be selected from within a range of 20% to 50%.

In an example, a system for cardiac function assistance can comprise: a first wearable device which is worn by a person on a first external location of the person's body, wherein the first wearable device measures the value of blood pressure from the first location, a second wearable device which is worn by a person on a second external location of the person's body, wherein the second wearable device measures the value of blood pressure from the second location; a first implanted blood pump which selectively increases blood flow to the first external location of the person's body, wherein the first implanted blood pump is selectively activated and/or the operation of the first implanted blood pump is adjusted when the value of blood pressure from the first location is X % lower or Y % higher than a benchmark range of values; and a second implanted blood pump which selectively increases blood flow to the second external location of the person's body, wherein the second implanted blood pump is selectively activated and/or the operation of the second implanted blood pump is adjusted when the value of blood pressure from the second location is X % lower or Y % higher than a benchmark range of values. In an example, X % can be a percentage selected from within a range of 10% to 50%. In an example, Y % can be a percentage selected from within a range of 10% to 50%.

In an example, the operation of an implanted blood pump in a first location can be selectively adjusted based on comparison of the value of blood pressure measured from that first location relative to the value of blood pressure measured from a second location. In an example, an implanted blood pump in a first location can be selectively adjusted when the value of blood pressure measured from that first location is at least X % lower or Y % higher than the value of blood pressure measured from a second location. In an example, X % can be a percentage selected from within a range of 10% to 50%. In an example, Y % can be a percentage selected from within a range of 10% to 50%. In an example, implanted blood pumps in a plurality of internal locations can be selectively adjusted based on multivariate analysis of values of blood pressure measured from a plurality of external locations. In an example, a plurality of implanted blood pumps in different locations in a person's vasculature can comprise a distributed network of circulation assisting devices for maintenance of proper blood circulation throughout different body regions.

In an example, a system for cardiac function assistance can comprise: a first wearable device which is worn by a person on a first external location of the person's body, wherein the first wearable device measures the value of blood pressure from this first location, a second wearable device which is worn by a person on a second external location of the person's body, wherein the second wearable device measures the value of a biometric a first implanted blood pump which selectively increases blood flow to the first external location of the person's body, wherein the first implanted blood pump is selectively activated and/or the operation of the first implanted blood pump is adjusted when the value of blood pressure from the first location is at least X % lower or Y % higher than the value of blood pressure from the second location; and a second implanted blood pump which selectively increases blood flow to the second external location of the person's body, wherein the second implanted blood pump is selectively activated and/or the operation of the second implanted blood pump is adjusted when the value of blood pressure from the second location is at least X % lower or Y % higher than the value of blood pressure from the first location.

In an example, a rapid loss in blood pressure in a first body region relative to a second body region may indicate hemorrhaging in the first body region. In an example, the operation of a non-central (peripheral) blood pump which increases blood flow to a first body region can be adjusted based on a rapid loss in blood pressure as measured by a wearable device on an external location of that first body region. In an example, the operation of a non-central (peripheral) blood pump which controls blood flow to a first body region can be adjusted to reduce blood flow to that region in response to a rapid loss in blood pressure in that body region. In an example, a distributed system of non-central (peripheral) blood pumps which assist in blood circulation to different body regions can be useful in combat or other environments in which there is potential rapid blood loss through injury and/or trauma. In an example, having a plurality of wearable devices at different external locations can detect rapid blood loss in a given region and adjust the corresponding blood pump to that region to reduce blood loss.

In an example, multivariate analysis of blood pressure, blood volume variation, and other biometric parameters from sensors on wearable devices at different external locations of a person's body can be analyzed in real time to detect rapid blood loss from a selected body region. In an example, rapid blood loss from a given body region can indicate hemorrhaging due to injury or trauma. In an example, blood flow to a given body region suffering from rapid blood loss due to hemorrhaging can be reduced by selective adjustment of one or more non-central (peripheral) blood pumps which control blood flow to that body region. In an example, a non-central (peripheral) blood pump can have a first operational mode in which it increases blood flow above normal flow levels and a second operational mode in which it decreases blood flow below normal flow levels. In an example, the second operational mode can be activated for a given body region when there is hemorrhaging in that body region due to injury or trauma. There must be safeguards to ensure that activation of a second operational mode does not cause undesirable blood flow reduction or tissue death, but, done properly, such as system could provide results similar to real-time application of external wound pressure to stop bleeding from wounds. This could possibly save lives.

In an example, a system for cardiac function assistance can comprise: a first wearable device (such as a ring or band) which is worn by a person on their right hand or arm which collects data on the level of a biometric parameter (such as oxygenation level) concerning their right hand or arm; a second wearable device (such as a ring or band) which is worn by a person on their left hand or arm which collects data on the level of a biometric parameter (such as oxygenation level) concerning their left hand or arm; a first implanted blood pump which selectively increases blood flow to their right hand and/or arm, wherein the operation of this first implanted blood pump is adjusted based on the level of biometric parameter (such as oxygenation level) concerning their right hand or arm; and a second implanted blood pump which selectively increases blood flow to their left hand and/or arm, wherein the operation of this second implanted blood pump is adjusted based on the level of biometric parameter (such as oxygenation level) concerning their left hand or arm.

In an example, a system for cardiac function assistance can comprise: a first wearable device (such as a band or sock) which is worn by a person on their right foot or leg which collects data on the level of a biometric parameter (such as oxygenation level) concerning their right foot or leg; a second wearable device (such as a band or sock) which is worn by a person on their left foot or leg which collects data on the level of a biometric parameter (such as oxygenation level) concerning their left foot or leg; a first implanted blood pump which selectively increases blood flow to their right foot and/or leg, wherein the operation of this first implanted blood pump is adjusted based on the level of biometric parameter (such as oxygenation level) concerning their right foot or leg; and a second implanted blood pump which selectively increases blood flow to their left foot and/or leg, wherein the operation of this second implanted blood pump is adjusted based on the level of biometric parameter (such as oxygenation level) concerning their left foot or leg.

In an example, a system for cardiac function assistance can comprise: a first wearable device (such as a ring or band) which is worn by a person on their hand or arm which collects data on the level of a biometric parameter (such as oxygenation level) concerning their hand or arm; a second wearable device (such as a band or sock) which is worn by a person on their foot or leg which collects data on the level of a biometric parameter (such as oxygenation level) concerning their foot or leg; a first implanted blood pump which selectively increases blood flow to their hand and/or arm, wherein the operation of this first implanted blood pump is adjusted based on the level of biometric parameter (such as oxygenation level) concerning their hand or arm; a second implanted blood pump which selectively increases blood flow to their foot and/or leg, wherein the operation of this second implanted blood pump is adjusted based on the level of biometric parameter (such as oxygenation level) concerning their foot or leg.

In an example, a wearable device of a system can comprise a light-emitting member (such as an LED) which is configured to direct light toward the person's body. In an example, this light can be infrared light, near-infrared light, ultraviolet light, and visible and/or white light. In an example, this light can be coherent and/or laser light. In an example, a light-energy receiver can receive this directed light after it has been reflected from, or passed through, the person's body tissue and/or fluid. In an example, data from the light-energy receiver can be analyzed to determine how the spectrum of directed light has been changed by reflection from, or passage through, the person's body tissue and/or fluid. In an example, changes in the spectrum of light energy due to interaction with a person's body tissue and/or fluid can be analyzed to measure (changes in) the chemical composition of body tissue and/or fluid.

In an example, a wearable device for collecting data on a biometric parameter can include a plurality of spectroscopic sensors. In an example, a spectroscopic sensor can further comprise one or more light-energy emitters (e.g. light sources) which direct light-energy toward a body tissue and/or fluid and one or more light-energy receivers (e.g. photoreceptors) which receive light-energy which has been transmitted through or reflected by body tissue and/or fluid. In an example, a wearable device for collecting data on a biometric parameter can include a plurality of light-energy emitters which emit light-energy toward a person's body tissue and/or fluid. In an example, a wearable device for collecting data on a biometric parameter can include a plurality of light-energy receivers which receive light-energy which has been transmitted through a person's body tissue and/or fluid or reflected by the person's body tissue and/or fluid. In an example, a wearable device for collecting data on a biometric parameter can include a plurality of light-energy emitters and a single light-energy receiver. In an example, a wearable device for collecting data on a biometric parameter can include a single light-energy emitter and a plurality of light-energy receivers.

In an example, different spectroscopic sensors in a plurality of spectroscopic sensors can differ with respect to the angles at which they direct light beams toward a person's body. In an example, a first subset of spectroscopic sensors in a plurality of spectroscopic sensors can direct light beams toward a person's body at a first angle and a second subset of spectroscopic sensors in the plurality of spectroscopic sensors can direct light beams toward the person's body at a second angle. In an example, this angle can be with respect to the proximal surface of a person's body. In an example, this angle can be with respect to the surface of a wearable device from which the light beams are emitted.

In an example, different spectroscopic sensors in a plurality of spectroscopic sensors can differ with respect to the color, frequency, and/or spectrum of light beams which they direct toward a person's body. In an example, a first subset of spectroscopic sensors in a plurality of spectroscopic sensors can direct light beams with a first color, frequency, and/or spectrum toward a person's body and a second subset of spectroscopic sensors in the plurality of spectroscopic sensors can direct light beams with a second color, frequency, and/or spectrum toward the person's body.

In an example, different spectroscopic sensors in a plurality of spectroscopic sensors can differ with respect to the power or intensity of light beams which they direct toward a person's body. In an example, a first subset of spectroscopic sensors in a plurality of spectroscopic sensors can direct light beams with a first level of power or intensity toward a person's body and a second subset of spectroscopic sensors in the plurality of spectroscopic sensors can direct light beams with a second level of power or intensity toward the person's body.

In an example, different spectroscopic sensors in a plurality of spectroscopic sensors can differ with respect to the body tissue depth from which light beams are reflected back to light-energy receivers. In an example, a first subset of spectroscopic sensors in a plurality of spectroscopic sensors can receive light beams reflected from a first tissue depth and a second subset of spectroscopic sensors in the plurality of spectroscopic sensors can receive light beams reflected from a second tissue depth.

In an example, different spectroscopic sensors in a plurality of spectroscopic sensors can differ with respect to the polarization or coherence of light beams which where they direct toward a person's body. In an example, a first subset of spectroscopic sensors in a plurality of spectroscopic sensors can direct light beams with a first orientation or degree of polarization or coherence toward a person's body and a second subset of spectroscopic sensors in the plurality of spectroscopic sensors can direct light beams with a second orientation or degree of polarization or coherence toward the person's body.

In an example, different spectroscopic sensors in a plurality of spectroscopic sensors can differ with respect to the timing and/or synchronization of light beams directed toward a person's body. In an example, light beam emission from different light-energy emitters can be sequenced and/or multiplexed. In an example, light beam emission and reception between different associated pairs of light-energy emitters and receivers can be sequenced to isolate measurement of biometric values from different tissue depths and/or locations. In an example, emission and reception of light-energy between different pairs of light-energy emitters and light-energy receivers can be multiplexed. In an example, emission of light-energy from multiple light-energy emitters can be sequenced and/or multiplexed to be received by a single light-energy receiver at different times.

In an example, different spectroscopic sensors in a plurality of spectroscopic sensors can differ with respect to the location on a person's body where they direct light beams and/or the location on a wearable device from which they emit light beams. In an example, a first subset of spectroscopic sensors in a plurality of spectroscopic sensors can direct light beams toward a first location on a person's body and a second subset of spectroscopic sensors in the plurality of spectroscopic sensors can direct light beams toward a second location on the person's body. In an example, a first subset of spectroscopic sensors in a plurality of spectroscopic sensors can direct light beams toward a first side of a portion of a person's body and a second subset of spectroscopic sensors in the plurality of spectroscopic sensors can direct light beams toward a second side of the portion of the person's body. In an example, a first subset of spectroscopic sensors in a plurality of spectroscopic sensors can direct light beams from a first location on a wearable device and a second subset of spectroscopic sensors in the plurality of spectroscopic sensors can direct light beams from a second location on a wearable device.

In an example, spectroscopic sensors in a plurality of spectroscopic sensors can be configured to be distributed around (at least half of) the circumference of a person's finger, wrist, arm, ankle, or leg. In an example, spectroscopic sensors in a plurality of spectroscopic sensors can be distributed around (at least half of) the circumference of a wearable device which encircles a portion of a person's body. In an example, spectroscopic sensors in a plurality of spectroscopic sensors can be distributed around (at least half of) the circumference of a finger ring, smart watch band, wrist band, arm band, ankle band, or smart sock.

In an example, a plurality of spectroscopic sensors can comprise a circumferential array of spectroscopic sensors around (at least half of the circumference of) a person's finger, wrist, arm, ankle, or toe. In an example, a plurality of spectroscopic sensors can comprise a ring or circle of spectroscopic sensors around (at least half of the circumference of) a person's finger, wrist, arm, ankle, or toe. In an example, a plurality of spectroscopic sensors can be incorporated into the band of a smart watch (or wrist band) or fitness band. In an example, a plurality of spectroscopic sensors can be incorporated into the side pieces of eyeglasses. In an example, a plurality of spectroscopic sensors can comprise a cylindrical matrix or grid of spectroscopic sensors.

In an example, light-energy emitters and light-energy receivers in a plurality of spectroscopic sensors can be distributed around (at least half of) the circumference of a portion of a person's body (such as a person's finger, wrist, arm, ankle, or leg) in a circumferentially-alternating manner, wherein circumferentially-alternating means repeatedly alternating between a light-energy emitter and a light-energy receiver around (at least half of) the circumference of the portion of the person's body. In an example, light-energy emitters and light-energy receivers in a plurality of spectroscopic sensors can be pair-wise associated at opposite sides of the circumference of a portion of a person's body (such as a person's finger, wrist, arm, ankle, or leg), wherein pair-wise associated at opposite sides means that each light-energy emitter is associated with a light-energy receiver which located on the (diametrically) opposite side of the body portion.

In an example, different light-energy emitters can differ with respect to the angles at which they direct light beams toward a person's body. In an example, a first subset of light-energy emitters can direct light beams toward a person's body at a first angle and a second subset of light-energy emitters can direct light beams toward the person's body at a second angle. In an example, this angle can be with respect to the proximal surface of a person's body. In an example, this angle can be with respect to the surface of a wearable device from which the light beams are emitted. In an example, a first light-energy emitter can emit light with a first light projection and/or body incidence angle and a second light-energy emitter can emit light with a second light projection and/or body incidence angle.

In an example, different light-energy emitters can differ with respect to the color, frequency, and/or spectrum of light beams which they direct toward a person's body. In an example, a first subset of light-energy emitters can direct light beams with a first color, frequency, and/or spectrum toward a person's body and a second subset of light-energy emitters can direct light beams with a second color, frequency, and/or spectrum toward the person's body. In an example, a light-energy emitter can emit light energy whose frequency and/or spectrum changes over time. In an example, a light-energy emitter can emit a sequence of light pulses at different selected frequencies.

In an example, a wearable device can comprise a first light-energy emitter and a second light-energy emitter. In an example, a first light-energy emitter can emit light with a first light frequency, color, and/or spectrum and a second light-energy emitter can emit light with a second light frequency, color, and/or spectrum. In an example, light from the first light-energy emitter can reflect primarily from a first depth, breadth, location, and/or type of body tissue and light from the second light-energy emitter can reflect primarily from a first depth, breadth, location, and/or type of body tissue. In an example, first and second light-energy emitters can emit light simultaneously. In an example, first and second light-energy emitters can emit light in a selected chronological sequence and/or timing pattern.

In an example, a first light-energy emitter can emit light-energy with a first light wavelength (or wavelength range or spectral distribution) and a second light-energy emitter can simultaneously emit light-energy with a second light wavelength (or wavelength range or spectral distribution) during the same time period. In an example, a first light-energy emitter can emit light-energy with a first light wavelength (or wavelength range or spectral distribution) and a second light-energy emitter can simultaneously emit light-energy with a second light wavelength (or wavelength range or spectral distribution) during the same time period in order to measure different physiological parameters, analytes, or conditions.

In an example, different light-energy emitters can emit light with different wavelengths or wavelength ranges based on data from one or more biometric sensors detecting different biological or physiological parameters or conditions. In an example, different emitters can emit light with different wavelengths or wavelength ranges based on data from one or more biometric sensors when a person is engaged in different types of activities. In an example, different emitters can emit light with different wavelengths or wavelength ranges based on data from one or more environmental sensors in response to different environmental parameters or conditions.

In an example, a first light-energy receiver can receive light-energy with a first light wavelength (or wavelength range or spectral distribution) and a second light-energy receiver can simultaneously receive light-energy with a second light wavelength (or wavelength range or spectral distribution) during the same time period. In an example, a first light-energy receiver can receive light-energy with a first light wavelength (or wavelength range or spectral distribution) and a second light-energy receiver can simultaneously receive light-energy with a second light wavelength (or wavelength range or spectral distribution) during the same time period in order to simultaneously measure different physiological parameters, analytes, or conditions.

In an example, a light-energy emitter can emit light-energy with a first light wavelength (or wavelength range or spectral distribution) during a first time period and can emit light-energy with a second light wavelength (or wavelength range or spectral distribution) during a second time period. In an example, a light-energy emitter can emit light-energy with a first light wavelength (or wavelength range or spectral distribution) during a first time period and can emit light-energy with a second light wavelength (or wavelength range or spectral distribution) during a second time period in order to measure different physiological parameters, analytes, or conditions. In an example, a light-energy emitter can automatically cycle through light-energy emissions with a variety of wavelengths (or wavelength ranges or spectral distributions) during different time periods in order to measure different physiological parameters, analytes, or conditions.

In an example, a light-energy emitter can emit light-energy with a first light wavelength (or wavelength range or spectral distribution) during a first time period and can emit light-energy with a second light wavelength (or wavelength range or spectral distribution) during a second time period in response to changing environmental conditions. In an example, a light-energy emitter can emit light-energy with a first light wavelength (or wavelength range or spectral distribution) during a first time period and can emit light-energy with a second light wavelength (or wavelength range or spectral distribution) during a second time period in response to changing biometric results. In an example, a light-energy emitter can emit light-energy with a first light wavelength (or wavelength range or spectral distribution) during a first time period and can emit light-energy with a second light wavelength (or wavelength range or spectral distribution) during a second time period in response to changing physiological conditions.

In an example, a light-energy receiver can receive light-energy with a first light wavelength (or wavelength range or spectral distribution) during a first time period and can receive light-energy with a second light wavelength (or wavelength range or spectral distribution) during a second time period. In an example, a light-energy receiver can receive light-energy with a first light wavelength (or wavelength range or spectral distribution) during a first time period and can receive light-energy with a second light wavelength (or wavelength range or spectral distribution) during a second time period in order to measure different physiological parameters, analytes, or conditions. In an example, a light-energy receiver can automatically cycle through light-energy emissions with a variety of wavelengths (or wavelength ranges or spectral distributions) during a different time periods in order to measure different physiological parameters, analytes, or conditions.

In an example, a light-energy receiver can receive light-energy with a first light wavelength (or wavelength range or spectral distribution) during a first time period and can receive light-energy with a second light wavelength (or wavelength range or spectral distribution) during a second time period in response to changing environmental conditions. In an example, a light-energy receiver can receive light-energy with a first light wavelength (or wavelength range or spectral distribution) during a first time period and can receive light-energy with a second light wavelength (or wavelength range or spectral distribution) during a second time period in response to changing biometric results. In an example, a light-energy receiver can receive light-energy with a first light wavelength (or wavelength range or spectral distribution) during a first time period and can receive light-energy with a second light wavelength (or wavelength range or spectral distribution) during a second time period in response to changing physiological conditions.

In an example, different light-energy emitters can differ with respect to the power or intensity of light beams which they direct toward a person's body. In an example, a first subset of light-energy emitters can direct light beams with a first level of power or intensity toward a person's body and a second subset of light-energy emitters can direct light beams with a second level of power or intensity toward the person's body.

In an example, different light-energy emitters and receivers can differ with respect to the body tissue depth from which light beams are reflected back to light-energy receivers. In an example, a first subset of light-energy receivers can receive light beams reflected from a first tissue depth and a second subset of light-energy receivers can receive light beams reflected from a second tissue depth. In an example, light from the first light-energy emitter can reflect primarily from a first depth, breadth, location, and/or type of body tissue and light from the second light-energy emitter can reflect primarily from a first depth, breadth, location, and/or type of body tissue.

In an example, different light-energy emitters can differ with respect to the polarization or coherence of light beams which where they direct toward a person's body. In an example, a first subset of light-energy emitters can direct light beams with a first orientation or degree of polarization or coherence toward a person's body and a second subset of light-energy emitters can direct light beams with a second orientation or degree of polarization or coherence toward the person's body. In an example, a wearable device can comprise a first light-energy emitter and a second light-energy emitter. In an example, the first light-energy emitter can emit light with a first light coherence, polarization, and/or phase and the second light-energy emitter can emit light with a second light coherence, polarization, and/or phase.

In an example, a wearable device can comprise an array, grid, and/or matrix of light-energy emitters which differ in one or more parameters selected from the group consisting of: location and/or distance from a light-energy receiver; distance to body surface; light beam frequency, color, and/or spectrum; light beam coherence, polarity, and/or phase; light beam power and/or intensity; light beam projection and/or body incidence angle; light beam duration; light beam size; and light beam focal distance. In an example, a system can comprise an array, grid, and/or matrix of light-energy receivers which differ in: location and/or distance from a light-energy emitter; and/or distance to body surface.

In an example, different light-energy emitters can differ with respect to the location on a person's body where they direct light beams and/or the location on a wearable device from which they emit light beams. In an example, a first subset of light-energy emitters can direct light beams toward a first location on a person's body and a second subset of light-energy emitters can direct light beams toward a second location on the person's body. In an example, a first subset of light-energy emitters can direct light beams toward a first side of a portion of a person's body and a second subset of light-energy emitters can direct light beams toward a second side of the portion of the person's body. In an example, a first subset of light-energy emitters can direct light beams from a first location on a wearable device and a second subset of light-energy emitters can direct light beams from a second location on a wearable device.

In an example, light-energy emitters and receivers can be configured to be distributed around (at least half of) the circumference of a person's finger, wrist, arm, ankle, or leg. In an example, light-energy emitters and receivers can be distributed around (at least half of) the circumference of a wearable device which encircles a portion of a person's body. In an example, light-energy emitters and receivers can be distributed around (at least half of) the circumference of a finger ring, smart watch band, wrist band, arm band, ankle band, or smart sock.

In an example, a plurality of light-energy emitters and receivers can comprise a circumferential array of light-energy emitters and receivers around (at least half of the circumference of) a person's finger, wrist, arm, ankle, or toe. In an example, a plurality of light-energy emitters and receivers can comprise a ring or circle of light-energy emitters and receivers around (at least half of the circumference of) a person's finger, wrist, arm, ankle, or toe. In an example, a plurality of light-energy emitters and receivers can be incorporated into the band of a smart watch (or wrist band) or fitness band. In an example, a plurality of light-energy emitters and receivers can be incorporated into the side pieces of eyeglasses. In an example, a plurality of light-energy emitters and receivers can comprise a cylindrical matrix or grid of spectroscopic sensors.

In an example, a wearable device can comprise a plurality of spectroscopic sensors. In an example, different spectroscopic sensors in a plurality of spectroscopic sensors can differ with respect to being at different locations around (at least half of) the circumference of a finger, wrist, arm, ankle, or toe. In an example, a plurality of spectroscopic sensors can comprise a ring of paired light-energy emitters and light-energy receivers around a finger, wrist, arm, ankle, or tow, wherein a light-energy emitter and light-energy receiver in pair are on opposite sides of the finger, wrist, arm, ankle, or tow. In an example, a plurality of spectroscopic sensors can comprise a ring of paired light-energy emitters and light-energy receivers around a finger, wrist, arm, ankle, or tow, wherein a light-energy emitter and light-energy receiver in pair are next to each other in the ring, and wherein light-energy emitters and receivers alternate around the ring. In an example, a plurality of spectroscopic sensors can comprise a plurality of light-energy emitters which are in optical communication with a single light-energy receiver. In an example, a plurality of spectroscopic sensors can comprise a single light-energy emitter which is in optical communication with a plurality of light-energy receivers.

In an example, a light-energy emitter can emit light along a first vector and a light-energy receiver can receive light along a second vector. In an example, the second vector can be substantially reversed from (e.g. 180-degree reflection) and parallel to the first vector. In an example, the second vector can be substantially perpendicular to (e.g. 90-degree angle relative to) the first vector. In an example, the second vector can be reversed from the first vector and symmetric to the first vector with respect to a virtual vector which extends outward in a perpendicular manner from the surface of a person's body. In an example, a system can include one or more light guides which direct light-energy from a first location, angle, and/or transmission vector to a second location, angle, and/or transmission vector. In an example, different light-energy emitters can emit light rays at different angles with respect to a device surface. In an example, different light-energy emitters can emit light rays at different angles with respect to a body surface. In an example, these angles can be between 60 and 120 degrees.

In an example, a spectroscopic sensor can comprise both a light-energy emitter and a light-energy receiver. In an example, a light-energy emitter and a light-energy receiver which are in optical communication with each other can comprise a spectroscopic sensor. In an example, a light-energy receiver can receive light which has been emitted by the light-energy emitter and then transmitted through or reflected from body tissue and/or fluid. In an example, a light-energy emitter and light-energy receiver can be paired such that light energy from a selected light-energy emitter is received by a selected light-energy receiver after that light energy has been transmitted through or reflected by body tissue and/or fluid.

In an example, a spectroscopic sensor can comprise a light-energy receiver alone (without a light-energy emitter) if it uses ambient light which has been reflected from or transmitted through body tissue and/or fluid. In an example, changes in the spectrum of ambient light which has been reflected from or transmitted through body tissue and/or fluid can be analyzed to measure biometric parameters with respect to the molecular composition of body tissue and/or fluid. In an example, a light-energy receiver which receives ambient light after that light has interacted with body tissue and/or fluid can be referred to as a spectroscopy sensor. In an example, an ambient light source can be solar radiation or artificial lighting in a person's environment.

In an example, a light-energy receiver can be optically isolated from light from a light-energy emitter which has not yet passed through or been reflected by body tissue and/or fluid. In an example, a light-energy receiver can be optically isolated from ambient light which has not yet passed through or been reflected by body tissue and/or fluid. In an example, a light-energy receiver can be optically isolated by means of a light blocking ring, layer, coating, cladding, or other component of the wearable device. In an example, a light-energy receiver can be optically isolated by a compressible, elastomeric, and/or inflatable ring between a light-energy receiver and the surface of a person's body. In an example, a light-energy receiver can be optically isolated by a compressible, elastomeric, and/or inflatable polygon-shaped barrier between a light-energy receiver and the surface of a person's body. In an example, a polygon-shaped barrier can have a square or hexagonal shape.

In an example, a wearable device of this system can have one or more light-energy emitters. In an example, one or more light-energy emitters can be light emitting diodes (LEDs). In an example, one or more light-energy emitters can emit coherent light. In an example, one or more light-energy emitters can be lasers. In an example, a light-energy emitter can emit infrared, near-infrared light, or ultraviolet light. In an example, a light-energy emitter can emit white light. In an example, a light-energy emitter can be selected from the group consisting of: light emitting diode (LED), coherent light source, organic light emitting diode (OLED), laser, laser diode, infrared light-energy emitter, multi-wavelength source, resonant cavity light emitting diode (RCLED), super-luminescent light emitting diode (SLED), and ultraviolet light-energy emitter. In an example, a light-energy receiver can be selected from the group consisting of: photodetector, photoresistor, avalanche photodiode (APD), charge-coupled device (CCD), complementary metal-oxide semiconductor (CMOS), infrared detector, infrared photoconductor, infrared photodiode, light dependent resistor (LDR), optoelectric sensor, photoconductor, photodiode, photomultiplier, and phototransistor.

In an example, a light-energy emitter can be a red-light laser. In an example, a light-energy emitter can be a green-light laser. In an example, a wearable device can have both a red-light laser and a green-light laser. In an example, a red light-energy emitter can be in optical communication with a first light-energy receiver (after the red light has interacted with body tissue and/or fluid) and a green light-energy emitter can be in optical communication with a second light-energy receiver (after the green light has interacted with body tissue and/or fluid). In an example, a wearable device can comprise a prism and/or filter which splits ambient light into red light and green light, wherein the red light is in optical communication with a first light-energy receiver (after the red light has interacted with body tissue and/or fluid) and the green light is in optical communication with a second light-energy receiver (after the green light has interacted with body tissue and/or fluid).

In an example, a wearable device can have a red light-energy emitter and an infrared light-energy emitter. In an example, a red light-energy emitter can be in optical communication with a first light-energy receiver (after the red light has interacted with body tissue and/or fluid) and an infrared light-energy emitter can be in optical communication with a second light-energy receiver (after the infrared light has interacted with body tissue and/or fluid).

In an example, a wearable device can have a first light-energy emitter which emits light with a wavelength of 660 nm and second light-energy emitter which emits light with a wavelength of 940 nm. In an example, a wearable device can have a first light-energy emitter which emits light with a wavelength within the range of 600 to 700 nm and second light-energy emitter which emits light with a wavelength within the range of 850 to 950 nm. In an example, the first light-energy emitter can be in optical communication with a first light-energy receiver (after its light has interacted with body tissue and/or fluid) and the second light-energy emitter can be in optical communication with a second light-energy receiver (after its light has interacted with body tissue and/or fluid). In an example, body oxygenation can be estimated based on the ratio of changes in the spectra of light beams from the two light-energy emitters due to those light beams having been transmitted through or reflected by body tissue and/or fluid.

In an example, a wearable device of this system can comprise one or more paired sets of light-energy emitters and light-energy receivers. In an example, each paired set can be configured so that light emitted from the light-energy receiver is received by the light-energy receiver after the light has been transmitted through or reflected from body tissue and/or fluid. In an example, different sets of light-energy emitters and receivers can have different locations wherein light is transmitted through or reflected by a person's body. In an example, a first pair comprising a light-energy emitter and a light-energy receiver can reflect light from a body surface at a first location and a second pair comprising a light-energy emitter and a light-energy receiver can reflect light from a body surface at a second location. In an example, different sets of light-energy emitters and receivers can have different angles at which light is transmitted through or reflected by a person's body. In an example, a first pair comprising a light-energy emitter and a light-energy receiver can reflect light from a body surface at a first angle and a second pair comprising a light-energy emitter and a light-energy receiver can reflect light from a body surface at a second angle.

In an example, pairs of light-energy emitters and light-energy receivers can be distributed around the circumference of a wearable device (such as a finger ring, watch band, wrist band, arm band, or ankle band) such that at least one pair is in close contact with the surface of a person's body regardless of rotation and/or shifting of the wearable device. In an example, pairs of light-energy emitters and light-energy receivers can be distributed around the circumference of a wearable device (such as a finger ring, watch band, wrist band, arm band, or ankle band) such that the light beam from at least one light-energy emitter is substantially perpendicular to the proximal surface of a person's body regardless of rotation and/or shifting of the wearable device.

In an example, a wearable device of this system can include one or more light-blocking layers, coatings, or claddings. In an example, a wearable device can include one or more light-reflecting layers, coatings, or claddings. In an example, a wearable device can include one or more mirrors. In an example, a light-blocking and/or light-reflecting layer, coating, and/or cladding can be opaque. In an example, a light-blocking and/or light-reflecting layer, coating, and/or cladding can comprise a black or sliver coating. In an example, a light-blocking and/or light-reflecting layer, coating, and/or cladding can be Mylar. In an example, a light-blocking and/or light-reflecting layer, coating, and/or cladding can prevent the direct transmission of light from a light-energy emitter to a light-energy receiver apart from transmission through or reflection from body tissue and/or fluid. In an example, a light-blocking and/or light-reflecting layer, coating, and/or cladding can optically isolate a light-energy receiver from ambient light. In an example, a light-blocking and/or light-reflecting layer, coating, and/or cladding can reduce or prevent the direct transmission of ambient light to a light-energy receiver apart from transmission through or reflection from body tissue and/or fluid.

In an example, a wearable device of this system can include a light barrier between a light-energy emitter and a light-energy receiver which reduces or eliminates the direct transmission of light energy from the emitter to the receiver. In an example, a light barrier can be located between a light-energy receiver and a person's skin. In an example, a light barrier can be opaque. In an example, a light barrier can be compressible, flexible, and/or elastic. In an example, a light barrier can comprise compressible foam. In an example, a light barrier can be an inflatable member (such as a balloon) which is filled with a gas or liquid. In an example, a light barrier can have a linear shape. In an example, a light barrier can have a circular, elliptical, sinusoidal, or other arcuate shape. In an example, a light barrier can surround a light-energy receiver. In an example, a light barrier can surround a light-energy emitter.

In an example, a wearable device of this system can include one or more light filters. In an example, a light filter can partially absorb and/or block light transmission between a light-energy emitter and body tissue. In an example, a light filter can partially absorb and/or block light transmission between ambient light and body tissue. In an example, a light filter can partially absorb and/or block light transmission between body tissue and a light-energy receiver. In an example, a wearable device can comprise two or more light filters which are alternately moved into the path of light beams from a light-energy emitter. In an example, one or more light filters can partially absorb and/or block one or more selected light wavelengths, wavelength ranges, frequencies, and/or frequency ranges. In an example, a light filter may absorb and/or block infrared or ultraviolet light. In an example, a light filter can selectively allow transmission of only infrared light or only ultraviolet light. In an example, a light filter can be made from one or more materials selected from the group consisting of: acrylic, crystal, glass, high-durometer plastic, low-durometer plastic, optical-pass material, polycarbonate, polyethylene, polymer, polyurethane, resin, sapphire, and transparent polymer. In an example, a light filter can be made by adding a light-absorbing dye to acrylic, crystal, glass, plastic, polycarbonate, polyethylene, polymer, polyurethane, resin, and/or a transparent polymer.

In an example, a wearable device of this system can include one or more lenses. In an example, a wearable device can include a lens which selectively refracts and/or focuses light. In an example, a lens can selectively refract and/or focus light transmission between a light-energy emitter and body tissue. In an example, a lens can selectively refract and/or focus light transmission between ambient light and body tissue. In an example, a lens can selectively refract and/or focus light transmission between body tissue and a light-energy receiver. In an example, a lens can be selected from the group consisting of: biconcave, biconvex, collimating, columnar, concave, converging, convex, diverging, fluid lens, Fresnel, multiple lenses, negative meniscus, planoconcave, planoconvex, polarizing, positive meniscus, prismatic, and variable-focal lens. In an example, a lens can be made from one or more materials selected from the group consisting of: acrylic, crystal, glass, high-durometer plastic, low-durometer plastic, optical-pass material, polycarbonate, polyethylene, polymer, polyurethane, resin, sapphire, and transparent polymer.

In an example, a wearable device of this system can include a light guide. In an example, a light guide can be flexible. In an example, a light guide can be generally cylindrical and/or columnar. In an example, a light guide can have a refractive index of at least 3.141. In an example, a light guide can be made from one or more materials selected from the group consisting of: acrylic, crystal, elastomeric light-transmissive material, glass, high-durometer plastic, low-durometer plastic, optical-pass material, polycarbonate, polyethylene, polymer, polyurethane, resin, sapphire, and transparent polymer.

In an example, a plurality of light-energy emitters can co-linear. In an example, a plurality of light-energy emitters and a light-energy receiver can be co-linear. In an example, a plurality of light-energy emitters can be configured in a polygonal array in proximity to a light-energy receiver. In an example, a plurality of light-energy emitters can be configured in a polygonal array which includes a light-energy receiver. In an example, a plurality of light-energy emitters can be configured in a polygonal array around a light-energy receiver. In an example, a plurality of light-energy emitters can be configured in a circular array in proximity to a light-energy receiver. In an example, a plurality of light-energy emitters can be configured in a circular array around a light-energy receiver. In an example, a plurality of light-energy emitters can emit light in a circular sequence around a central light-energy receiver.

In an example, an array of light-energy emitters can have a square or rectangular shape. In an example, an array of light-energy emitters can have a hexagonal shape. In an example, an array of light-energy emitters can have a circular shape. In an example, an array of light-energy emitters can have a sunburst (e.g. radial spoke) shape. In an example, an array of light-energy emitters can have a cylindrical and/or ring shape. In an example, an array of light-energy emitters and receivers can have a square or rectangular shape. In an example, an array of light-energy emitters and receivers can have a hexagonal shape. In an example, an array of light-energy emitters and receivers can have a circular shape. In an example, an array of light-energy emitters and receivers can have a sunburst (e.g. radial spoke) shape. In an example, an array of light-energy emitters and receivers can have a cylindrical and/or ring shape.

In an example, the depths, breadths, locations, and/or types of body tissue or fluid from which light beams from a plurality of light-energy emitters are reflected can be determined by a selected geometric configuration of the plurality of light-energy emitters and a light-energy receiver. In an example, a selected geometric configuration of a plurality of light-energy emitters and a light-energy receiver can be designed to most accurately measure an analyte level in the body. In an example, the geometric configuration of a plurality of light-energy emitters and a light-energy receiver can be adjusted automatically (in an iterative manner) by a system in order to more accurately measure an analyte level in the body for a specific person, for a specific type of activity, or for a specific configuration of the system relative to the person's body surface.

In an example, the geometric configuration of a plurality of light-energy emitters and a light-energy receiver can be adjusted automatically to maintain accurate measurement of an analyte level in the body even if the system shifts and/or moves relative to the person's body surface. In an example, a system can automatically vary the geometric configuration of a plurality of light-energy emitters and a light-energy receiver in order to scan through a range of tissue depths, locations, and/or types in order to measure an analyte level in the body more accurately. In an example, a plurality of light-energy emitters can emit light simultaneously. In an example, a plurality of light-energy emitters can emit light in a selected chronological sequence and/or timing pattern.

In an example, a wearable device can include a linear array, grid, and/or matrix of light-energy emitters. In an example, a wearable device can include a rectangular array, grid, and/or matrix of light-energy emitters. In an example, a wearable device can include a circular or elliptical array, grid, and/or matrix of light-energy emitters. In an example, a wearable device can include a checkerboard array, grid, and/or matrix of light-energy emitters. In an example, a wearable device can include a three-dimensional stacked array, grid, and/or matrix of light-energy emitters. In an example, a wearable device can include a sunburst and/or radial-spoke array, grid, and/or matrix of light-energy emitters. In an example, a wearable device can include a sinusoidal array, grid, and/or matrix of light-energy emitters.

In an example, a wearable device can include a linear array, grid, and/or matrix of light-energy receivers. In an example, a wearable device can include a rectangular array, grid, and/or matrix of light-energy receivers. In an example, a wearable device can include a circular or elliptical array, grid, and/or matrix of light-energy receivers. In an example, a wearable device can include a checkerboard array, grid, and/or matrix of light-energy receivers. In an example, a wearable device can include a three-dimensional stacked array, grid, and/or matrix of light-energy receivers. In an example, a wearable device can include a sunburst and/or radial-spoke array, grid, and/or matrix of light-energy receivers. In an example, a wearable device can include a sinusoidal array, grid, and/or matrix of light-energy receivers.

In an example, a wearable device can include a linear array, grid, and/or matrix of (alternating) light-energy emitters and receivers. In an example, a wearable device can include a rectangular array, grid, and/or matrix of (alternating) light-energy emitters and receivers. In an example, a wearable device can include a circular or elliptical array, grid, and/or matrix of (alternating) light-energy emitters and receivers. In an example, a wearable device can include a checkerboard array, grid, and/or matrix of (alternating) light-energy emitters and receivers. In an example, a wearable device can include a three-dimensional stacked array, grid, and/or matrix of (alternating) light-energy emitters and receivers. In an example, a wearable device can include a sunburst and/or radial-spoke array, grid, and/or matrix of (alternating) light-energy emitters and receivers. In an example, a wearable device can include a sinusoidal array, grid, and/or matrix of (alternating) light-energy emitters and receivers.

In an example, a wearable device for collecting data on a biometric parameter concerning a person's body can include a first light-energy emitter and a second light-energy emitter. In an example, the first light-energy emitter can have a first location relative to the person's body and the second light-energy emitter can have a second location relative to the person's body. In an example, the first light-energy emitter can emit light at a first angle with respect to the surface of a person's body and the second light-energy emitter can emit light at a second angle with respect to the surface of a person's body. In an example, the first light-energy emitter can emit light with a first wavelength (or spectral distribution) and the second light-energy emitter can emit light with a second wavelength (or spectral distribution).

In an example, a system can have two (or more) light-energy emitters. In an example, a first light-energy emitter can be separated from a second light-energy emitter by a selected distance. In an example, this selected distance can be expressed in inches and be within the range of $1/16"$ to $2"$. In an example, this selected distance can be expressed in metric units and be within the range of 2 mm to 5 cm. In an example, if this distance is along a circumferential axis, this selected distance can be expressed in (compass or polar coordinate) degrees and be within the range of 2 degrees to 60 degrees.

In an example, a light-energy emitter can be part of an arcuate band. In an example, a light-energy emitter can be part of a housing which is held on a person's body by an arcuate band. In an example, a system can comprise an array, grid, and/or matrix of two or more light-energy emitters with a proximal-to-distal orientation. In an example, a system can comprise an array, grid, and/or matrix of two or more light-energy emitters along a proximal-to-distal axis. In an example, a system can comprise an array, grid, and/or matrix of two or more light-energy emitters with a circumferential orientation. In an example, a system can comprise an array, grid, and/or matrix of two or more light-energy emitters along a circumferential axis.

In an example, a system can have two (or more) light-energy receivers. In an example, a first light-energy receiver can be separated from a second light-energy receiver by a selected distance. In an example, this selected distance can be expressed in inches and be within the range of $1/16"$ to $2"$. In an example, this selected distance can be expressed in metric units and be within the range of 2 mm to 5 cm. In an example, if this distance is along a circumferential axis, this selected distance can be expressed in (compass or polar coordinate) degrees and be within the range of 2 degrees to 60 degrees.

In an example, a light-energy receiver can be part of an arcuate band. In an example, a light-energy receiver can be part of a housing which is held on a person's body by an arcuate band. In an example, a system can comprise an array, grid, and/or matrix of two or more light-energy receivers with a proximal-to-distal orientation. In an example, a system can comprise an array, grid, and/or matrix of two or more light-energy receivers along a proximal-to-distal axis. In an example, a system can comprise an array, grid, and/or matrix of two or more light-energy receivers with a circumferential orientation. In an example, a system can comprise an array, grid, and/or matrix of two or more light-energy receivers along a circumferential axis.

In an example, a light-energy emitter can emit light from the inward side of a wearable device toward the surface of a person's body (e.g. finger, wrist, arm, ear, or leg). In an example, a light-energy receiver can receive light into the inward side of a wearable device which has been transmitted through or reflected by body tissue and/or fluid. In an example, there can be a flexible and/or compressible light barrier between a light-energy emitter and a light-energy receiver. In an example, a light-energy emitter and a light-energy receiver can be on the same circumferential line (e.g. circle) of a wearable device, but at different radial locations around this circumference. In an example, a light-energy emitter and a light-energy receiver can be on the same radial location around a wearable device, but on different circumferential lines (e.g. circles).

In an example, an array of emitters and/or receivers can have a circumferential axis and a proximal-to-distal axis. In an example, this array can have at least three emitters and/or receivers along a circumferential axis and at least two emitters and/or receivers along a proximal-to-distal axis. In an example, an array can be formed from a plurality of sets of emitters and receivers, wherein each set forms the vertexes of a square or rectangle. In an example, an array can be formed from a plurality of sets of emitters and receivers, wherein each set forms the vertexes of a hexagon. In an example, an array can be formed from a plurality of sets of emitters and receivers, wherein each set forms a circle.

In an example, an array, grid, and/or matrix of two or more light-energy emitters can span up to 10% of the cross-sectional circumference of a part of a person's body such as a finger, wrist, arm, ankle, or leg. In an example, an array, grid, and/or matrix of two or more light-energy emitters can span between 10% and 25% of the cross-sectional circumference of a part of a person's body such as a finger, wrist, arm, ankle, or leg. In an example, an array, grid, and/or matrix of two or more light-energy emitters can span between 25% and 50% of the cross-sectional circumference of a part of a person's body such as a finger, wrist, arm, ankle, or leg. In an example, an array, grid, and/or matrix of two or more light-energy emitters can span between 50% and 100% of the cross-sectional circumference of a part of a person's body such as a finger, wrist, arm, ankle, or leg.

In an example, an array, grid, and/or matrix of two or more light-energy receivers can span up to 10% of the cross-sectional circumference of a part of a person's body such as a finger, wrist, arm, ankle, or leg. In an example, an array, grid, and/or matrix of two or more light-energy receivers can span between 10% and 25% of the cross-sectional circumference of a part of a person's body such as a finger, wrist, arm, ankle, or leg. In an example, an array, grid, and/or matrix of two or more light-energy receivers can span between 25% and 50% of the cross-sectional circumference of a part of a person's body such as a finger, wrist, arm, ankle, or leg. In an example, an array, grid, and/or matrix of two or more light-energy receivers can span between 50% and 100% of the cross-sectional circumference of a part of a person's body such as a finger, wrist, arm, ankle, or leg.

In an example, an array, grid, and/or matrix of (alternating) light-energy emitters and receivers can span up to 10% of the circumference of a part of a person's body such as a finger, wrist, arm, ankle, or leg. In an example, an array, grid, and/or matrix of (alternating) light-energy emitters and receivers can span between 10% and 25% of the circumference of a part of a person's body such as a finger, wrist, arm, ankle, or leg. In an example, an array, grid, and/or matrix of (alternating) light-energy emitters and receivers can span between 25% and 50% of the circumference of a part of a person's body such as a finger, wrist, arm, ankle, or leg. In an example, an array, grid, and/or matrix of (alternating) light-energy emitters and receivers can span between 50% and 100% of the circumference of a part of a person's body such as a finger, wrist, arm, ankle, or leg.

In an example, compass coordinates can be defined for the circumference of a wearable device with the 0-degree point being the most ventral point when the wearable device is worn, the 90-degree point being one-quarter of the way around the circumference in a clockwise direction from the 0-degree point, the 180-degree point being opposite the 0-degree point, and the 270-degree point being one-quarter of the way around the circumference in a clockwise direction from the 180-degree point. In an example, a light-energy emitter can be separated from a light-energy receiver by between 1 and 15 degrees. In an example, a light-energy emitter can be separated from a light-energy receiver by between 10 and 45 degrees. In an example, a light-energy emitter can be separated from a light-energy receiver by more than 44 degrees. In an example, a light-energy emitter can be separated from a light-energy receiver by 45, 60, 90, or 180 degrees. In an example, a plurality of light-energy receivers can be distributed around (at least half of) the circumference of a wearable device, being pair-wise separated from each other by between 10 and 45 degrees. In an example, a plurality of light-energy receivers can be distributed around (at least half of) the circumference of a wearable device, being pair-wise separated from each other by 45, 60, 90, or 180 degrees.

In an example, a system can have a circumferential array, matrix, or grid of four or more emitters, each of which is separated from the nearest other emitter by a distance within the range of 1/16" to 2". In an example, a system can have a circumferential array, matrix, or grid of four or more emitters, each of which is separated from the nearest other emitter by a distance within the range of 2 mm to 5 cm. In an example, a system can have a circumferential array, matrix, or grid of four or more emitters, each of which is separated from the nearest other emitter by a distance within the range of 2 degrees to 60 degrees. In an example, a system can have a circumferential array of emitters which spans between 25% and 100% of the cross-sectional perimeter circumference of a part of the body (e.g. finger, wrist, arm, ankle, or leg) to which the system is attached. In an example, this circumferential array of emitters can be even spaced or distributed, with the same pair-wise distance or number of degrees between adjacent emitters.

In an example, a system can have a circumferential array, matrix, or grid of four or more receivers, each of which is separated from the nearest other receiver by a distance within the range of 1/16" to 2". In an example, a system can have a circumferential array, matrix, or grid of four or more receivers, each of which is separated from the nearest other receiver by a distance within the range of 2 mm to 5 cm. In an example, a system can have a circumferential array, matrix, or grid of four or more receivers, each of which is separated from the nearest other receiver by a distance within the range of 2 degrees to 60 degrees. In an example, a system can have a circumferential array of receivers which spans between 25% and 100% of the cross-sectional perimeter circumference of a part of the body (e.g. finger, wrist, arm, ankle, or leg) to which the system is attached. In an example, this circumferential array of receivers can be even spaced or distributed, with the same pair-wise distance or number of degrees between adjacent receivers.

In an example, different light-energy emitters and receivers can differ with respect to the timing and/or synchronization of light beams directed toward a person's body. In an example, light beam emission from different light-energy emitters can be sequenced and/or multiplexed. In an example, light beam emission and reception between different associated pairs of light-energy emitters and receivers can be sequenced to isolate measurement of biometric values from different tissue depths and/or locations. In an example, emission and reception of light-energy between different pairs of light-energy emitters and light-energy receivers can be multiplexed. In an example, emission of light-energy from multiple light-energy emitters can be sequenced and/or multiplexed to be received by a single light-energy receiver at different times.

In an example, a first light-energy emitter can emit light during a first time period and a second light-energy emitter can emit light during a second time period. In an example, a first light-energy receiver can receive light during a first time period and the second light-energy receiver can receive light during a second time period. In an example, the first light-energy emitter can emit light during a first environmental condition and the second light-energy emitter can emit light during a second environmental condition. In an example, the first light-energy emitter can emit light when the person is engaged in a first type of physical activity and the second light-energy emitter can emit light when the person is engaged in a second type of physical activity.

In an example, the angle of a beam of light emitted from a light-energy emitter can be changed over time to create a chronological sequence of beams of light with different projection and/or body incidence angles. In an example, the power or intensity of a beam of light emitted from a light-energy emitter can be changed over time to create a chronological sequence of beams of light with different power or intensity levels. Such sequences can help to more accurately measure an analyte level in the body.

In an example, the depth, breadth, location, and/or type of body tissue or fluid from which light from a light-energy emitter is reflected can be changed by adjusting the coherence, polarization, and/or phase of light emitted from the light-energy emitter. In an example, the coherence, polarization, and/or phase of light emitted from the light-energy emitter can be adjusted in order to more accurately measure an analyte level in the body. In an example, the coherence, polarization, and/or phase of light emitted from the light-energy emitter can be adjusted automatically (in an iterative manner) by a system in order to more accurately measure an analyte level in the body for a specific person, for a specific type of activity, or for a specific configuration of the system relative to the person's body surface.

In an example, the coherence, polarization, and/or phase of light emitted from the light-energy emitter can be adjusted automatically to maintain accurate measurement of an analyte level in the body even if the system shifts and/or moves relative to the person's body surface. In an example, a system can automatically vary the coherence, polarization, and/or phase of light from a light-energy emitter to scan through a range of tissue depths, locations, and/or types in order to obtain more accurate measurement of an analyte level in the body. In an example, a system can further comprise one or more optical filters or lenses which change the coherence, polarization, and/or phase of light emitted by a light-energy emitter.

In an example, the depth, breadth, location, and/or type of body tissue or fluid from which light from a light-energy emitter is reflected can be changed by adjusting the frequency, color, and/or spectrum of light emitted from the light-energy emitter. In an example, the frequency, color, and/or spectrum of light emitted from the light-energy emitter can be adjusted in order to more accurately measure an analyte level in the body. In an example, the frequency, color, and/or spectrum of light emitted from the light-energy emitter can be adjusted automatically (in an iterative manner) by a system in order to more accurately measure an analyte level in the body for a specific person, for a specific type of activity, or for a specific configuration of the system relative to the person's body surface.

In an example, the frequency, color, and/or spectrum of light emitted from the light-energy emitter can be adjusted automatically to maintain accurate measurement of an analyte level in the body even if the system shifts and/or moves relative to the person's body surface. In an example, a system can automatically vary the frequency, color, and/or spectrum of light from a light-energy emitter to scan through a range of tissue depths, locations, and/or types in order to obtain more accurate measurement of an analyte level in the body. In an example, a system can further comprise one or more optical filters or lenses which change the frequency, color, and/or spectrum of light emitted by a light-energy emitter. In an example, the frequency, color, and/or spectrum of a beam of light emitted from a light-energy emitter can be changed over time to create a chronological sequence of beams of light with different frequencies, colors, and/or spectrums.

In an example, the frequency, color, and/or spectrum of a beam of light emitted from a light-energy emitter can be changed in response to specific environmental conditions (e.g. temperature or humidity) and/or specific activities in which the person wearing a system is engaged (e.g. high level of movement, eating, sleeping, etc.) in order to more accurately measure an analyte level in the body. In an example, the projection angle of a beam of light emitted from a light-energy emitter can be changed in response to specific environmental conditions (e.g. temperature or humidity) and/or specific activities in which the person wearing a system is engaged (e.g. high level of movement, eating, sleeping, etc.) in order to more accurately measure an analyte level in the body. In an example, the power and/or intensity of a beam of light emitted from a light-energy emitter can be changed in response to specific environmental conditions (e.g. temperature or humidity) and/or specific activities in which the person wearing a system is engaged (e.g. high level of movement, eating, sleeping, etc.) in order to more accurately measure an analyte level in the body.

In an example, the geometric configuration of a light-energy emitter and a plurality of light-energy receivers can be adjusted automatically (in an iterative manner) by a system in order to more accurately measure an analyte level in the body for a specific person, for a specific type of activity, or for a specific configuration of the system relative to the person's body surface. In an example, the geometric configuration of a light-energy emitter and a plurality of light-energy receivers can be adjusted automatically to maintain accurate measurement of an analyte level in the body even if the system shifts and/or moves relative to the person's body surface. In an example, a system can automatically vary the geometric configuration of a light-energy emitter and a plurality of light-energy receivers in order to scan through a range of tissue depths, locations, and/or types in order to measure an analyte level in the body more accurately.

In an example, a light-energy emitter (or light-energy receiver) can be automatically moved relative to a wearable housing which holds it. In an example, a light-energy emitter (or light-energy receiver) can be automatically tilted, rotated, raised, or lowered by an actuator. In an example, a light-energy emitter (or light-energy receiver) can be automatically tilted, rotated, raised, or lowered if the wearable housing which holds it moves relative to the body surface on which it is worn. In an example, a light-energy emitter (or light-energy receiver) can be automatically tilted, rotated, raised, or lowered in order to maintain a selected distance (or distance range) from the surface of a person's body. In an example, a light-energy emitter (or light-energy receiver) can be automatically tilted, rotated, raised, or lowered in order to maintain a selected angle (or angle range) with respect to the surface of a person's body.

In an example, a wearable device can further comprise a rotating member which holds a light-energy emitter, a light-energy receiver, or both. In an example, rotation of this member can be done manually. In an example, this rotation can be done automatically by one or more actuators. In an example, the distance between a light-energy emitter and a light-energy receiver can be adjusted by rotating the rotating member. In an example, the location of a light-energy emitter and/or a light-energy receiver relative to a person's body can be adjusted by rotating the rotating member. In an example, movement of a light-energy emitter, a light-energy receiver, or both by a rotating member can enable more accurate measurement of an analyte level in the body. In an example, such movement of a light-energy emitter, a light-energy receiver, or both can enable customization of a system to the anatomy of a specific person for more accurate measurement of that person's analyte level.

In an example, the depth, breadth, location, and/or type of body tissue or fluid from which light from a light-energy emitter is reflected can be changed by adjusting the angle of light emitted from the light-energy emitter. In an example, the angle of light emitted from the light-energy emitter can be adjusted in order to more accurately measure an analyte level in the body. In an example, the angle of light emitted from the light-energy emitter can be adjusted automatically (in an iterative manner) by a system in order to more accurately measure an analyte level in the body for a specific person, for a specific type of activity, or for a specific configuration of the system relative to the person's body surface. In an example, the angle of light emitted from the light-energy emitter can be adjusted automatically to maintain accurate measurement of an analyte level in the body even if the system shifts and/or moves relative to the person's body surface. In an example, a system can automatically vary the angle of light from a light-energy emitter to scan through a range of tissue depths, locations, and/or types in order to obtain more accurate measurement of an analyte level in the body. In an example, a system can further comprise one or more optical filters or lenses which change the projection and/or body incidence angle of a light beam emitted by a light-energy emitter.

In an example, the depth, breadth, location, and/or type of body tissue or fluid from which light from a light-energy emitter is reflected can be changed by adjusting the power and/or intensity of light emitted from the light-energy emitter. In an example, the power and/or intensity of light emitted from the light-energy emitter can be adjusted in order to more accurately measure an analyte level in the body. In an example, the power and/or intensity of light emitted from the light-energy emitter can be adjusted automatically (in an iterative manner) by a system in order to more accurately measure an analyte level in the body for a specific person, for a specific type of activity, or for a specific configuration of the system relative to the person's body surface. In an example, the power and/or intensity of light emitted from the light-energy emitter can be adjusted automatically to maintain accurate measurement of an analyte level in the body even if the system shifts and/or moves relative to the person's body surface. In an example, a system can automatically vary the power and/or intensity of light from a light-energy emitter to scan through a range of tissue depths, locations, and/or types in order to obtain more accurate measurement of an analyte level in the body.

In an example, the depth, breadth, location, and/or type of body tissue or fluid from which light from a light-energy emitter is reflected and received by a light-energy receiver can be changed by adjusting the distance between a light-energy emitter and a light-energy receiver. In an example, the distance between a light-energy emitter and a light-energy receiver can be adjusted in order to more accurately measure an analyte level in the body. In an example, the distance between a light-energy emitter and a light-energy receiver can be adjusted automatically (in an iterative manner) by a system in order to more accurately measure an analyte level in the body for a specific person, for a specific type of activity, or for a specific configuration of the system relative to the person's body surface. In an example, the distance between a light-energy emitter and a light-energy receiver can be adjusted automatically to maintain accurate measurement of an analyte level in the body even if the system shifts and/or moves relative to the person's body surface. In an example, a system can automatically vary the distance between a light-energy emitter and a light-energy receiver to scan through a range of tissue depths, locations, and/or types in order to obtain more accurate measurement of an analyte level in the body.

In an example, a wearable device can further comprise a track, channel, or slot along which a light-energy emitter, a light-energy receiver, or both can be moved. In an example, this movement can be done automatically by one or more actuators. In an example, this track, channel, or slot can have a circumferential orientation. In an example, this track, channel, or slot can have a proximal-to-distal orientation. In an example, the distance between a light-energy emitter and a light-energy receiver can be adjusted by moving the emitter, the receiver, or both along such a track, channel, or slot. In an example, the location of a light-energy emitter and/or a light-energy receiver relative to a person's body can be adjusted by moving the emitter, the receiver, or both along such a track, channel, or slot. In an example, movement of a light-energy emitter, a light-energy receiver, or both along a track, channel, or slot can enable more accurate measurement of an analyte level in the body. In an example, movement of a light-energy emitter, a light-energy receiver, or both along a track, channel, or slot can enable customization of a wearable device to the anatomy of a specific person for more accurate measurement of that person's analyte level.

In an example, a beam of light can: be emitted by the light-energy emitter along a first vector; hit body tissue; reflect back from the body tissue; pass through a lens or light guide; and enter the light-energy receiver along a second vector which is reversed from and parallel to the first vector. In an example, a beam of light can: be emitted by the light-energy emitter along a first vector; hit body tissue; reflect back from the body tissue; pass through a rotating and/or tilting lens or light guide; and enter the light-energy receiver along a second vector which is reversed from and parallel to the first vector. In an example, a beam of light can: be emitted by the light-energy emitter along a first vector; hit body tissue; reflect back from the body tissue; pass through a lens or light guide which is rotated and/or tilted by an actuator; and enter the light-energy receiver along a second vector which is reversed from and parallel to the first vector.

In an example, the beam of light emitted by a light-energy emitter can be automatically moved by using an actuator to automatically move a lens (or light guide) through which this beam is transmitted. In an example, the beam of light emitted by a light-energy emitter can be automatically moved by using an actuator to automatically rotate, tilt, raise, or lower a lens (or light guide) through which this beam is transmitted. In an example, the beam of light emitted by a light-energy emitter can be automatically moved by using an actuator to automatically change the focal distance of a lens (or light guide) through which this beam is transmitted. In an example, the beam of light emitted by a light-energy emitter can be automatically moved by using an actuator to automatically move a light guide through which this beam is transmitted. In an example, the beam of light emitted by a light-energy emitter can be automatically moved by using an actuator to automatically rotate, tilt, raise, or lower a light guide through which this beam is transmitted. In an example, the beam of light emitted by a light-energy emitter can be automatically moved by using an actuator to automatically move a light reflector (such as a mirror) from which this beam is reflected. In an example, the beam of light emitted by a light-energy emitter can be automatically moved by using an actuator to automatically rotate, tilt, raise, or lower a light reflector (such as a mirror) from which this beam is reflected.

In an example, a blood pump can be incorporated into an artificial blood flow lumen and/or vessel. In an example, an artificial blood flow lumen and/or vessel can be implanted into fluid communication with a natural blood vessel by one or more connecting members or connection methods selected from the group consisting of: endovascular and/or transluminal insertion and expansion, surgical anastomosis, surgical sutures, purse string suture, drawstring, pull tie, friction fit, surgical staples, tissue adhesive, gel, fluid seal, chemical bonding, cauterization, blood vessel connector and/or joint, vessel branch, twist connector, helical threads or screw connector, connection port, interlocking joints, tongue and groove connection, flanged connector, beveled ridge, magnetic connection, plug connector, circumferential ring, inflatable ring, and snap connector.

In an example, an implanted blood flow lumen can be selected from the group consisting of: artificial vessel segment, bioengineered vessel segment, transplanted vessel segment, artificial vessel joint, vessel branch, stent or other expandable mesh or framework, artificial lumen, manufactured catheter, manufactured tube, valve, vessel valve segment, multi-channel lumen, blood pump housing, and elastic blood chamber. In an example, an implanted blood flow lumen can have a longitudinal axis which is relatively straight. In an example, an implanted blood flow lumen can have a longitudinal axis which is arcuate. In an example, an implanted blood flow lumen can have a longitudinal axis which follows the shape of longitudinal axis of the natural blood vessel with which the implanted blood flow lumen is in fluid communication.

In another example, an implanted blood flow lumen containing a blood pump can spliced into a natural blood vessel (from an upstream location to a downstream location) so as to entirely replace a longitudinal segment of the natural blood vessel. An advantage of this splicing approach is that blood flow need not be bifurcated; this can reduce potential thrombogenesis from flow junctures. Even when blood flows are divided among multiple intra-luminal channels within an implanted blood flow lumen, there is greater design flexibility in an entirely-manufactured blood flow lumen. This design flexibility can be used to create hemodynamic flow patterns which minimize thrombogenesis despite the splitting of blood flows. A potential disadvantage of this splicing approach is that it involves the removal of a longitudinal segment of the natural blood vessel.

In another example, an implanted blood flow lumen can be configured to be implanted at least partially outside the walls of the natural blood vessel with which the implanted blood flow lumen is in fluid communication. In an example, an implanted blood flow lumen can bifurcate (and then reconverge) blood flow from an upstream location to a downstream location. In an example, an implanted blood flow lumen can divide pre-implantation blood flow through a natural blood vessel from an upstream location to a downstream location into a first blood flow and a second blood flow. In an example, these two blood flows can flow in parallel (in terms of flow dynamics even if not parallel in terms of geometry) for a while. In an example, these first and second flows can diverge at an upstream location and then reconverge at a downstream location.

In an example, this system can further comprise one or more components selected from the group consisting of: accelerometer, augmented reality eyewear, chemiresistor, electromagnetic energy sensor, human-to-computer interface, photodetector, acoustic energy sensor, breathing rate sensor, digital camera, galvanic skin response (GSR) sensor, microphone, solar panel, VR eyewear, brain oxygenation sensor, deely bobbers, eye muscle (EOG) sensor, microchip, skin conductance sensor, vibrating component, and drug pump.

In an example data from wearable sensors can be analyzed using an analytical method selected from the group consisting of: Analysis of Variance (ANOVA), Artificial Neural Network (ANN), Auto-Regressive (AR) Modeling, Bayesian Analysis, Bonferroni Analysis (BA), Centroid Analysis, Chi-Squared Analysis, Cluster Analysis, Correlation, Covariance, Data Normalization (DN), Decision Tree Analysis (DTA), Discrete Fourier transform (DFT), Discriminant Analysis (DA), Edgar AI Analysis, Carlavian Curve Analysis (CCA), and Empirical Mode Decomposition (EMD).

In an example, this system can further comprise one or more components selected from the group consisting of: barometric pressure sensor, chewing sensor, electromyographic (EMG) sensor, hydration sensor, photoplethysmography (PPG) sensor, stretch sensor, allergen sensor, capacitive sensor, electrical resistance sensor, gyroscope, multiaxial accelerometer, drug reservoir, battery, cholesterol sensor, electronic tablet, hygrometry sensor, piezoelectric sensor, swallow sensor, bend sensor, chromatographic sensor, and electronically-functional eyewear.

In an example data from wearable sensors can be analyzed using an analytical method selected from the group consisting of: Factor Analysis (FA), Fast Fourier Transform (FFT), Feature Vector Analysis (FVA), Fisher Linear Discriminant, Fourier Transformation (FT) Method, Fuzzy Logic (FL) Modeling, Gaussian Model (GM), Generalized Auto-Regressive Conditional Heteroscedasticity (GARCH) Modeling, Hidden Markov Model (HMM), Independent Components Analysis (ICA), Inter-Band Power Ratio, Inter-Channel Power Ratio, Inter-Montage Power Mean, Inter-Montage Ratio, Kalman Filter (KF), Kernel Estimation, Laplacian Filter, and Laplacian Montage Analysis.

In an example, this system can further comprise one or more components selected from the group consisting of: impedance sensor, piezoresistive sensor, sweat sensor, biochemical sensor, compass, electrophoresis sensor, inclinometer, pneumography sensor, temperature sensor, ambient temperature sensor, cardiotachometer, electromagnetic actuator, home automation control system, oximeter, blood glucose sensor, computer-to-human interface, energy transducer to generate energy from ambient electromagnetic energy, and inertial sensor.

In an example data from wearable sensors can be analyzed using an analytical method selected from the group consisting of: Least Squares Estimation, Linear Regression, Linear Transform, Logit Model, Machine Learning (ML), Markov Model, Maximum Entropy Modeling, Maximum Likelihood, Mean Power, Multi-Band Covariance Analysis, Multi-Channel Covariance Analysis, and Multivariate Linear Regression.

In an example, this system can further comprise one or more components selected from the group consisting of: pollution sensor, thermal energy sensor, blood pressure sensor, conductive fabric, energy transducer to generate energy from body motion or kinetic energy, keypad, power source, thermistor, blood reservoir, conductivity sensor, energy transducer to generate energy from body thermal energy, magnetic field sensor, pressure sensor, thermocouple, buzzer, display screen, global positioning system (GPS), mobile phone, and speaker.

In an example data from wearable sensors can be analyzed using an analytical method selected from the group consisting of: Multivariate Logit, Multivariate Regression, Naive Bayes Classifier, Neural Network, Non-Linear Programming, Non-negative Matrix Factorization (NMF), Power Spectral Density, Power Spectrum Analysis, Principal Components Analysis (PCA), Probit Model, and Quadratic Minimum Distance Classifier.

In an example, this system can further comprise one or more components selected from the group consisting of: wireless data receiver, buttons, digital memory, gesture recognition interface, microprocessor, sound-emitting member, wireless communication module, amino acid sensor, cell phone, electromagnetic conductivity sensor, home electronics portal, oximetry sensor, AR eyewear, chemical sensor, electromagnetic energy emitter, home thermostat, pH level sensor, action potential sensor, caloric intake monitor, glucose sensor, motion sensor, spectrophotometer, altitude sensor, capnography sensor, electrocardiographic (ECG) sensor, and Hall-effect sensor.

In an example data from wearable sensors can be analyzed using an analytical method selected from the group consisting of: Random Forest (RF), Random Forest Analysis (RFA), Regression Model, Signal Amplitude (SA), Signal Averaging, Signal Decomposition, Sine Wave Compositing, Singular Value Decomposition (SVD), Spine Function, Support Vector and/or Machine (SVM), Time Domain Analysis, Time Frequency Analysis, Time Series Model, Trained Bayes Classifier, Variance, Waveform Identification, Wavelet Analysis, and Wavelet Transformation.

In an example, this system can further comprise one or more components selected from the group consisting of: neural impulse sensor, ballistocardiographic sensor, chemoreceptor, electromagnetic impedance sensor, humidity sensor, photodiode, strain gauge, ambient humidity sensor, carbon dioxide level, electrochemical sensor, heart rate monitor, olfactory sensor, ambient noise sensor, cardiopulmonary function sensor, electrogoniometer, hemoencephalography (HEG) sensor, optoelectronic sensor, brain-to-computer interface (BCI), and dial.

In an example, this system can further comprise one or more components selected from the group consisting of: food consumption sensor, microfluidic sensor, smart phone, voice recognition interface, air quality sensor, capacitance hygrometry sensor, electric motor, goniometer, motor, speech recognition interface, wireless data transmitter, brain activity sensor, data processor, environmental oxygen level sensor, Micro Electro Mechanical System (MEMS), pulse rate sensor, touch screen, ambient light sensor, and carbon monoxide sensor. In an example, this system can further comprise one or more components selected from the group consisting of: electroencephalographic (EEG) sensor, heart rate variability sensor, one-way valve, blood volume sensor, control unit, energy transmitted through inductively-coupled coils, magnetometer, pulse oximetry sensor, and thrombus-catching net.

In an example, a system for cardiac function assistance can comprise: a wearable device, wherein the wearable device further comprises a light-energy emitter, a light-energy receiver, a data processor, and a power source; wherein the wearable device collects data on a biometric parameter; and an implanted cardiac pacemaker; wherein operation of the implanted cardiac pacemaker is controlled and/or adjusted based on analysis of the data on the biometric parameter.

In an example, a system for cardiac function assistance can comprise: a wearable device which is worn by a person; wherein the wearable device further comprises a light-energy emitter, a light-energy receiver, a data processor, a power source, and a first data transmitter and/or receiver; wherein light energy from the light-energy emitter is transmitted through or reflected from the person's body tissue and/or fluid before it reaches the light-energy receiver; and wherein a change in the spectrum of light energy received by the light-energy receiver due to transmission of the light energy through body tissue and/or fluid or reflection of the light energy from body tissue and/or fluid is analyzed to estimate a value of a biometric parameter concerning the person's body; and an implanted cardiac pacemaker and a second data transmitter and/or receiver which are implanted in the person's body, wherein operation of the implanted cardiac pacemaker is controlled and/or adjusted based on the estimated value of the biometric parameter.

In an example, a system for cardiac function assistance can comprise: a finger ring, smart watch, wrist band, ankle band, ear ring, or smart sock which is worn by a person; wherein the finger ring, smart watch, wrist band, ankle band, ear ring, or smart sock further comprises a light-energy emitter, a light-energy receiver, a data processor, a power source, and a first data transmitter and/or receiver; wherein light energy from the light-energy emitter is transmitted through or reflected from the person's body tissue and/or fluid before it reaches the light-energy receiver; and wherein a change in the spectrum of light energy received by the light-energy receiver due to transmission of the light energy through body tissue and/or fluid or reflection of the light energy from body tissue and/or fluid is analyzed to estimate the person's body oxygenation level; and an implanted cardiac pacemaker and a second data transmitter and/or receiver which are implanted in the person's body, wherein operation of the implanted cardiac pacemaker is controlled and/or adjusted based on the person's body oxygenation level.

In an example, a system for cardiac function assistance can comprise: a wearable device, wherein the wearable device further comprises a light-energy emitter, a light-energy receiver, a data processor, and a power source; wherein the wearable device collects data on a biometric parameter; and an implanted central blood pump; wherein operation of the implanted central blood pump is controlled and/or adjusted based on analysis of the data on the biometric parameter.

In an example, a system for cardiac function assistance can comprise: a wearable device which is worn by a person; wherein the wearable device further comprises a light-energy emitter, a light-energy receiver, a data processor, a power source, and a first data transmitter and/or receiver; wherein light energy from the light-energy emitter is transmitted through or reflected from the person's body tissue and/or fluid before it reaches the light-energy receiver; and wherein a change in the spectrum of light energy received by the light-energy receiver due to transmission of the light energy through body tissue and/or fluid or reflection of the light energy from body tissue and/or fluid is analyzed to estimate a value of a biometric parameter concerning the person's body; and an implanted central blood pump and a second data transmitter and/or receiver which are implanted in the person's body, wherein operation of the implanted central blood pump is controlled and/or adjusted based on the estimated value of the biometric parameter.

In an example, a system for cardiac function assistance can comprise: a finger ring, smart watch, wrist band, ankle band, ear ring, or smart sock which is worn by a person; wherein the finger ring, smart watch, wrist band, ankle band, ear ring, or smart sock further comprises a light-energy emitter, a light-energy receiver, a data processor, a power source, and a first data transmitter and/or receiver; wherein light energy from the light-energy emitter is transmitted through or reflected from the person's body tissue and/or fluid before it reaches the light-energy receiver; and wherein a change in the spectrum of light energy received by the light-energy receiver due to transmission of the light energy through body tissue and/or fluid or reflection of the light energy from body tissue and/or fluid is analyzed to estimate the person's body oxygenation level; and an implanted central blood pump and a second data transmitter and/or receiver which are implanted in the person's body, wherein operation of the implanted central blood pump is controlled and/or adjusted based on the person's body oxygenation level.

In an example, a closed loop system for human circulatory assistance comprising: a first wearable device which is worn by a person on a first external location of the person's body; wherein the first wearable device further comprises a first light-energy emitter, a first light-energy receiver, a first data processor, and a first power source; and wherein the first wearable device collects data on a biometric parameter from the first location; a second wearable device which is worn by a person on a second external location of the person's body; wherein the second wearable device further comprises a second light-energy emitter, a second light-energy receiver, a second data processor, and a second power source; and wherein the second wearable device collects data on the biometric parameter from the second location; a first implanted non-central blood pump, wherein the first implanted non-central blood pump selectively increases blood flow to the first external location of the person's body based on the value of the biometric parameter at the first external location; and a second implanted non-central blood pump, wherein the second implanted non-central blood pump selectively increases blood flow to the second external location of the person's body based on the value of the biometric parameter at the second external location.

In an example, a system for cardiac function assistance can comprise: (1) a first wearable device which is worn by a person on a first external location of the person's body; wherein the wearable device further comprises a first light-energy emitter, a first light-energy receiver, a first data processor, a first power source, and a first data transmitter and/or receiver; wherein light energy from the first light-energy emitter is transmitted through or reflected from the person's body tissue and/or fluid before it reaches the first light-energy receiver; and wherein a change in the spectrum of light energy received by the first light-energy receiver due to transmission of the light energy through body tissue and/or fluid or reflection of the light energy from body tissue and/or fluid is analyzed to estimate a first value of a biometric parameter concerning the person's body; (2) a second wearable device which is worn by a person on a second external location of the person's body; wherein the wearable device further comprises a second light-energy emitter, a second light-energy receiver, a second data processor, a second power source, and a second data transmitter and/or receiver; wherein light energy from the second light-energy emitter is transmitted through or reflected from the person's body tissue and/or fluid before it reaches the second light-energy receiver; and wherein a change in the spectrum of light energy received by the second light-energy receiver due to transmission of the light energy through body tissue and/or fluid or reflection of the light energy from body tissue and/or fluid is analyzed to estimate a second value of a biometric parameter concerning the person's body; (3) a first implanted non-central blood pump, wherein the first implanted non-central blood pump selectively increases blood flow to the first external location of the person's body based on the first value of the biometric parameter; and (4) a second implanted non-central blood pump, wherein the second implanted non-central blood pump selectively increases blood flow to the second external location of the person's body based on the second value of the biometric parameter.

In an example, a system for cardiac function assistance can comprise: (1) a first finger ring, smart watch, wrist band, ankle band, ear ring, or smart sock which is worn by a person on a first external location of the person's body; wherein the finger ring, smart watch, wrist band, ankle band, ear ring, or smart sock further comprises a first light-energy emitter, a first light-energy receiver, a first data processor, a first power source, and a first data transmitter and/or receiver; wherein light energy from the first light-energy emitter is transmitted through or reflected from the person's body tissue and/or fluid before it reaches the first light-energy receiver; and wherein a change in the spectrum of light energy received by the first light-energy receiver due to transmission of the light energy through body tissue and/or fluid or reflection of the light energy from body tissue and/or fluid is analyzed to estimate a first value of the person's body oxygenation level; (2) a second finger ring, smart watch, wrist band, ankle band, ear ring, or smart sock which is worn by a person on a second external location of the person's body; wherein the finger ring, smart watch, wrist band, ankle band, ear ring, or smart sock further comprises a second light-energy emitter, a second light-energy receiver, a second data processor, a second power source, and a second data transmitter and/or receiver; wherein light energy from the second light-energy emitter is transmitted through or reflected from the person's body tissue and/or fluid before it reaches the second light-energy receiver; and wherein a change in the spectrum of light energy received by the second light-energy receiver due to transmission of the light energy through body tissue and/or fluid or reflection of the light energy from body tissue and/or fluid is analyzed to estimate a second value of the person's body oxygenation level; (3) a first implanted non-central blood pump, wherein the first implanted non-central blood pump selectively increases blood flow to the first external location of the person's body based on the first value of the person's body oxygenation level; and (4) a second implanted non-central blood pump, wherein the second implanted non-central blood pump selectively increases blood flow to the second external location of the person's body based on the second value of the person's body oxygenation level.

Photoplethysmography (PPG) is a method which analyzes variation in the amount (and spectral distribution) of light which is caused by reflection of the light from (or transmission of the light through) body tissue in order to measure one or more biometric parameters (such as heart rate or heart rate variation). Changes in the shape of blood vessels and flow of blood through body tissue change the amount (and spectral distribution) of light which is reflected from, or transmitted through, the body tissue. Wearable photoplethysmography (PPG) devices include at least one light emitter (whose light is directed toward body tissue) and at least one light receiver (which receives this light after it has been reflected from, or transmitted through, the body tissue).

Biometric information from a wearable photoplethysmography (PPG) device can be used to adjust the operation of an implanted device such as a cardiac pacemaker, creating a peripheral feedback loop or (in the extreme) closed-loop system for improving cardiac function, maintaining peripheral tissue health, and/or managing a heart condition. Measurement of one or more biometric parameters from one or more peripheral locations (such as a person's ears, fingers, or feet) can provide information on cardiac function and peripheral tissue health which is not available from a central location such as a person's heart or abdomen. A wearable photoplethysmography (PPG) device and an implanted cardiac pacemaker can together comprise a system for improving cardiac function, maintaining peripheral tissue health, and/or treating a heart condition. Such a system can provide a feedback loop for automatic adjustment and optimal operation of a person's cardiac pacemaker based on biometric parameters measured from one or more peripheral locations on the person's body.

In an example, a system for cardiac rhythm management can comprise an implanted cardiac pacemaker whose operation is automatically adjusted based on one or more biometric parameters which are measured by a wearable photoplethysmography (PPG) device. In an example, a peripheral feedback system with both a wearable PPG device and an implanted cardiac pacemaker can help to treat congestive heart failure. In an example, a peripheral feedback system with both a wearable PPG device and a implanted cardiac pacemaker can be used to help diagnosis and/or treat a condition selected from the group consisting of arrhythmia, arteriosclerosis, atherosclerosis, atherosclerotic pathology, fibrillation, autonomic dysfunction, cardio-pulmonary health, congestive heart failure, endothelial dysfunction, hypovolemia, peripheral arterial disease, poor peripheral circulation, premature ventricular contraction, stress level, and tachycardia.

In an example, a wearable photoplethysmography (PPG) device can collect information on light which has been reflected from, or transmitted through, body tissue in order to measure one or more biometric parameters selected from the group consisting of Heart Rate (HR), Heart Rate Variability (HRV), Blood Volume Pulse (BVP), Inter-Beat Interval (IBI), Peak-to-Peak Interval (PPI), Blood Pulse Rate (BPR), Blood Volume Pulse (BVP), Blood Volume Amplitude (BVP), Peak Amplitude (PA), Pulse Area, Pulse Transit Time (PTT), Standard Deviation of Average Normal to Normal Beat (SDANN), Systolic Amplitude, Systolic Peak Amplitude, Blood Pressure, Oxygen Saturation, VO2, VO2max, Hydration Level, and Respiration and/or Breathing Rate.

In an example, the operation of an implanted cardiac pacemaker can be changed by changing one or more operating parameters selected from the group consisting of frequency of heart stimulations, atrioventricular (AV) pacing interval, interventricular (IV) pacing interval, coordination between stimulations of different heart chambers, timing of stimulations of different heart chambers, location(s) of the heart to which electromagnetic energy is delivered, regularity of heart stimulations, magnitude of heart stimulations, voltage of heart stimulations, initiation of heart stimulations, and cessation of heart stimulations.

In an example, a wearable photoplethysmography (PPG) device can be worn on a person's body at location which is selected from the group consisting of a person's ear (e.g. ear lobe or ear canal), nose (e.g. septum), forehead, neck, hand (e.g. finger), wrist, arm, toe, ankle, leg, and waist. In an example, a wearable photoplethysmography (PPG) device can be embodied in a wearable device with a form which is selected from the group consisting of earbud, hearing aid, ear ring, headset, headphone, nose ring, eyeglasses, necklace, collar, finger ring, wrist band, smart watch, smart cuff, bracelet, arm band, sleeve, toe ring, sock, ankle band, and belt.

In an example, one or more light emitters of a wearable photoplethysmography (PPG) device can be of a type which is selected from the group consisting of light emitting diode (LED), laser diode (LD), micro-plasma emitter, and incandescent bulb. In an example, a first light emitter can emit light in a first wavelength (or frequency band) and a second light emitter can emit light in a second wavelength (or frequency band or color) which is different than the first wavelength (or frequency band or color). In an example, a light emitter can emit light with a variable (e.g. scanning) wavelength (of frequency). In an example, the light can be infrared light, near-infrared light, or ultraviolet light. In an example, the light can be coherent light. In an example, a light emitter can be a laser.

In an example, a first light emitter can emit light in a first direction (e.g. vector) and a second light emitter can emit light in a second direction (e.g. vector) which is different than the first direction (e.g. vector). In an example, the first and second directions (e.g. vectors) can be parallel to each other. In an example, the first and second directions (e.g. vectors) can be coaxial. In an example, the first and second directions (e.g. vectors) can be perpendicular to each other. In an example, the first and/or second directions (e.g. vectors) can be moved by one or more electromagnetic actuators. In an example, the first and/or second directions (e.g. vectors) can be moved by an array of moving micromirrors.

In an example, a first light emitter can emit light from a first (radial) location relative to a body member and a second light emitter can emit light from a second (radial) location relative to the body member which is different than the first location. In an example, wearable photoplethysmography (PPG) device can comprise a circumferential array of light emitters which are distributed around the circumference of a body member such as a finger, wrist, or arm. In an example, a first light emitter can emit light at a first time and a second light emitter can emit light at a second time which is different than the first time.

In an example, one or more light receivers of a wearable photoplethysmography (PPG) device can be selected from the group consisting of photodetector, optical detector, photodiode, and phototransistor. In an example, a first light receiver can receive light from a first (radial) location relative to a body member and a second light receiver can receive light from a second (radial) location relative to the body member which is different than the first location. In an example, wearable photoplethysmography (PPG) device can comprise a circumferential array of light emitters and light receivers which are distributed around the circumference of a body member such as a finger, wrist, or arm.

In an example, a wearable photoplethysmography (PPG) device can further include one or more light guides (such as lenses, mirrors, or prisms) which direct the paths of light rays between the light emitter and a person's body or between the person's body and the light receiver. In an example, a wearable photoplethysmography (PPG) device can further include one or more light barriers between a light emitter and a light receiver to block transmission of light from the emitter to the receiver except through body tissue. In an example, a wearable photoplethysmography (PPG) device can include one or more light barriers between the environment and a light receiver to block transmission of ambient light to the light receiver. In an example, a wearable photoplethysmography (PPG) device can further comprise an inertial motion sensor (such as an accelerometer and/or a gyroscope).

In an example, a wearable photoplethysmography (PPG) device can also include compressible foam which holds a light emitter, a light receiver, and/or a light guide snugly against a person's body. This can reduce measurement errors due to body motion. In an example, a wearable photoplethysmography (PPG) device can include a spring or elastic member whose tension and/or length is adjusted to hold a light emitter, a light receiver, and/or a light guide snugly against a person's body. In an example, a wearable photoplethysmography (PPG) device can include an inflatable member or an electromagnetic actuator which holds a light emitter, a light receiver, and/or a light guide snugly against a person's body to reduce errors due to body motion. In an example, a spring, elastic member, inflatable member, and/or electromagnetic actuator can be adjusted in response to motion detected by a motion sensor in order to hold a light emitter, a light receiver, and/or a light guide more snugly against a person's body when the body is moving a lot.

In an example, a peripheral feedback system for cardiac rhythm management can comprise: (a) a first implanted photoplethysmography (PPG) device, wherein the first PPG device is implanted in a first peripheral location (e.g. arm or leg) of a person's body, wherein the first implanted PPG device further comprises at least one first light emitter and at least one first light receiver, wherein changes in the amount (and/or spectrum) of light from the first light emitter which is received by the first light receiver caused by reflection of the light from (or transmission of the light through) body tissue at the first peripheral location are analyzed in order to measure pulse magnitude; (b) a second implanted photoplethysmography (PPG) device, wherein the second PPG device is implanted in a second peripheral location (e.g. arm or leg) of a person's body, wherein the second implanted PPG device further comprises at least one second light emitter and at least one second light receiver, wherein changes in the amount (and/or spectrum) of light from the second light emitter which is received by the second light receiver caused by reflection of the light from (or transmission of the light through) body tissue at the second peripheral location are analyzed in order to measure pulse magnitude; and (c) an implanted cardiac pacemaker, wherein the operation of the implanted cardiac pacemaker is automatically adjusted based on comparison and/or multivariate analysis of the pulse magnitude values measured by the first implanted PPG device and the second implanted PPG device.

In an example, a system for treating congestive heart failure can comprise: (a) a first implanted photoplethysmography (PPG) device, wherein the first PPG device is implanted in a first peripheral location (e.g. arm or leg) of a person's body, wherein the first implanted PPG device further comprises at least one first light emitter and at least one first light receiver, wherein changes in the amount (and/or spectrum) of light from the first light emitter which is received by the first light receiver caused by reflection of the light from (or transmission of the light through) body tissue at the first peripheral location are analyzed in order to measure pulse magnitude; (b) a second implanted photoplethysmography (PPG) device, wherein the second PPG device is implanted in a second peripheral location (e.g. arm or leg) of a person's body, wherein the second implanted PPG device further comprises at least one second light emitter and at least one second light receiver, wherein changes in the amount (and/or spectrum) of light from the second light emitter which is received by the second light receiver caused by reflection of the light from (or transmission of the light through) body tissue at the second peripheral location are analyzed in order to measure pulse magnitude; and (c) an implanted cardiac pacemaker, wherein the operation of the implanted cardiac pacemaker is automatically adjusted based on comparison and/or multivariate analysis of the pulse magnitude values measured by the first implanted PPG device and the second implanted PPG device.

In one embodiment, a peripheral feedback system for cardiac rhythm management can comprise: (a) a first wearable photoplethysmography (PPG) device which is configured to be worn on the person's right arm, wherein the first wearable PPG device has at least one first light emitter and at least one first light receiver, wherein variation in the amount (and/or spectrum) of light from the first light emitter which is received by the first light receiver caused by reflection of the light from (or transmission of the light through) the right arm is analyzed in order to measure one or more biometric parameters from the person's right arm; (b) a second wearable photoplethysmography (PPG) device which is configured to be worn on the person's left arm, wherein the second wearable PPG device has at least one second light emitter and at least one second light receiver, wherein variation in the amount (and/or spectrum) of light from the second light emitter which is received by the second light receiver caused by reflection of the light from (or transmission of the light through) the left arm is analyzed in order to measure the one or more biometric parameters from the person's left arm; and (c) an implanted cardiac pacemaker, wherein the operation of the implanted cardiac pacemaker is automatically adjusted based on multivariate comparison and/or analysis of the values of the one or more biometric parameters measured from the person's right arm and left arm.

In an example, a feedback system for cardiac rhythm management can comprise: (a) a first wearable photoplethysmography (PPG) device which is configured to be worn at a first location on a person's body, wherein the first wearable PPG device has at least one first light emitter and at least one first light receiver, wherein variation in the amount (and/or spectrum) of light from the first light emitter which is received by the first light receiver caused by reflection of the light from (or transmission of the light through) body tissue is analyzed in order to measure one or more biometric parameters from the first location; (b) a second wearable photoplethysmography (PPG) device which is configured to be worn at a second location on the person's body, wherein the second wearable PPG device has at least one second light emitter and at least one second light receiver, wherein variation in the amount (and/or spectrum) of light from the second light emitter which is received by the second light receiver caused by reflection of the light from (or transmission of the light through) body tissue is analyzed in order to measure one or more biometric parameters from the second location; and (c) an implanted cardiac pacemaker, wherein the operation of the implanted cardiac pacemaker is automatically adjusted based on differences between values of the one or more biometric parameters measured at the first and second locations, and wherein the operation of the implanted cardiac pacemaker is automatically adjusted by adjusting one or more of operating parameters selected from the group consisting of: Amplitude (e.g. Atrial Pulse, Ventricular Pulse, Current, Voltage); AV Delay (e.g. Post Pacing, Post Sensing, Minimum); Blanking Period (e.g. Ventricular); Coordination/Timing (e.g. Between Different Chambers); Electrode (e.g. Locations, Combination, Polarity); Frequency (e.g. Pulse, Heart Stimulations); Initiation or Cessation (e.g. Pacing, Stimulation); Mode (e.g. Pacing); Pacing Interval (e.g. AV, IV, VV); Polarity (e.g. Pacing); Pulse Width (e.g. Atrial, Ventricular); Rate (e.g. Basic, Upper Tracking, Hysteresis); Refractory Extension (e.g. Atrial); Refractory Period (e.g. Atrial, Ventricular, Post-Ventricular); Sensing (e.g. Atrial, Polarity, Ventricular, Polarity); and Sensitivity (e.g. Atrial).

In an example, a peripheral feedback system for cardiac rhythm management can comprise: (a) a first wearable photoplethysmography (PPG) device which is configured to be worn on the person's right arm, wherein the first wearable PPG device has at least one first light emitter and at least one first light receiver, wherein variation in the amount (and/or spectrum) of light from the first light emitter which is received by the first light receiver caused by reflection of the light from (or transmission of the light through) body tissue is analyzed in order to measure one or more biometric parameters from the person's right arm; (b) a second wearable photoplethysmography (PPG) device which is configured to be worn on the person's left arm, wherein the second wearable PPG device has at least one second light emitter and at least one second light receiver, wherein variation in the amount (and/or spectrum) of light from the second light emitter which is received by the second light receiver caused by reflection of the light from (or transmission of the light through) body tissue is analyzed in order to measure the one or more biometric parameters from the person's left arm; and (c) an implanted cardiac pacemaker, wherein the operation of the implanted cardiac pacemaker is automatically adjusted based on multivariate comparison and/or analysis of the values of the one or more biometric parameters measured from the person's right arm and left arm, and wherein the operation of the implanted cardiac pacemaker is automatically adjusted by adjusting one or more of operating parameters selected from the group consisting of: Amplitude (e.g. Atrial Pulse, Ventricular Pulse, Current, Voltage); AV Delay (e.g. Post Pacing, Post Sensing, Minimum); Blanking Period (e.g. Ventricular); Coordination/Timing (e.g. Between Different Chambers); Electrode (e.g. Locations, Combination, Polarity); Frequency (e.g. Pulse, Heart Stimulations); Initiation or Cessation (e.g. Pacing, Stimulation); Mode (e.g. Pacing); Pacing Interval (e.g. AV, IV, VV); Polarity (e.g. Pacing); Pulse Width (e.g. Atrial, Ventricular); Rate (e.g. Basic, Upper Tracking, Hysteresis); Refractory Extension (e.g. Atrial); Refractory Period (e.g. Atrial, Ventricular, Post-Ventricular); Sensing (e.g. Atrial, Polarity, Ventricular, Polarity); and Sensitivity (e.g. Atrial).

In one embodiment, a peripheral feedback system for cardiac rhythm management can comprise: (a) a first wearable photoplethysmography (PPG) device which is configured to be worn on (or in) a person's right ear, wherein the first wearable PPG device has at least one first light emitter and at least one first light receiver, and wherein variation in the amount (and/or spectrum) of light from the first light emitter which is received by the first light receiver caused by reflection of the light from (or transmission of the light through) body tissue is analyzed in order to measure one or more biometric parameters from the first location; (b) a second wearable photoplethysmography (PPG) device which is configured to be worn on (or in) a person's left ear, wherein the second wearable PPG device has at least one second light emitter and at least one second light receiver, and wherein variation in the amount (and/or spectrum) of light from the second light emitter which is received by the second light receiver caused by reflection of the light from (or transmission of the light through) body tissue is analyzed in order to measure one or more biometric parameters from the second location; and (c) an implanted cardiac pacemaker, wherein the operation of the implanted cardiac pacemaker is automatically adjusted based on multivariate analysis of the one or more biometric parameters measured from the person's right ear and left ear.

In an example, a system for treating congestive heart failure can comprise: (a) a first wearable photoplethysmography (PPG) device which is configured to be worn on (or in) the person's right ear, wherein the first wearable PPG device has at least one first light emitter and at least one first light receiver, wherein variation in the amount (and/or spectrum) of light from the first light emitter which is received by the first light receiver caused by reflection of the light from (or transmission of the light through) body tissue is analyzed in order to measure one or more biometric parameters from the person's right ear; (b) a second wearable photoplethysmography (PPG) device which is configured to be worn on (or in) the person's left ear, wherein the second wearable PPG device has at least one second light emitter and at least one second light receiver, wherein variation in the amount (and/or spectrum) of light from the second light emitter which is received by the second light receiver caused by reflection of the light from (or transmission of the light through) body tissue is analyzed in order to measure the one or more biometric parameters from the person's left ear; and (c) an implanted cardiac pacemaker, wherein the operation of the implanted cardiac pacemaker is automatically adjusted based on multivariate comparison and/or analysis of the values of the one or more biometric parameters measured from the person's right ear and left ear.

In an example, a system for treating congestive heart failure can comprise: (a) a first wearable photoplethysmography (PPG) device which is configured to be worn on the person's right foot, wherein the first wearable PPG device has at least one first light emitter and at least one first light receiver, wherein variation in the amount (and/or spectrum) of light from the first light emitter which is received by the first light receiver caused by reflection of the light from (or transmission of the light through) body tissue is analyzed in order to measure one or more biometric parameters from the person's right foot; (b) a second wearable photoplethysmography (PPG) device which is configured to be worn on the person's left foot, wherein the second wearable PPG device has at least one second light emitter and at least one second light receiver, wherein variation in the amount (and/or spectrum) of light from the second light emitter which is received by the second light receiver caused by reflection of the light from (or transmission of the light through) body tissue is analyzed in order to measure the one or more biometric parameters from the person's left foot; and (c) an implanted cardiac pacemaker, wherein the operation of the implanted cardiac pacemaker is automatically adjusted based on multivariate comparison and/or analysis of the values of the one or more biometric parameters measured from the person's right foot and left foot.

In one embodiment, a feedback system for cardiac rhythm management can comprise: (a) a first wearable photoplethysmography (PPG) device with at least one first light emitter and at least one first light receiver which is worn on the right side of a person's body, wherein changes in the amount (and/or spectrum) of light from the first light emitter which is received by the first light receiver caused by reflection of the light from (or transmission of the light through) body tissue are analyzed in order to measure heart rate variability from the right side of the person's body; (b)

a second wearable photoplethysmography (PPG) device with at least one second light emitter and at least one second light receiver which is worn on the left side of a person's body, wherein changes in the amount (and/or spectrum) of light from the second light emitter which is received by the second light receiver caused by reflection of the light from (or transmission of the light through) body tissue are analyzed in order to measure heart rate variability on the left side of the person's body; and (c) an implanted cardiac pacemaker whose operation is automatically adjusted in response to differences in the heart rate variability between the right side and the left side of the person's body.

In an example, a peripheral feedback system for cardiac rhythm management can comprise: (a) a first wearable photoplethysmography (PPG) device with at least one first light emitter and at least one first light receiver which is worn on a person's right arm, wherein variation in the amount (and/or spectrum) of light from the first light emitter which is received by the first light receiver caused by reflection of the light from (or transmission of the light through) body tissue of the right arm is analyzed in order to measure systolic amplitude from the person's right arm; (b) a second wearable photoplethysmography (PPG) device with at least one second light emitter and at least one second light receiver which is worn on a person's left arm, wherein variation in the amount (and/or spectrum) of light from the second light emitter which is received by the second light receiver caused by reflection of the light from (or transmission of the light through) body tissue of the left arm is analyzed in order to measure systolic amplitude from the person's left arm; and (c) an implanted cardiac pacemaker, wherein the operation of the implanted cardiac pacemaker is automatically adjusted based on comparison and/or multivariate analysis of systolic amplitude from the person's right arm vs. systolic amplitude from the person's left arm; and wherein the operation of the implanted cardiac pacemaker is automatically adjusted by adjusting one or more of operating parameters selected from the group consisting of: Amplitude (e.g. Atrial Pulse, Ventricular Pulse, Current, Voltage); AV Delay (e.g. Post Pacing, Post Sensing, Minimum); Blanking Period (e.g. Ventricular); Coordination/Timing (e.g. Between Different Chambers); Electrode (e.g. Locations, Combination, Polarity); Frequency (e.g. Pulse, Heart Stimulations); Initiation or Cessation (e.g. Pacing, Stimulation); Mode (e.g. Pacing); Pacing Interval (e.g. AV, IV, VV); Polarity (e.g. Pacing); Pulse Width (e.g. Atrial, Ventricular); Rate (e.g. Basic, Upper Tracking, Hysteresis); Refractory Extension (e.g. Atrial); Refractory Period (e.g. Atrial, Ventricular, Post-Ventricular); Sensing (e.g. Atrial, Polarity, Ventricular, Polarity); and Sensitivity (e.g. Atrial).

In one embodiment, a peripheral feedback system for cardiac rhythm management can comprise: (a) a first wearable photoplethysmography (PPG) device worn on the right side of a person's body with at least one first light emitter and at least one first light receiver, wherein variation in the amount (and/or spectrum) of light from the first light emitter received by the first light receiver which is caused by reflection of the light from (or transmission of the light through) body tissue is analyzed in order to measure one or more biometric parameters from the right side of the person's body; (b) a second wearable photoplethysmography (PPG) device worn on the left side of a person's body with at least one second light emitter and at least one second light receiver, wherein variation in the amount (and/or spectrum) of light from the second light emitter received by the second light receiver which is caused by reflection of the light from (or transmission of the light through) body tissue is analyzed in order to measure one or more biometric parameters from the left side of the person's body; and (c) an implanted cardiac pacemaker, wherein the operation of the implanted cardiac pacemaker is automatically adjusted based on the values of the one or more biometric parameters from the right side and the left side of the person's body.

In an example, a feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters selected from the group consisting blood pressure; and (b) an implanted cardiac pacemaker whose frequency of heart contraction stimulations is automatically decreased in response to a high blood pressure measured by the PPG device.

In an example, a peripheral feedback system for cardiac rhythm management can comprise: (a) a wearable photoplethysmography (PPG) device with a light emitter and a light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker whose operation is automatically adjusted based on the measured values of the one or more biometric parameters. In another example, a peripheral feedback system for cardiac rhythm management can comprise: (a) a wearable photoplethysmography (PPG) device with a ring of light emitters and light receivers around a person's finger, wherein changes in the amount (and/or spectrum) of light from the light emitters which is received by the light receivers caused by reflection of the light from (or transmission of the light through) body tissue are analyzed in order to measure one or more biometric parameters; and (b) an implanted cardiac pacemaker whose operation is automatically adjusted based on the one or more biometric parameters. Alternatively, a peripheral feedback system for cardiac rhythm management can comprise: (a) a wearable photoplethysmography (PPG) device with at least one light emitter and at least one light receiver, wherein changes in light from the at least one light emitter which is received by the at least one light receiver caused by reflection of the light from (or transmission of the light through) body tissue are analyzed in order to measure one or more biometric parameters, and wherein a first light receiver receives light from a first (radial) location relative to a body member and a second light receiver receives light from a second (radial) location relative to the body member which is different than the first location; and (b) an implanted cardiac pacemaker whose operation is automatically adjusted based on the measured values of the one or more biometric parameters.

In one embodiment, a feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters selected from the group consisting of Heart Rate (HR), Heart Rate Variability (HRV), Blood Volume Pulse (BVP), Inter-Beat Interval (IBI), Peak-to-Peak Interval (PPI), Blood Pulse Rate (BPR), Blood Volume Pulse (BVP), Blood Volume Amplitude (BVP), Peak Amplitude (PA), Pulse Area, Pulse Transit Time (PTT), Standard Deviation of Average Normal to Normal Beat (SDANN), Systolic Amplitude, Systolic Peak Amplitude, Blood Pressure, Oxygen Saturation, VO2, VO2max, Hydration Level, and Respiration and/or Breathing Rate; and (b) an implanted cardiac pacemaker whose operation is automatically adjusted based on the one or more biometric parameters, wherein the operation of the implanted cardiac pacemaker is adjusted by changing one or more operating parameters selected from the group consisting of frequency of heart contraction stimulations, atrioventricular (AV) pacing interval, interventricular (IV) pacing interval, coordination between contraction stimulations of different heart chambers, timing of contraction stimulations of different heart chambers, location(s) of the heart to which electromagnetic energy is delivered, regularity of heart contraction stimulations, magnitude of heart contraction stimulations, voltage of heart contraction stimulations, initiation of heart contraction stimulations, and cessation of heart contraction stimulations.

In an example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters selected from the group consisting of Heart Rate (HR), Heart Rate Variability (HRV), Blood Volume Pulse (BVP), Inter-Beat Interval (IBI), Peak-to-Peak Interval (PPI), Blood Pulse Rate (BPR), Blood Volume Pulse (BVP), Blood Volume Amplitude (BVP), Peak Amplitude (PA), Pulse Area, Pulse Transit Time (PTT), Standard Deviation of Average Normal to Normal Beat (SDANN), Systolic Amplitude, Systolic Peak Amplitude, Blood Pressure, Oxygen Saturation, VO2, VO2max, Hydration Level, and Respiration and/or Breathing Rate; and (b) an implanted cardiac pacemaker whose operation is automatically adjusted based on the one or more biometric parameters, wherein the operation of the implanted cardiac pacemaker is adjusted by changing one or more operating parameters selected from the group consisting of—the pattern of heart contraction stimulations, atrioventricular (AV) pacing interval, interventricular (IV) pacing interval, coordination between contraction stimulations of different heart chambers, timing of contraction stimulations of different heart chambers, location(s) of the heart to which electromagnetic energy is delivered, regularity of heart contraction stimulations, magnitude of heart contraction stimulations, voltage of heart contraction stimulations, initiation of heart contraction stimulations, and cessation of heart contraction stimulations.

In an example, a peripheral feedback system for cardiac rhythm management can comprise: (a) a smart watch with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters selected from the group consisting of Heart Rate (HR), Heart Rate Variability (HRV), Blood Volume Pulse (BVP), Inter-Beat Interval (IBI), Peak-to-Peak Interval (PPI), Blood Pulse Rate (BPR), Blood Volume Pulse (BVP), Blood Volume Amplitude (BVP), Peak Amplitude (PA), Pulse Area, Pulse Transit Time (PTT), Standard Deviation of Average Normal to Normal Beat (SDANN), Systolic Amplitude, Systolic Peak Amplitude, Blood Pressure, Oxygen Saturation, VO2, VO2max, Hydration Level, and Respiration and/or Breathing Rate; and (b) an implanted cardiac pacemaker whose operation is automatically adjusted based on the one or more biometric parameters, wherein the operation of the implanted cardiac pacemaker is adjusted by changing one or more operating parameters selected from the group consisting of—the pattern of heart electromagnetic energy stimulations, atrioventricular (AV) pacing interval, interventricular (IV) pacing interval, coordination between electromagnetic energy stimulations of different heart chambers, timing of electromagnetic energy stimulations of different heart chambers, location(s) of the heart to which electromagnetic energy is delivered, regularity of heart electromagnetic energy stimulations, magnitude of heart contraction electromagnetic energy stimulations, voltage of heart electromagnetic energy stimulations, initiation of heart electromagnetic energy stimulations, and cessation of heart electromagnetic energy stimulations.

In one embodiment, a peripheral feedback system for cardiac rhythm management can comprise: (a) a leg band with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters selected from the group consisting of Heart Rate (HR), Heart Rate Variability (HRV), Blood Volume Pulse (BVP), Inter-Beat Interval (IBI), Peak-to-Peak Interval (PPI), Blood Pulse Rate (BPR), Blood Volume Pulse (BVP), Blood Volume Amplitude (BVP), Peak Amplitude (PA), Pulse Area, Pulse Transit Time (PTT), Standard Deviation of Average Normal to Normal Beat (SDANN), Systolic Amplitude, Systolic Peak Amplitude, Blood Pressure, Oxygen Saturation, VO2, VO2max, Hydration Level, and Respiration and/or Breathing Rate; and (b) an implanted cardiac pacemaker whose operation is automatically adjusted based on the one or more biometric parameters, wherein the operation of the implanted cardiac pacemaker is adjusted by changing one or more operating parameters selected from the group consisting of—the pattern of heart electromagnetic energy stimulations, atrioventricular (AV) pacing interval, interventricular (IV) pacing interval, coordination between electromagnetic energy stimulations of different heart chambers, timing of electromagnetic energy stimulations of different heart chambers, location(s) of the heart to which electromagnetic energy is delivered, regularity of heart electromagnetic energy stimulations, magnitude of heart contraction electromagnetic energy stimulations, voltage of heart electromagnetic energy stimulations, initiation of heart electromagnetic energy stimulations, and cessation of heart electromagnetic energy stimulations.

In an example, a feedback system for cardiac rhythm management can comprise: (a) an ear bud or hearing aid with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters selected from the group consisting of Heart Rate (HR), Heart Rate Variability (HRV), Blood Volume Pulse (BVP), Inter-Beat Interval (IBI), Peak-to-Peak Interval (PPI), Blood Pulse Rate (BPR), Blood Volume Pulse (BVP), Blood Volume Amplitude (BVP), Peak Amplitude (PA), Pulse Area, Pulse Transit Time (PTT), Standard Deviation of Average Normal to Normal Beat (SDANN), Systolic Amplitude, Systolic Peak Amplitude, Blood Pressure, Oxygen Saturation, VO2, VO2max, Hydration Level, and Respiration and/or Breathing Rate; and (b) an implanted cardiac pacemaker whose operation is automatically adjusted based on the one or more biometric parameters.

In one embodiment, a peripheral feedback system for cardiac rhythm management can comprise: (a) a wrist band with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters selected from the group consisting of Heart Rate (HR), Heart Rate Variability (HRV), Blood Volume Pulse (BVP), Inter-Beat Interval (IBI), Peak-to-Peak Interval (PPI), Blood Pulse Rate (BPR), Blood Volume Pulse (BVP), Blood Volume Amplitude (BVP), Peak Amplitude (PA), Pulse Area, Pulse Transit Time (PTT), Standard Deviation of Average Normal to Normal Beat (SDANN), Systolic Amplitude, Systolic Peak Amplitude, Blood Pressure, Oxygen Saturation, VO2, VO2max, Hydration Level, and Respiration and/or Breathing Rate; and (b) an implanted cardiac pacemaker whose operation is automatically adjusted based on the one or more biometric parameters. In another example, a peripheral feedback system for cardiac rhythm management can comprise: (a) a pair of glasses with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker whose operation is automatically adjusted based on the one or more biometric parameters, wherein the operation of the implanted cardiac pacemaker is adjusted by changing one or more operating parameters selected from the group consisting of—the pattern of heart electromagnetic energy stimulations, atrioventricular (AV) pacing interval, interventricular (IV) pacing interval, coordination between electromagnetic energy stimulations of different heart chambers, timing of electromagnetic energy stimulations of different heart chambers, location(s) of the heart to which electromagnetic energy is delivered, regularity of heart electromagnetic energy stimulations, magnitude of heart contraction electromagnetic energy stimulations, voltage of heart electromagnetic energy stimulations, initiation of heart electromagnetic energy stimulations, and cessation of heart electromagnetic energy stimulations.

In an example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker whose operation is automatically adjusted based on the one or more biometric parameters, wherein the operation of the implanted cardiac pacemaker is adjusted by changing one or more operating parameters selected from the group consisting of—the pattern of heart electromagnetic energy stimulations, atrioventricular (AV) pacing interval, interventricular (IV) pacing interval, coordination between electromagnetic energy stimulations of different heart chambers, timing of electromagnetic energy stimulations of different heart chambers, location(s) of the heart to which electromagnetic energy is delivered, regularity of heart electromagnetic energy stimulations, magnitude of heart electromagnetic energy stimulations, voltage of heart electromagnetic energy stimulations, initiation of heart electromagnetic energy stimulations, and cessation of heart electromagnetic energy stimulations.

In one embodiment, a system for treating cardiac arrhythmia can comprise: (a) a wearable photoplethysmography (PPG) device with at least one light emitter and at least one light receiver, wherein changes in the spectral distribution (and/or amount) of light from the light emitter which is received by the light receiver caused by reflection of the light from (or transmission of the light through) body tissue are analyzed in order to measure one or more biometric parameters selected from the group consisting of Heart Rate (HR), Heart Rate Variability (HRV), Blood Volume Pulse (BVP), Inter-Beat Interval (IBI), Peak-to-Peak Interval (PPI), Blood Pulse Rate (BPR), Blood Volume Pulse (BVP), Blood Volume Amplitude (BVP), Peak Amplitude (PA), Pulse Area, Pulse Transit Time (PTT), Standard Deviation of Average Normal to Normal Beat (SDANN), Systolic Amplitude, Systolic Peak Amplitude, Blood Pressure, Oxygen Saturation, VO2, VO2max, Hydration Level, and Respiration and/or Breathing Rate; and (b) an implanted cardiac pacemaker whose operation is automatically adjusted based on the one or more biometric parameters, wherein the operation of the implanted cardiac pacemaker is adjusted by changing one or more operating parameters selected from the group consisting of frequency of heart contraction stimulations, atrioventricular (AV) pacing interval, interventricular (IV) pacing interval, coordination between contraction stimulations of different heart chambers, timing of contraction stimulations of different heart chambers, location(s) of the heart to which electromagnetic energy is delivered, regularity of heart contraction stimulations, magnitude of heart contraction stimulations, voltage of heart contraction stimulations, initiation of heart contraction stimulations, and cessation of heart contraction stimulations.

In an example, a feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters selected from the group consisting blood volume amplitude or peak amplitude; and (b) an implanted cardiac pacemaker whose pacing interval is automatically decreased in response to a high blood volume amplitude or peak amplitude measured by the PPG device. Alternatively, a peripheral feedback system for cardiac rhythm management can comprise: (a) a wearable photoplethysmography (PPG) device with a plurality of light emitters and a single light receiver, wherein changes in the amount (and/or spectrum) of light from the light emitters which is received by the light receiver caused by reflection of the light from (or transmission of the light through) body tissue are analyzed in order to measure pulse transit time; and (b) an implanted cardiac pacemaker whose pacing rate is automatically reduced in response to a low pulse transit time measured by the PPG device.

In an example, a peripheral feedback system for cardiac rhythm management can comprise: (a) a wearable photoplethysmography (PPG) device with a single light emitter and a plurality of light receivers, wherein changes in the amount (and/or spectrum) of light from the light emitter which is received by the light receivers caused by reflection of the light from (or transmission of the light through) body tissue are analyzed in order to measure one or more biometric parameters selected from the group consisting of Heart Rate (HR), Heart Rate Variability (HRV), Blood Volume Pulse (BVP), Inter-Beat Interval (IBI), Peak-to-Peak Interval (PPI), Blood Pulse Rate (BPR), Blood Volume Pulse (BVP), Blood Volume Amplitude (BVP), Peak Amplitude (PA), Pulse Area, Pulse Transit Time (PTT), Standard Deviation of Average Normal to Normal Beat (SDANN), Systolic Amplitude, Systolic Peak Amplitude, Blood Pressure, Oxygen Saturation, VO2, VO2max, Hydration Level, and Respiration and/or Breathing Rate; and (b) an implanted cardiac pacemaker whose pacing rate is automatically reduced in response to a low value for the one or more biometric parameters measured by the PPG device.

In an example, a peripheral feedback system for cardiac rhythm management can comprise: (a) a wearable photoplethysmography (PPG) device with a plurality of light emitters and a single light receiver, wherein changes in the amount (and/or spectrum) of light from the light emitters which is received by the light receiver caused by reflection of the light from (or transmission of the light through) body tissue are analyzed in order to measure one or more biometric parameters selected from the group consisting of blood volume pulse; and (b) an implanted cardiac pacemaker whose stimulation amplitude (e.g. atrial pulse amplitude, ventricular pulse amplitude, current, and/or voltage) is automatically reduced in response to a high blood volume pulse measured by the PPG device. In another example, a feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters selected from the group consisting blood pressure; and (b) an implanted cardiac pacemaker whose voltage of heart contraction stimulations is automatically decreased in response to a high blood pressure measured by the PPG device.

In one embodiment, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure blood volume pulse, inter-beat interval, peak-to-peak interval, blood pulse rate, or blood volume pulse; and (b) an implanted cardiac pacemaker, wherein the frequency of electromagnetic energy stimulations by the implanted cardiac pacemaker is automatically adjusted based on measured blood volume pulse, inter-beat interval, peak-to-peak interval, blood pulse rate, or blood volume pulse. In another example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure pulse transit time; and (b) an implanted cardiac pacemaker, wherein the frequency of electromagnetic energy stimulations by the implanted cardiac pacemaker is automatically decreased in response to a high pulse transit time.

In an example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure Standard Deviation of Average Normal to Normal Beat (SDANN), Systolic Amplitude, or Systolic Peak Amplitude; and (b) an implanted cardiac pacemaker, wherein the frequency of electromagnetic energy stimulations by the implanted cardiac pacemaker is automatically adjusted based on measured Standard Deviation of Average Normal to Normal Beat (SDANN), Systolic Amplitude, or Systolic Peak Amplitude. Alternatively, a feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure Heart Rate (HR) and/or Heart Rate Variability (HRV); and (b) an implanted cardiac pacemaker, wherein the frequency of heart contractions stimulated by the implanted cardiac pacemaker is automatically increased or decreased based on Heart Rate (HR) and/or Heart Rate Variability (HRV) measured by the photoplethysmography (PPG) device.

In one embodiment, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure Heart Rate Variability (HRV); and (b) an implanted cardiac pacemaker, wherein the frequency of heart contractions stimulated by the implanted cardiac pacemaker is automatically decreased based on a high Heart Rate Variability (HRV) measured by the photoplethysmography (PPG) device. In another example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure heart rate; and (b) an implanted cardiac pacemaker, wherein the frequency of electromagnetic energy stimulations by the implanted cardiac pacemaker is automatically adjusted based on measured heart rate.

In one embodiment, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure blood pressure; and (b) an implanted cardiac pacemaker, wherein the inter-chamber timing of electromagnetic energy stimulations by the implanted cardiac pacemaker is automatically adjusted based on measured blood pressure. Alternatively, a feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure heart rate variability; and (b) an implanted cardiac pacemaker, wherein the inter-chamber timing of electromagnetic energy stimulations by the implanted cardiac pacemaker is automatically adjusted based on measured heart rate variability.

In an example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure heart rate variability; and (b) an implanted cardiac pacemaker, wherein the magnitude and/or voltage of electromagnetic energy stimulations by the implanted cardiac pacemaker is automatically adjusted based on measured heart rate variability. In another example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure blood pressure; and (b) an implanted cardiac pacemaker, wherein the magnitude and/or voltage of electromagnetic energy stimulations by the implanted cardiac pacemaker is automatically decreased in response to high blood pressure.

In one embodiment, a peripheral feedback system for cardiac rhythm management can comprise: (a) a wearable photoplethysmography (PPG) device with a light emitter and a light receiver, wherein variation in the amount (and/or spectrum) of light from the light emitter received by the light receiver caused by reflection of the light from (or transmission of the light through) body tissue is analyzed in order to measure heart rate; and (b) an implanted cardiac pacemaker, wherein the magnitude of electromagnetic stimulations of the heart by the implanted cardiac pacemaker is automatically reduced in response to a high heart rate measured by the PPG device. Alternatively, a feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure hydration level; and (b) an implanted cardiac pacemaker, wherein the magnitude of electromagnetic stimulations of the heart by the pacemaker is automatically decreased in response to a high hydration level measured by the PPG device.

In an example, a closed-loop system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the one or more measured biometric parameters. In another example, a peripheral feedback system for cardiac rhythm management can comprise: (a) a finger ring which functions as a wearable photoplethysmography (PPG) device with at least one light emitter on one side of a person's finger and at least one light receiver on the opposite side of the person's finger, wherein changes in the amount (and/or spectrum) of light from the light emitter which is received by the light receiver caused by reflection of the light from (or transmission of the light through) the finger are analyzed in order to measure one or more biometric parameters; and (b) an implanted cardiac pacemaker, wherein the operation of the implanted cardiac pacemaker is automatically adjusted based on the values of the one or more biometric parameters.

In an example, a peripheral feedback system for cardiac rhythm management can comprise: (a) a headset which functions as a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the values of the one or more biometric parameters. In another example, a peripheral feedback system for cardiac rhythm management can comprise: (a) a pair of eyeglasses which functions as a wearable photoplethysmography (PPG) device with at least one light emitter on a portion of the eyeglasses which rests on an ear and at least one light receiver on the portion of the eyeglasses which rests on the ear, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the values of the one or more biometric parameters.

In one embodiment, a peripheral feedback system for cardiac rhythm management can comprise: (a) a wearable photoplethysmography (PPG) device with a circumferential array of light emitters which are evenly distributed around the radial circumference of a body member (such as a finger, wrist, or arm) and at least one light receiver, wherein changes in the amount (and/or spectrum) of light from the light emitters which is received by the light receiver caused by reflection of the light from (or transmission of the light through) body tissue are analyzed in order to measure one or more biometric parameters, and; and (b) an implanted cardiac pacemaker, wherein the operation of the implanted cardiac pacemaker is automatically adjusted based on the one or more biometric parameters. In another example, a feedback system for cardiac rhythm management can comprise: (a) a wearable photoplethysmography (PPG) device with a circumferential array of pairs of light emitters and light receivers around the circumference of a body member (such as a finger, wrist, or arm), wherein changes in the amount (and/or spectrum) of light from the light emitters which is received by the light receivers due to reflection from (or transmission of the light through) body tissue are analyzed in order to measure one or more biometric parameters, and; and (b) an implanted cardiac pacemaker, wherein the operation of the implanted cardiac pacemaker is automatically adjusted based on the one or more biometric parameters.

In an example, a peripheral feedback system for cardiac rhythm management can comprise: (a) a wearable photoplethysmography (PPG) device with a first light emitter, a second light emitter, and a light receiver, wherein the second light emitter is between the first light emitter and the light receiver, and wherein changes in the amount (and/or spectrum) of light from the first and/or second light emitters which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the one or more biometric parameters. In another example, a feedback system for cardiac rhythm management can comprise: (a) a wearable photoplethysmography (PPG) device with a first light emitter which emits light along a first vector, a second light emitter which emits light along a second vector, wherein the first and second vectors are co-linear, and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the one or more biometric parameters.

In one embodiment, a peripheral feedback system for cardiac rhythm management can comprise: (a) a wearable photoplethysmography (PPG) device with a first light emitter, a second light emitter, and at least one light receiver, wherein changes in the amount (and/or spectrum) of light from the light emitter which is received by the light receiver caused by reflection of the light from (or transmission of the light through) body tissue are analyzed in order to measure one or more biometric parameters, and wherein the first light emitter emits light from a location within a first radial quadrant around a body member and the second light emitter emits light from a location within a second radial quadrant around the body member; and (b) an implanted cardiac pacemaker, wherein the operation of the implanted cardiac pacemaker is automatically adjusted based on the one or more biometric parameters. In another example, a peripheral feedback system for cardiac rhythm management can comprise: (a) a wearable photoplethysmography (PPG) device with a plurality of paired light emitters and light receivers which are distributed around the band of a smart watch, wherein changes in the amount (and/or spectrum) of light from the light emitters which is received by the light receivers due to reflection from (or transmission of the light through) body tissue are analyzed in order to measure one or more biometric parameters, and; and (b) an implanted cardiac pacemaker, wherein the operation of the implanted cardiac pacemaker is automatically adjusted based on the one or more biometric parameters.

In an example, a peripheral feedback system for cardiac rhythm management can comprise: (a) a wearable photoplethysmography (PPG) device with an array of light emitters and light receivers on the inside circumferential surface of a finger ring, wherein changes in the amount (and/or spectrum) of light from the light emitters which is received by the light receivers due to reflection from (or transmission of the light through) body tissue are analyzed in order to measure one or more biometric parameters, and; and (b) an implanted cardiac pacemaker, wherein the operation of the implanted cardiac pacemaker is automatically adjusted based on the one or more biometric parameters. In another example, a peripheral feedback system for cardiac rhythm management can comprise: (a) a wearable photoplethysmography (PPG) device with an array of light emitters and light receivers on an device which is configured to be (partially) inserted into a person's ear canal, wherein changes in the amount (and/or spectrum) of light from the light emitters which is received by the light receivers due to reflection from (or transmission of the light through) body tissue are analyzed in order to measure one or more biometric parameters, and; and (b) an implanted cardiac pacemaker, wherein the operation of the implanted cardiac pacemaker is automatically adjusted based on the one or more biometric parameters.

In an example, a feedback system for cardiac rhythm management can comprise: (a) a wearable photoplethysmography (PPG) device which is configured to be (partially) inserted into a person's ear canal, wherein this device has at least one light emitter and at least one light receiver, and wherein changes in the amount (and/or spectrum) of light from the light emitters which is received by the light receivers due to reflection from (or transmission of the light through) body tissue are analyzed in order to measure the person's blood pressure, and; and (b) an implanted cardiac pacemaker, wherein the operation of the implanted cardiac pacemaker is automatically adjusted based on blood pressure measured by the PPG device. In another example, a peripheral feedback system for cardiac rhythm management can comprise: (a) a wearable photoplethysmography (PPG) device can be eyewear with an array of light emitters and light receivers, wherein changes in the amount (and/or spectrum) of light from the light emitters which is received by the light receivers due to reflection from (or transmission of the light through) body tissue are analyzed in order to measure one or more biometric parameters, and; and (b) an implanted cardiac pacemaker, wherein the operation of the implanted cardiac pacemaker is automatically adjusted based on the one or more biometric parameters.

In one embodiment, a feedback system for cardiac rhythm management can comprise: (a) a wearable photoplethysmography (PPG) device with at least one light emitter and at least one light receiver, wherein variation in the amount (and/or spectrum) of light from the light emitter which is received by the light receiver caused by reflection of the light from (or transmission of the light through) body tissue is analyzed in order to measure one or more biometric parameters; and (b) an implanted cardiac pacemaker, wherein the operation of the implanted cardiac pacemaker is automatically adjusted based on the one or more biometric parameters, and wherein the operation of the implanted cardiac pacemaker is automatically adjusted by adjusting (ventricular) blanking period. In another example, a peripheral feedback system for cardiac rhythm management can comprise: (a) a wearable photoplethysmography (PPG) device with at least one light emitter and at least one light receiver, wherein variation in the amount (and/or spectrum) of light from the light emitter which is received by the light receiver caused by reflection of the light from (or transmission of the light through) body tissue is analyzed in order to measure one or more biometric parameters; and (b) an implanted cardiac pacemaker, wherein the operation of the implanted cardiac pacemaker is automatically adjusted based on the one or more biometric parameters, and wherein the operation of the implanted cardiac pacemaker is automatically adjusted by initiating or stopping electromagnetic stimulation.

In an example, a feedback system for cardiac rhythm management can comprise: (a) a wearable photoplethysmography (PPG) device with at least one light emitter and at least one light receiver, wherein variation in the amount (and/or spectrum) of light from the light emitter which is received by the light receiver caused by reflection of the light from (or transmission of the light through) body tissue is analyzed in order to measure one or more biometric parameters; and (b) an implanted cardiac pacemaker, wherein the operation of the implanted cardiac pacemaker is automatically adjusted based on the one or more biometric parameters, and wherein the operation of the implanted cardiac pacemaker is automatically adjusted by adjusting pacing polarity. In another example, a peripheral feedback system for cardiac rhythm management can comprise: (a) a wearable photoplethysmography (PPG) device with at least one light emitter and at least one light receiver, wherein variation in the amount (and/or spectrum) of light from the light emitter which is received by the light receiver caused by reflection of the light from (or transmission of the light through) body tissue is analyzed in order to measure one or more biometric parameters; and (b) an implanted cardiac pacemaker, wherein the operation of the implanted cardiac pacemaker is automatically adjusted based on the one or more biometric parameters, and wherein the operation of the implanted cardiac pacemaker is automatically adjusted by adjusting (atrial, ventricular, or post-ventricular) refractory period.

In one embodiment, a peripheral feedback system for cardiac rhythm management can comprise: (a) a wearable photoplethysmography (PPG) device with at least one light emitter and at least one light receiver, wherein variation in the amount (and/or spectrum) of light from the light emitter which is received by the light receiver caused by reflection of the light from (or transmission of the light through) body tissue is analyzed in order to measure blood pressure; and (b) an implanted cardiac pacemaker, wherein the operation of the implanted cardiac pacemaker is automatically adjusted based on blood pressure, and wherein the operation of the implanted cardiac pacemaker is automatically adjusted by adjusting pacing frequency (e.g. pulse, heart stimulations), pacing interval (e.g. AV, IV, VV), and/or pacing rate (e.g. basic, upper tracking, hysteresis). In another example, a peripheral feedback system for cardiac rhythm management can comprise: (a) a wearable photoplethysmography (PPG) device with at least one light emitter and at least one light receiver, wherein periodic variation in the amount (and/or spectrum) of light from the light emitter which is received by the light receiver caused by reflection of the light from (or transmission of the light through) body tissue is analyzed in order to measure one or more biometric parameters; and (b) an implanted cardiac pacemaker, wherein the operation of the implanted cardiac pacemaker is automatically adjusted based on the one or more biometric parameters.

In an example, a peripheral feedback system for cardiac rhythm management can comprise: (a) a wearable photoplethysmography (PPG) device with a plurality of light emitters and a plurality of light receivers, wherein variation in the amount (and/or spectrum) of light from the light emitters which is received by the light receivers caused by reflection of the light from (or transmission of the light through) body tissue is analyzed in order to measure one or more biometric parameters; and (b) an implanted cardiac pacemaker, wherein the operation of the implanted cardiac pacemaker is automatically adjusted based on the one or more biometric parameters.

In an example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver after transmission through body tissue are analyzed in order to measure one or more biometric parameters; and (b) an implanted cardiac pacemaker, wherein the operation of the implanted cardiac pacemaker is automatically adjusted based on the one or more biometric parameters, and wherein the operation of the implanted cardiac pacemaker is adjusted by changing one or more pacemaker operating parameters selected from the group consisting of frequency of heart contraction stimulations, atrioventricular (AV) pacing interval, interventricular (IV) pacing interval, coordination between contraction stimulations of different heart chambers, timing of contraction stimulations of different heart chambers, location(s) of the heart to which electromagnetic energy is delivered, regularity of heart contraction stimulations, magnitude of heart contraction stimulations, voltage of heart contraction stimulations, initiation of heart contraction stimulations, and cessation of heart contraction stimulations.

In an example, a feedback system for cardiac rhythm management can comprise: (a) a wearable photoplethysmography (PPG) device with at least one light emitter on a first side of a person's earlobe and at least one light receiver on a second side of the person's earlobe, where the second side is opposite the first side, and wherein changes in the amount (and/or spectrum) of light from the light emitter which is received by the light receiver after transmission through the earlobe are analyzed in order to measure one or more biometric parameters; and (b) an implanted cardiac pacemaker, wherein the operation of the implanted cardiac pacemaker is automatically adjusted based on the one or more biometric parameters, and wherein the operation of the implanted cardiac pacemaker is adjusted by changing the frequency of heart contraction stimulations. In another example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the one or more biometric parameters, and wherein the operation of the implanted cardiac pacemaker is adjusted by changing the regularity of heart contraction stimulations.

In one embodiment, a feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the one or more measured biometric parameters. In another example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure systolic amplitude or peak amplitude; and (b) an implanted cardiac pacemaker, wherein the operation of the implanted cardiac pacemaker is automatically adjusted based on measured systolic amplitude or peak amplitude.

In an example, a feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure respiration and/or breathing rate; and (b) an implanted cardiac pacemaker, wherein the operation of the implanted cardiac pacemaker is automatically adjusted based on respiration and/or breathing rate. In another example, a peripheral feedback system for cardiac rhythm management can comprise: (a) a wearable photoplethysmography (PPG) device with at least one laser and at least one light receiver, wherein changes in the amount (and/or spectrum) of light from the laser which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the one or more biometric parameters.

In one embodiment, a peripheral feedback system for cardiac rhythm management can comprise: (a) a wearable photoplethysmography (PPG) device with at least one coherent light emitter (e.g. laser) and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the one or more biometric parameters. In another example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters, and wherein the angle at which light from the light emitter enters body tissue is changed by an array of moving micromirrors; and (b) an implanted cardiac pacemaker, wherein the operation of the implanted cardiac pacemaker is automatically adjusted based on the one or more biometric parameters.

In an example, a peripheral feedback system for cardiac rhythm management can comprise: (a) a wearable photoplethysmography (PPG) device worn around the circumference of a body member (such as a person's finger, wrist, or arm) with at least one light emitter and at least one light receiver located on the same radial quadrant of the circumference, wherein variation in (the amount) light from the light emitter which is received by the light receiver caused by reflection of the light from (or transmission of the light through) body tissue is analyzed in order to measure one or more biometric parameters; and (b) an implanted cardiac pacemaker, wherein the operation of the implanted cardiac pacemaker is automatically adjusted based on the one or more biometric parameters. In another example, a feedback system for cardiac rhythm management can comprise: (a) a wearable photoplethysmography (PPG) device which is at least partially inserted into a person's ear canal, wherein wearable PPG device further comprises at least one light emitter and at least one light receiver, and wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the measured values of the biometric parameters.

In an example, a peripheral feedback system for cardiac rhythm management can comprise: (a) a wearable photoplethysmography (PPG) device worn on a person's nose, wherein wearable PPG device further comprises at least one light emitter and at least one light receiver, and wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the measured values of the biometric parameters. In another example, a feedback system for cardiac rhythm management can comprise: (a) a wearable photoplethysmography (PPG) device worn on a person's finger, wherein wearable PPG device further comprises at least one light emitter and at least one light receiver, and wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the measured values of the biometric parameters.

In an example, a peripheral feedback system for cardiac rhythm management can comprise: (a) a smart bandage which is adhered to a person's body, wherein the smart bandage functions as a wearable photoplethysmography (PPG) device, wherein the smart bandage further comprises at least one light emitter and at least one light receiver, and wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the measured values of the biometric parameters. In another example, a feedback system for cardiac rhythm management can comprise: (a) an implanted photoplethysmography (PPG) device, wherein the PPG device is implanted within a peripheral location in a person's body, wherein the PPG device further comprises at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the one or more biometric parameters measured by the PPG device at the peripheral location in the person's body.

In one embodiment, a peripheral feedback system for cardiac rhythm management can comprise: (a) a garment cuff or sleeve which functions as a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the values of the one or more biometric parameters. In another example, a peripheral feedback system for cardiac rhythm management can comprise: (a) a hearing aid which functions as a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the values of the one or more biometric parameters.

In an example, a system for cardiac rhythm management can comprise: (a) a wearable photoplethysmography (PPG) device with a light emitter and a light receiver, wherein variation in the amount (and/or spectrum) of light from the light emitter received by the light receiver caused by reflection of the light from body tissue is analyzed in order to measure one or more biometric parameters; and (b) an implanted cardiac pacemaker, wherein the operation of the implanted cardiac pacemaker is automatically adjusted based on measured values of the one or more biometric parameters.

In one embodiment, a system for treating arteriosclerosis or atherosclerosis can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed to measure one or more biometric parameters selected from the group consisting of Heart Rate (HR), Heart Rate Variability (HRV), Blood Volume Pulse (BVP), Inter-Beat Interval (IBI), Peak-to-Peak Interval (PPI), Blood Pulse Rate (BPR), Blood Volume Pulse (BVP), Blood Volume Amplitude (BVP), Peak Amplitude (PA), Pulse Area, Pulse Transit Time (PTT), Standard Deviation of Average Normal to Normal Beat (SDANN), Systolic Amplitude, Systolic Peak Amplitude, Blood Pressure, Oxygen Saturation, VO2, VO2max, Hydration Level, and Respiration and/or Breathing Rate; and (b) an implanted cardiac pacemaker, wherein the operation of the implanted cardiac pacemaker is automatically adjusted based on the one or more biometric parameters measured by the wearable photoplethysmography (PPG) device, and wherein the operation of the implanted cardiac pacemaker is changed by changing one or more pacemaker operating parameters selected from the group consisting of frequency of heart contraction stimulations, atrioventricular (AV) pacing interval, interventricular (IV) pacing interval, coordination between contraction stimulations of different heart chambers, timing of contraction stimulations of different heart chambers, location(s) of the heart to which electromagnetic energy is delivered, regularity of heart contraction stimulations, magnitude of heart contraction stimulations, voltage of heart contraction stimulations, initiation of heart contraction stimulations, and cessation of heart contraction stimulations.

In an example, a system for treating congestive heart failure can comprise: (a) a belt or waist band which functions as a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the values of the one or more biometric parameters. In another example, a system for treating congestive heart failure can comprise: (a) a headset which functions as a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the values of the one or more biometric parameters.

In one embodiment, a system for treating congestive heart failure can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed to measure one or more biometric parameters selected from the group consisting of blood pressure; and (b) an implanted cardiac pacemaker, wherein the operation of the implanted cardiac pacemaker is automatically adjusted based on the one or more biometric parameters measured by the wearable photoplethysmography (PPG) device, and wherein the operation of the implanted cardiac pacemaker is changed by changing one or more pacemaker operating parameters selected from the group consisting of frequency of heart contraction stimulations, atrioventricular (AV) pacing interval, interventricular (IV) pacing interval, coordination between contraction stimulations of different heart chambers, timing of contraction stimulations of different heart chambers, location(s) of the heart to which electromagnetic energy is delivered, regularity of heart contraction stimulations, magnitude of heart contraction stimulations, voltage of heart contraction stimulations, initiation of heart contraction stimulations, and cessation of heart contraction stimulations.

In an example, a system for treating congestive heart failure can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure blood pressure; and (b) an implanted cardiac pacemaker, wherein the operation of the implanted cardiac pacemaker is automatically adjusted based on blood pressure. In another example, a system for treating congestive heart failure can comprise: (a) hearing aid which functions as a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the values of the one or more biometric parameters.

In an example, a system for treating hypovolemia can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed to measure one or more biometric parameters selected from the group consisting of Heart Rate (HR), Heart Rate Variability (HRV), Blood Volume Pulse (BVP), Inter-Beat Interval (IBI), Peak-to-Peak Interval (PPI), Blood Pulse Rate (BPR), Blood Volume Pulse (BVP), Blood Volume Amplitude (BVP), Peak Amplitude (PA), Pulse Area, Pulse Transit Time (PTT), Standard Deviation of Average Normal to Normal Beat (SDANN), Systolic Amplitude, Systolic Peak Amplitude, Blood Pressure, Oxygen Saturation, VO2, VO2max, Hydration Level, and Respiration and/or Breathing Rate; and (b) an implanted cardiac pacemaker, wherein the operation of the implanted cardiac pacemaker is automatically adjusted based on the one or more biometric parameters measured by the wearable photoplethysmography (PPG) device, and wherein the operation of the implanted cardiac pacemaker is changed by changing one or more pacemaker operating parameters selected from the group consisting of frequency of heart contraction stimulations, atrioventricular (AV) pacing interval, interventricular (IV) pacing interval, coordination between contraction stimulations of different heart chambers, timing of contraction stimulations of different heart chambers, location(s) of the heart to which electromagnetic energy is delivered, regularity of heart contraction stimulations, magnitude of heart contraction stimulations, voltage of heart contraction stimulations, initiation of heart contraction stimulations, and cessation of heart contraction stimulations.

In an example, a system for treating ventricular fibrillation can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed to measure one or more biometric parameters selected from the group consisting of Heart Rate (HR), Heart Rate Variability (HRV), Blood Volume Pulse (BVP), Inter-Beat Interval (IBI), Peak-to-Peak Interval (PPI), Blood Pulse Rate (BPR), Blood Volume Pulse (BVP), Blood Volume Amplitude (BVP), Peak Amplitude (PA), Pulse Area, Pulse Transit Time (PTT), Standard Deviation of Average Normal to Normal Beat (SDANN), Systolic Amplitude, Systolic Peak Amplitude, Blood Pressure, Oxygen Saturation, VO2, VO2max, Hydration Level, and Respiration and/or Breathing Rate; and (b) an implanted cardiac pacemaker, wherein the operation of the implanted cardiac pacemaker is automatically adjusted based on the one or more biometric parameters measured by the wearable photoplethysmography (PPG) device, and wherein the operation of the implanted cardiac pacemaker is changed by changing one or more pacemaker operating parameters selected from the group consisting of frequency of heart contraction stimulations, atrioventricular (AV) pacing interval, interventricular (IV) pacing interval, coordination between contraction stimulations of different heart chambers, timing of contraction stimulations of different heart chambers, location(s) of the heart to which electromagnetic energy is delivered, regularity of heart contraction stimulations, magnitude of heart contraction stimulations, voltage of heart contraction stimulations, initiation of heart contraction stimulations, and cessation of heart contraction stimulations.

In one embodiment, a peripheral feedback system for cardiac rhythm management can comprise: (a) a wearable photoplethysmography (PPG) device with at least one light emitter and at least one light receiver, wherein variation in the amount (and/or spectrum) of light from the light emitter which is received by the light receiver caused by reflection of the light from (or transmission of the light through) body tissue is analyzed in order to measure one or more biometric parameters selected from the group consisting of blood pulse rate; and (b) an implanted cardiac pacemaker, wherein the operation of the implanted cardiac pacemaker is automatically adjusted based on the blood pulse rate, and wherein the operation of the implanted cardiac pacemaker is automatically adjusted by adjusting one or more of operating parameters selected from the group consisting of: Amplitude (e.g. Atrial Pulse, Ventricular Pulse, Current, Voltage); AV Delay (e.g. Post Pacing, Post Sensing, Minimum); Blanking Period (e.g. Ventricular); Coordination/Timing (e.g. Between Different Chambers); Electrode (e.g. Locations, Combination, Polarity); Frequency (e.g. Pulse, Heart Stimulations); Initiation or Cessation (e.g. Pacing, Stimulation); Mode (e.g. Pacing); Pacing Interval (e.g. AV, IV, VV); Polarity (e.g. Pacing); Pulse Width (e.g. Atrial, Ventricular); Rate (e.g. Basic, Upper Tracking, Hysteresis); Refractory Extension (e.g. Atrial); Refractory Period (e.g. Atrial, Ventricular, Post-Ventricular); Sensing (e.g. Atrial, Polarity, Ventricular, Polarity); and Sensitivity (e.g. Atrial).

In an example, a peripheral feedback system for cardiac rhythm management can comprise: (a) a wearable photoplethysmography (PPG) device with at least one light emitter and at least one light receiver, wherein variation in the amount (and/or spectrum) of light from the light emitter which is received by the light receiver caused by reflection of the light from (or transmission of the light through) body tissue is analyzed in order to measure heart rate; and (b) an implanted cardiac pacemaker, wherein the operation of the implanted cardiac pacemaker is automatically adjusted based on the one or more biometric parameters, and wherein the operation of the implanted cardiac pacemaker is automatically adjusted by adjusting one or more of operating parameters selected from the group consisting of: Amplitude (e.g. Atrial Pulse, Ventricular Pulse, Current, Voltage); AV Delay (e.g. Post Pacing, Post Sensing, Minimum); Blanking Period (e.g. Ventricular); Coordination/Timing (e.g. Between Different Chambers); Electrode (e.g. Locations, Combination, Polarity); Frequency (e.g. Pulse, Heart Stimulations); Initiation or Cessation (e.g. Pacing, Stimulation); Mode (e.g. Pacing); Pacing Interval (e.g. AV, IV, VV); Polarity (e.g. Pacing); Pulse Width (e.g. Atrial, Ventricular); Rate (e.g. Basic, Upper Tracking, Hysteresis); Refractory Extension (e.g. Atrial); Refractory Period (e.g. Atrial, Ventricular, Post-Ventricular); Sensing (e.g. Atrial, Polarity, Ventricular, Polarity); and Sensitivity (e.g. Atrial).

In one embodiment, a peripheral feedback system for cardiac rhythm management can comprise: (a) a wrist band or smart watch which is worn by a person, wherein the wrist band or smart watch has at least one light emitter and at least one light receiver, wherein the finger ring functions as a wearable photoplethysmography (PPG) device, wherein variation in the amount (and/or spectrum) of light from the light emitter which is received by the light receiver caused by reflection of the light from (or transmission of the light through) body tissue is analyzed in order to measure one or more biometric parameters selected from the group consisting of Heart Rate (HR), Heart Rate Variability (HRV), Blood Volume Pulse (BVP), Inter-Beat Interval (IBI), Peak-to-Peak Interval (PPI), Blood Pulse Rate (BPR), Blood Volume Pulse (BVP), Blood Volume Amplitude (BVP), Peak Amplitude (PA), Pulse Area, Pulse Transit Time (PTT), Standard Deviation of Average Normal to Normal Beat (SDANN), Systolic Amplitude, Systolic Peak Amplitude, Blood Pressure, Oxygen Saturation, VO2, VO2max, Hydration Level, and Respiration and/or Breathing Rate; and (b) an implanted cardiac pacemaker, wherein the operation of the implanted cardiac pacemaker is automatically adjusted based on the one or more biometric parameters, and wherein the operation of the implanted cardiac pacemaker is automatically adjusted by adjusting one or more of operating parameters selected from the group consisting of: Amplitude (e.g. Atrial Pulse, Ventricular Pulse, Current, Voltage); AV Delay (e.g. Post Pacing, Post Sensing, Minimum); Blanking Period (e.g. Ventricular); Coordination/Timing (e.g. Between Different Chambers); Electrode (e.g. Locations, Combination, Polarity); Frequency (e.g. Pulse, Heart Stimulations); Initiation or Cessation (e.g. Pacing, Stimulation); Mode (e.g. Pacing); Pacing Interval (e.g. AV, IV, VV); Polarity (e.g. Pacing); Pulse Width (e.g. Atrial, Ventricular); Rate (e.g. Basic, Upper Tracking, Hysteresis); Refractory Extension (e.g. Atrial); Refractory Period (e.g. Atrial, Ventricular, Post-Ventricular); Sensing (e.g. Atrial, Polarity, Ventricular, Polarity); and Sensitivity (e.g. Atrial).

In an example, a system for treating congestive heart failure can comprise: (a) a wearable photoplethysmography (PPG) device with at least one light emitter and at least one light receiver, wherein variation in the amount (and/or spectrum) of light from the light emitter which is received by the light receiver caused by reflection of the light from (or transmission of the light through) body tissue is analyzed in order to measure blood volume; and (b) an implanted cardiac pacemaker, wherein the operation of the implanted cardiac pacemaker is automatically adjusted based on the one or more biometric parameters, and wherein the operation of the implanted cardiac pacemaker is automatically adjusted by adjusting one or more of operating parameters selected from the group consisting of: Amplitude (e.g. Atrial Pulse, Ventricular Pulse, Current, Voltage); AV Delay (e.g. Post Pacing, Post Sensing, Minimum); Blanking Period (e.g. Ventricular); Coordination/Timing (e.g. Between Different Chambers); Electrode (e.g. Locations, Combination, Polarity); Frequency (e.g. Pulse, Heart Stimulations); Initiation or Cessation (e.g. Pacing, Stimulation); Mode (e.g. Pacing); Pacing Interval (e.g. AV, IV, VV); Polarity (e.g. Pacing); Pulse Width (e.g. Atrial, Ventricular); Rate (e.g. Basic, Upper Tracking, Hysteresis); Refractory Extension (e.g. Atrial); Refractory Period (e.g. Atrial, Ventricular, Post-Ventricular); Sensing (e.g. Atrial, Polarity, Ventricular, Polarity); and Sensitivity (e.g. Atrial).

In one embodiment, a feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure systolic amplitude or peak amplitude; and (b) an implanted cardiac pacemaker, wherein the pacing interval of the pacemaker is decreased in response to high systolic amplitude or peak amplitude as measured by the PPG device. In another example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure oxygen saturation, VO2, and/or VO2max; and (b) an implanted cardiac pacemaker, wherein the pacing rate of the implanted cardiac pacemaker is automatically increased in response to low oxygen saturation, VO2, and/or VO2max measured by the PPG device.

In an example, a feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure Blood Volume Pulse (BVP), Inter-Beat Interval (IBI), Peak-to-Peak Interval (PPI), Blood Pulse Rate (BPR), or Blood Volume Pulse (BVP); and (b) an implanted cardiac pacemaker, wherein the pattern of electromagnetic energy stimulations by the implanted cardiac pacemaker is automatically adjusted based on Blood Volume Pulse (BVP), Inter-Beat Interval (IBI), Peak-to-Peak Interval (PPI), Blood Pulse Rate (BPR), or Blood Volume Pulse (BVP). In another example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure heart rate; and (b) an implanted cardiac pacemaker, wherein the pattern of electromagnetic energy stimulations by the implanted cardiac pacemaker is automatically adjusted based on measured heart rate.

In an example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure blood pressure; and (b) an implanted cardiac pacemaker, wherein the rate of electromagnetic energy stimulations by the implanted cardiac pacemaker is automatically decreased in response to high blood pressure measured by the wearable PPG device. In another example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure Heart Rate (HR); and (b) an implanted cardiac pacemaker, wherein the rate of heart contractions stimulated by the implanted cardiac pacemaker is automatically decreased in response to a high Heart Rate (HR) as measured by the photoplethysmography (PPG) device.

In an example, a peripheral feedback system for cardiac rhythm management can comprise: (a) a wearable photoplethysmography (PPG) device with a first light emitter which emits light in a first wavelength (or frequency band or color), a second light emitter which emits light in a second wavelength (or frequency band or color) wherein the second wavelength is different than the first wavelength, and a light receiver; wherein changes in the amount (and/or spectrum) of light from the first and/or second light emitters which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the one or more biometric parameters. In another example, a feedback system for cardiac rhythm management can comprise: (a) a wearable photoplethysmography (PPG) device; wherein the PPG device further comprises at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and wherein the wearable PPG device further comprises an inertial motion sensor (such as combination of an accelerometer and/or gyroscope); and (b) an implanted cardiac pacemaker, wherein the operation of the implanted cardiac pacemaker is automatically adjusted based on the one or more measured biometric parameters.

In one embodiment, a peripheral feedback system for cardiac rhythm management can comprise: (a) a wearable photoplethysmography (PPG) device; wherein the PPG device further comprises at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and wherein the wearable PPG device further comprises one or more light guides (such as lenses, mirrors, or prisms) which direct the paths of light rays between a light emitter and a person's body or between the person's body and a light receiver; and (b) an implanted cardiac pacemaker, wherein the operation of the implanted cardiac pacemaker is automatically adjusted based on the one or more measured biometric parameters.

In an example, a feedback system for cardiac rhythm management can comprise: (a) a first implanted photoplethysmography (PPG) device, wherein the first PPG device is implanted in a first peripheral location (e.g. arm or leg) of a person's body, wherein the first implanted PPG device further comprises at least one first light emitter and at least one first light receiver, wherein changes in the amount (and/or spectrum) of light from the first light emitter which is received by the first light receiver caused by reflection of the light from (or transmission of the light through) body tissue at the first peripheral location are analyzed in order to measure one or more biometric parameters; (b) a second implanted photoplethysmography (PPG) device, wherein the second PPG device is implanted in a second peripheral location (e.g. arm or leg) of a person's body, wherein the second implanted PPG device further comprises at least one second light emitter and at least one second light receiver, wherein changes in the amount (and/or spectrum) of light from the second light emitter which is received by the second light receiver caused by reflection of the light from (or transmission of the light through) body tissue at the second peripheral location are analyzed in order to measure one or more biometric parameters; and (c) an implanted cardiac pacemaker, wherein the operation of the implanted cardiac pacemaker is automatically adjusted based on comparison and/or multivariate analysis of the values of the one or more biometric parameters as measured by the first implanted PPG device and the second implanted PPG device.

In one embodiment, a system for treating congestive heart failure can comprise: (a) a first implanted photoplethysmography (PPG) device, wherein the first PPG device is implanted in a first peripheral location (e.g. arm or leg) of a person's body, wherein the first implanted PPG device further comprises at least one first light emitter and at least one first light receiver, wherein changes in the amount (and/or spectrum) of light from the first light emitter which is received by the first light receiver caused by reflection of the light from (or transmission of the light through) body tissue at the first peripheral location are analyzed in order to measure one or more biometric parameters; (b) a second implanted photoplethysmography (PPG) device, wherein the second PPG device is implanted in a second peripheral location (e.g. arm or leg) of a person's body, wherein the second implanted PPG device further comprises at least one second light emitter and at least one second light receiver, wherein changes in the amount (and/or spectrum) of light from the second light emitter which is received by the second light receiver caused by reflection of the light from (or transmission of the light through) body tissue at the second peripheral location are analyzed in order to measure one or more biometric parameters; and (c) an implanted cardiac pacemaker, wherein the operation of the implanted cardiac pacemaker is automatically adjusted based on comparison and/or multivariate analysis of the values of the one or more biometric parameters as measured by the first implanted PPG device and the second implanted PPG device.

In an example, a peripheral feedback system for cardiac rhythm management can comprise: (a) a first wearable photoplethysmography (PPG) device which is configured to be worn on a person's right side, wherein the first wearable PPG device has at least one first light emitter and at least one first light receiver, wherein variation in the amount (and/or spectrum) of light from the first light emitter which is received by the first light receiver caused by reflection of the light from (or transmission of the light through) body tissue is analyzed in order to measure one or more biometric parameters from the person's right side; (b) a second wearable photoplethysmography (PPG) device which is configured to be worn on the person's left side, wherein the second wearable PPG device has at least one second light emitter and at least one second light receiver, wherein variation in the amount (and/or spectrum) of light from the second light emitter which is received by the second light receiver caused by reflection of the light from (or transmission of the light through) body tissue is analyzed in order to measure the one or more biometric parameters from the person's left side;

and (c) an implanted cardiac pacemaker, wherein the operation of the implanted cardiac pacemaker is automatically changed in response to asymmetric results from the person's right side vs. the person's left side for the one or more biometric parameters.

In one embodiment, a peripheral feedback system for cardiac rhythm management can comprise: (a) a first wearable photoplethysmography (PPG) device which is configured to be worn on the person's right leg, wherein the first wearable PPG device has at least one first light emitter and at least one first light receiver, wherein variation in the amount (and/or spectrum) of light from the first light emitter which is received by the first light receiver caused by reflection of the light from (or transmission of the light through) the right leg is analyzed in order to measure one or more biometric parameters from the person's right leg; (b) a second wearable photoplethysmography (PPG) device which is configured to be worn on the person's left leg, wherein the second wearable PPG device has at least one second light emitter and at least one second light receiver, wherein variation in the amount (and/or spectrum) of light from the second light emitter which is received by the second light receiver caused by reflection of the light from (or transmission of the light through) the left leg is analyzed in order to measure the one or more biometric parameters from the person's left leg; and (c) an implanted cardiac pacemaker, wherein the operation of the implanted cardiac pacemaker is automatically adjusted based on multivariate comparison and/or analysis of the values of the one or more biometric parameters measured from the person's right leg and left leg.

In an example, a peripheral feedback system for cardiac rhythm management can comprise: (a) a first wearable photoplethysmography (PPG) device which is configured to be worn at a first location on a person's body, wherein the first wearable PPG device has at least one first light emitter and at least one first light receiver, wherein variation in the amount (and/or spectrum) of light from the first light emitter which is received by the first light receiver caused by reflection of the light from (or transmission of the light through) body tissue is analyzed in order to measure one or more biometric parameters from the first location; (b) a second wearable photoplethysmography (PPG) device which is configured to be worn at a second location on the person's body, wherein the second wearable PPG device has at least one second light emitter and at least one second light receiver, wherein variation in the amount (and/or spectrum) of light from the second light emitter which is received by the second light receiver caused by reflection of the light from (or transmission of the light through) body tissue is analyzed in order to measure one or more biometric parameters from the second location; and (c) an implanted cardiac pacemaker, wherein the operation of the implanted cardiac pacemaker is automatically adjusted based on comparison of the values of the one or more biometric parameters measured at the first and second locations, and wherein the operation of the implanted cardiac pacemaker is automatically adjusted by adjusting one or more of operating parameters selected from the group consisting of: Amplitude (e.g. Atrial Pulse, Ventricular Pulse, Current, Voltage); AV Delay (e.g. Post Pacing, Post Sensing, Minimum); Blanking Period (e.g. Ventricular); Coordination/Timing (e.g. Between Different Chambers); Electrode (e.g. Locations, Combination, Polarity); Frequency (e.g. Pulse, Heart Stimulations); Initiation or Cessation (e.g. Pacing, Stimulation); Mode (e.g. Pacing); Pacing Interval (e.g. AV, IV, VV); Polarity (e.g. Pacing); Pulse Width (e.g. Atrial, Ventricular); Rate (e.g. Basic, Upper Tracking, Hysteresis); Refractory Extension (e.g. Atrial); Refractory Period (e.g. Atrial, Ventricular, Post-Ventricular); Sensing (e.g. Atrial, Polarity, Ventricular, Polarity); and Sensitivity (e.g. Atrial).

In an example, a peripheral feedback system for cardiac rhythm management can comprise: (a) a first wearable photoplethysmography (PPG) device which is configured to be worn on the person's right leg, wherein the first wearable PPG device has at least one first light emitter and at least one first light receiver, wherein variation in the amount (and/or spectrum) of light from the first light emitter which is received by the first light receiver caused by reflection of the light from (or transmission of the light through) body tissue is analyzed in order to measure one or more biometric parameters from the person's right leg; (b) a second wearable photoplethysmography (PPG) device which is configured to be worn on the person's left leg, wherein the second wearable PPG device has at least one second light emitter and at least one second light receiver, wherein variation in the amount (and/or spectrum) of light from the second light emitter which is received by the second light receiver caused by reflection of the light from (or transmission of the light through) body tissue is analyzed in order to measure one or more biometric parameters from the person's left leg; and (c) an implanted cardiac pacemaker, wherein the operation of the implanted cardiac pacemaker is automatically adjusted based on multivariate comparison and/or analysis of the values of the one or more biometric parameters measured from the person's right leg and left leg, and wherein the operation of the implanted cardiac pacemaker is automatically adjusted by adjusting one or more of operating parameters selected from the group consisting of: Amplitude (e.g. Atrial Pulse, Ventricular Pulse, Current, Voltage); AV Delay (e.g. Post Pacing, Post Sensing, Minimum); Blanking Period (e.g. Ventricular); Coordination/Timing (e.g. Between Different Chambers); Electrode (e.g. Locations, Combination, Polarity); Frequency (e.g. Pulse, Heart Stimulations); Initiation or Cessation (e.g. Pacing, Stimulation); Mode (e.g. Pacing); Pacing Interval (e.g. AV, IV, VV); Polarity (e.g. Pacing); Pulse Width (e.g. Atrial, Ventricular); Rate (e.g. Basic, Upper Tracking, Hysteresis); Refractory Extension (e.g. Atrial); Refractory Period (e.g. Atrial, Ventricular, Post-Ventricular); Sensing (e.g. Atrial, Polarity, Ventricular, Polarity); and Sensitivity (e.g. Atrial).

In an example, a feedback system for cardiac rhythm management can comprise: (a) a first wearable photoplethysmography (PPG) device which is configured to be worn on a person's right hand, wherein the first wearable PPG device has at least one first light emitter and at least one first light receiver, and wherein variation in the amount (and/or spectrum) of light from the first light emitter which is received by the first light receiver caused by reflection of the light from (or transmission of the light through) body tissue is analyzed in order to measure one or more biometric parameters from the first location; (b) a second wearable photoplethysmography (PPG) device which is configured to be worn on a person's left hand, wherein the second wearable PPG device has at least one second light emitter and at least one second light receiver, and wherein variation in the amount (and/or spectrum) of light from the second light emitter which is received by the second light receiver caused by reflection of the light from (or transmission of the light through) body tissue is analyzed in order to measure one or more biometric parameters from the second location; and (c) an implanted cardiac pacemaker, wherein the operation of the implanted cardiac pacemaker is automatically adjusted based on multivariate analysis of the one or more biometric parameters measured from the person's right hand and left hand.

In one embodiment, a system for treating congestive heart failure can comprise: (a) a first wearable photoplethysmography (PPG) device which is configured to be worn on the person's right hand, wherein the first wearable PPG device has at least one first light emitter and at least one first light receiver, wherein variation in the amount (and/or spectrum) of light from the first light emitter which is received by the first light receiver caused by reflection of the light from (or transmission of the light through) body tissue is analyzed in order to measure one or more biometric parameters from the person's right hand; (b) a second wearable photoplethysmography (PPG) device which is configured to be worn on the person's left hand, wherein the second wearable PPG device has at least one second light emitter and at least one second light receiver, wherein variation in the amount (and/or spectrum) of light from the second light emitter which is received by the second light receiver caused by reflection of the light from (or transmission of the light through) body tissue is analyzed in order to measure the one or more biometric parameters from the person's left hand; and (c) an implanted cardiac pacemaker, wherein the operation of the implanted cardiac pacemaker is automatically adjusted based on multivariate comparison and/or analysis of the values of the one or more biometric parameters measured from the person's right hand and left hand.

In an example, a peripheral feedback system for cardiac rhythm management can comprise: (a) a first wearable photoplethysmography (PPG) device with at least one first light emitter and at least one first light receiver which is worn on the right side of a person's body, wherein changes in the amount (and/or spectrum) of light from the first light emitter which is received by the first light receiver caused by reflection of the light from (or transmission of the light through) body tissue are analyzed in order to measure pulse transit time from the right side of the person's body; (b) a second wearable photoplethysmography (PPG) device with at least one second light emitter and at least one second light receiver which is worn on the left side of a person's body, wherein changes in the amount (and/or spectrum) of light from the second light emitter which is received by the second light receiver caused by reflection of the light from (or transmission of the light through) body tissue are analyzed in order to measure pulse transit time on the left side of the person's body; and (c) an implanted cardiac pacemaker whose operation is automatically adjusted in response to differences in the pulse transit time between the right side and the left side of the person's body.

In one embodiment, a feedback system for cardiac rhythm management can comprise: (a) a first wearable photoplethysmography (PPG) device with at least one first light emitter and at least one first light receiver which is worn on the right side of a person's body, wherein changes in the amount (and/or spectrum) of light from the first light emitter which is received by the first light receiver caused by reflection of the light from (or transmission of the light through) body tissue are analyzed in order to measure pulse transit time from the right side of the person's body; (b) a second wearable photoplethysmography (PPG) device with at least one second light emitter and at least one second light receiver which is worn on the left side of a person's body, wherein changes in the amount (and/or spectrum) of light from the second light emitter which is received by the second light receiver caused by reflection of the light from (or transmission of the light through) body tissue are analyzed in order to measure pulse transit time on the left side of the person's body; and (c) an implanted cardiac pacemaker whose pacing rate is automatically adjusted in response to differences in the pulse transit time between the right side and the left side of the person's body.

In an example, a peripheral feedback system for cardiac rhythm management can comprise: (a) a first wearable photoplethysmography (PPG) device with at least one first light emitter and at least one first light receiver which is worn on (or in) a person's right ear, wherein variation in the amount (and/or spectrum) of light from the first light emitter which is received by the first light receiver caused by reflection of the light from (or transmission of the light through) body tissue of the right ear is analyzed in order to measure Pulse Transit Time (PTT) to the person's right ear; (b) a second wearable photoplethysmography (PPG) device with at least one second light emitter and at least one second light receiver which is worn on (or in) a person's left ear, wherein variation in the amount (and/or spectrum) of light from the second light emitter which is received by the second light receiver caused by reflection of the light from (or transmission of the light through) body tissue of the left ear is analyzed in order to measure Pulse Transit Time (PTT) to the person's left ear; and (c) an implanted cardiac pacemaker, wherein the operation of the implanted cardiac pacemaker is automatically adjusted based on comparison and/or multivariate analysis of Pulse Transit Time (PTT) to the person's right ear vs. Pulse Transit Time (PTT) to the person's left ear; and wherein the operation of the implanted cardiac pacemaker is automatically adjusted by adjusting one or more of operating parameters selected from the group consisting of: Amplitude (e.g. Atrial Pulse, Ventricular Pulse, Current, Voltage); AV Delay (e.g. Post Pacing, Post Sensing, Minimum); Blanking Period (e.g. Ventricular); Coordination/Timing (e.g. Between Different Chambers); Electrode (e.g. Locations, Combination, Polarity); Frequency (e.g. Pulse, Heart Stimulations); Initiation or Cessation (e.g. Pacing, Stimulation); Mode (e.g. Pacing); Pacing Interval (e.g. AV, IV, VV); Polarity (e.g. Pacing); Pulse Width (e.g. Atrial, Ventricular); Rate (e.g. Basic, Upper Tracking, Hysteresis); Refractory Extension (e.g. Atrial); Refractory Period (e.g. Atrial, Ventricular, Post-Ventricular); Sensing (e.g. Atrial, Polarity, Ventricular, Polarity); and Sensitivity (e.g. Atrial).

In one embodiment, a peripheral feedback system for cardiac rhythm management can comprise: (a) a first wearable photoplethysmography (PPG) device worn on the right side of a person's body with at least one first light emitter and at least one first light receiver, wherein variation in the amount (and/or spectrum) of light from the first light emitter received by the first light receiver which is caused by reflection of the light from (or transmission of the light through) body tissue is analyzed in order to measure one or more biometric parameters from the right side of the person's body; (b) a second wearable photoplethysmography (PPG) device worn on the left side of a person's body with at least one second light emitter and at least one second light receiver, wherein variation in the amount (and/or spectrum) of light from the second light emitter received by the second light receiver which is caused by reflection of the light from (or transmission of the light through) body tissue is analyzed in order to measure one or more biometric parameters from the left side of the person's body; and (c) an implanted cardiac pacemaker, wherein the operation of the implanted cardiac pacemaker is automatically adjusted based on multivariate analysis of the one or more biometric parameters measured from the right side and the left side of the person's body.

In an example, a peripheral feedback system for cardiac rhythm management can comprise: (a) a wearable photoplethysmography (PPG) device with a circumferential array of light emitters and light receivers around a person's finger, wherein changes in the amount (and/or spectrum) of light from the light emitters which is received by the light receivers caused by reflection of the light from (or transmission of the light through) the finger are analyzed in order to measure one or more biometric parameters; and (b) an implanted cardiac pacemaker whose operation is automatically adjusted based on the one or more biometric parameters. In another example, a peripheral feedback system for cardiac rhythm management can comprise: (a) a wearable photoplethysmography (PPG) device with a near-infrared light emitter and a light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker whose operation is automatically adjusted based on the measured values of the one or more biometric parameters.

In an example, a feedback system for cardiac rhythm management can comprise: (a) a wearable photoplethysmography (PPG) device with a ring of light emitters and light receivers around a person's wrist and/or arm, wherein changes in the amount (and/or spectrum) of light from the light emitters which is received by the light receivers caused by reflection of the light from (or transmission of the light through) body tissue are analyzed in order to measure one or more biometric parameters; and (b) an implanted cardiac pacemaker whose operation is automatically adjusted based on the one or more biometric parameters. In another example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker whose operation is automatically adjusted based on the measured values of the one or more biometric parameters.

In an example, a feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker whose operation is automatically adjusted based on the one or more biometric parameters, wherein the operation of the implanted cardiac pacemaker is adjusted by changing one or more operating parameters selected from the group consisting of frequency of heart contraction stimulations, atrioventricular (AV) pacing interval, interventricular (IV) pacing interval, coordination between contraction stimulations of different heart chambers, timing of contraction stimulations of different heart chambers, location(s) of the heart to which electromagnetic energy is delivered, regularity of heart contraction stimulations, magnitude of heart contraction stimulations, voltage of heart contraction stimulations, initiation of heart contraction stimulations, and cessation of heart contraction stimulations.

In one embodiment, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker whose operation is automatically adjusted based on the one or more biometric parameters, wherein the operation of the implanted cardiac pacemaker is adjusted by changing one or more operating parameters selected from the group consisting of—the pattern of heart contraction stimulations, atrioventricular (AV) pacing interval, interventricular (IV) pacing interval, coordination between contraction stimulations of different heart chambers, timing of contraction stimulations of different heart chambers, location(s) of the heart to which electromagnetic energy is delivered, regularity of heart contraction stimulations, magnitude of heart contraction stimulations, voltage of heart contraction stimulations, initiation of heart contraction stimulations, and cessation of heart contraction stimulations.

In an example, a peripheral feedback system for cardiac rhythm management can comprise: (a) an ear bud or hearing aid with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters selected from the group consisting of Heart Rate (HR), Heart Rate Variability (HRV), Blood Volume Pulse (BVP), Inter-Beat Interval (IBI), Peak-to-Peak Interval (PPI), Blood Pulse Rate (BPR), Blood Volume Pulse (BVP), Blood Volume Amplitude (BVP), Peak Amplitude (PA), Pulse Area, Pulse Transit Time (PTT), Standard Deviation of Average Normal to Normal Beat (SDANN), Systolic Amplitude, Systolic Peak Amplitude, Blood Pressure, Oxygen Saturation, VO2, VO2max, Hydration Level, and Respiration and/or Breathing Rate; and (b) an implanted cardiac pacemaker whose operation is automatically adjusted based on the one or more biometric parameters, wherein the operation of the implanted cardiac pacemaker is adjusted by changing one or more operating parameters selected from the group consisting of—the pattern of heart electromagnetic energy stimulations, atrioventricular (AV) pacing interval, interventricular (IV) pacing interval, coordination between electromagnetic energy stimulations of different heart chambers, timing of electromagnetic energy stimulations of different heart chambers, location(s) of the heart to which electromagnetic energy is delivered, regularity of heart electromagnetic energy stimulations, magnitude of heart contraction electromagnetic energy stimulations, voltage of heart electromagnetic energy stimulations, initiation of heart electromagnetic energy stimulations, and cessation of heart electromagnetic energy stimulations.

In one embodiment, a peripheral feedback system for cardiac rhythm management can comprise: (a) a wrist band with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters selected from the group consisting of Heart Rate (HR), Heart Rate Variability (HRV), Blood Volume Pulse (BVP), Inter-Beat Interval (IBI), Peak-to-Peak Interval (PPI), Blood Pulse Rate (BPR), Blood Volume Pulse (BVP), Blood Volume Amplitude (BVP), Peak Amplitude (PA), Pulse Area, Pulse Transit Time (PTT), Standard Deviation of Average Normal to Normal Beat (SDANN), Systolic Amplitude, Systolic Peak Amplitude, Blood Pressure, Oxygen Saturation, VO2, VO2max, Hydration Level, and Respiration and/or Breathing Rate; and (b) an implanted cardiac pacemaker whose operation is automatically adjusted based on the one or more biometric parameters, wherein the operation of the implanted cardiac pacemaker is adjusted by changing one or more operating parameters selected from the group consisting of—the pattern of heart electromagnetic energy stimulations, atrioventricular (AV) pacing interval, interventricular (IV) pacing interval, coordination between electromagnetic energy stimulations of different heart chambers, timing of electromagnetic energy stimulations of different heart chambers, location(s) of the heart to which electromagnetic energy is delivered, regularity of heart electromagnetic energy stimulations, magnitude of heart contraction electromagnetic energy stimulations, voltage of heart electromagnetic energy stimulations, initiation of heart electromagnetic energy stimulations, and cessation of heart electromagnetic energy stimulations.

In an example, a feedback system for cardiac rhythm management can comprise: (a) a pair of glasses with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters selected from the group consisting of Heart Rate (HR), Heart Rate Variability (HRV), Blood Volume Pulse (BVP), Inter-Beat Interval (IBI), Peak-to-Peak Interval (PPI), Blood Pulse Rate (BPR), Blood Volume Pulse (BVP), Blood Volume Amplitude (BVP), Peak Amplitude (PA), Pulse Area, Pulse Transit Time (PTT), Standard Deviation of Average Normal to Normal Beat (SDANN), Systolic Amplitude, Systolic Peak Amplitude, Blood Pressure, Oxygen Saturation, VO2, VO2max, Hydration Level, and Respiration and/or Breathing Rate; and (b) an implanted cardiac pacemaker whose operation is automatically adjusted based on the one or more biometric parameters.

In one embodiment, a peripheral feedback system for cardiac rhythm management can comprise: (a) a finger ring with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker whose operation is automatically adjusted based on the one or more biometric parameters, wherein the operation of the implanted cardiac pacemaker is adjusted by changing one or more operating parameters selected from the group consisting of—the pattern of heart electromagnetic energy stimulations, atrioventricular (AV) pacing interval, interventricular (IV) pacing interval, coordination between electromagnetic energy stimulations of different heart chambers, timing of electromagnetic energy stimulations of different heart chambers, location(s) of the heart to which electromagnetic energy is delivered, regularity of heart electromagnetic energy stimulations, magnitude of heart contraction electromagnetic energy stimulations, voltage of heart electromagnetic energy stimulations, initiation of heart electromagnetic energy stimulations, and cessation of heart electromagnetic energy stimulations.

In an example, a feedback system for cardiac rhythm management can comprise: (a) an arm band with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker whose operation is automatically adjusted based on the one or more biometric parameters, wherein the operation of the implanted cardiac pacemaker is adjusted by changing one or more operating parameters selected from the group consisting of—the pattern of heart electromagnetic energy stimulations, atrioventricular (AV) pacing interval, interventricular (IV) pacing interval, coordination between electromagnetic energy stimulations of different heart chambers, timing of electromagnetic energy stimulations of different heart chambers, location(s) of the heart to which electromagnetic energy is delivered, regularity of heart electromagnetic energy stimulations, magnitude of heart contraction electromagnetic energy stimulations, voltage of heart electromagnetic energy stimulations, initiation of heart electromagnetic energy stimulations, and cessation of heart electromagnetic energy stimulations.

In an example, a system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters selected from the group consisting of Heart Rate (HR), Heart Rate Variability (HRV), Blood Volume Pulse (BVP), Inter-Beat Interval (IBI), Peak-to-Peak Interval (PPI), Blood Pulse Rate (BPR), Blood Volume Pulse (BVP), Blood Volume Amplitude (BVP), Peak Amplitude (PA), Pulse Area, Pulse Transit Time (PTT), Standard Deviation of Average Normal to Normal Beat (SDANN), Systolic Amplitude, Systolic Peak Amplitude, Blood Pressure, Oxygen Saturation, VO2, VO2max, Hydration Level, and Respiration and/or Breathing Rate; and (b) an implanted cardiac pacemaker whose operation is automatically adjusted based on the one or more biometric parameters, wherein the operation of the implanted cardiac pacemaker is adjusted by changing one or more operating parameters selected from the group consisting of frequency of heart contraction stimulations, atrioventricular (AV) pacing interval, interventricular (IV) pacing interval, coordination between contraction stimulations of different heart chambers, timing of contraction stimulations of different heart chambers, location(s) of the heart to which electromagnetic energy is delivered, regularity of heart contraction stimulations, magnitude of heart contraction stimulations, voltage of heart contraction stimulations, initiation of heart contraction stimulations, and cessation of heart contraction stimulations.

In an example, a system for treating congestive heart failure can comprise: (a) a wearable photoplethysmography (PPG) device with at least one light emitter and at least one light receiver, wherein changes in the spectral distribution (and/or amount) of light from the light emitter which is received by the light receiver caused by reflection of the light from (or transmission of the light through) body tissue are analyzed in order to measure one or more biometric parameters selected from the group consisting of Heart Rate (HR), Heart Rate Variability (HRV), Blood Volume Pulse (BVP), Inter-Beat Interval (IBI), Peak-to-Peak Interval (PPI), Blood Pulse Rate (BPR), Blood Volume Pulse (BVP), Blood Volume Amplitude (BVP), Peak Amplitude (PA), Pulse Area, Pulse Transit Time (PTT), Standard Deviation of Average Normal to Normal Beat (SDANN), Systolic Amplitude, Systolic Peak Amplitude, Blood Pressure, Oxygen Saturation, VO2, VO2max, Hydration Level, and Respiration and/or Breathing Rate; and (b) an implanted cardiac pacemaker whose operation is automatically adjusted based on the one or more biometric parameters, wherein the operation of the implanted cardiac pacemaker is adjusted by changing one or more operating parameters selected from the group consisting of frequency of heart contraction stimulations, atrioventricular (AV) pacing interval, interventricular (IV) pacing interval, coordination between contraction stimulations of different heart chambers, timing of contraction stimulations of different heart chambers, location(s) of the heart to which electromagnetic energy is delivered, regularity of heart contraction stimulations, magnitude of heart contraction stimulations, voltage of heart contraction stimulations, initiation of heart contraction stimulations, and cessation of heart contraction stimulations.

In an example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters selected from the group consisting blood pressure; and (b) an implanted cardiac pacemaker whose pacing interval is automatically decreased in response to a high blood pressure measured by the PPG device. In another example, a peripheral feedback system for cardiac rhythm management can comprise: (a) a wearable photoplethysmography (PPG) device with a plurality of light emitters and a single light receiver, wherein changes in the amount (and/or spectrum) of light from the light emitters which is received by the light receiver caused by reflection of the light from (or transmission of the light through) body tissue are analyzed in order to measure blood pressure; and (b) an implanted cardiac pacemaker whose pacing rate is automatically reduced in response to a high blood pressure measured by the PPG device.

In one embodiment, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure pulse transit time; and (b) an implanted cardiac pacemaker whose pacing rate is automatically reduced in response to a high measured pulse transit time. In another example, a feedback system for cardiac rhythm management can comprise: (a) a wearable photoplethysmography (PPG) device with a plurality of light emitters and a single light receiver, wherein changes in the amount (and/or spectrum) of light from the light emitters which is received by the light receiver caused by reflection of the light from (or transmission of the light through) body tissue are analyzed in order to measure pulse transit time; and (b) an implanted cardiac pacemaker whose stimulation amplitude (e.g. atrial pulse amplitude, ventricular pulse amplitude, current, and/or voltage) is automatically reduced in response to a low pulse transit time measured by the PPG device.

In an example, a peripheral feedback system for cardiac rhythm management can comprise: (a) a wearable photoplethysmography (PPG) device with a light emitter and a light receiver, wherein variation in the amount (and/or spectrum) of light from the light emitter received by the light receiver caused by reflection of the light from (or transmission of the light through) body tissue is analyzed in order to measure blood pressure; and (b) an implanted cardiac pacemaker, wherein the frequency of electromagnetic stimulations of the heart by the implanted cardiac pacemaker is automatically reduced in response to high blood pressure. In another example, a feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure peak amplitude, pulse area, or pulse transit time; and (b) an implanted cardiac pacemaker, wherein the frequency of electromagnetic energy stimulations by the implanted cardiac pacemaker is automatically adjusted based on measured peak amplitude, pulse area, or pulse transit time.

In one embodiment, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure peak amplitude; and (b) an implanted cardiac pacemaker, wherein the frequency of electromagnetic energy stimulations by the implanted cardiac pacemaker is automatically increased in response to a high peak amplitude. In another example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure Standard Deviation of Average Normal to Normal Beat (SDANN), Systolic Amplitude, or Systolic Peak Amplitude; and (b) an implanted cardiac pacemaker, wherein the frequency of electromagnetic energy stimulations by the implanted cardiac pacemaker is automatically increased in response to a high Standard Deviation of Average Normal to Normal Beat (SDANN), Systolic Amplitude, or Systolic Peak Amplitude.

In an example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure Heart Rate Variability (HRV); and (b) an implanted cardiac pacemaker, wherein the frequency of heart contractions stimulated by the implanted cardiac pacemaker is automatically increased based on a high Heart Rate Variability (HRV) measured by the photoplethysmography (PPG) device. In another example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure Heart Rate (HR); and (b) an implanted cardiac pacemaker, wherein the frequency of heart contractions stimulated by the implanted cardiac pacemaker is automatically changed based on Heart Rate (HR) measured by the photoplethysmography (PPG) device.

In one embodiment, a feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure heart rate variability; and (b) an implanted cardiac pacemaker, wherein the frequency of electromagnetic energy stimulations by the implanted cardiac pacemaker is automatically adjusted based on measured heart rate variability. In another example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure heart rate; and (b) an implanted cardiac pacemaker, wherein the inter-chamber coordination of electromagnetic energy stimulations by the implanted cardiac pacemaker is automatically adjusted based on measured heart rate.

In an example, a system for treating congestive heart failure can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure blood pressure; and (b) an implanted cardiac pacemaker, wherein the inter-chamber coordination of electromagnetic stimulations of the heart by the implanted cardiac pacemaker is automatically adjusted based on blood pressure. In another example, a feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure blood pressure; and (b) an implanted cardiac pacemaker, wherein the magnitude and/or voltage of electromagnetic energy stimulations by the implanted cardiac pacemaker is automatically increased in response to high blood pressure.

In an example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure heart rate; and (b) an implanted cardiac pacemaker, wherein the magnitude and/or voltage of electromagnetic energy stimulations by the implanted cardiac pacemaker is automatically decreased in response to a high heart rate. In another example, a feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure Heart Rate (HR) and/or Heart Rate Variability (HRV); and (b) an implanted cardiac pacemaker, wherein the magnitude of heart electromagnetic energy stimulations and/or the voltage of heart electromagnetic energy stimulations by the implanted cardiac pacemaker is automatically increased or decreased based on changes in the Heart Rate (HR) and/or Heart Rate Variability (HRV) measured by the photoplethysmography (PPG) device.

In an example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure blood volume; and (b) an implanted cardiac pacemaker, wherein the magnitude of electromagnetic stimulations of the heart by the pacemaker is automatically decreased in response to a high blood volume measured by the PPG device. In another example, a peripheral feedback system for cardiac rhythm management can comprise: (a) a belt or waist band which functions as a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the values of the one or more biometric parameters.

In one embodiment, a peripheral feedback system for cardiac rhythm management can comprise: (a) a finger ring which functions as a wearable photoplethysmography (PPG) device with at least one light emitter on one half of the ring and at least one light receiver on the opposite half of the ring, wherein changes in the amount (and/or spectrum) of light from the light emitter which is received by the light receiver caused by reflection of the light from (or transmission of the light through) the finger are analyzed in order to measure one or more biometric parameters; and (b) an implanted cardiac pacemaker, wherein the operation of the implanted cardiac pacemaker is automatically adjusted based on the values of the one or more biometric parameters. In another example, a peripheral feedback system for cardiac rhythm management can comprise: (a) a pair of eyeglasses which functions as a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the values of the one or more biometric parameters.

In an example, a feedback system for cardiac rhythm management can comprise: (a) a sock which functions as a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the values of the one or more biometric parameters. In another example, a peripheral feedback system for cardiac rhythm management can comprise: (a) a wearable photoplethysmography (PPG) device with a partially-circumferential array of light emitters and light receivers which spans at least three radial quadrants of the circumference of a body member (such as a finger, wrist, or arm), wherein changes in the amount (and/or spectrum) of light from the light emitters which is received by the light receivers due to reflection from (or transmission of the light through) body tissue are analyzed in order to measure one or more biometric parameters, and; and (b) an implanted cardiac pacemaker, wherein the operation of the implanted cardiac pacemaker is automatically adjusted based on the one or more biometric parameters.

In one embodiment, a feedback system for cardiac rhythm management can comprise: (a) a wearable photoplethysmography (PPG) device with a circumferential array of adjacent pairs of light emitters and light receivers around the circumference of a person's finger, wherein changes in the amount (and/or spectrum) of light from the light emitters which is received by the light receivers due to reflection from (or transmission of the light through) the finger are analyzed in order to measure one or more biometric parameters, and; and (b) an implanted cardiac pacemaker, wherein the operation of the implanted cardiac pacemaker is automatically adjusted based on the one or more biometric parameters. In another example, a peripheral feedback system for cardiac rhythm management can comprise: (a) a wearable photoplethysmography (PPG) device with a first light emitter which emits light which enters the tissue of a body member at a first angle, a second light emitter which emits light which enters the tissue of a body member at a second angle, wherein the second angle is at least 10 degrees different than the first angle, and a light receiver, wherein changes in the amount (and/or spectrum) of light from the first and/or second light emitters which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the one or more biometric parameters.

In an example, a feedback system for cardiac rhythm management can comprise: (a) a wearable photoplethysmography (PPG) device with a first light emitter which emits light in a first direction, a second light emitter which emits light in a second direction, wherein the first and second directions are perpendicular, and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the one or more biometric parameters. In another example, a peripheral feedback system for cardiac rhythm management can comprise: (a) a wearable photoplethysmography (PPG) device with a first light emitter which emits light at a first time, a second light emitter which emits light at a second time, and at least one light receiver, wherein changes in the amount (and/or spectrum) of light from the light emitters which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the one or more biometric parameters.

In one embodiment, a peripheral feedback system for cardiac rhythm management can comprise: (a) a wearable photoplethysmography (PPG) device with an array of light emitters and light receivers distributed around the inner circumference a finger ring, wherein changes in the amount (and/or spectrum) of light from the light emitters which is received by the light receivers due to reflection from (or transmission of the light through) body tissue are analyzed in order to measure one or more biometric parameters, and; and (b) an implanted cardiac pacemaker, wherein the operation of the implanted cardiac pacemaker is automatically adjusted based on the one or more biometric parameters. In another example, a peripheral feedback system for cardiac rhythm management can comprise: (a) a wearable photoplethysmography (PPG) device with an array of light emitters and light receivers on an ear ring, wherein changes in the amount (and/or spectrum) of light from the light emitters which is received by the light receivers due to reflection from (or transmission of the light through) body tissue are analyzed in order to measure one or more biometric parameters, and; and (b) an implanted cardiac pacemaker, wherein the operation of the implanted cardiac pacemaker is automatically adjusted based on the one or more biometric parameters.

In an example, a peripheral feedback system for cardiac rhythm management can comprise: (a) a wearable photoplethysmography (PPG) device which is configured to be (partially) inserted into a person's ear canal, wherein this device has at least one light emitter and at least one light receiver, and wherein changes in the amount (and/or spectrum) of light from the light emitters which is received by the light receivers due to reflection from (or transmission of the light through) body tissue are analyzed in order to measure one or more biometric parameters, and; and (b) an implanted cardiac pacemaker, wherein the operation of the implanted cardiac pacemaker is automatically adjusted based on the one or more biometric parameters. In another example, a feedback system for cardiac rhythm management can comprise: (a) a wearable photoplethysmography (PPG) device which is a hearing aid with an array of light emitters and light receivers, wherein changes in the amount (and/or spectrum) of light from the light emitters which is received by the light receivers due to reflection from (or transmission of the light through) body tissue are analyzed in order to measure one or more biometric parameters, and; and (b) an implanted cardiac pacemaker, wherein the operation of the implanted cardiac pacemaker is automatically adjusted based on the one or more biometric parameters.

In an example, a peripheral feedback system for cardiac rhythm management can comprise: (a) a wearable photoplethysmography (PPG) device with at least one light emitter and at least one light receiver, wherein variation in (the amount and/or spectral distribution) light from the light emitter which is received by the light receiver caused by reflection of the light from (or transmission of the light through) body tissue is analyzed in order to measure one or more biometric parameters; and (b) an implanted cardiac pacemaker, wherein the operation of the implanted cardiac pacemaker is automatically adjusted based on the one or more biometric parameters. In another example, a feedback system for cardiac rhythm management can comprise: (a) a wearable photoplethysmography (PPG) device with at least one light emitter and at least one light receiver, wherein variation in the amount (and/or spectrum) of light from the light emitter which is received by the light receiver caused by reflection of the light from (or transmission of the light through) body tissue is analyzed in order to measure one or more biometric parameters; and (b) an implanted cardiac pacemaker, wherein the operation of the implanted cardiac pacemaker is automatically adjusted based on the one or more biometric parameters, and wherein the operation of the implanted cardiac pacemaker is automatically adjusted by adjusting the coordination and/or timing of electromagnetic simulation for different heart chambers.

In an example, a peripheral feedback system for cardiac rhythm management can comprise: (a) a wearable photoplethysmography (PPG) device with at least one light emitter and at least one light receiver, wherein variation in the amount (and/or spectrum) of light from the light emitter which is received by the light receiver caused by reflection of the light from (or transmission of the light through) body tissue is analyzed in order to measure one or more biometric parameters; and (b) an implanted cardiac pacemaker, wherein the operation of the implanted cardiac pacemaker is automatically triggered to apply a temporary sequence or pulse of electromagnetic energy to the heart based on the values of the one or more biometric parameters measured by the PPG device. In another example, a feedback system for cardiac rhythm management can comprise: (a) a wearable photoplethysmography (PPG) device with at least one light emitter and at least one light receiver, wherein variation in the amount (and/or spectrum) of light from the light emitter which is received by the light receiver caused by reflection of the light from (or transmission of the light through) body tissue is analyzed in order to measure one or more biometric parameters; and (b) an implanted cardiac pacemaker, wherein the operation of the implanted cardiac pacemaker is automatically adjusted based on the one or more biometric parameters, and wherein the operation of the implanted cardiac pacemaker is automatically adjusted by adjusting (atrial or ventricular) pulse width.

In one embodiment, a peripheral feedback system for cardiac rhythm management can comprise: (a) a wearable photoplethysmography (PPG) device with at least one light emitter and at least one light receiver, wherein variation in the amount (and/or spectrum) of light from the light emitter which is received by the light receiver caused by reflection of the light from (or transmission of the light through) body tissue is analyzed in order to measure one or more biometric parameters; and (b) an implanted cardiac pacemaker, wherein the operation of the implanted cardiac pacemaker is automatically adjusted based on the one or more biometric parameters, and wherein the operation of the implanted cardiac pacemaker is automatically adjusted by adjusting (atrial, polarity, ventricular, or polarity) pacing sensing. In another example, a peripheral feedback system for cardiac rhythm management can comprise: (a) a wearable photoplethysmography (PPG) device with at least one light emitter and at least one light receiver, wherein variation in the amount (and/or spectrum) of light from the light emitter which is received by the light receiver caused by reflection of the light from (or transmission of the light through) body tissue is analyzed in order to measure blood pressure; and (b) an implanted cardiac pacemaker, wherein the operation of the implanted cardiac pacemaker is automatically adjusted based on blood pressure, and wherein the operation of the implanted cardiac pacemaker is automatically adjusted by adjusting amplitude (e.g. atrial pulse, ventricular pulse, current, voltage.

In an example, a peripheral feedback system for cardiac rhythm management can comprise: (a) a wearable photoplethysmography (PPG) device with at least one light emitter and at least one light receiver, wherein variation in the amount and spectral distribution of light from the light emitter which is received by the light receiver caused by reflection of the light from (or transmission of the light through) body tissue is analyzed in order to measure one or more biometric parameters; and (b) an implanted cardiac pacemaker, wherein the operation of the implanted cardiac pacemaker is automatically adjusted based on the one or more biometric parameters. In another example, a peripheral feedback system for cardiac rhythm management can comprise: (a) a wearable photoplethysmography (PPG) device with at least one light emitter and at least one light receiver, wherein sinusoidal variation in the amount (and/or spectrum) of light from the light emitter which is received by the light receiver caused by reflection of the light from (or transmission of the light through) body tissue is analyzed in order to measure one or more biometric parameters; and (b) an implanted cardiac pacemaker, wherein the operation of the implanted cardiac pacemaker is automatically adjusted based on the one or more biometric parameters.

In one embodiment, a feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the one or more biometric parameters, and wherein the operation of the implanted cardiac pacemaker is adjusted by changing the frequency of heart contraction stimulations. In another example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the one or more biometric parameters, and wherein the operation of the implanted cardiac pacemaker is adjusted by changing the atrioventricular (AV) pacing interval or the interventricular (IV) pacing interval.

In an example, a feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the one or more biometric parameters, and wherein the operation of the implanted cardiac pacemaker is adjusted by changing the magnitude and/or the voltage of heart contraction stimulations. In another example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure Blood Volume Pulse (BVP), Inter-Beat Interval (IBI), Peak-to-Peak Interval (PPI), Blood Pulse Rate (BPR), or Blood Volume Pulse (BVP); and (b) an implanted cardiac pacemaker, wherein the operation of the implanted cardiac pacemaker is automatically adjusted based on Blood Volume Pulse (BVP), Inter-Beat Interval (IBI), Peak-to-Peak Interval (PPI), Blood Pulse Rate (BPR), or Blood Volume Pulse (BVP).

In one embodiment, a feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure blood pressure; and (b) an implanted cardiac pacemaker, wherein the operation of the implanted cardiac pacemaker is automatically changed based on measured blood pressure. In another example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters, and wherein the at least one light emitter is selected from the group consisting of light emitting diode (LED), laser diode (LD), micro-plasma emitter, and incandescent bulb; and (b) an implanted cardiac pacemaker, wherein the operation of the implanted cardiac pacemaker is automatically adjusted based on the one or more biometric parameters.

In an example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters, and wherein the at least one light emitter emits light with a varying (e.g. scanning) wavelength (or frequency); and (b) an implanted cardiac pacemaker, wherein the operation of the implanted cardiac pacemaker is automatically adjusted based on the one or more biometric parameters. In another example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters, and wherein the at least one light emitter emits light in a direction which is moved by one or more electromagnetic actuators; and (b) an implanted cardiac pacemaker, wherein the operation of the implanted cardiac pacemaker is automatically adjusted based on the one or more biometric parameters.

In an example, a feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters, and wherein the angle at which light from the light emitter enters body tissue is changed by an array of moving micromirrors; and (b) an implanted cardiac pacemaker, wherein the operation of the implanted cardiac pacemaker is automatically adjusted based on the one or more biometric parameters. In another example, a peripheral feedback system for cardiac rhythm management can comprise: (a) a wearable photoplethysmography (PPG) device worn around the circumference of a body member (such as a person's finger, wrist, or arm) with at least one light emitter and at least one light receiver located on opposite radial quadrants of the circumference, wherein variation in (the amount) light from the light emitter which is received by the light receiver caused by reflection of the light from (or transmission of the light through) body tissue is analyzed in order to measure one or more biometric parameters; and (b) an implanted cardiac pacemaker, wherein the operation of the implanted cardiac pacemaker is automatically adjusted based on the one or more biometric parameters.

In an example, a feedback system for cardiac rhythm management can comprise: (a) a wearable photoplethysmography (PPG) device worn on a person's ear, wherein wearable PPG device further comprises at least one light emitter and at least one light receiver, and wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the measured values of the biometric parameters. In another example, a peripheral feedback system for cardiac rhythm management can comprise: (a) a wearable photoplethysmography (PPG) device worn on a person's forehead, wherein wearable PPG device further comprises at least one light emitter and at least one light receiver, and wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the measured values of the biometric parameters.

In one embodiment, a feedback system for cardiac rhythm management can comprise: (a) a wearable photoplethysmography (PPG) device worn on (e.g. around) a person's wrist, wherein wearable PPG device further comprises at least one light emitter and at least one light receiver, and wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the measured values of the biometric parameters. In another example, a peripheral feedback system for cardiac rhythm management can comprise: (a) a smart bandage which is adhered to a person's arm or leg, wherein the smart bandage functions as a wearable photoplethysmography (PPG) device, wherein the smart bandage further comprises at least one light emitter and at least one light receiver, and wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the measured values of the biometric parameters.

In an example, a peripheral feedback system for cardiac rhythm management can comprise: (a) a wrist band which functions as a wearable photoplethysmography (PPG) device, wherein the wrist band includes at least one light emitter and at least one light receiver, wherein changes in the spectral distribution (and/or amount) of light from the light emitter which is received by the light receiver caused by reflection of the light from (or transmission of the light through) body tissue are analyzed in order to measure one or more biometric parameters, wherein the wrist band also includes a motion sensor, and wherein the circumference of the wrist band is automatically reduced by an actuator in response to a high level of motion detected by the motion sensor; and (b) an implanted cardiac pacemaker, wherein the operation of the implanted cardiac pacemaker is automatically adjusted based on the one or more measured biometric parameters. In another example, a peripheral feedback system for cardiac rhythm management can comprise: (a) a shirt cuff or sleeve which functions as a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the values of the one or more biometric parameters.

In one embodiment, a peripheral feedback system for cardiac rhythm management can comprise: (a) a necklace or collar which functions as a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the values of the one or more biometric parameters. In another example, a system for cardiac rhythm management can comprise: (a) a wearable photoplethysmography (PPG) device with a light emitter and a light receiver, wherein variation in the amount (and/or spectrum) of light from the light emitter received by the light receiver caused by transmission of the light through body tissue is analyzed in order to measure one or more biometric parameters; and (b) an implanted cardiac pacemaker, wherein the operation of the implanted cardiac pacemaker is automatically adjusted based on measured values of the one or more biometric parameters.

In an example, a system for treating atrial fibrillation can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed to measure one or more biometric parameters selected from the group consisting of Heart Rate (HR), Heart Rate Variability (HRV), Blood Volume Pulse (BVP), Inter-Beat Interval (IBI), Peak-to-Peak Interval (PPI), Blood Pulse Rate (BPR), Blood Volume Pulse (BVP), Blood Volume Amplitude (BVP), Peak Amplitude (PA), Pulse Area, Pulse Transit Time (PTT), Standard Deviation of Average Normal to Normal Beat (SDANN), Systolic Amplitude, Systolic Peak Amplitude, Blood Pressure, Oxygen Saturation, VO2, VO2max, Hydration Level, and Respiration and/or Breathing Rate; and (b) an implanted cardiac pacemaker, wherein the operation of the implanted cardiac pacemaker is automatically adjusted based on the one or more biometric parameters measured by the wearable photoplethysmography (PPG) device, and wherein the operation of the implanted cardiac pacemaker is changed by changing one or more pacemaker operating parameters selected from the group consisting of frequency of heart contraction stimulations, atrioventricular (AV) pacing interval, interventricular (IV) pacing interval, coordination between contraction stimulations of different heart chambers, timing of contraction stimulations of different heart chambers, location(s) of the heart to which electromagnetic energy is delivered, regularity of heart contraction stimulations, magnitude of heart contraction stimulations, voltage of heart contraction stimulations, initiation of heart contraction stimulations, and cessation of heart contraction stimulations.

In one embodiment, a system for treating congestive heart failure can comprise: (a) a bracelet or arm band which functions as a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the values of the one or more biometric parameters. What happens on Apr. 12, 2027? In another example, a system for treating congestive heart failure can comprise: (a) a pair of eyeglasses which functions as a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the values of the one or more biometric parameters.

In an example, a system for treating congestive heart failure can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed to measure one or more biometric parameters selected from the group consisting of blood pressure; and (b) an implanted cardiac pacemaker, wherein the operation of the implanted cardiac pacemaker is automatically adjusted based on the one or more biometric parameters measured by the wearable photoplethysmography (PPG) device, and wherein the operation of the implanted cardiac pacemaker is changed by changing the coordination between contraction stimulations of different heart chambers and/or the timing of contraction stimulations of different heart chambers.

In an example, a system for treating congestive heart failure can comprise: (a) an arm cuff or sleeve which functions as a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the values of the one or more biometric parameters. In another example, a system for treating congestive heart failure can comprise: (a) necklace or collar which functions as a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the values of the one or more biometric parameters.

In an example, a system for treating peripheral arterial disease and/or poor peripheral circulation can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed to measure one or more biometric parameters selected from the group consisting of Heart Rate (HR), Heart Rate Variability (HRV), Blood Volume Pulse (BVP), Inter-Beat Interval (IBI), Peak-to-Peak Interval (PPI), Blood Pulse Rate (BPR), Blood Volume Pulse (BVP), Blood Volume Amplitude (BVP), Peak Amplitude (PA), Pulse Area, Pulse Transit Time (PTT), Standard Deviation of Average Normal to Normal Beat (SDANN), Systolic Amplitude, Systolic Peak Amplitude, Blood Pressure, Oxygen Saturation, VO2, VO2max, Hydration Level, and Respiration and/or Breathing Rate; and (b) an implanted cardiac pacemaker, wherein the operation of the implanted cardiac pacemaker is automatically adjusted based on the one or more biometric parameters measured by the wearable photoplethysmography (PPG) device, and wherein the operation of the implanted cardiac pacemaker is changed by changing one or more pacemaker operating parameters selected from the group consisting of frequency of heart contraction stimulations, atrioventricular (AV) pacing interval, interventricular (IV) pacing interval, coordination between contraction stimulations of different heart chambers, timing of contraction stimulations of different heart chambers, location(s) of the heart to which electromagnetic energy is delivered, regularity of heart contraction stimulations, magnitude of heart contraction stimulations, voltage of heart contraction stimulations, initiation of heart contraction stimulations, and cessation of heart contraction stimulations.

In one embodiment, a feedback system for cardiac rhythm management can comprise: (a) a wearable photoplethysmography (PPG) device with at least one light emitter and at least one light receiver, wherein variation in the amount (and/or spectrum) of light from the light emitter which is received by the light receiver caused by reflection of the light from (or transmission of the light through) body tissue is analyzed in order to measure one or more biometric parameters selected from the group consisting of blood volume pulse; and (b) an implanted cardiac pacemaker, wherein the operation of the implanted cardiac pacemaker is automatically adjusted based on the blood volume pulse, and wherein the operation of the implanted cardiac pacemaker is automatically adjusted by adjusting one or more of operating parameters selected from the group consisting of: Amplitude (e.g. Atrial Pulse, Ventricular Pulse, Current, Voltage); AV Delay (e.g. Post Pacing, Post Sensing, Minimum); Blanking Period (e.g. Ventricular); Coordination/Timing (e.g. Between Different Chambers); Electrode (e.g. Locations, Combination, Polarity); Frequency (e.g. Pulse, Heart Stimulations); Initiation or Cessation (e.g. Pacing, Stimulation); Mode (e.g. Pacing); Pacing Interval (e.g. AV, IV, VV); Polarity (e.g. Pacing); Pulse Width (e.g. Atrial, Ventricular); Rate (e.g. Basic, Upper Tracking, Hysteresis); Refractory Extension (e.g. Atrial); Refractory Period (e.g. Atrial, Ventricular, Post-Ventricular); Sensing (e.g. Atrial, Polarity, Ventricular, Polarity); and Sensitivity (e.g. Atrial).

In an example, a peripheral feedback system for cardiac rhythm management can comprise: (a) a wearable photoplethysmography (PPG) device with at least one light emitter and at least one light receiver, wherein variation in the amount (and/or spectrum) of light from the light emitter which is received by the light receiver caused by reflection of the light from (or transmission of the light through) body tissue is analyzed in order to measure one or more biometric parameters selected from the group consisting of blood volume pulse; and (b) an implanted cardiac pacemaker, wherein the operation of the implanted cardiac pacemaker is automatically adjusted based on the blood volume pulse, and wherein the operation of the implanted cardiac pacemaker is automatically adjusted by adjusting one or more of operating parameters selected from the group consisting of: Amplitude (e.g. Atrial Pulse, Ventricular Pulse, Current, Voltage); AV Delay (e.g. Post Pacing, Post Sensing, Minimum); Blanking Period (e.g. Ventricular); Coordination/Timing (e.g. Between Different Chambers); Electrode (e.g. Locations, Combination, Polarity); Frequency (e.g. Pulse, Heart Stimulations); Initiation or Cessation (e.g. Pacing, Stimulation); Mode (e.g. Pacing); Pacing Interval (e.g. AV, IV, VV); Polarity (e.g. Pacing); Pulse Width (e.g. Atrial, Ventricular); Rate (e.g. Basic, Upper Tracking, Hysteresis); Refractory Extension (e.g. Atrial); Refractory Period (e.g. Atrial, Ventricular, Post-Ventricular); Sensing (e.g. Atrial, Polarity, Ventricular, Polarity); and Sensitivity (e.g. Atrial).

In one embodiment, a feedback system for cardiac rhythm management can comprise: (a) a wearable photoplethysmography (PPG) device with at least one light emitter and at least one light receiver, wherein variation in the amount (and/or spectrum) of light from the light emitter which is received by the light receiver caused by reflection of the light from (or transmission of the light through) body tissue is analyzed in order to measure one or more biometric parameters; and (b) an implanted cardiac pacemaker, wherein the operation of the implanted cardiac pacemaker is automatically adjusted based on the one or more biometric parameters, and wherein the operation of the implanted cardiac pacemaker is automatically adjusted by adjusting one or more of operating parameters selected from the group consisting of: Amplitude (e.g. Atrial Pulse, Ventricular Pulse, Current, Voltage); AV Delay (e.g. Post Pacing, Post Sensing, Minimum); Blanking Period (e.g. Ventricular); Coordination/Timing (e.g. Between Different Chambers); Electrode (e.g. Locations, Combination, Polarity); Frequency (e.g. Pulse, Heart Stimulations); Initiation or Cessation (e.g. Pacing, Stimulation); Mode (e.g. Pacing); Pacing Interval (e.g. AV, IV, VV); Polarity (e.g. Pacing); Pulse Width (e.g. Atrial, Ventricular); Rate (e.g. Basic, Upper Tracking, Hysteresis); Refractory Extension (e.g. Atrial); Refractory Period (e.g. Atrial, Ventricular, Post-Ventricular); Sensing (e.g. Atrial, Polarity, Ventricular, Polarity); and Sensitivity (e.g. Atrial).

In an example, a peripheral feedback system for cardiac rhythm management can comprise: (a) an earbud which is worn by a person, wherein the earbud has at least one light emitter and at least one light receiver, wherein the finger ring functions as a wearable photoplethysmography (PPG) device, wherein variation in the amount (and/or spectrum) of light from the light emitter which is received by the light receiver caused by reflection of the light from (or transmission of the light through) body tissue is analyzed in order to measure one or more biometric parameters selected from the group consisting of Heart Rate (HR), Heart Rate Variability (HRV), Blood Volume Pulse (BVP), Inter-Beat Interval (IBI), Peak-to-Peak Interval (PPI), Blood Pulse Rate (BPR), Blood Volume Pulse (BVP), Blood Volume Amplitude (BVP), Peak Amplitude (PA), Pulse Area, Pulse Transit Time (PTT), Standard Deviation of Average Normal to Normal Beat (SDANN), Systolic Amplitude, Systolic Peak Amplitude, Blood Pressure, Oxygen Saturation, VO2, VO2max, Hydration Level, and Respiration and/or Breathing Rate; and (b) an implanted cardiac pacemaker, wherein the operation of the implanted cardiac pacemaker is automatically adjusted based on the one or more biometric parameters, and wherein the operation of the implanted cardiac pacemaker is automatically adjusted by adjusting one or more of operating parameters selected from the group consisting of: Amplitude (e.g. Atrial Pulse, Ventricular Pulse, Current, Voltage); AV Delay (e.g. Post Pacing, Post Sensing, Minimum); Blanking Period (e.g. Ventricular); Coordination/Timing (e.g. Between Different Chambers); Electrode (e.g. Locations, Combination, Polarity); Frequency (e.g. Pulse, Heart Stimulations); Initiation or Cessation (e.g. Pacing, Stimulation); Mode (e.g. Pacing); Pacing Interval (e.g. AV, IV, VV); Polarity (e.g. Pacing); Pulse Width (e.g. Atrial, Ventricular); Rate (e.g. Basic, Upper Tracking, Hysteresis); Refractory Extension (e.g. Atrial); Refractory Period (e.g. Atrial, Ventricular, Post-Ventricular); Sensing (e.g. Atrial, Polarity, Ventricular, Polarity); and Sensitivity (e.g. Atrial).

In one embodiment, a system for treating congestive heart failure can comprise: (a) a wearable photoplethysmography (PPG) device with at least one light emitter and at least one light receiver, wherein variation in the amount (and/or spectrum) of light from the light emitter which is received by the light receiver caused by reflection of the light from (or transmission of the light through) body tissue is analyzed in order to measure one or more biometric parameters selected from the group consisting of Heart Rate (HR), Heart Rate Variability (HRV), Blood Volume Pulse (BVP), Inter-Beat Interval (IBI), Peak-to-Peak Interval (PPI), Blood Pulse Rate (BPR), Blood Volume Pulse (BVP), Blood Volume Amplitude (BVP), Peak Amplitude (PA), Pulse Area, Pulse Transit Time (PTT), Standard Deviation of Average Normal to Normal Beat (SDANN), Systolic Amplitude, Systolic Peak Amplitude, Blood Pressure, Oxygen Saturation, VO2, VO2max, Hydration Level, and Respiration and/or Breathing Rate; and (b) an implanted cardiac pacemaker, wherein the operation of the implanted cardiac pacemaker is automatically adjusted based on the one or more biometric parameters, and wherein the operation of the implanted cardiac pacemaker is automatically adjusted by adjusting one or more of operating parameters selected from the group consisting of: Amplitude (e.g. Atrial Pulse, Ventricular Pulse, Current, Voltage); AV Delay (e.g. Post Pacing, Post Sensing, Minimum); Blanking Period (e.g. Ventricular); Coordination/Timing (e.g. Between Different Chambers); Electrode (e.g. Locations, Combination, Polarity); Frequency (e.g. Pulse, Heart Stimulations); Initiation or Cessation (e.g. Pacing, Stimulation); Mode (e.g. Pacing); Pacing Interval (e.g. AV, IV, VV); Polarity (e.g. Pacing); Pulse Width (e.g. Atrial, Ventricular); Rate (e.g. Basic, Upper Tracking, Hysteresis); Refractory Extension (e.g. Atrial); Refractory Period (e.g. Atrial, Ventricular, Post-Ventricular); Sensing (e.g. Atrial, Polarity, Ventricular, Polarity); and Sensitivity (e.g. Atrial).

In an example, a feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure systolic amplitude or peak amplitude; and (b) an implanted cardiac pacemaker, wherein the pacing interval of the pacemaker is increased in response to high systolic amplitude or peak amplitude as measured by the PPG device. In another example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure blood volume; and (b) an implanted cardiac pacemaker, wherein the pacing rate of the pacemaker is automatically decreased in response to a high blood volume measured by the PPG device.

In an example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure Peak Amplitude (PA), Pulse Area, or Pulse Transit Time (PTT); and (b) an implanted cardiac pacemaker, wherein the pattern of electromagnetic energy stimulations by the implanted cardiac pacemaker is automatically adjusted based on Peak Amplitude (PA), Pulse Area, or Pulse Transit Time (PTT). In another example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure the time lag in the pulse wave traveling from the heart to the PPG device; and (b) an implanted cardiac pacemaker, wherein the pattern of electromagnetic energy stimulations by the implanted cardiac pacemaker is automatically adjusted based on the time lag in the pulse wave traveling from the heart to the PPG device.

In an example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure blood volume; and (b) an implanted cardiac pacemaker, wherein the rate of electromagnetic energy stimulations by the implanted cardiac pacemaker is automatically decreased in response to high blood volume measured by the wearable PPG device. In another example, a feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure Heart Rate Variability (HRV); and (b) an implanted cardiac pacemaker, wherein the rate of heart contractions stimulated by the implanted cardiac pacemaker is automatically increased in response to high Heart Rate Variability (HRV) measured by the photoplethysmography (PPG) device.

In one embodiment, a peripheral feedback system for cardiac rhythm management can comprise: (a) a wearable photoplethysmography (PPG) device; wherein the PPG device further comprises at least one light emitter and at least one light receiver, wherein changes in the spectral distribution (and/or amount) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the one or more measured biometric parameters. In another example, a feedback system for cardiac rhythm management can comprise: (a) a wearable photoplethysmography (PPG) device; wherein the PPG device further comprises at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and wherein the wearable PPG device further comprises one or more electromagnetic actuators which hold one or more light emitters, light receivers, and/or light guides snugly against a person's body in order to reduce errors due to body motion; and (b) an implanted cardiac pacemaker, wherein the operation of the implanted cardiac pacemaker is automatically adjusted based on the one or more measured biometric parameters.

In an example, a peripheral feedback system for cardiac rhythm management can comprise: (a) a wearable photoplethysmography (PPG) device; wherein the PPG device further comprises at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and wherein the wearable PPG device includes compressible foam which holds one or more light emitters, light receivers, and/or light guides snugly against a person's body to reduce measurement errors due to body motion; and (b) an implanted cardiac pacemaker, wherein the operation of the implanted cardiac pacemaker is automatically adjusted based on the one or more measured biometric parameters.

In one embodiment, a feedback system for cardiac rhythm management can comprise: (a) a first implanted photoplethysmography (PPG) device, wherein the first PPG device is implanted in a first peripheral location (e.g. arm or leg) of a person's body, wherein the first implanted PPG device further comprises at least one first light emitter and at least one first light receiver, wherein changes in the amount (and/or spectrum) of light from the first light emitter which is received by the first light receiver caused by reflection of the light from (or transmission of the light through) body tissue at the first peripheral location are analyzed in order to measure blood pressure; (b) a second implanted photoplethysmography (PPG) device, wherein the second PPG device is implanted in a second peripheral location (e.g. arm or leg) of a person's body, wherein the second implanted PPG device further comprises at least one second light emitter and at least one second light receiver, wherein changes in the amount (and/or spectrum) of light from the second light emitter which is received by the second light receiver caused by reflection of the light from (or transmission of the light through) body tissue at the second peripheral location are analyzed in order to measure blood pressure; and (c) an implanted cardiac pacemaker, wherein the operation of the implanted cardiac pacemaker is automatically adjusted based on comparison and/or multivariate analysis of the blood pressure values measured by the first implanted PPG device and the second implanted PPG device.

In an example, a system for treating congestive heart failure can comprise: (a) a first implanted photoplethysmography (PPG) device, wherein the first PPG device is implanted in a first peripheral location (e.g. arm or leg) of a person's body, wherein the first implanted PPG device further comprises at least one first light emitter and at least one first light receiver, wherein changes in the amount (and/or spectrum) of light from the first light emitter which is received by the first light receiver caused by reflection of the light from (or transmission of the light through) body tissue at the first peripheral location are analyzed in order to measure blood pressure; (b) a second implanted photoplethysmography (PPG) device, wherein the second PPG device is implanted in a second peripheral location (e.g. arm or leg) of a person's body, wherein the second implanted PPG device further comprises at least one second light emitter and at least one second light receiver, wherein changes in the amount (and/or spectrum) of light from the second light emitter which is received by the second light receiver caused by reflection of the light from (or transmission of the light through) body tissue at the second peripheral location are analyzed in order to measure blood pressure; and (c) an implanted cardiac pacemaker, wherein the operation of the implanted cardiac pacemaker is automatically adjusted based on comparison and/or multivariate analysis of the blood pressure values measured by the first implanted PPG device and the second implanted PPG device.

In one embodiment, a peripheral feedback system for cardiac rhythm management can comprise: (a) a first wearable photoplethysmography (PPG) device which is configured to be worn on (or in) a person's right ear, wherein the first wearable PPG device has at least one first light emitter and at least one first light receiver, wherein variation in the amount (and/or spectrum) of light from the first light emitter which is received by the first light receiver caused by reflection of the light from (or transmission of the light through) the right ear is analyzed in order to measure one or more biometric parameters from the person's right ear; (b) a second wearable photoplethysmography (PPG) device which is configured to be worn on (or in) the person's left ear, wherein the second wearable PPG device has at least one second light emitter and at least one second light receiver, wherein variation in the amount (and/or spectrum) of light from the second light emitter which is received by the second light receiver caused by reflection of the light from (or transmission of the light through) the left ear is analyzed in order to measure the one or more biometric parameters from the person's left ear; and (c) an implanted cardiac pacemaker, wherein the operation of the implanted cardiac pacemaker is automatically adjusted based on multivariate comparison and/or analysis of the values of the one or more biometric parameters measured from the person's right ear and left ear.

In an example, a peripheral feedback system for cardiac rhythm management can comprise: (a) a first wearable photoplethysmography (PPG) device which is configured to be worn on the person's right foot, wherein the first wearable PPG device has at least one first light emitter and at least one first light receiver, wherein variation in the amount (and/or spectrum) of light from the first light emitter which is received by the first light receiver caused by reflection of the light from (or transmission of the light through) the right foot is analyzed in order to measure one or more biometric parameters from the person's right foot; (b) a second wearable photoplethysmography (PPG) device which is configured to be worn on the person's left foot, wherein the second wearable PPG device has at least one second light emitter and at least one second light receiver, wherein variation in the amount (and/or spectrum) of light from the second light emitter which is received by the second light receiver caused by reflection of the light from (or transmission of the light through) the left foot is analyzed in order to measure the one or more biometric parameters from the person's left foot; and (c) an implanted cardiac pacemaker, wherein the operation of the implanted cardiac pacemaker is automatically adjusted based on multivariate comparison and/or analysis of the values of the one or more biometric parameters measured from the person's right foot and left foot.

In an example, a peripheral feedback system for cardiac rhythm management can comprise: (a) a first wearable photoplethysmography (PPG) device which is configured to be worn on (or in) the person's right ear, wherein the first wearable PPG device has at least one first light emitter and at least one first light receiver, wherein variation in the amount (and/or spectrum) of light from the first light emitter which is received by the first light receiver caused by reflection of the light from (or transmission of the light through) body tissue is analyzed in order to measure one or more biometric parameters from the person's right ear; (b) a second wearable photoplethysmography (PPG) device which is configured to be worn on (or in) the person's left ear, wherein the second wearable PPG device has at least one second light emitter and at least one second light receiver, wherein variation in the amount (and/or spectrum) of light from the second light emitter which is received by the second light receiver caused by reflection of the light from (or transmission of the light through) body tissue is analyzed in order to measure the one or more biometric parameters from the person's left ear; and (c) an implanted cardiac pacemaker, wherein the operation of the implanted cardiac pacemaker is automatically adjusted based on multivariate comparison and/or analysis of the values of the one or more biometric parameters measured from the person's right ear and left ear, and wherein the operation of the implanted cardiac pacemaker is automatically adjusted by adjusting one or more of operating parameters selected from the group consisting of: Amplitude (e.g. Atrial Pulse, Ventricular Pulse, Current, Voltage); AV Delay (e.g. Post Pacing, Post Sensing, Minimum); Blanking Period (e.g. Ventricular); Coordination/Timing (e.g. Between Different Chambers); Electrode (e.g. Locations, Combination, Polarity); Frequency (e.g. Pulse, Heart Stimulations); Initiation or Cessation (e.g. Pacing, Stimulation); Mode (e.g. Pacing); Pacing Interval (e.g. AV, IV, VV); Polarity (e.g. Pacing); Pulse Width (e.g. Atrial, Ventricular); Rate (e.g. Basic, Upper Tracking, Hysteresis); Refractory Extension (e.g. Atrial); Refractory Period (e.g. Atrial, Ventricular, Post-Ventricular); Sensing (e.g. Atrial, Polarity, Ventricular, Polarity); and Sensitivity (e.g. Atrial).

In an example, a peripheral feedback system for cardiac rhythm management can comprise: (a) a first wearable photoplethysmography (PPG) device which is configured to be worn on the person's right foot, wherein the first wearable PPG device has at least one first light emitter and at least one first light receiver, wherein variation in the amount (and/or spectrum) of light from the first light emitter which is received by the first light receiver caused by reflection of the light from (or transmission of the light through) body tissue is analyzed in order to measure one or more biometric parameters from the person's right foot; (b) a second wearable photoplethysmography (PPG) device which is configured to be worn on the person's left foot, wherein the second wearable PPG device has at least one second light emitter and at least one second light receiver, wherein variation in the amount (and/or spectrum) of light from the second light emitter which is received by the second light receiver caused by reflection of the light from (or transmission of the light through) body tissue is analyzed in order to measure the one or more biometric parameters from the person's left foot; and (c) an implanted cardiac pacemaker, wherein the operation of the implanted cardiac pacemaker is automatically adjusted based on multivariate comparison and/or analysis of the values of the one or more biometric parameters measured from the person's right foot and left foot, and wherein the operation of the implanted cardiac pacemaker is automatically adjusted by adjusting one or more of operating parameters selected from the group consisting of: Amplitude (e.g. Atrial Pulse, Ventricular Pulse, Current, Voltage); AV Delay (e.g. Post Pacing, Post Sensing, Minimum); Blanking Period (e.g. Ventricular); Coordination/Timing (e.g. Between Different Chambers); Electrode (e.g. Locations, Combination, Polarity); Frequency (e.g. Pulse, Heart Stimulations); Initiation or Cessation (e.g. Pacing, Stimulation); Mode (e.g. Pacing); Pacing Interval (e.g. AV, IV, VV); Polarity (e.g. Pacing); Pulse Width (e.g. Atrial, Ventricular); Rate (e.g. Basic, Upper Tracking, Hysteresis); Refractory Extension (e.g. Atrial); Refractory Period (e.g. Atrial, Ventricular, Post-Ventricular); Sensing (e.g. Atrial, Polarity, Ventricular, Polarity); and Sensitivity (e.g. Atrial).

In one embodiment, a feedback system for cardiac rhythm management can comprise: (a) a first wearable photoplethysmography (PPG) device which is configured to be worn on a person's right leg, wherein the first wearable PPG device has at least one first light emitter and at least one first light receiver, and wherein variation in the amount (and/or spectrum) of light from the first light emitter which is received by the first light receiver caused by reflection of the light from (or transmission of the light through) body tissue is analyzed in order to measure one or more biometric parameters from the first location; (b) a second wearable photoplethysmography (PPG) device which is configured to be worn on a person's left leg, wherein the second wearable PPG device has at least one second light emitter and at least one second light receiver, and wherein variation in the amount (and/or spectrum) of light from the second light emitter which is received by the second light receiver caused by reflection of the light from (or transmission of the light through) body tissue is analyzed in order to measure one or more biometric parameters from the second location; and (c) an implanted cardiac pacemaker, wherein the operation of the implanted cardiac pacemaker is automatically adjusted based on multivariate analysis of the one or more biometric parameters measured from the person's right leg and left leg.

In an example, a system for treating congestive heart failure can comprise: (a) a first wearable photoplethysmography (PPG) device which is configured to be worn on the person's right arm, wherein the first wearable PPG device has at least one first light emitter and at least one first light receiver, wherein variation in the amount (and/or spectrum) of light from the first light emitter which is received by the first light receiver caused by reflection of the light from (or transmission of the light through) body tissue is analyzed in order to measure one or more biometric parameters from the person's right arm; (b) a second wearable photoplethysmography (PPG) device which is configured to be worn on the person's left arm, wherein the second wearable PPG device has at least one second light emitter and at least one second light receiver, wherein variation in the amount (and/or spectrum) of light from the second light emitter which is received by the second light receiver caused by reflection of the light from (or transmission of the light through) body tissue is analyzed in order to measure the one or more biometric parameters from the person's left arm; and (c) an implanted cardiac pacemaker, wherein the operation of the implanted cardiac pacemaker is automatically adjusted based on multivariate comparison and/or analysis of the values of the one or more biometric parameters measured from the person's right arm and left arm.

In one embodiment, a peripheral feedback system for cardiac rhythm management can comprise: (a) a first wearable photoplethysmography (PPG) device with at least one first light emitter and at least one first light receiver which is worn on the right side of a person's body, wherein changes in the amount (and/or spectrum) of light from the first light emitter which is received by the first light receiver caused by reflection of the light from (or transmission of the light through) body tissue are analyzed in order to measure blood pressure from the right side of the person's body; (b) a second wearable photoplethysmography (PPG) device with at least one second light emitter and at least one second light receiver which is worn on the left side of a person's body, wherein changes in the amount (and/or spectrum) of light from the second light emitter which is received by the second light receiver caused by reflection of the light from (or transmission of the light through) body tissue are analyzed in order to measure blood pressure on the left side of the person's body; and (c) an implanted cardiac pacemaker whose operation is automatically adjusted in response to differences in the blood pressure between the right side and the left side of the person's body.

In an example, a feedback system for cardiac rhythm management can comprise: (a) a first wearable photoplethysmography (PPG) device with at least one first light emitter and at least one first light receiver which is worn on (or in) a person's right ear, wherein variation in the amount (and/or spectrum) of light from the first light emitter which is received by the first light receiver caused by reflection of the light from (or transmission of the light through) body tissue of the right ear is analyzed in order to measure systolic amplitude from the person's right ear; (b) a second wearable photoplethysmography (PPG) device with at least one second light emitter and at least one second light receiver which is worn on (or in) a person's left ear, wherein variation in the amount (and/or spectrum) of light from the second light emitter which is received by the second light receiver caused by reflection of the light from (or transmission of the light through) body tissue of the left ear is analyzed in order to measure systolic amplitude from the person's left ear; and (c) an implanted cardiac pacemaker, wherein the operation of the implanted cardiac pacemaker is automatically adjusted based on comparison and/or multivariate analysis of systolic amplitude from the person's right ear vs. systolic amplitude from the person's left ear; and wherein the operation of the implanted cardiac pacemaker is automatically adjusted by adjusting one or more of operating parameters selected from the group consisting of: Amplitude (e.g. Atrial Pulse, Ventricular Pulse, Current, Voltage); AV Delay (e.g. Post Pacing, Post Sensing, Minimum); Blanking Period (e.g. Ventricular); Coordination/Timing (e.g. Between Different Chambers); Electrode (e.g. Locations, Combination, Polarity); Frequency (e.g. Pulse, Heart Stimulations); Initiation or Cessation (e.g. Pacing, Stimulation); Mode (e.g. Pacing); Pacing Interval (e.g. AV, IV, VV); Polarity (e.g. Pacing); Pulse Width (e.g. Atrial, Ventricular); Rate (e.g. Basic, Upper Tracking, Hysteresis); Refractory Extension (e.g. Atrial); Refractory Period (e.g. Atrial, Ventricular, Post-Ventricular); Sensing (e.g. Atrial, Polarity, Ventricular, Polarity); and Sensitivity (e.g. Atrial).

In one embodiment, a peripheral feedback system for cardiac rhythm management can comprise: (a) a first wearable photoplethysmography (PPG) device with at least one first light emitter and at least one first light receiver which is worn on a person's right leg, wherein variation in the amount (and/or spectrum) of light from the first light emitter which is received by the first light receiver caused by reflection of the light from (or transmission of the light through) body tissue of the right leg is analyzed in order to measure Pulse Transit Time (PTT) to the person's right leg; (b) a second wearable photoplethysmography (PPG) device with at least one second light emitter and at least one second light receiver which is worn on a person's left leg, wherein variation in the amount (and/or spectrum) of light from the second light emitter which is received by the second light receiver caused by reflection of the light from (or transmission of the light through) body tissue of the left leg is analyzed in order to measure Pulse Transit Time (PTT) to the person's left leg; and (c) an implanted cardiac pacemaker, wherein the operation of the implanted cardiac pacemaker is automatically adjusted based on comparison and/or multivariate analysis of Pulse Transit Time (PTT) to the person's right leg vs. Pulse Transit Time (PTT) to the person's left leg; and wherein the operation of the implanted cardiac pacemaker is automatically adjusted by adjusting one or more of operating parameters selected from the group consisting of: Amplitude (e.g. Atrial Pulse, Ventricular Pulse, Current, Voltage); AV Delay (e.g. Post Pacing, Post Sensing, Minimum); Blanking Period (e.g. Ventricular); Coordination/Timing (e.g. Between Different Chambers); Electrode (e.g. Locations, Combination, Polarity); Frequency (e.g. Pulse, Heart Stimulations); Initiation or Cessation (e.g. Pacing, Stimulation); Mode (e.g. Pacing); Pacing Interval (e.g. AV, IV, VV); Polarity (e.g. Pacing); Pulse Width (e.g. Atrial, Ventricular); Rate (e.g. Basic, Upper Tracking, Hysteresis); Refractory Extension (e.g. Atrial); Refractory Period (e.g. Atrial, Ventricular, Post-Ventricular); Sensing (e.g. Atrial, Polarity, Ventricular, Polarity); and Sensitivity (e.g. Atrial).

In an example, a feedback system for cardiac rhythm management can comprise: (a) a first wearable photoplethysmography (PPG) device worn on the right side of a person's body with at least one first light emitter and at least one first light receiver, wherein variation in the amount (and/or spectrum) of light from the first light emitter received by the first light receiver which is caused by reflection of the light from (or transmission of the light through) body tissue is analyzed in order to measure one or more biometric parameters from the right side of the person's body; (b) a second wearable photoplethysmography (PPG) device worn on the left side of a person's body with at least one second light emitter and at least one second light receiver, wherein variation in the amount (and/or spectrum) of light from the second light emitter received by the second light receiver which is caused by reflection of the light from (or transmission of the light through) body tissue is analyzed in order to measure one or more biometric parameters from the left side of the person's body; and (c) an implanted cardiac pacemaker, wherein the operation of the implanted cardiac pacemaker is automatically adjusted based on differences between the one or more biometric parameters measured from the right side and the left side of the person's body.

In an example, a peripheral feedback system for cardiac rhythm management can comprise: (a) a wearable photoplethysmography (PPG) device with a circumferential array of light emitters and light receivers around a person's wrist and/or arm, wherein changes in the amount (and/or spectrum) of light from the light emitters which is received by the light receivers caused by reflection of the light from (or transmission of the light through) body tissue are analyzed in order to measure one or more biometric parameters; and (b) an implanted cardiac pacemaker whose operation is automatically adjusted based on the one or more biometric parameters. Alternatively, a peripheral feedback system for cardiac rhythm management can comprise: (a) a wearable photoplethysmography (PPG) device with a plurality of light emitters and a single light receiver, wherein changes in the amount (and/or spectrum) of light from the light emitters which is received by the light receiver caused by reflection of the light from (or transmission of the light through) body tissue are analyzed in order to measure one or more biometric parameters selected from the group consisting of Heart Rate (HR), Heart Rate Variability (HRV), Blood Volume Pulse (BVP), Inter-Beat Interval (IBI), Peak-to-Peak Interval (PPI), Blood Pulse Rate (BPR), Blood Volume Pulse (BVP), Blood Volume Amplitude (BVP), Peak Amplitude (PA), Pulse Area, Pulse Transit Time (PTT), Standard Deviation of Average Normal to Normal Beat (SDANN), Systolic Amplitude, Systolic Peak Amplitude, Blood Pressure, Oxygen Saturation, VO2, VO2max, Hydration Level, and Respiration and/or Breathing Rate; and (b) an implanted cardiac pacemaker whose operation is automatically adjusted based on the one or more biometric parameters.

In an example, a peripheral feedback system for cardiac rhythm management can comprise: (a) a wearable photoplethysmography (PPG) device with a single light emitter and a plurality of light receivers, wherein changes in the amount (and/or spectrum) of light from the light emitter which is received by the light receivers caused by reflection of the light from (or transmission of the light through) body tissue are analyzed in order to measure one or more biometric parameters selected from the group consisting of Heart Rate (HR), Heart Rate Variability (HRV), Blood Volume Pulse (BVP), Inter-Beat Interval (IBI), Peak-to-Peak Interval (PPI), Blood Pulse Rate (BPR), Blood Volume Pulse (BVP), Blood Volume Amplitude (BVP), Peak Amplitude (PA), Pulse Area, Pulse Transit Time (PTT), Standard Deviation of Average Normal to Normal Beat (SDANN), Systolic Amplitude, Systolic Peak Amplitude, Blood Pressure, Oxygen Saturation, VO2, VO2max, Hydration Level, and Respiration and/or Breathing Rate; and (b) an implanted cardiac pacemaker whose operation is automatically adjusted based on measured value of the one or more biometric parameters.

In one embodiment, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters selected from the group consisting of Heart Rate (HR), Heart Rate Variability (HRV), Blood Volume Pulse (BVP), Inter-Beat Interval (IBI), Peak-to-Peak Interval (PPI), Blood Pulse Rate (BPR), Blood Volume Pulse (BVP), Blood Volume Amplitude (BVP), Peak Amplitude (PA), Pulse Area, Pulse Transit Time (PTT), Standard Deviation of Average Normal to Normal Beat (SDANN), Systolic Amplitude, Systolic Peak Amplitude, Blood Pressure, Oxygen Saturation, VO2, VO2max, Hydration Level, and Respiration and/or Breathing Rate; and (b) an implanted cardiac pacemaker whose operation is automatically adjusted based on the one or more biometric parameters.

In an example, a feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters selected from the group consisting of Heart Rate (HR), Heart Rate Variability (HRV), Blood Volume Pulse (BVP), Inter-Beat Interval (IBI), Peak-to-Peak Interval (PPI), Blood Pulse Rate (BPR), Blood Volume Pulse (BVP), Blood Volume Amplitude (BVP), Peak Amplitude (PA), Pulse Area, Pulse Transit Time (PTT), Standard Deviation of Average Normal to Normal Beat (SDANN), Systolic Amplitude, Systolic Peak Amplitude, Blood Pressure, Oxygen Saturation, VO2, VO2max, Hydration Level, and Respiration and/or Breathing Rate; and (b) an implanted cardiac pacemaker whose operation is automatically adjusted based on the one or more biometric parameters, wherein the operation of the implanted cardiac pacemaker is adjusted by changing one or more operating parameters selected from the group consisting of frequency of heart electromagnetic energy stimulations, atrioventricular (AV) pacing interval, interventricular (IV) pacing interval, coordination between electromagnetic energy stimulations of different heart chambers, timing of electromagnetic energy stimulations of different heart chambers, location(s) of the heart to which electromagnetic energy is delivered, regularity of heart electromagnetic energy stimulations, magnitude of heart contraction electromagnetic energy stimulations, voltage of heart electromagnetic energy stimulations, initiation of heart electromagnetic energy stimulations, and cessation of heart electromagnetic energy stimulations.

In one embodiment, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters selected from the group consisting of Heart Rate (HR), Heart Rate Variability (HRV), Blood Volume Pulse (BVP), Inter-Beat Interval (IBI), Peak-to-Peak Interval (PPI), Blood Pulse Rate (BPR), Blood Volume Pulse (BVP), Blood Volume Amplitude (BVP), Peak Amplitude (PA), Pulse Area, Pulse Transit Time (PTT), Standard Deviation of Average Normal to Normal Beat (SDANN), Systolic Amplitude, Systolic Peak Amplitude, Blood Pressure, Oxygen Saturation, VO2, VO2max, Hydration Level, and Respiration and/or Breathing Rate; and (b) an implanted cardiac pacemaker whose operation is automatically adjusted based on the one or more biometric parameters, wherein the operation of the implanted cardiac pacemaker is adjusted by changing one or more operating parameters selected from the group consisting of—the pattern of heart electromagnetic energy stimulations, atrioventricular (AV) pacing interval, interventricular (IV) pacing interval, coordination between electromagnetic energy stimulations of different heart chambers, timing of electromagnetic energy stimulations of different heart chambers, location(s) of the heart to which electromagnetic energy is delivered, regularity of heart electromagnetic energy stimulations, magnitude of heart contraction electromagnetic energy stimulations, voltage of heart electromagnetic energy stimulations, initiation of heart electromagnetic energy stimulations, and cessation of heart electromagnetic energy stimulations.

In an example, a feedback system for cardiac rhythm management can comprise: (a) a pair of glasses with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters selected from the group consisting of Heart Rate (HR), Heart Rate Variability (HRV), Blood Volume Pulse (BVP), Inter-Beat Interval (IBI), Peak-to-Peak Interval (PPI), Blood Pulse Rate (BPR), Blood Volume Pulse (BVP), Blood Volume Amplitude (BVP), Peak Amplitude (PA), Pulse Area, Pulse Transit Time (PTT), Standard Deviation of Average Normal to Normal Beat (SDANN), Systolic Amplitude, Systolic Peak Amplitude, Blood Pressure, Oxygen Saturation, VO2, VO2max, Hydration Level, and Respiration and/or Breathing Rate; and (b) an implanted cardiac pacemaker whose operation is automatically adjusted based on the one or more biometric parameters, wherein the operation of the implanted cardiac pacemaker is adjusted by changing one or more operating parameters selected from the group consisting of—the pattern of heart electromagnetic energy stimulations, atrioventricular (AV) pacing interval, interventricular (IV) pacing interval, coordination between electromagnetic energy stimulations of different heart chambers, timing of electromagnetic energy stimulations of different heart chambers, location(s) of the heart to which electromagnetic energy is delivered, regularity of heart electromagnetic energy stimulations, magnitude of heart contraction electromagnetic energy stimulations, voltage of heart electromagnetic energy stimulations, initiation of heart electromagnetic energy stimulations, and cessation of heart electromagnetic energy stimulations.

In one embodiment, a peripheral feedback system for cardiac rhythm management can comprise: (a) a finger ring with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters selected from the group consisting of Heart Rate (HR), Heart Rate Variability (HRV), Blood Volume Pulse (BVP), Inter-Beat Interval (IBI), Peak-to-Peak Interval (PPI), Blood Pulse Rate (BPR), Blood Volume Pulse (BVP), Blood Volume Amplitude (BVP), Peak Amplitude (PA), Pulse Area, Pulse Transit Time (PTT), Standard Deviation of Average Normal to Normal Beat (SDANN), Systolic Amplitude, Systolic Peak Amplitude, Blood Pressure, Oxygen Saturation, VO2, VO2max, Hydration Level, and Respiration and/or Breathing Rate; and (b) an implanted cardiac pacemaker whose operation is automatically adjusted based on the one or more biometric parameters.

In an example, a feedback system for cardiac rhythm management can comprise: (a) an arm band with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters selected from the group consisting of Heart Rate (HR), Heart Rate Variability (HRV), Blood Volume Pulse (BVP), Inter-Beat Interval (IBI), Peak-to-Peak Interval (PPI), Blood Pulse Rate (BPR), Blood Volume Pulse (BVP), Blood Volume Amplitude (BVP), Peak Amplitude (PA), Pulse Area, Pulse Transit Time (PTT), Standard Deviation of Average Normal to Normal Beat (SDANN), Systolic Amplitude, Systolic Peak Amplitude, Blood Pressure, Oxygen Saturation, VO2, VO2max, Hydration Level, and Respiration and/or Breathing Rate; and (b) an implanted cardiac pacemaker whose operation is automatically adjusted based on the one or more biometric parameters.

In an example, a peripheral feedback system for cardiac rhythm management can comprise: (a) a smart watch with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker whose operation is automatically adjusted based on the one or more biometric parameters, wherein the operation of the implanted cardiac pacemaker is adjusted by changing one or more operating parameters selected from the group consisting of—the pattern of heart electromagnetic energy stimulations, atrioventricular (AV) pacing interval, interventricular (IV) pacing interval, coordination between electromagnetic energy stimulations of different heart chambers, timing of electromagnetic energy stimulations of different heart chambers, location(s) of the heart to which electromagnetic energy is delivered, regularity of heart electromagnetic energy stimulations, magnitude of heart contraction electromagnetic energy stimulations, voltage of heart electromagnetic energy stimulations, initiation of heart electromagnetic energy stimulations, and cessation of heart electromagnetic energy stimulations.

In an example, a peripheral feedback system for cardiac rhythm management can comprise: (a) a leg band with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker whose operation is automatically adjusted based on the one or more biometric parameters, wherein the operation of the implanted cardiac pacemaker is adjusted by changing one or more operating parameters selected from the group consisting of—the pattern of heart electromagnetic energy stimulations, atrioventricular (AV) pacing interval, interventricular (IV) pacing interval, coordination between electromagnetic energy stimulations of different heart chambers, timing of electromagnetic energy stimulations of different heart chambers, location(s) of the heart to which electromagnetic energy is delivered, regularity of heart electromagnetic energy stimulations, magnitude of heart contraction electromagnetic energy stimulations, voltage of heart electromagnetic energy stimulations, initiation of heart electromagnetic energy stimulations, and cessation of heart electromagnetic energy stimulations.

In one embodiment, a system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure two biometric parameters selected from the group consisting of Heart Rate (HR), Heart Rate Variability (HRV), Blood Volume Pulse (BVP), Inter-Beat Interval (IBI), Peak-to-Peak Interval (PPI), Blood Pulse Rate (BPR), Blood Volume Pulse (BVP), Blood Volume Amplitude (BVP), Peak Amplitude (PA), Pulse Area, Pulse Transit Time (PTT), Standard Deviation of Average Normal to Normal Beat (SDANN), Systolic Amplitude, Systolic Peak Amplitude, Blood Pressure, Oxygen Saturation, VO2, VO2max, Hydration Level, and Respiration and/or Breathing Rate; and (b) an implanted cardiac pacemaker whose operation is automatically adjusted based on the one or more biometric parameters, wherein the operation of the implanted cardiac pacemaker is adjusted by changing two operating parameters selected from the group consisting of frequency of heart contraction stimulations, atrioventricular (AV) pacing interval, interventricular (IV) pacing interval, coordination between contraction stimulations of different heart chambers, timing of contraction stimulations of different heart chambers, location(s) of the heart to which electromagnetic energy is delivered, regularity of heart contraction stimulations, magnitude of heart contraction stimulations, voltage of heart contraction stimulations, initiation of heart contraction stimulations, and cessation of heart contraction stimulations.

In an example, a system for treating congestive heart failure can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters selected from the group consisting of Heart Rate (HR), Heart Rate Variability (HRV), Blood Volume Pulse (BVP), Inter-Beat Interval (IBI), Peak-to-Peak Interval (PPI), Blood Pulse Rate (BPR), Blood Volume Pulse (BVP), Blood Volume Amplitude (BVP), Peak Amplitude (PA), Pulse Area, Pulse Transit Time (PTT), Standard Deviation of Average Normal to Normal Beat (SDANN), Systolic Amplitude, Systolic Peak Amplitude, Blood Pressure, Oxygen Saturation, VO2, VO2max, Hydration Level, and Respiration and/or Breathing Rate; and (b) an implanted cardiac pacemaker whose operation is automatically adjusted based on the one or more biometric parameters, wherein the operation of the implanted cardiac pacemaker is adjusted by changing one or more operating parameters selected from the group consisting of—the pattern of heart electromagnetic energy stimulations, atrioventricular (AV) pacing interval, interventricular (IV) pacing interval, coordination between electromagnetic energy stimulations of different heart chambers, timing of electromagnetic energy stimulations of different heart chambers, location(s) of the heart to which electromagnetic energy is delivered, regularity of heart electromagnetic energy stimulations, magnitude of heart contraction electromagnetic energy stimulations, voltage of heart electromagnetic energy stimulations, initiation of heart electromagnetic energy stimulations, and cessation of heart electromagnetic energy stimulations. In another example, a peripheral feedback system for cardiac rhythm management can comprise: (a) a wearable photoplethysmography (PPG) device with a plurality of light emitters and a single light receiver, wherein changes in the amount (and/or spectrum) of light from the light emitters which is received by the light receiver caused by reflection of the light from (or transmission of the light through) body tissue are analyzed in order to measure heart rate; and (b) an implanted cardiac pacemaker whose pacing rate is automatically reduced in response to a high heart rate measured by the PPG device.

In one embodiment, a peripheral feedback system for cardiac rhythm management can comprise: (a) a wearable photoplethysmography (PPG) device with a single light emitter and a plurality of light receivers, wherein changes in the amount (and/or spectrum) of light from the light emitter which is received by the light receivers caused by reflection of the light from (or transmission of the light through) body tissue are analyzed in order to measure one or more biometric parameters selected from the group consisting of Heart Rate (HR), Heart Rate Variability (HRV), Blood Volume Pulse (BVP), Inter-Beat Interval (IBI), Peak-to-Peak Interval (PPI), Blood Pulse Rate (BPR), Blood Volume Pulse (BVP), Blood Volume Amplitude (BVP), Peak Amplitude (PA), Pulse Area, Pulse Transit Time (PTT), Standard Deviation of Average Normal to Normal Beat (SDANN), Systolic Amplitude, Systolic Peak Amplitude, Blood Pressure, Oxygen Saturation, VO2, VO2max, Hydration Level, and Respiration and/or Breathing Rate; and (b) an implanted cardiac pacemaker whose pacing rate is automatically adjusted based on measured values of the one or more biometric parameters. Alternatively, a feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure pulse transit time; and (b) an implanted cardiac pacemaker whose pacing rate is automatically increased in response to a high measured pulse transit time.

In an example, a peripheral feedback system for cardiac rhythm management can comprise: (a) a wearable photoplethysmography (PPG) device with a plurality of light emitters and a single light receiver, wherein changes in the amount (and/or spectrum) of light from the light emitters which is received by the light receiver caused by reflection of the light from (or transmission of the light through) body tissue are analyzed in order to measure blood pressure; and (b) an implanted cardiac pacemaker whose stimulation amplitude (e.g. atrial pulse amplitude, ventricular pulse amplitude, current, and/or voltage) is automatically reduced in response to a high blood pressure measured by the PPG device. In another example, a feedback system for cardiac rhythm management can comprise: (a) a wearable photoplethysmography (PPG) device with a light emitter and a light receiver, wherein variation in the amount (and/or spectrum) of light from the light emitter received by the light receiver caused by reflection of the light from (or transmission of the light through) body tissue is analyzed in order to measure heart rate; and (b) an implanted cardiac pacemaker, wherein the frequency of electromagnetic stimulations of the heart by the implanted cardiac pacemaker is automatically reduced in response to a high heart rate measured by the PPG device.

In one embodiment, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure peak amplitude; and (b) an implanted cardiac pacemaker, wherein the frequency of electromagnetic energy stimulations by the implanted cardiac pacemaker is automatically decreased in response to a high peak amplitude. Alternatively, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure pulse area; and (b) an implanted cardiac pacemaker, wherein the frequency of electromagnetic energy stimulations by the implanted cardiac pacemaker is automatically increased in response to a high pulse area.

In an example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure Standard Deviation of Average Normal to Normal Beat (SDANN), Systolic Amplitude, or Systolic Peak Amplitude; and (b) an implanted cardiac pacemaker, wherein the frequency of electromagnetic energy stimulations by the implanted cardiac pacemaker is automatically decreased in response to a high Standard Deviation of Average Normal to Normal Beat (SDANN), Systolic Amplitude, or Systolic Peak Amplitude. In another example, a feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure Heart Rate (HR); and (b) an implanted cardiac pacemaker, wherein the frequency of heart contractions stimulated by the implanted cardiac pacemaker is automatically increased based on a high Heart Rate (HR) measured by the photoplethysmography (PPG) device.

In an example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure Heart Rate Variability (HRV); and (b) an implanted cardiac pacemaker, wherein the frequency of heart contractions stimulated by the implanted cardiac pacemaker is automatically changed based on Heart Rate Variability (HRV) measured by the photoplethysmography (PPG) device. In another example, a system for treating congestive heart failure can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure blood pressure; and (b) an implanted cardiac pacemaker, wherein the frequency of electromagnetic stimulations of the heart by the implanted cardiac pacemaker is automatically adjusted based on blood pressure.

In an example, a feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure heart rate; and (b) an implanted cardiac pacemaker, wherein the inter-chamber timing of electromagnetic energy stimulations by the implanted cardiac pacemaker is automatically adjusted based on measured heart rate. Alternatively, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure blood pressure; and (b) an implanted cardiac pacemaker, wherein the magnitude and/or voltage of electromagnetic energy stimulations by the implanted cardiac pacemaker is automatically adjusted based on measured blood pressure.

In one embodiment, a feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure heart rate; and (b) an implanted cardiac pacemaker, wherein the magnitude and/or voltage of electromagnetic energy stimulations by the implanted cardiac pacemaker is automatically increased in response to a high heart rate. In another example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure heart rate variability; and (b) an implanted cardiac pacemaker, wherein the magnitude and/or voltage of electromagnetic energy stimulations by the implanted cardiac pacemaker is automatically decreased in response to high heart rate variability.

In an example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure Heart Rate (HR) and/or Heart Rate Variability (HRV); and (b) an implanted cardiac pacemaker, wherein the magnitude of heart electromagnetic energy stimulations and/or the voltage of heart electromagnetic energy stimulations by the implanted cardiac pacemaker is automatically changed based on the Heart Rate (HR) and/or Heart Rate Variability (HRV) measured by the photoplethysmography (PPG) device. Alternatively, a system for treating congestive heart failure can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure blood pressure; and (b) an implanted cardiac pacemaker, wherein the magnitude of electromagnetic stimulations of the heart by the implanted cardiac pacemaker is automatically adjusted based on blood pressure.

In one embodiment, a peripheral feedback system for cardiac rhythm management can comprise: (a) a bracelet or arm band which functions as a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the values of the one or more biometric parameters. In another example, a peripheral feedback system for cardiac rhythm management can comprise: (a) a finger ring which functions as a wearable photoplethysmography (PPG) device with at least two light emitters on one half of the ring and at least two light receivers on the opposite half of the ring, wherein changes in the amount (and/or spectrum) of light from the light emitters which is received by the light receivers caused by reflection of the light from (or transmission of the light through) the finger are analyzed in order to measure one or more biometric parameters; and (b) an implanted cardiac pacemaker, wherein the operation of the implanted cardiac pacemaker is automatically adjusted based on the values of the one or more biometric parameters.

In an example, a feedback system for cardiac rhythm management can comprise: (a) a pair of eyeglasses which functions as a wearable photoplethysmography (PPG) device, wherein the pair of eyeglasses has at least one portion which curves behind a person's ear, wherein there is at least one light emitter and at least one light receiver on this portion, and wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the values of the one or more biometric parameters. In another example, a peripheral feedback system for cardiac rhythm management can comprise: (a) a toe ring which functions as a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the values of the one or more biometric parameters.

In one embodiment, a feedback system for cardiac rhythm management can comprise: (a) a wearable photoplethysmography (PPG) device with a partially-circumferential array of light emitters and light receivers which spans at least two radial quadrants of the circumference of a body member (such as a finger, wrist, or arm), wherein changes in the amount (and/or spectrum) of light from the light emitters which is received by the light receivers due to reflection from (or transmission of the light through) body tissue are analyzed in order to measure one or more biometric parameters, and; and (b) an implanted cardiac pacemaker, wherein the operation of the implanted cardiac pacemaker is automatically adjusted based on the one or more biometric parameters. Alternatively, a peripheral feedback system for cardiac rhythm management can comprise: (a) a wearable photoplethysmography (PPG) device with a circumferential array of opposite-side pairs light emitters and light receivers around the circumference of a person's finger, wherein changes in the amount (and/or spectrum) of light from the light emitters which is received by the light receivers due to reflection from (or transmission of the light through) the finger are analyzed in order to measure one or more biometric parameters, and; and (b) an implanted cardiac pacemaker, wherein the operation of the implanted cardiac pacemaker is automatically adjusted based on the one or more biometric parameters.

In an example, a feedback system for cardiac rhythm management can comprise: (a) a wearable photoplethysmography (PPG) device with a first light emitter, a second light emitter, and at least one light receiver, wherein changes in the amount (and/or spectrum) of light from the first and/or second light emitters which is received by the light receiver caused by reflection of the light from (or transmission of the light through) body tissue are analyzed in order to measure one or more biometric parameters, and wherein the first light emitter emits light in a first direction and the second light emitter emits light in a second direction which is different than the first direction; and (b) an implanted cardiac pacemaker, wherein the operation of the implanted cardiac pacemaker is automatically adjusted based on the one or more biometric parameters. In another example, a peripheral feedback system for cardiac rhythm management can comprise: (a) a wearable photoplethysmography (PPG) device with a first light emitter which emits light in a first direction, a second light emitter which emits light in a second direction, wherein the first and second directions are parallel, and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the one or more biometric parameters.

In an example, a peripheral feedback system for cardiac rhythm management can comprise: (a) a wearable photoplethysmography (PPG) device with a first light emitter which emits light at a first frequency at a first time, a second light emitter which emits light at a second frequency at a second time, and at least one light receiver, wherein changes in the amount (and/or spectrum) of light from the light emitters which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the one or more biometric parameters. Alternatively, a peripheral feedback system for cardiac rhythm management can comprise: (a) a wearable photoplethysmography (PPG) device with an array of pairs of light emitters and light receivers which are distributed around the inner circumference a finger ring, wherein changes in the amount (and/or spectrum) of light from the light emitters which is received by the light receivers due to reflection from (or transmission of the light through) body tissue are analyzed in order to measure one or more biometric parameters, and; and (b) an implanted cardiac pacemaker, wherein the operation of the implanted cardiac pacemaker is automatically adjusted based on the one or more biometric parameters.

In an example, a peripheral feedback system for cardiac rhythm management can comprise: (a) a wearable photoplethysmography (PPG) device with a light emitter held against the ventral side of a person's earlobe and a light receiver held against the dorsal side of the earlobe, or vice versa, wherein changes in the amount (and/or spectrum) of light from the light emitters which is received by the light receivers due to reflection from (or transmission of the light through) body tissue are analyzed in order to measure one or more biometric parameters, and; and (b) an implanted cardiac pacemaker, wherein the operation of the implanted cardiac pacemaker is automatically adjusted based on the one or more biometric parameters. In another example, a feedback system for cardiac rhythm management can comprise: (a) a wearable photoplethysmography (PPG) device which is configured to be (partially) inserted into a person's ear canal, wherein this device has at least one light emitter and at least one light receiver, and wherein changes in the amount (and/or spectrum) of light from the light emitters which is received by the light receivers due to reflection from (or transmission of the light through) body tissue are analyzed in order to measure the person's heart rate, and; and (b) an implanted cardiac pacemaker, wherein the operation of the implanted cardiac pacemaker is automatically adjusted based on heart rate measured by the PPG device.

In one embodiment, a peripheral feedback system for cardiac rhythm management can comprise: (a) a wearable photoplethysmography (PPG) device which is a headset with an array of light emitters and light receivers, wherein changes in the amount (and/or spectrum) of light from the light emitters which is received by the light receivers due to reflection from (or transmission of the light through) body tissue are analyzed in order to measure one or more biometric parameters, and; and (b) an implanted cardiac pacemaker, wherein the operation of the implanted cardiac pacemaker is automatically adjusted based on the one or more biometric parameters. In another example, a feedback system for cardiac rhythm management can comprise: (a) a wearable photoplethysmography (PPG) device with at least one light emitter and at least one light receiver, wherein variation in the amount (and/or spectrum) of light from the light emitter which is received by the light receiver caused by reflection of the light from (or transmission of the light through) body tissue is analyzed in order to measure one or more biometric parameters; and (b) an implanted cardiac pacemaker, wherein the operation of the implanted cardiac pacemaker is automatically adjusted based on the one or more biometric parameters, and wherein the operation of the implanted cardiac pacemaker is automatically adjusted by adjusting stimulation amplitude (e.g. atrial pulse, ventricular pulse, current, voltage).

In an example, a peripheral feedback system for cardiac rhythm management can comprise: (a) a wearable photoplethysmography (PPG) device with at least one light emitter and at least one light receiver, wherein variation in the amount (and/or spectrum) of light from the light emitter which is received by the light receiver caused by reflection of the light from (or transmission of the light through) body tissue is analyzed in order to measure one or more biometric parameters; and (b) an implanted cardiac pacemaker, wherein the operation of the implanted cardiac pacemaker is automatically adjusted based on the one or more biometric parameters, and wherein the operation of the implanted cardiac pacemaker is automatically adjusted by adjusting the locations, combinations, and/or polarity of the electrodes selected to apply electromagnetic simulation to the person's heart. Alternatively, a feedback system for cardiac rhythm management can comprise: (a) a wearable photoplethysmography (PPG) device with at least one light emitter and at least one light receiver, wherein variation in the amount (and/or spectrum) of light from the light emitter which is received by the light receiver caused by reflection of the light from (or transmission of the light through) body tissue is analyzed in order to measure one or more biometric parameters; and (b) an implanted cardiac pacemaker, wherein the operation of the implanted cardiac pacemaker is automatically adjusted based on the one or more biometric parameters, and wherein the operation of the implanted cardiac pacemaker is automatically adjusted by changing pacing mode.

In one embodiment, a peripheral feedback system for cardiac rhythm management can comprise: (a) a wearable photoplethysmography (PPG) device with at least one light emitter and at least one light receiver, wherein variation in the amount (and/or spectrum) of light from the light emitter which is received by the light receiver caused by reflection of the light from (or transmission of the light through) body tissue is analyzed in order to measure one or more biometric parameters; and (b) an implanted cardiac pacemaker, wherein the operation of the implanted cardiac pacemaker is automatically adjusted based on the one or more biometric parameters, and wherein the operation of the implanted cardiac pacemaker is automatically adjusted by adjusting the (basic, upper tracking, or hysteresis) pacing rate. In another example, a peripheral feedback system for cardiac rhythm management can comprise: (a) a wearable photoplethysmography (PPG) device with at least one light emitter and at least one light receiver, wherein variation in the amount (and/or spectrum) of light from the light emitter which is received by the light receiver caused by reflection of the light from (or transmission of the light through) body tissue is analyzed in order to measure one or more biometric parameters; and (b) an implanted cardiac pacemaker, wherein the operation of the implanted cardiac pacemaker is automatically adjusted based on the one or more biometric parameters, and wherein the operation of the implanted cardiac pacemaker is automatically adjusted by adjusting (atrial) pacing sensitivity.

In an example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the one or more biometric parameters, and wherein the operation of the implanted cardiac pacemaker is adjusted by changing one or more pacemaker operating parameters selected from the group consisting of frequency of heart contraction stimulations, atrioventricular (AV) pacing interval, interventricular (IV) pacing interval, coordination between contraction stimulations of different heart chambers, timing of contraction stimulations of different heart chambers, location(s) of the heart to which electromagnetic energy is delivered, regularity of heart contraction stimulations, magnitude of heart contraction stimulations, voltage of heart contraction stimulations, initiation of heart contraction stimulations, and cessation of heart contraction stimulations.

In one embodiment, a peripheral feedback system for cardiac rhythm management can comprise: (a) a wearable photoplethysmography (PPG) device with at least one light emitter and at least one light receiver, wherein variation in the spectral distribution of light from the light emitter which is received by the light receiver caused by reflection of the light from (or transmission of the light through) body tissue is analyzed in order to measure one or more biometric parameters; and (b) an implanted cardiac pacemaker, wherein the operation of the implanted cardiac pacemaker is automatically adjusted based on the one or more biometric parameters.

In an example, a feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the one or more biometric parameters, and wherein the operation of the implanted cardiac pacemaker is adjusted by changing one or more pacemaker operating parameters selected from the group consisting of frequency of heart contraction stimulations, atrioventricular (AV) pacing interval, interventricular (IV) pacing interval, coordination between contraction stimulations of different heart chambers, timing of contraction stimulations of different heart chambers, location(s) of the heart to which electromagnetic energy is delivered, regularity of heart contraction stimulations, magnitude of heart contraction stimulations, voltage of heart contraction stimulations, initiation of heart contraction stimulations, and cessation of heart contraction stimulations. Alternatively, a peripheral feedback system for cardiac rhythm management can comprise: (a) a wearable photoplethysmography (PPG) device with at least one light emitter on a first side of a person's wrist and at least one light receiver on a second side of the person's wrist, where the second side is opposite the first side, and wherein changes in the amount (and/or spectrum) of light from the light emitter which is received by the light receiver after transmission through the wrist are analyzed in order to measure one or more biometric parameters; and (b) an implanted cardiac pacemaker, wherein the operation of the implanted cardiac pacemaker is automatically adjusted based on the one or more biometric parameters, and wherein the operation of the implanted cardiac pacemaker is adjusted by changing the frequency of heart contraction stimulations.

In an example, a feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the one or more biometric parameters, and wherein the operation of the implanted cardiac pacemaker is adjusted by changing the coordination between contraction stimulations of different heart chambers and/or the timing of contraction stimulations of different heart chambers. In another example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the one or more biometric parameters, and wherein the operation of the implanted cardiac pacemaker is adjusted by initiating stimulation of heart contractions.

In an example, a feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure Peak Amplitude (PA), Pulse Area, or Pulse Transit Time (PTT); and (b) an implanted cardiac pacemaker, wherein the operation of the implanted cardiac pacemaker is automatically adjusted based on Peak Amplitude (PA), Pulse Area, or Pulse Transit Time (PTT). In another example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure oxygen saturation, VO2, and/or VO2max; and (b) an implanted cardiac pacemaker, wherein the operation of the implanted cardiac pacemaker is automatically adjusted based on oxygen saturation, VO2, and/or VO2max.

In one embodiment, a peripheral feedback system for cardiac rhythm management can comprise: (a) a wearable photoplethysmography (PPG) device with at least one light emitting diode (LED) and at least one light receiver, wherein changes in the amount (and/or spectrum) of light from the LED which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the one or more biometric parameters. Alternatively, a peripheral feedback system for cardiac rhythm management can comprise: (a) a wearable photoplethysmography (PPG) device with at least one light emitter and at least one light receiver, wherein the at least one light emitter emits light with periodic variation of wavelength (or frequency) within a selected wavelength (or frequency) range, and wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the one or more biometric parameters.

In an example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters, and wherein the at least one light emitter emits light whose path is varied by one or more electromagnetic actuators; and (b) an implanted cardiac pacemaker, wherein the operation of the implanted cardiac pacemaker is automatically adjusted based on the one or more biometric parameters. In another example, a feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters, and wherein the angle at which light from the light emitter enters body tissue is changed by an array of moving microlenses; and (b) an implanted cardiac pacemaker, wherein the operation of the implanted cardiac pacemaker is automatically adjusted based on the one or more biometric parameters.

In one embodiment, a peripheral feedback system for cardiac rhythm management can comprise: (a) a wearable photoplethysmography (PPG) device worn around the circumference of a body member (such as a person's finger, wrist, or arm) with at least one light emitter and at least one light receiver located on each radial quadrant of the circumference, wherein variation in (the amount) light from the light emitters which is received by the light receivers caused by reflection of the light from (or transmission of the light through) body tissue is analyzed in order to measure one or more biometric parameters; and (b) an implanted cardiac pacemaker, wherein the operation of the implanted cardiac pacemaker is automatically adjusted based on the one or more biometric parameters. Alternatively, a feedback system for cardiac rhythm management can comprise: (a) a wearable photoplethysmography (PPG) device which is attached to a person's outer ear, wherein wearable PPG device further comprises at least one light emitter and at least one light receiver, and wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the measured values of the biometric parameters.

In an example, a peripheral feedback system for cardiac rhythm management can comprise: (a) a wearable photoplethysmography (PPG) device worn on (or around) a person's neck, wherein wearable PPG device further comprises at least one light emitter and at least one light receiver, and wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the measured values of the biometric parameters. In another example, a feedback system for cardiac rhythm management can comprise: (a) a wearable photoplethysmography (PPG) device worn on (e.g. around) a person's arm, wherein wearable PPG device further comprises at least one light emitter and at least one light receiver, and wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the measured values of the biometric parameters.

In one embodiment, a peripheral feedback system for cardiac rhythm management can comprise: (a) a wearable photoplethysmography (PPG) device which is worn on (e.g. around) a person's toe, wherein wearable PPG device further comprises at least one light emitter and at least one light receiver, and wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the measured values of the biometric parameters. In another example, a peripheral feedback system for cardiac rhythm management can comprise: (a) an ankle band which functions as a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the values of the one or more biometric parameters.

In an example, a peripheral feedback system for cardiac rhythm management can comprise: (a) an ear ring which functions as a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the values of the one or more biometric parameters. Alternatively, a peripheral feedback system for cardiac rhythm management can comprise: (a) a smart watch and/or wrist band which functions as a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the values of the one or more biometric parameters.

In an example, a system for cardiac rhythm management can comprise: (a) a wearable photoplethysmography (PPG) device with a light emitter and a light receiver, wherein variation in the spectrum of light from the light emitter received by the light receiver caused by reflection of the light from body tissue is analyzed in order to measure one or more biometric parameters; and (b) an implanted cardiac pacemaker, wherein the operation of the implanted cardiac pacemaker is automatically adjusted based on measured values of the one or more biometric parameters.

In an example, a system for treating autonomic dysfunction can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed to measure one or more biometric parameters selected from the group consisting of Heart Rate (HR), Heart Rate Variability (HRV), Blood Volume Pulse (BVP), Inter-Beat Interval (IBI), Peak-to-Peak Interval (PPI), Blood Pulse Rate (BPR), Blood Volume Pulse (BVP), Blood Volume Amplitude (BVP), Peak Amplitude (PA), Pulse Area, Pulse Transit Time (PTT), Standard Deviation of Average Normal to Normal Beat (SDANN), Systolic Amplitude, Systolic Peak Amplitude, Blood Pressure, Oxygen Saturation, VO2, VO2max, Hydration Level, and Respiration and/or Breathing Rate; and (b) an implanted cardiac pacemaker, wherein the operation of the implanted cardiac pacemaker is automatically adjusted based on the one or more biometric parameters measured by the wearable photoplethysmography (PPG) device, and wherein the operation of the implanted cardiac pacemaker is changed by changing one or more pacemaker operating parameters selected from the group consisting of frequency of heart contraction stimulations, atrioventricular (AV) pacing interval, interventricular (IV) pacing interval, coordination between contraction stimulations of different heart chambers, timing of contraction stimulations of different heart chambers, location(s) of the heart to which electromagnetic energy is delivered, regularity of heart contraction stimulations, magnitude of heart contraction stimulations, voltage of heart contraction stimulations, initiation of heart contraction stimulations, and cessation of heart contraction stimulations.

In one embodiment, a system for treating congestive heart failure can comprise: (a) a finger ring which functions as a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the values of the one or more biometric parameters. In another example, a system for treating congestive heart failure can comprise: (a) a toe ring, sock, or ankle band which functions as a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the values of the one or more biometric parameters.

In an example, a system for treating congestive heart failure can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed to measure one or more biometric parameters selected from the group consisting of Heart Rate (HR) and/or Heart Rate Variability (HRV); and (b) an implanted cardiac pacemaker, wherein the operation of the implanted cardiac pacemaker is automatically adjusted based on the one or more biometric parameters measured by the wearable photoplethysmography (PPG) device, and wherein the operation of the implanted cardiac pacemaker is changed by changing one or more pacemaker operating parameters selected from the group consisting of frequency of heart contraction stimulations, atrioventricular (AV) pacing interval, interventricular (IV) pacing interval, coordination between contraction stimulations of different heart chambers, timing of contraction stimulations of different heart chambers, location(s) of the heart to which electromagnetic energy is delivered, regularity of heart contraction stimulations, magnitude of heart contraction stimulations, voltage of heart contraction stimulations, initiation of heart contraction stimulations, and cessation of heart contraction stimulations.

In one embodiment, a system for treating congestive heart failure can comprise: (a) an ear ring which functions as a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the values of the one or more biometric parameters. Alternatively, a system for treating congestive heart failure can comprise: (a) smart watch and/or wrist band which functions as a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the values of the one or more biometric parameters.

In an example, a system for treating premature ventricular contraction can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed to measure one or more biometric parameters selected from the group consisting of Heart Rate (HR), Heart Rate Variability (HRV), Blood Volume Pulse (BVP), Inter-Beat Interval (IBI), Peak-to-Peak Interval (PPI), Blood Pulse Rate (BPR), Blood Volume Pulse (BVP), Blood Volume Amplitude (BVP), Peak Amplitude (PA), Pulse Area, Pulse Transit Time (PTT), Standard Deviation of Average Normal to Normal Beat (SDANN), Systolic Amplitude, Systolic Peak Amplitude, Blood Pressure, Oxygen Saturation, VO2, VO2max, Hydration Level, and Respiration and/or Breathing Rate; and (b) an implanted cardiac pacemaker, wherein the operation of the implanted cardiac pacemaker is automatically adjusted based on the one or more biometric parameters measured by the wearable photoplethysmography (PPG) device, and wherein the operation of the implanted cardiac pacemaker is changed by changing one or more pacemaker operating parameters selected from the group consisting of frequency of heart contraction stimulations, atrioventricular (AV) pacing interval, interventricular (IV) pacing interval, coordination between contraction stimulations of different heart chambers, timing of contraction stimulations of different heart chambers, location(s) of the heart to which electromagnetic energy is delivered, regularity of heart contraction stimulations, magnitude of heart contraction stimulations, voltage of heart contraction stimulations, initiation of heart contraction stimulations, and cessation of heart contraction stimulations.

In one embodiment, a feedback system for cardiac rhythm management can comprise: (a) a wearable photoplethysmography (PPG) device with at least one light emitter and at least one light receiver, wherein variation in the amount (and/or spectrum) of light from the light emitter which is received by the light receiver caused by reflection of the light from (or transmission of the light through) body tissue is analyzed in order to measure one or more biometric parameters selected from the group consisting of inter-beat interval; and (b) an implanted cardiac pacemaker, wherein the operation of the implanted cardiac pacemaker is automatically adjusted based on the inter-beat interval, and wherein the operation of the implanted cardiac pacemaker is automatically adjusted by adjusting one or more of operating parameters selected from the group consisting of: Amplitude (e.g. Atrial Pulse, Ventricular Pulse, Current, Voltage); AV Delay (e.g. Post Pacing, Post Sensing, Minimum); Blanking Period (e.g. Ventricular); Coordination/Timing (e.g. Between Different Chambers); Electrode (e.g. Locations, Combination, Polarity); Frequency (e.g. Pulse, Heart Stimulations); Initiation or Cessation (e.g. Pacing, Stimulation); Mode (e.g. Pacing); Pacing Interval (e.g. AV, IV, VV); Polarity (e.g. Pacing); Pulse Width (e.g. Atrial, Ventricular); Rate (e.g. Basic, Upper Tracking, Hysteresis); Refractory Extension (e.g. Atrial); Refractory Period (e.g. Atrial, Ventricular, Post-Ventricular); Sensing (e.g. Atrial, Polarity, Ventricular, Polarity); and Sensitivity (e.g. Atrial).

In an example, a peripheral feedback system for cardiac rhythm management can comprise: (a) a wearable photoplethysmography (PPG) device with at least one light emitter and at least one light receiver, wherein variation in the amount (and/or spectrum) of light from the light emitter which is received by the light receiver caused by reflection of the light from (or transmission of the light through) body tissue is analyzed in order to measure one or more biometric parameters selected from the group consisting of Pulse Transit Time (PTT), Standard Deviation of Average Normal to Normal Beat (SDANN), Systolic Amplitude, and Systolic Peak Amplitude; and (b) an implanted cardiac pacemaker, wherein the operation of the implanted cardiac pacemaker is automatically adjusted based on the one or more biometric parameters, and wherein the operation of the implanted cardiac pacemaker is automatically adjusted by adjusting one or more of operating parameters selected from the group consisting of: Amplitude (e.g. Atrial Pulse, Ventricular Pulse, Current, Voltage); AV Delay (e.g. Post Pacing, Post Sensing, Minimum); Blanking Period (e.g. Ventricular); Coordination/Timing (e.g. Between Different Chambers); Electrode (e.g. Locations, Combination, Polarity); Frequency (e.g. Pulse, Heart Stimulations); Initiation or Cessation (e.g. Pacing, Stimulation); Mode (e.g. Pacing); Pacing Interval (e.g. AV, IV, VV); Polarity (e.g. Pacing); Pulse Width (e.g. Atrial, Ventricular); Rate (e.g. Basic, Upper Tracking, Hysteresis); Refractory Extension (e.g. Atrial); Refractory Period (e.g. Atrial, Ventricular, Post-Ventricular); Sensing (e.g. Atrial, Polarity, Ventricular, Polarity); and Sensitivity (e.g. Atrial).

In an example, a feedback system for cardiac rhythm management can comprise: (a) a wearable photoplethysmography (PPG) device with at least one light emitter and at least one light receiver, wherein variation in the amount (and/or spectrum) of light from the light emitter which is received by the light receiver caused by reflection of the light from (or transmission of the light through) body tissue is analyzed in order to measure one or more biometric parameters selected from the group consisting of Heart Rate (HR), Heart Rate Variability (HRV), Blood Volume Pulse (BVP), Inter-Beat Interval (IBI), Peak-to-Peak Interval (PPI), Blood Pulse Rate (BPR), Blood Volume Pulse (BVP), Blood Volume Amplitude (BVP), Peak Amplitude (PA), Pulse Area, Pulse Transit Time (PTT), Standard Deviation of Average Normal to Normal Beat (SDANN), Systolic Amplitude, Systolic Peak Amplitude, Blood Pressure, Oxygen Saturation, VO2, VO2max, Hydration Level, and Respiration and/or Breathing Rate; and (b) an implanted cardiac pacemaker, wherein the operation of the implanted cardiac pacemaker is automatically adjusted based on the one or more biometric parameters, and wherein the operation of the implanted cardiac pacemaker is automatically adjusted by adjusting one or more of operating parameters selected from the group consisting of: Amplitude (e.g. Atrial Pulse, Ventricular Pulse, Current, Voltage); AV Delay (e.g. Post Pacing, Post Sensing, Minimum); Blanking Period (e.g. Ventricular); Coordination/Timing (e.g. Between Different Chambers); Electrode (e.g. Locations, Combination, Polarity); Frequency (e.g. Pulse, Heart Stimulations); Initiation or Cessation (e.g. Pacing, Stimulation); Mode (e.g. Pacing); Pacing Interval (e.g. AV, IV, VV); Polarity (e.g. Pacing); Pulse Width (e.g. Atrial, Ventricular); Rate (e.g. Basic, Upper Tracking, Hysteresis); Refractory Extension (e.g. Atrial); Refractory Period (e.g. Atrial, Ventricular, Post-Ventricular); Sensing (e.g. Atrial, Polarity, Ventricular, Polarity); and Sensitivity (e.g. Atrial).

In an example, a peripheral feedback system for cardiac rhythm management can comprise: (a) a peripheral implanted photoplethysmography (PPG) device, wherein the PPG device is implanted within a person's arm or leg, wherein the PPG device at least one light emitter and at least one light receiver, wherein variation in the amount (and/or spectrum) of light from the light emitter which is received by the light receiver caused by reflection of the light from (or transmission of the light through) body tissue is analyzed in order to measure one or more biometric parameters selected from the group consisting of peripheral Heart Rate (HR), Heart Rate Variability (HRV), Blood Volume Pulse (BVP), Inter-Beat Interval (IBI), Peak-to-Peak Interval (PPI), Blood Pulse Rate (BPR), Blood Volume Pulse (BVP), Blood Volume Amplitude (BVP), Peak Amplitude (PA), Pulse Area, Pulse Transit Time (PTT), Standard Deviation of Average Normal to Normal Beat (SDANN), Systolic Amplitude, Systolic Peak Amplitude, Blood Pressure, Oxygen Saturation, VO2, VO2max, Hydration Level, and Respiration and/or Breathing Rate; and (b) an implanted cardiac pacemaker, wherein the operation of the implanted cardiac pacemaker is automatically adjusted based on the one or more biometric parameters, and wherein the operation of the implanted cardiac pacemaker is automatically adjusted by adjusting one or more of operating parameters selected from the group consisting of: Amplitude (e.g. Atrial Pulse, Ventricular Pulse, Current, Voltage); AV Delay (e.g. Post Pacing, Post Sensing, Minimum); Blanking Period (e.g. Ventricular); Coordination/Timing (e.g. Between Different Chambers); Electrode (e.g. Locations, Combination, Polarity); Frequency (e.g. Pulse, Heart Stimulations); Initiation or Cessation (e.g. Pacing, Stimulation); Mode (e.g. Pacing); Pacing Interval (e.g. AV, IV, VV); Polarity (e.g. Pacing); Pulse Width (e.g. Atrial, Ventricular); Rate (e.g. Basic, Upper Tracking, Hysteresis); Refractory Extension (e.g. Atrial); Refractory Period (e.g. Atrial, Ventricular, Post-Ventricular); Sensing (e.g. Atrial, Polarity, Ventricular, Polarity); and Sensitivity (e.g. Atrial).

In one embodiment, a system for treating congestive heart failure can comprise: (a) a wearable photoplethysmography (PPG) device with at least one light emitter and at least one light receiver, wherein variation in the amount (and/or spectrum) of light from the light emitter which is received by the light receiver caused by reflection of the light from (or transmission of the light through) body tissue is analyzed in order to measure blood pressure; and (b) an implanted cardiac pacemaker, wherein the operation of the implanted cardiac pacemaker is automatically adjusted based on blood pressure, and wherein the operation of the implanted cardiac pacemaker is automatically adjusted by adjusting pacing coordination/timing between different chambers; electrode stimulation locations, combinations, or polarity; and/r pacing mode. In another example, a feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure systolic amplitude or peak amplitude; and (b) an implanted cardiac pacemaker, wherein the pacing interval of the pacemaker is increased in response to high systolic amplitude or peak amplitude as measured by the PPG device.

In an example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure systolic amplitude or peak amplitude; and (b) an implanted cardiac pacemaker, wherein the pacing voltage or current is decreased in response to high systolic amplitude or peak amplitude as measured by the PPG device. In another example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure Standard Deviation of Average Normal to Normal Beat (SDANN), Systolic Amplitude, or Systolic Peak Amplitude; and (b) an implanted cardiac pacemaker, wherein the pattern of electromagnetic energy stimulations by the implanted cardiac pacemaker is automatically adjusted based on measured Standard Deviation of Average Normal to Normal Beat (SDANN), Systolic Amplitude, or Systolic Peak Amplitude.

In one embodiment, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure heart rate variability; and (b) an implanted cardiac pacemaker, wherein the pattern of electromagnetic energy stimulations by the implanted cardiac pacemaker is automatically adjusted based on measured heart rate variability. Alternatively, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure Heart Rate (HR) and/or Heart Rate Variability (HRV); and (b) an implanted cardiac pacemaker, wherein the rate of heart contractions stimulated by the implanted cardiac pacemaker is automatically increased or decreased based on Heart Rate (HR) and/or Heart Rate Variability (HRV) measured by the photoplethysmography (PPG) device.

In an example, a feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure Heart Rate Variability (HRV); and (b) an implanted cardiac pacemaker, wherein the rate of heart contractions stimulated by the implanted cardiac pacemaker is automatically decreased in response to high on Heart Rate Variability (HRV) measured by the photoplethysmography (PPG) device. In another example, a peripheral feedback system for cardiac rhythm management can comprise: (a) a wearable photoplethysmography (PPG) device; wherein the PPG device further comprises at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and wherein the wearable PPG device further comprises a spring whose tension and/or length is adjusted to hold a light emitter, a light receiver, and/or a light guide snugly against a person's body; and (b) an implanted cardiac pacemaker, wherein the operation of the implanted cardiac pacemaker is automatically adjusted based on the one or more measured biometric parameters.

In one embodiment, a feedback system for cardiac rhythm management can comprise: (a) a wearable photoplethysmography (PPG) device; wherein the PPG device further comprises at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and wherein the wearable PPG device further comprises one or more inflatable members which hold one or more light emitters, light receivers, and/or light guides snugly against a person's body to reduce errors due to body motion; and (b) an implanted cardiac pacemaker, wherein the operation of the implanted cardiac pacemaker is automatically adjusted based on the one or more measured biometric parameters.

In an example, a peripheral feedback system for cardiac rhythm management can comprise: (a) a wearable photoplethysmography (PPG) device; wherein the PPG device further comprises at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; wherein the wearable PPG device further comprises an inertial motion sensor (such as combination of an accelerometer and/or gyroscope); and wherein the wearable PPG device further comprises one or more springs, elastic members, inflatable members, and/or electromagnetic actuators which are automatically adjusted in response to motion detected by a inertial motion sensor in order to hold one or more light emitters, light receivers, and/or a light guides snugly against a person's body even when a person's body is moving a lot; and (b) an implanted cardiac pacemaker, wherein the operation of the implanted cardiac pacemaker is automatically adjusted based on the one or more measured biometric parameters.

In an example, a feedback system for cardiac rhythm management can comprise: (a) a first implanted photoplethysmography (PPG) device, wherein the first PPG device is implanted in a first peripheral location (e.g. arm or leg) of a person's body, wherein the first implanted PPG device further comprises at least one first light emitter and at least one first light receiver, wherein changes in the amount (and/or spectrum) of light from the first light emitter which is received by the first light receiver caused by reflection of the light from (or transmission of the light through) body tissue at the first peripheral location are analyzed in order to measure blood volume; (b) a second implanted photoplethysmography (PPG) device, wherein the second PPG device is implanted in a second peripheral location (e.g. arm or leg) of a person's body, wherein the second implanted PPG device further comprises at least one second light emitter and at least one second light receiver, wherein changes in the amount (and/or spectrum) of light from the second light emitter which is received by the second light receiver caused by reflection of the light from (or transmission of the light through) body tissue at the second peripheral location are analyzed in order to measure blood volume; and (c) an implanted cardiac pacemaker, wherein the operation of the implanted cardiac pacemaker is automatically adjusted based on comparison and/or multivariate analysis of the blood volume values measured by the first implanted PPG device and the second implanted PPG device.

In an example, a system for treating congestive heart failure can comprise: (a) a first implanted photoplethysmography (PPG) device, wherein the first PPG device is implanted in a first peripheral location (e.g. arm or leg) of a person's body, wherein the first implanted PPG device further comprises at least one first light emitter and at least one first light receiver, wherein changes in the amount (and/or spectrum) of light from the first light emitter which is received by the first light receiver caused by reflection of the light from (or transmission of the light through) body tissue at the first peripheral location are analyzed in order to measure blood volume; (b) a second implanted photoplethysmography (PPG) device, wherein the second PPG device is implanted in a second peripheral location (e.g. arm or leg) of a person's body, wherein the second implanted PPG device further comprises at least one second light emitter and at least one second light receiver, wherein changes in the amount (and/or spectrum) of light from the second light emitter which is received by the second light receiver caused by reflection of the light from (or transmission of the light through) body tissue at the second peripheral location are analyzed in order to measure blood volume; and (c) an implanted cardiac pacemaker, wherein the operation of the implanted cardiac pacemaker is automatically adjusted based on comparison and/or multivariate analysis of the blood volume values measured by the first implanted PPG device and the second implanted PPG device.

In one embodiment, a peripheral feedback system for cardiac rhythm management can comprise: (a) a first wearable photoplethysmography (PPG) device which is configured to be worn on the person's right hand, wherein the first wearable PPG device has at least one first light emitter and at least one first light receiver, wherein variation in the amount (and/or spectrum) of light from the first light emitter which is received by the first light receiver caused by reflection of the light from (or transmission of the light through) the right hand is analyzed in order to measure one or more biometric parameters from the person's right hand; (b) a second wearable photoplethysmography (PPG) device which is configured to be worn on the person's left hand, wherein the second wearable PPG device has at least one second light emitter and at least one second light receiver, wherein variation in the amount (and/or spectrum) of light from the second light emitter which is received by the second light receiver caused by reflection of the light from (or transmission of the light through) the left hand is analyzed in order to measure the one or more biometric parameters from the person's left hand; and (c) an implanted cardiac pacemaker, wherein the operation of the implanted cardiac pacemaker is automatically adjusted based on multivariate comparison and/or analysis of the values of the one or more biometric parameters measured from the person's right hand and left hand.

In an example, a peripheral feedback system for cardiac rhythm management can comprise: (a) a first wearable photoplethysmography (PPG) device which is configured to be worn at a first location on a person's body, wherein the first wearable PPG device has at least one first light emitter and at least one first light receiver, wherein variation in the amount (and/or spectrum) of light from the first light emitter which is received by the first light receiver caused by reflection of the light from (or transmission of the light through) body tissue is analyzed in order to measure one or more biometric parameters from the first location; (b) a second wearable photoplethysmography (PPG) device which is configured to be worn at a second location on the person's body, wherein the second wearable PPG device has at least one second light emitter and at least one second light receiver, wherein variation in the amount (and/or spectrum) of light from the second light emitter which is received by the second light receiver caused by reflection of the light from (or transmission of the light through) body tissue is analyzed in order to measure one or more biometric parameters from the second location; and (c) an implanted cardiac pacemaker, wherein the operation of the implanted cardiac pacemaker is automatically adjusted based multivariate analysis of the one or more biometric parameters from the first and second locations, and wherein the operation of the implanted cardiac pacemaker is automatically adjusted by adjusting one or more of operating parameters selected from the group consisting of: Amplitude (e.g. Atrial Pulse, Ventricular Pulse, Current, Voltage); AV Delay (e.g. Post Pacing, Post Sensing, Minimum); Blanking Period (e.g. Ventricular); Coordination/Timing (e.g. Between Different Chambers); Electrode (e.g. Locations, Combination, Polarity); Frequency (e.g. Pulse, Heart Stimulations); Initiation or Cessation (e.g. Pacing, Stimulation); Mode (e.g. Pacing); Pacing Interval (e.g. AV, IV, VV); Polarity (e.g. Pacing); Pulse Width (e.g. Atrial, Ventricular); Rate (e.g. Basic, Upper Tracking, Hysteresis); Refractory Extension (e.g. Atrial); Refractory Period (e.g. Atrial, Ventricular, Post-Ventricular); Sensing (e.g. Atrial, Polarity, Ventricular, Polarity); and Sensitivity (e.g. Atrial).

In one embodiment, a peripheral feedback system for cardiac rhythm management can comprise: (a) a first wearable photoplethysmography (PPG) device which is configured to be worn on the person's right hand, wherein the first wearable PPG device has at least one first light emitter and at least one first light receiver, wherein variation in the amount (and/or spectrum) of light from the first light emitter which is received by the first light receiver caused by reflection of the light from (or transmission of the light through) body tissue is analyzed in order to measure one or more biometric parameters from the person's right hand; (b) a second wearable photoplethysmography (PPG) device which is configured to be worn on the person's left hand, wherein the second wearable PPG device has at least one second light emitter and at least one second light receiver, wherein variation in the amount (and/or spectrum) of light from the second light emitter which is received by the second light receiver caused by reflection of the light from (or transmission of the light through) body tissue is analyzed in order to measure the one or more biometric parameters from the person's left hand; and (c) an implanted cardiac pacemaker, wherein the operation of the implanted cardiac pacemaker is automatically adjusted based on multivariate comparison and/or analysis of the values of the one or more biometric parameters measured from the person's right hand and left hand, and wherein the operation of the implanted cardiac pacemaker is automatically adjusted by adjusting one or more of operating parameters selected from the group consisting of: Amplitude (e.g. Atrial Pulse, Ventricular Pulse, Current, Voltage); AV Delay (e.g. Post Pacing, Post Sensing, Minimum); Blanking Period (e.g. Ventricular); Coordination/Timing (e.g. Between Different Chambers); Electrode (e.g. Locations, Combination, Polarity); Frequency (e.g. Pulse, Heart Stimulations); Initiation or Cessation (e.g. Pacing, Stimulation); Mode (e.g. Pacing); Pacing Interval (e.g. AV, IV, VV); Polarity (e.g. Pacing); Pulse Width (e.g. Atrial, Ventricular); Rate (e.g. Basic, Upper Tracking, Hysteresis); Refractory Extension (e.g. Atrial); Refractory Period (e.g. Atrial, Ventricular, Post-Ventricular); Sensing (e.g. Atrial, Polarity, Ventricular, Polarity); and Sensitivity (e.g. Atrial).

In an example, a peripheral feedback system for cardiac rhythm management can comprise: (a) a first wearable photoplethysmography (PPG) device which is configured to be worn at a first location on a person's body, wherein the first wearable PPG device has at least one first light emitter and at least one first light receiver, and wherein variation in the amount (and/or spectrum) of light from the first light emitter which is received by the first light receiver caused by reflection of the light from (or transmission of the light through) body tissue is analyzed in order to measure one or more biometric parameters from the first location; (b) a second wearable photoplethysmography (PPG) device which is configured to be worn at a second location on the person's body, wherein the second wearable PPG device has at least one second light emitter and at least one second light receiver, and wherein variation in the amount (and/or spectrum) of light from the second light emitter which is received by the second light receiver caused by reflection of the light from (or transmission of the light through) body tissue is analyzed in order to measure one or more biometric parameters from the second location; and (c) an implanted cardiac pacemaker, wherein the operation of the implanted cardiac pacemaker is automatically adjusted based on multivariate analysis of the one or more biometric parameters measured from the first and second locations.

In one embodiment, a feedback system for cardiac rhythm management can comprise: (a) a first wearable photoplethysmography (PPG) device which is configured to be worn on a person's right foot, wherein the first wearable PPG device has at least one first light emitter and at least one first light receiver, and wherein variation in the amount (and/or spectrum) of light from the first light emitter which is received by the first light receiver caused by reflection of the light from (or transmission of the light through) body tissue is analyzed in order to measure one or more biometric parameters from the first location; (b) a second wearable photoplethysmography (PPG) device which is configured to be worn on a person's left foot, wherein the second wearable PPG device has at least one second light emitter and at least one second light receiver, and wherein variation in the amount (and/or spectrum) of light from the second light emitter which is received by the second light receiver caused by reflection of the light from (or transmission of the light through) body tissue is analyzed in order to measure one or more biometric parameters from the second location; and (c) an implanted cardiac pacemaker, wherein the operation of the implanted cardiac pacemaker is automatically adjusted based on multivariate analysis of one or more biometric parameters measured from the person's right foot and left foot. In an example, you put data from your right foot in, you put data from your right foot out, and then you shake it all about.

In an example, a system for treating congestive heart failure can comprise: (a) a first wearable photoplethysmography (PPG) device which is configured to be worn on the person's right leg, wherein the first wearable PPG device has at least one first light emitter and at least one first light receiver, wherein variation in the amount (and/or spectrum) of light from the first light emitter which is received by the first light receiver caused by reflection of the light from (or transmission of the light through) body tissue is analyzed in order to measure one or more biometric parameters from the person's right leg; (b) a second wearable photoplethysmography (PPG) device which is configured to be worn on the person's left leg, wherein the second wearable PPG device has at least one second light emitter and at least one second light receiver, wherein variation in the amount (and/or spectrum) of light from the second light emitter which is received by the second light receiver caused by reflection of the light from (or transmission of the light through) body tissue is analyzed in order to measure the one or more biometric parameters from the person's left leg; and (c) an implanted cardiac pacemaker, wherein the operation of the implanted cardiac pacemaker is automatically adjusted based on multivariate comparison and/or analysis of the values of the one or more biometric parameters measured from the person's right leg and left leg.

In an example, a peripheral feedback system for cardiac rhythm management can comprise: (a) a first wearable photoplethysmography (PPG) device with at least one first light emitter and at least one first light receiver which is worn on the right side of a person's body, wherein changes in the amount (and/or spectrum) of light from the first light emitter which is received by the first light receiver caused by reflection of the light from (or transmission of the light through) body tissue are analyzed in order to measure blood volume from the right side of the person's body; (b) a second wearable photoplethysmography (PPG) device with at least one second light emitter and at least one second light receiver which is worn on the left side of a person's body, wherein changes in the amount (and/or spectrum) of light from the second light emitter which is received by the second light receiver caused by reflection of the light from (or transmission of the light through) body tissue are analyzed in order to measure blood volume on the left side of the person's body; and (c) an implanted cardiac pacemaker whose operation is automatically adjusted in response to differences in the blood volume between the right side and the left side of the person's body.

In an example, a feedback system for cardiac rhythm management can comprise: (a) a first wearable photoplethysmography (PPG) device with at least one first light emitter and at least one first light receiver which is worn on a person's right leg, wherein variation in the amount (and/or spectrum) of light from the first light emitter which is received by the first light receiver caused by reflection of the light from (or transmission of the light through) body tissue of the right leg is analyzed in order to measure systolic amplitude from the person's right leg; (b) a second wearable photoplethysmography (PPG) device with at least one second light emitter and at least one second light receiver which is worn on a person's left leg, wherein variation in the amount (and/or spectrum) of light from the second light emitter which is received by the second light receiver caused by reflection of the light from (or transmission of the light through) body tissue of the left leg is analyzed in order to measure systolic amplitude from the person's left leg; and (c) an implanted cardiac pacemaker, wherein the operation of the implanted cardiac pacemaker is automatically adjusted based on comparison and/or multivariate analysis of systolic amplitude from the person's right leg vs. systolic amplitude from the person's left leg; and wherein the operation of the implanted cardiac pacemaker is automatically adjusted by adjusting one or more of operating parameters selected from the group consisting of: Amplitude (e.g. Atrial Pulse, Ventricular Pulse, Current, Voltage); AV Delay (e.g. Post Pacing, Post Sensing, Minimum); Blanking Period (e.g. Ventricular); Coordination/Timing (e.g. Between Different Chambers); Electrode (e.g. Locations, Combination, Polarity); Frequency (e.g. Pulse, Heart Stimulations); Initiation or Cessation (e.g. Pacing, Stimulation); Mode (e.g. Pacing); Pacing Interval (e.g. AV, IV, VV); Polarity (e.g. Pacing); Pulse Width (e.g. Atrial, Ventricular); Rate (e.g. Basic, Upper Tracking, Hysteresis); Refractory Extension (e.g. Atrial); Refractory Period (e.g. Atrial, Ventricular, Post-Ventricular); Sensing (e.g. Atrial, Polarity, Ventricular, Polarity); and Sensitivity (e.g. Atrial).

In an example, a peripheral feedback system for cardiac rhythm management can comprise: (a) a first wearable photoplethysmography (PPG) device with at least one first light emitter and at least one first light receiver which is worn on a person's right arm, wherein variation in the amount (and/or spectrum) of light from the first light emitter which is received by the first light receiver caused by reflection of the light from (or transmission of the light through) body tissue of the right arm is analyzed in order to measure Pulse Transit Time (PTT) to the person's right arm; (b) a second wearable photoplethysmography (PPG) device with at least one second light emitter and at least one second light receiver which is worn on a person's left arm, wherein variation in the amount (and/or spectrum) of light from the second light emitter which is received by the second light receiver caused by reflection of the light from (or transmission of the light through) body tissue of the left arm is analyzed in order to measure Pulse Transit Time (PTT) to the person's left arm; and (c) an implanted cardiac pacemaker, wherein the operation of the implanted cardiac pacemaker is automatically adjusted based on comparison and/or multivariate analysis of Pulse Transit Time (PTT) to the person's right arm vs. Pulse Transit Time (PTT) to the person's left arm; and wherein the operation of the implanted cardiac pacemaker is automatically adjusted by adjusting one or more of operating parameters selected from the group consisting of: Amplitude (e.g. Atrial Pulse, Ventricular Pulse, Current, Voltage); AV Delay (e.g. Post Pacing, Post Sensing, Minimum); Blanking Period (e.g. Ventricular); Coordination/Timing (e.g. Between Different Chambers); Electrode (e.g. Locations, Combination, Polarity); Frequency (e.g. Pulse, Heart Stimulations); Initiation or Cessation (e.g. Pacing, Stimulation); Mode (e.g. Pacing); Pacing Interval (e.g. AV, IV, VV); Polarity (e.g. Pacing); Pulse Width (e.g. Atrial, Ventricular); Rate (e.g. Basic, Upper Tracking, Hysteresis); Refractory Extension (e.g. Atrial); Refractory Period (e.g. Atrial, Ventricular, Post-Ventricular); Sensing (e.g. Atrial, Polarity, Ventricular, Polarity); and Sensitivity (e.g. Atrial).

In one embodiment, a feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters selected from the group consisting blood volume amplitude or peak amplitude; and (b) an implanted cardiac pacemaker whose frequency of heart contraction stimulations is automatically decreased in response to a high blood volume amplitude or peak amplitude measured by the PPG device. Alternatively, a peripheral feedback system for cardiac rhythm management can comprise: (a) a wearable photoplethysmography (PPG) device with a coherent light emitter and a light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker whose operation is automatically adjusted based on the measured values of the one or more biometric parameters.

In an example, a peripheral feedback system for cardiac rhythm management can comprise: (a) a wearable photoplethysmography (PPG) device with a ring of light emitters and light receivers around a body member, wherein changes in the amount (and/or spectrum) of light from the light emitters which is received by the light receivers caused by reflection of the light from (or transmission of the light through) body tissue are analyzed in order to measure one or more biometric parameters; and (b) an implanted cardiac pacemaker whose operation is automatically adjusted based on the one or more biometric parameters. In another example, a peripheral feedback system for cardiac rhythm management can comprise: (a) a wearable photoplethysmography (PPG) device with at least one light emitter and at least one light receiver, wherein changes in light from the at least one light emitter which is received by the at least one light receiver caused by reflection of the light from (or transmission of the light through) body tissue are analyzed in order to measure one or more biometric parameters, and wherein at least one light receiver is selected from the group consisting of photodetector, optical detector, photodiode, and phototransistor; and (b) an implanted cardiac pacemaker whose operation is automatically adjusted based on the measured values of the one or more biometric parameters.

In one embodiment, a feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure pulse transit time; and (b) an implanted cardiac pacemaker whose operation is automatically adjusted based on the measured pulse transit time. In another example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker whose operation is automatically adjusted based on the one or more biometric parameters, wherein the operation of the implanted cardiac pacemaker is adjusted by changing one or more operating parameters selected from the group consisting of frequency of heart electromagnetic energy stimulations, atrioventricular (AV) pacing interval, interventricular (IV) pacing interval, coordination between electromagnetic energy stimulations of different heart chambers, timing of electromagnetic energy stimulations of different heart chambers, location(s) of the heart to which electromagnetic energy is delivered, regularity of heart electromagnetic energy stimulations, magnitude of heart electromagnetic energy stimulations, voltage of heart electromagnetic energy stimulations, initiation of heart electromagnetic energy stimulations, and cessation of heart electromagnetic energy stimulations.

In an example, a feedback system for cardiac rhythm management can comprise: (a) a finger ring with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters selected from the group consisting of Heart Rate (HR), Heart Rate Variability (HRV), Blood Volume Pulse (BVP), Inter-Beat Interval (IBI), Peak-to-Peak Interval (PPI), Blood Pulse Rate (BPR), Blood Volume Pulse (BVP), Blood Volume Amplitude (BVP), Peak Amplitude (PA), Pulse Area, Pulse Transit Time (PTT), Standard Deviation of Average Normal to Normal Beat (SDANN), Systolic Amplitude, Systolic Peak Amplitude, Blood Pressure, Oxygen Saturation, VO2, VO2max, Hydration Level, and Respiration and/or Breathing Rate; and (b) an implanted cardiac pacemaker whose operation is automatically adjusted based on the one or more biometric parameters, wherein the operation of the implanted cardiac pacemaker is adjusted by changing one or more operating parameters selected from the group consisting of—the pattern of heart electromagnetic energy stimulations, atrioventricular (AV) pacing interval, interventricular (IV) pacing interval, coordination between electromagnetic energy stimulations of different heart chambers, timing of electromagnetic energy stimulations of different heart chambers, location(s) of the heart to which electromagnetic energy is delivered, regularity of heart electromagnetic energy stimulations, magnitude of heart contraction electromagnetic energy stimulations, voltage of heart electromagnetic energy stimulations, initiation of heart electromagnetic energy stimulations, and cessation of heart electromagnetic energy stimulations.

In one embodiment, a peripheral feedback system for cardiac rhythm management can comprise: (a) an arm band with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters selected from the group consisting of Heart Rate (HR), Heart Rate Variability (HRV), Blood Volume Pulse (BVP), Inter-Beat Interval (IBI), Peak-to-Peak Interval (PPI), Blood Pulse Rate (BPR), Blood Volume Pulse (BVP), Blood Volume Amplitude (BVP), Peak Amplitude (PA), Pulse Area, Pulse Transit Time (PTT), Standard Deviation of Average Normal to Normal Beat (SDANN), Systolic Amplitude, Systolic Peak Amplitude, Blood Pressure, Oxygen Saturation, VO2, VO2max, Hydration Level, and Respiration and/or Breathing Rate; and (b) an implanted cardiac pacemaker whose operation is automatically adjusted based on the one or more biometric parameters, wherein the operation of the implanted cardiac pacemaker is adjusted by changing one or more operating parameters selected from the group consisting of—the pattern of heart electromagnetic energy stimulations, atrioventricular (AV) pacing interval, interventricular (IV) pacing interval, coordination between electromagnetic energy stimulations of different heart chambers, timing of electromagnetic energy stimulations of different heart chambers, location(s) of the heart to which electromagnetic energy is delivered, regularity of heart electromagnetic energy stimulations, magnitude of heart contraction electromagnetic energy stimulations, voltage of heart electromagnetic energy stimulations, initiation of heart electromagnetic energy stimulations, and cessation of heart electromagnetic energy stimulations.

In an example, a feedback system for cardiac rhythm management can comprise: (a) a smart watch with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters selected from the group consisting of Heart Rate (HR), Heart Rate Variability (HRV), Blood Volume Pulse (BVP), Inter-Beat Interval (IBI), Peak-to-Peak Interval (PPI), Blood Pulse Rate (BPR), Blood Volume Pulse (BVP), Blood Volume Amplitude (BVP), Peak Amplitude (PA), Pulse Area, Pulse Transit Time (PTT), Standard Deviation of Average Normal to Normal Beat (SDANN), Systolic Amplitude, Systolic Peak Amplitude, Blood Pressure, Oxygen Saturation, VO2, VO2max, Hydration Level, and Respiration and/or Breathing Rate; and (b) an implanted cardiac pacemaker whose operation is automatically adjusted based on the one or more biometric parameters. Alternatively, a peripheral feedback system for cardiac rhythm management can comprise: (a) a leg band with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters selected from the group consisting of Heart Rate (HR), Heart Rate Variability (HRV), Blood Volume Pulse (BVP), Inter-Beat Interval (IBI), Peak-to-Peak Interval (PPI), Blood Pulse Rate (BPR), Blood Volume Pulse (BVP), Blood Volume Amplitude (BVP), Peak Amplitude (PA), Pulse Area, Pulse Transit Time (PTT), Standard Deviation of Average Normal to Normal Beat (SDANN), Systolic Amplitude, Systolic Peak Amplitude, Blood Pressure, Oxygen Saturation, VO2, VO2max, Hydration Level, and Respiration and/or Breathing Rate; and (b) an implanted cardiac pacemaker whose operation is automatically adjusted based on the one or more biometric parameters.

In an example, a peripheral feedback system for cardiac rhythm management can comprise: (a) an ear bud or hearing aid with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker whose operation is automatically adjusted based on the one or more biometric parameters, wherein the operation of the implanted cardiac pacemaker is adjusted by changing one or more operating parameters selected from the group consisting of—the pattern of heart electromagnetic energy stimulations, atrioventricular (AV) pacing interval, interventricular (IV) pacing interval, coordination between electromagnetic energy stimulations of different heart chambers, timing of electromagnetic energy stimulations of different heart chambers, location(s) of the heart to which electromagnetic energy is delivered, regularity of heart electromagnetic energy stimulations, magnitude of heart contraction electromagnetic energy stimulations, voltage of heart electromagnetic energy stimulations, initiation of heart electromagnetic energy stimulations, and cessation of heart electromagnetic energy stimulations.

In an example, a peripheral feedback system for cardiac rhythm management can comprise: (a) a wrist band with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker whose operation is automatically adjusted based on the one or more biometric parameters, wherein the operation of the implanted cardiac pacemaker is adjusted by changing one or more operating parameters selected from the group consisting of—the pattern of heart electromagnetic energy stimulations, atrioventricular (AV) pacing interval, interventricular (IV) pacing interval, coordination between electromagnetic energy stimulations of different heart chambers, timing of electromagnetic energy stimulations of different heart chambers, location(s) of the heart to which electromagnetic energy is delivered, regularity of heart electromagnetic energy stimulations, magnitude of heart contraction electromagnetic energy stimulations, voltage of heart electromagnetic energy stimulations, initiation of heart electromagnetic energy stimulations, and cessation of heart electromagnetic energy stimulations.

In one embodiment, a system for cardiac rhythm management can comprise: (a) a wearable photoplethysmography (PPG) device with at least one light emitter and at least one light receiver, wherein changes in the spectral distribution (and/or amount) of light from the light emitter which is received by the light receiver caused by reflection of the light from (or transmission of the light through) body tissue are analyzed in order to measure one or more biometric parameters selected from the group consisting of Heart Rate (HR), Heart Rate Variability (HRV), Blood Volume Pulse (BVP), Inter-Beat Interval (IBI), Peak-to-Peak Interval (PPI), Blood Pulse Rate (BPR), Blood Volume Pulse (BVP), Blood Volume Amplitude (BVP), Peak Amplitude (PA), Pulse Area, Pulse Transit Time (PTT), Standard Deviation of Average Normal to Normal Beat (SDANN), Systolic Amplitude, Systolic Peak Amplitude, Blood Pressure, Oxygen Saturation, VO2, VO2max, Hydration Level, and Respiration and/or Breathing Rate; and (b) an implanted cardiac pacemaker whose operation is automatically adjusted based on the one or more biometric parameters, wherein the operation of the implanted cardiac pacemaker is adjusted by changing one or more operating parameters selected from the group consisting of frequency of heart contraction stimulations, atrioventricular (AV) pacing interval, interventricular (IV) pacing interval, coordination between contraction stimulations of different heart chambers, timing of contraction stimulations of different heart chambers, location(s) of the heart to which electromagnetic energy is delivered, regularity of heart contraction stimulations, magnitude of heart contraction stimulations, voltage of heart contraction stimulations, initiation of heart contraction stimulations, and cessation of heart contraction stimulations.

In an example, a peripheral feedback system for cardiac rhythm management can comprise: (a) a wearable photoplethysmography (PPG) device with a single light emitter and a plurality of light receivers, wherein changes in the amount (and/or spectrum) of light from the light emitter which is received by the light receivers caused by reflection of the light from (or transmission of the light through) body tissue are analyzed in order to measure one or more biometric parameters selected from the group consisting of Heart Rate (HR), Heart Rate Variability (HRV), Blood Volume Pulse (BVP), Inter-Beat Interval (IBI), Peak-to-Peak Interval (PPI), Blood Pulse Rate (BPR), Blood Volume Pulse (BVP), Blood Volume Amplitude (BVP), Peak Amplitude (PA), Pulse Area, Pulse Transit Time (PTT), Standard Deviation of Average Normal to Normal Beat (SDANN), Systolic Amplitude, Systolic Peak Amplitude, Blood Pressure, Oxygen Saturation, VO2, VO2max, Hydration Level, and Respiration and/or Breathing Rate; and (b) an implanted cardiac pacemaker whose pacing interval is automatically adjusted based on measured values of the one or more biometric parameters. In another example, a feedback system for cardiac rhythm management can comprise: (a) a wearable photoplethysmography (PPG) device with a plurality of light emitters and a single light receiver, wherein changes in the amount (and/or spectrum) of light from the light emitters which is received by the light receiver caused by reflection of the light from (or transmission of the light through) body tissue are analyzed in order to measure one or more biometric parameters selected from the group consisting of blood volume pulse; and (b) an implanted cardiac pacemaker whose pacing rate is automatically reduced in response to a high blood volume pulse measured by the PPG device.

In one embodiment, a peripheral feedback system for cardiac rhythm management can comprise: (a) a wearable photoplethysmography (PPG) device with a single light emitter and a plurality of light receivers, wherein changes in the amount (and/or spectrum) of light from the light emitter which is received by the light receivers caused by reflection of the light from (or transmission of the light through) body tissue are analyzed in order to measure one or more biometric parameters selected from the group consisting of Heart Rate (HR), Heart Rate Variability (HRV), Blood Volume Pulse (BVP), Inter-Beat Interval (IBI), Peak-to-Peak Interval (PPI), Blood Pulse Rate (BPR), Blood Volume Pulse (BVP), Blood Volume Amplitude (BVP), Peak Amplitude (PA), Pulse Area, Pulse Transit Time (PTT), Standard Deviation of Average Normal to Normal Beat (SDANN), Systolic Amplitude, Systolic Peak Amplitude, Blood Pressure, Oxygen Saturation, VO2, VO2max, Hydration Level, and Respiration and/or Breathing Rate; and (b) an implanted cardiac pacemaker whose pacing rate is automatically reduced in response to a high value for the one or more biometric parameters measured by the PPG device.

In an example, a feedback system for cardiac rhythm management can comprise: (a) a wearable photoplethysmography (PPG) device with a plurality of light emitters and a single light receiver, wherein changes in the amount (and/or spectrum) of light from the light emitters which is received by the light receiver caused by reflection of the light from (or transmission of the light through) body tissue are analyzed in order to measure heart rate; and (b) an implanted cardiac pacemaker whose stimulation amplitude (e.g. atrial pulse amplitude, ventricular pulse amplitude, current, and/or voltage) is automatically reduced in response to a high heart rate measured by the PPG device. Alternatively, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters selected from the group consisting blood volume amplitude or peak amplitude; and (b) an implanted cardiac pacemaker whose voltage of heart contraction stimulations is automatically decreased in response to a high blood volume amplitude or peak amplitude measured by the PPG device.

In one embodiment, a feedback system for cardiac rhythm management can comprise: (a) a wearable photoplethysmography (PPG) device with a light emitter and a light receiver, wherein variation in the amount (and/or spectrum) of light from the light emitter received by the light receiver caused by reflection of the light from (or transmission of the light through) body tissue is analyzed in order to measure blood pressure; and (b) an implanted cardiac pacemaker, wherein the frequency of electromagnetic stimulations of the heart by the implanted cardiac pacemaker is automatically reduced in response to high blood pressure measured by the PPG device. In another example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure pulse area; and (b) an implanted cardiac pacemaker, wherein the frequency of electromagnetic energy stimulations by the implanted cardiac pacemaker is automatically decreased in response to a high pulse area.

In an example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure pulse transit time; and (b) an implanted cardiac pacemaker, wherein the frequency of electromagnetic energy stimulations by the implanted cardiac pacemaker is automatically increased in response to a high pulse transit time. In another example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters selected from the group consisting of Heart Rate (HR), Heart Rate Variability (HRV), Blood Volume Pulse (BVP), Inter-Beat Interval (IBI), Peak-to-Peak Interval (PPI), Blood Pulse Rate (BPR), Blood Volume Pulse (BVP), Blood Volume Amplitude (BVP), Peak Amplitude (PA), Pulse Area, Pulse Transit Time (PTT), Standard Deviation of Average Normal to Normal Beat (SDANN), Systolic Amplitude, Systolic Peak Amplitude, Blood Pressure, Oxygen Saturation, VO2, VO2max, Hydration Level, and Respiration and/or Breathing Rate; and (b) an implanted cardiac pacemaker, wherein the frequency of heart contractions stimulated by the implanted cardiac pacemaker is automatically increased or decreased based on the one or more biometric parameters.

In an example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure Heart Rate (HR); and (b) an implanted cardiac pacemaker, wherein the frequency of heart contractions stimulated by the implanted cardiac pacemaker is automatically decreased based on a high Heart Rate (HR) measured by the photoplethysmography (PPG) device. Alternatively, a feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure blood pressure; and (b) an implanted cardiac pacemaker, wherein the frequency of electromagnetic energy stimulations by the implanted cardiac pacemaker is automatically adjusted based on measured blood pressure.

In an example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure blood pressure; and (b) an implanted cardiac pacemaker, wherein the inter-chamber coordination of electromagnetic energy stimulations by the implanted cardiac pacemaker is automatically adjusted based on measured blood pressure. In another example, a feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure heart rate variability; and (b) an implanted cardiac pacemaker, wherein the inter-chamber coordination of electromagnetic energy stimulations by the implanted cardiac pacemaker is automatically adjusted based on measured heart rate variability.

In one embodiment, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure heart rate; and (b) an implanted cardiac pacemaker, wherein the magnitude and/or voltage of electromagnetic energy stimulations by the implanted cardiac pacemaker is automatically adjusted based on measured heart rate. Alternatively, a feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure heart rate variability; and (b) an implanted cardiac pacemaker, wherein the magnitude and/or voltage of electromagnetic energy stimulations by the implanted cardiac pacemaker is automatically increased in response to high heart rate variability.

In an example, a peripheral feedback system for cardiac rhythm management can comprise: (a) a wearable photoplethysmography (PPG) device with a light emitter and a light receiver, wherein variation in the amount (and/or spectrum) of light from the light emitter received by the light receiver caused by reflection of the light from (or transmission of the light through) body tissue is analyzed in order to measure blood pressure; and (b) an implanted cardiac pacemaker, wherein the magnitude of electromagnetic stimulations of the heart by the implanted cardiac pacemaker is automatically reduced in response to high blood pressure measured by the PPG device. In another example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure oxygen saturation, VO2, and/or VO2max; and (b) an implanted cardiac pacemaker, wherein the magnitude of electromagnetic stimulation applied by the implanted cardiac pacemaker is automatically increased in response to low oxygen saturation, VO2, and/or VO2max measured by the PPG device.

In one embodiment, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure Heart Rate (HR) and/or Heart Rate Variability (HRV); and (b) an implanted cardiac pacemaker, wherein the operation by the implanted cardiac pacemaker is automatically adjusted based on Heart Rate (HR) and/or Heart Rate Variability (HRV) measured by the photoplethysmography (PPG) device. In another example, a peripheral feedback system for cardiac rhythm management can comprise: (a) a finger ring which functions as a wearable photoplethysmography (PPG) device with at least one light emitter and at least one light receiver, wherein changes in the amount (and/or spectrum) of light from the light emitter which is received by the light receiver caused by reflection of the light from (or transmission of the light through) the finger are analyzed in order to measure one or more biometric parameters; and (b) an implanted cardiac pacemaker, wherein the operation of the implanted cardiac pacemaker is automatically adjusted based on the values of the one or more biometric parameters.

In an example, a feedback system for cardiac rhythm management can comprise: (a) a pair of headphones which functions as a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the values of the one or more biometric parameters. Alternatively, a peripheral feedback system for cardiac rhythm management can comprise: (a) a pair of eyeglasses which functions as a wearable photoplethysmography (PPG) device, wherein the pair of eyeglasses has at least one portion which rests on top of a person's outer ear, wherein there is at least one light emitter and at least one light receiver on this portion, and wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the values of the one or more biometric parameters.

In one embodiment, a feedback system for cardiac rhythm management can comprise: (a) a wearable photoplethysmography (PPG) device with a circumferential array of light emitters (evenly) distributed around the circumference of a body member (such as a finger, wrist, or arm) and at least one light receiver, wherein changes in the amount (and/or spectrum) of light from the light emitters which is received by the light receiver caused by reflection of the light from (or transmission of the light through) body tissue are analyzed in order to measure one or more biometric parameters, and; and (b) an implanted cardiac pacemaker, wherein the operation of the implanted cardiac pacemaker is automatically adjusted based on the one or more biometric parameters. In another example, a peripheral feedback system for cardiac rhythm management can comprise: (a) a wearable photoplethysmography (PPG) device with a circumferential array of light emitters and light receivers which spans all four radial quadrants of the circumference of a body member (such as a finger, wrist, or arm), wherein changes in the amount (and/or spectrum) of light from the light emitters which is received by the light receivers due to reflection from (or transmission of the light through) body tissue are analyzed in order to measure one or more biometric parameters, and; and (b) an implanted cardiac pacemaker, wherein the operation of the implanted cardiac pacemaker is automatically adjusted based on the one or more biometric parameters.

In an example, a feedback system for cardiac rhythm management can comprise: (a) a wearable photoplethysmography (PPG) device with a first light emitter, a second light emitter, and a light receiver, wherein the light receiver is between the first light emitter and the second light emitter, and wherein changes in the amount (and/or spectrum) of light from the first and/or second light emitters which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the one or more biometric parameters. Alternatively, a peripheral feedback system for cardiac rhythm management can comprise: (a) a wearable photoplethysmography (PPG) device with a first light emitter, a second light emitter, and at least one light receiver, wherein changes in the amount (and/or spectrum) of light from the first and/or second light emitters which is received by the light receiver caused by reflection of the light from (or transmission of the light through) body tissue are analyzed in order to measure one or more biometric parameters, and wherein the first light emitter emits light along a first vector and the second light emitter emits light along a second vector which is different than the first vector; and (b) an implanted cardiac pacemaker, wherein the operation of the implanted cardiac pacemaker is automatically adjusted based on the one or more biometric parameters.

In an example, a peripheral feedback system for cardiac rhythm management can comprise: (a) a wearable photoplethysmography (PPG) device with a first light emitter, a second light emitter, and at least one light receiver, wherein changes in the amount (and/or spectrum) of light from the light emitter which is received by the light receiver caused by reflection of the light from (or transmission of the light through) body tissue are analyzed in order to measure one or more biometric parameters, and wherein the first light emitter emits light from a first (radial) location relative to a body member and the second light emitter emits light from a second (radial) location relative to the body member which is different than the first location; and (b) an implanted cardiac pacemaker, wherein the operation of the implanted cardiac pacemaker is automatically adjusted based on the one or more biometric parameters. In another example, a peripheral feedback system for cardiac rhythm management can comprise: (a) a wearable photoplethysmography (PPG) device with an array of light emitters and light receivers which are distributed along the band of a smart watch, wherein changes in the amount (and/or spectrum) of light from the light emitters which is received by the light receivers due to reflection from (or transmission of the light through) body tissue are analyzed in order to measure one or more biometric parameters, and; and (b) an implanted cardiac pacemaker, wherein the operation of the implanted cardiac pacemaker is automatically adjusted based on the one or more biometric parameters.

In an example, a feedback system for cardiac rhythm management can comprise: (a) a wearable photoplethysmography (PPG) device with an array of light emitters and light receivers on the inner surface of the housing of a smart watch, wherein changes in the amount (and/or spectrum) of light from the light emitters which is received by the light receivers due to reflection from (or transmission of the light through) body tissue are analyzed in order to measure one or more biometric parameters, and; and (b) an implanted cardiac pacemaker, wherein the operation of the implanted cardiac pacemaker is automatically adjusted based on the one or more biometric parameters. In another example, a peripheral feedback system for cardiac rhythm management can comprise: (a) a wearable photoplethysmography (PPG) device with an array of light emitters and light receivers on an earbud, wherein changes in the amount (and/or spectrum) of light from the light emitters which is received by the light receivers due to reflection from (or transmission of the light through) body tissue are analyzed in order to measure one or more biometric parameters, and; and (b) an implanted cardiac pacemaker, wherein the operation of the implanted cardiac pacemaker is automatically adjusted based on the one or more biometric parameters.

In one embodiment, a feedback system for cardiac rhythm management can comprise: (a) a wearable photoplethysmography (PPG) device which is configured to be (partially) inserted into a person's ear canal, wherein this device has at least one light emitter and at least one light receiver, and wherein changes in the amount (and/or spectrum) of light from the light emitters which is received by the light receivers due to reflection from (or transmission of the light through) body tissue are analyzed in order to measure the person's heart rate variability, and; and (b) an implanted cardiac pacemaker, wherein the operation of the implanted cardiac pacemaker is automatically adjusted based on heart rate variability measured by the PPG device. Alternatively, a peripheral feedback system for cardiac rhythm management can comprise: (a) a wearable photoplethysmography (PPG) device can be a pair of eyeglasses with an array of light emitters and light receivers, wherein changes in the amount (and/or spectrum) of light from the light emitters which is received by the light receivers due to reflection from (or transmission of the light through) body tissue are analyzed in order to measure one or more biometric parameters, and; and (b) an implanted cardiac pacemaker, wherein the operation of the implanted cardiac pacemaker is automatically adjusted based on the one or more biometric parameters.

In an example, a peripheral feedback system for cardiac rhythm management can comprise: (a) a wearable photoplethysmography (PPG) device with at least one light emitter and at least one light receiver, wherein variation in the amount (and/or spectrum) of light from the light emitter which is received by the light receiver caused by reflection of the light from (or transmission of the light through) body tissue is analyzed in order to measure one or more biometric parameters; and (b) an implanted cardiac pacemaker, wherein the operation of the implanted cardiac pacemaker is automatically adjusted based on the one or more biometric parameters, and wherein the operation of the implanted cardiac pacemaker is automatically adjusted by adjusting (post pacing, post sensing, or minimum) AV delay. In another example, a peripheral feedback system for cardiac rhythm management can comprise: (a) a wearable photoplethysmography (PPG) device with at least one light emitter and at least one light receiver, wherein variation in the amount (and/or spectrum) of light from the light emitter which is received by the light receiver caused by reflection of the light from (or transmission of the light through) body tissue is analyzed in order to measure one or more biometric parameters; and (b) an implanted cardiac pacemaker, wherein the operation of the implanted cardiac pacemaker is automatically adjusted based on the one or more biometric parameters, and wherein the operation of the implanted cardiac pacemaker is automatically adjusted by adjusting pacing (pulse) frequency.

In one embodiment, a feedback system for cardiac rhythm management can comprise: (a) a wearable photoplethysmography (PPG) device with at least one light emitter and at least one light receiver, wherein variation in the amount (and/or spectrum) of light from the light emitter which is received by the light receiver caused by reflection of the light from (or transmission of the light through) body tissue is analyzed in order to measure one or more biometric parameters; and (b) an implanted cardiac pacemaker, wherein the operation of the implanted cardiac pacemaker is automatically adjusted based on the one or more biometric parameters, and wherein the operation of the implanted cardiac pacemaker is automatically adjusted by adjusting (AV, IV, or VV) pacing interval. Alternatively, a peripheral feedback system for cardiac rhythm management can comprise: (a) a wearable photoplethysmography (PPG) device with at least one light emitter and at least one light receiver, wherein variation in the amount (and/or spectrum) of light from the light emitter which is received by the light receiver caused by reflection of the light from (or transmission of the light through) body tissue is analyzed in order to measure one or more biometric parameters; and (b) an implanted cardiac pacemaker, wherein the operation of the implanted cardiac pacemaker is automatically adjusted based on the one or more biometric parameters, and wherein the operation of the implanted cardiac pacemaker is automatically adjusted by adjusting (atrial) refractory extension.

In an example, a feedback system for cardiac rhythm management can comprise: (a) a wearable photoplethysmography (PPG) device with at least one light emitter and at least one light receiver, wherein variation in the amount (and/or spectrum) of light from the light emitter which is received by the light receiver caused by reflection of the light from (or transmission of the light through) body tissue is analyzed in order to measure heart rate (HR) and/or heart rate variability (HRV); and (b) an implanted cardiac pacemaker, wherein the operation of the implanted cardiac pacemaker is automatically adjusted based on heart rate (HR) and/or heart rate variability (HRV), and wherein the operation of the implanted cardiac pacemaker is automatically adjusted by adjusting pacing frequency (e.g. pulse, heart stimulations), pacing interval (e.g. AV, IV, VV), and/or pacing rate (e.g. basic, upper tracking, hysteresis). In another example, a peripheral feedback system for cardiac rhythm management can comprise: (a) a wearable photoplethysmography (PPG) device with at least one light emitter and at least one light receiver, wherein variation in the amount (and/or spectrum) of light from the light emitter which is received by the light receiver caused by reflection of the light from (or transmission of the light through) body tissue is analyzed in order to measure one or more biometric parameters; and (b) an implanted cardiac pacemaker, wherein the operation of the implanted cardiac pacemaker is automatically adjusted based on the one or more biometric parameters.

In one embodiment, a feedback system for cardiac rhythm management can comprise: (a) a wearable photoplethysmography (PPG) device with at least one light emitter and at least one light receiver, wherein sinusoidal variation in the spectral distribution of light from the light emitter which is received by the light receiver caused by reflection of the light from (or transmission of the light through) body tissue is analyzed in order to measure one or more biometric parameters; and (b) an implanted cardiac pacemaker, wherein the operation of the implanted cardiac pacemaker is automatically adjusted based on the one or more biometric parameters. In another example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from body tissue are analyzed in order to measure one or more biometric parameters; and (b) an implanted cardiac pacemaker, wherein the operation of the implanted cardiac pacemaker is automatically adjusted based on the one or more biometric parameters, and wherein the operation of the implanted cardiac pacemaker is adjusted by changing one or more pacemaker operating parameters selected from the group consisting of frequency of heart contraction stimulations, atrioventricular (AV) pacing interval, interventricular (IV) pacing interval, coordination between contraction stimulations of different heart chambers, timing of contraction stimulations of different heart chambers, location(s) of the heart to which electromagnetic energy is delivered, regularity of heart contraction stimulations, magnitude of heart contraction stimulations, voltage of heart contraction stimulations, initiation of heart contraction stimulations, and cessation of heart contraction stimulations.

In an example, a peripheral feedback system for cardiac rhythm management can comprise: (a) a wearable photoplethysmography (PPG) device with at least one light emitter on a first side of a person's finger and at least one light receiver on a second side of the person's finger, where the second side is opposite the first side, and wherein changes in the amount (and/or spectrum) of light from the light emitter which is received by the light receiver after transmission through the finger are analyzed in order to measure one or more biometric parameters; and (b) an implanted cardiac pacemaker, wherein the operation of the implanted cardiac pacemaker is automatically adjusted based on the one or more biometric parameters, and wherein the operation of the implanted cardiac pacemaker is adjusted by changing the frequency of heart contraction stimulations. Alternatively, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the one or more biometric parameters, and wherein the operation of the implanted cardiac pacemaker is adjusted by changing the location(s) of the electrode(s) selected to deliver electromagnetic energy to the person's heart.

In an example, a feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the one or more biometric parameters, and wherein the operation of the implanted cardiac pacemaker is adjusted by ceasing stimulation of heart contractions. In another example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure Standard Deviation of Average Normal to Normal Beat (SDANN); and (b) an implanted cardiac pacemaker, wherein the operation of the implanted cardiac pacemaker is automatically adjusted based on measured Standard Deviation of Average Normal to Normal Beat (SDANN).

In an example, a feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure hydration level; and (b) an implanted cardiac pacemaker, wherein the operation of the implanted cardiac pacemaker is automatically adjusted based on hydration level. Alternatively, a peripheral feedback system for cardiac rhythm management can comprise: (a) a wearable photoplethysmography (PPG) device with at least one light emitting diode (LED) and at least one photodetector, wherein changes in the amount (and/or spectrum) of light from the LED which is received by the photodetector caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the one or more biometric parameters.

In one embodiment, a feedback system for cardiac rhythm management can comprise: (a) a wearable photoplethysmography (PPG) device with at least one light emitter and at least one light receiver, wherein the at least one light emitter emits light with sinusoidal variation in wavelength (or frequency) within a selected wavelength (or frequency) range, and wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the one or more biometric parameters. In another example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters, and wherein the angle at which light from the light emitter enters body tissue is changed by activation of one or more electromagnetic actuators; and (b) an implanted cardiac pacemaker, wherein the operation of the implanted cardiac pacemaker is automatically adjusted based on the one or more biometric parameters.

In an example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters, and wherein the at least one light emitter emits light in a path which is changed by a Digital Micromirror Array (DMA); and (b) an implanted cardiac pacemaker, wherein the operation of the implanted cardiac pacemaker is automatically adjusted based on the one or more biometric parameters. In another example, a peripheral feedback system for cardiac rhythm management can comprise: (a) a wearable photoplethysmography (PPG) device worn around the circumference of a body member (such as a person's finger, wrist, or arm) with at least one light emitter and at least one light receiver of each of four radial quadrants around the circumference, wherein variation in (the amount) light from a light emitter in a quadrant received by a light receiver in that quadrant caused by reflection of the light from (or transmission of the light through) body tissue is analyzed in order to measure one or more biometric parameters; and (b) an implanted cardiac pacemaker, wherein the operation of the implanted cardiac pacemaker is automatically adjusted based on the one or more biometric parameters.

In one embodiment, a feedback system for cardiac rhythm management can comprise: (a) a wearable photoplethysmography (PPG) device worn on a person's earlobe, wherein wearable PPG device further comprises at least one light emitter and at least one light receiver, and wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the measured values of the biometric parameters. Alternatively, a peripheral feedback system for cardiac rhythm management can comprise: (a) a wearable photoplethysmography (PPG) device worn on a person's hand, wherein wearable PPG device further comprises at least one light emitter and at least one light receiver, and wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the measured values of the biometric parameters.

In an example, a feedback system for cardiac rhythm management can comprise: (a) a smart bandage worn on a person's body which functions as a wearable photoplethysmography (PPG) device, wherein the smart bandage further comprises at least one light emitter and at least one light receiver, and wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the measured values of the biometric parameters. In another example, a peripheral feedback system for cardiac rhythm management can comprise: (a) a wearable photoplethysmography (PPG) device, wherein the PPG device further comprises at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the one or more measured biometric parameters.

In one embodiment, a feedback system for cardiac rhythm management can comprise: (a) an arm cuff or sleeve which functions as a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the values of the one or more biometric parameters. Alternatively, a peripheral feedback system for cardiac rhythm management can comprise: (a) an earbud which functions as a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the values of the one or more biometric parameters.

In an example, a system for cardiac rhythm management can comprise: (a) a wearable photoplethysmography (PPG) device with a light emitter and a light receiver, wherein variation in the amount (and/or spectrum) of light from the light emitter received by the light receiver caused by reflection of the light from (or transmission of the light through) body tissue is analyzed in order to measure one or more biometric parameters; and (b) an implanted cardiac pacemaker, wherein the operation of the implanted cardiac pacemaker is automatically adjusted based on values of the one or more biometric parameters measured by the PPG device. In another example, a system for cardiac rhythm management can comprise: (a) a wearable photoplethysmography (PPG) device with a light emitter and a light receiver, wherein variation in the spectrum of light from the light emitter received by the light receiver caused by transmission of the light through body tissue is analyzed in order to measure one or more biometric parameters; and (b) an implanted cardiac pacemaker, wherein the operation of the implanted cardiac pacemaker is automatically adjusted based on measured values of the one or more biometric parameters.

In an example, a system for treating cardiac arrhythmia can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed to measure one or more biometric parameters selected from the group consisting of Heart Rate (HR), Heart Rate Variability (HRV), Blood Volume Pulse (BVP), Inter-Beat Interval (IBI), Peak-to-Peak Interval (PPI), Blood Pulse Rate (BPR), Blood Volume Pulse (BVP), Blood Volume Amplitude (BVP), Peak Amplitude (PA), Pulse Area, Pulse Transit Time (PTT), Standard Deviation of Average Normal to Normal Beat (SDANN), Systolic Amplitude, Systolic Peak Amplitude, Blood Pressure, Oxygen Saturation, VO2, VO2max, Hydration Level, and Respiration and/or Breathing Rate; and (b) an implanted cardiac pacemaker, wherein the operation of the implanted cardiac pacemaker is automatically adjusted based on the one or more biometric parameters measured by the wearable photoplethysmography (PPG) device, and wherein the operation of the implanted cardiac pacemaker is changed by changing one or more pacemaker operating parameters selected from the group consisting of frequency of heart contraction stimulations, atrioventricular (AV) pacing interval, interventricular (IV) pacing interval, coordination between contraction stimulations of different heart chambers, timing of contraction stimulations of different heart chambers, location(s) of the heart to which electromagnetic energy is delivered, regularity of heart contraction stimulations, magnitude of heart contraction stimulations, voltage of heart contraction stimulations, initiation of heart contraction stimulations, and cessation of heart contraction stimulations.

In an example, a system for treating congestive heart failure can comprise: (a) a pair of headphones which functions as a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the values of the one or more biometric parameters.

In one embodiment, a system for treating congestive heart failure can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed to measure one or more biometric parameters selected from the group consisting of Heart Rate (HR), Heart Rate Variability (HRV), Blood Volume Pulse (BVP), Inter-Beat Interval (IBI), Peak-to-Peak Interval (PPI), Blood Pulse Rate (BPR), Blood Volume Pulse (BVP), Blood Volume Amplitude (BVP), Peak Amplitude (PA), Pulse Area, Pulse Transit Time (PTT), Standard Deviation of Average Normal to Normal Beat (SDANN), Systolic Amplitude, Systolic Peak Amplitude, Blood Pressure, Oxygen Saturation, VO2, VO2max, Hydration Level, and Respiration and/or Breathing Rate; and (b) an implanted cardiac pacemaker, wherein the operation of the implanted cardiac pacemaker is automatically adjusted based on the one or more biometric parameters measured by the wearable photoplethysmography (PPG) device, and wherein the operation of the implanted cardiac pacemaker is changed by changing one or more pacemaker operating parameters selected from the group consisting of frequency of heart contraction stimulations, atrioventricular (AV) pacing interval, interventricular (IV) pacing interval, coordination between contraction stimulations of different heart chambers, timing of contraction stimulations of different heart chambers, location(s) of the heart to which electromagnetic energy is delivered, regularity of heart contraction stimulations, magnitude of heart contraction stimulations, voltage of heart contraction stimulations, initiation of heart contraction stimulations, and cessation of heart contraction stimulations.

In an example, a system for treating congestive heart failure can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure body hydration level; and (b) an implanted cardiac pacemaker, wherein the operation of the implanted cardiac pacemaker is automatically adjusted based on body hydration level. In another example, a system for treating congestive heart failure can comprise: (a) an earbud which functions as a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the values of the one or more biometric parameters.

In one embodiment, a system for treating endothelial dysfunction can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed to measure one or more biometric parameters selected from the group consisting of Heart Rate (HR), Heart Rate Variability (HRV), Blood Volume Pulse (BVP), Inter-Beat Interval (IBI), Peak-to-Peak Interval (PPI), Blood Pulse Rate (BPR), Blood Volume Pulse (BVP), Blood Volume Amplitude (BVP), Peak Amplitude (PA), Pulse Area, Pulse Transit Time (PTT), Standard Deviation of Average Normal to Normal Beat (SDANN), Systolic Amplitude, Systolic Peak Amplitude, Blood Pressure, Oxygen Saturation, VO2, VO2max, Hydration Level, and Respiration and/or Breathing Rate; and (b) an implanted cardiac pacemaker, wherein the operation of the implanted cardiac pacemaker is automatically adjusted based on the one or more biometric parameters measured by the wearable photoplethysmography (PPG) device, and wherein the operation of the implanted cardiac pacemaker is changed by changing one or more pacemaker operating parameters selected from the group consisting of frequency of heart contraction stimulations, atrioventricular (AV) pacing interval, interventricular (IV) pacing interval, coordination between contraction stimulations of different heart chambers, timing of contraction stimulations of different heart chambers, location(s) of the heart to which electromagnetic energy is delivered, regularity of heart contraction stimulations, magnitude of heart contraction stimulations, voltage of heart contraction stimulations, initiation of heart contraction stimulations, and cessation of heart contraction stimulations.

In an example, a system for treating tachycardia can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed to measure one or more biometric parameters selected from the group consisting of Heart Rate (HR), Heart Rate Variability (HRV), Blood Volume Pulse (BVP), Inter-Beat Interval (IBI), Peak-to-Peak Interval (PPI), Blood Pulse Rate (BPR), Blood Volume Pulse (BVP), Blood Volume Amplitude (BVP), Peak Amplitude (PA), Pulse Area, Pulse Transit Time (PTT), Standard Deviation of Average Normal to Normal Beat (SDANN), Systolic Amplitude, Systolic Peak Amplitude, Blood Pressure, Oxygen Saturation, VO2, VO2max, Hydration Level, and Respiration and/or Breathing Rate; and (b) an implanted cardiac pacemaker, wherein the operation of the implanted cardiac pacemaker is automatically adjusted based on the one or more biometric parameters measured by the wearable photoplethysmography (PPG) device, and wherein the operation of the implanted cardiac pacemaker is changed by changing one or more pacemaker operating parameters selected from the group consisting of frequency of heart contraction stimulations, atrioventricular (AV) pacing interval, interventricular (IV) pacing interval, coordination between contraction stimulations of different heart chambers, timing of contraction stimulations of different heart chambers, location(s) of the heart to which electromagnetic energy is delivered, regularity of heart contraction stimulations, magnitude of heart contraction stimulations, voltage of heart contraction stimulations, initiation of heart contraction stimulations, and cessation of heart contraction stimulations.

In one embodiment, a peripheral feedback system for cardiac rhythm management can comprise: (a) a wearable photoplethysmography (PPG) device with at least one light emitter and at least one light receiver, wherein variation in the amount (and/or spectrum) of light from the light emitter which is received by the light receiver caused by reflection of the light from (or transmission of the light through) body tissue is analyzed in order to measure one or more biometric parameters selected from the group consisting of peak-to-peak interval; and (b) an implanted cardiac pacemaker, wherein the operation of the implanted cardiac pacemaker is automatically adjusted based on the peak-to-peak interval, and wherein the operation of the implanted cardiac pacemaker is automatically adjusted by adjusting one or more of operating parameters selected from the group consisting of: Amplitude (e.g. Atrial Pulse, Ventricular Pulse, Current, Voltage); AV Delay (e.g. Post Pacing, Post Sensing, Minimum); Blanking Period (e.g. Ventricular); Coordination/Timing (e.g. Between Different Chambers); Electrode (e.g. Locations, Combination, Polarity); Frequency (e.g. Pulse, Heart Stimulations); Initiation or Cessation (e.g. Pacing, Stimulation); Mode (e.g. Pacing); Pacing Interval (e.g. AV, IV, VV); Polarity (e.g. Pacing); Pulse Width (e.g. Atrial, Ventricular); Rate (e.g. Basic, Upper Tracking, Hysteresis); Refractory Extension (e.g. Atrial); Refractory Period (e.g. Atrial, Ventricular, Post-Ventricular); Sensing (e.g. Atrial, Polarity, Ventricular, Polarity); and Sensitivity (e.g. Atrial).

In an example, a peripheral feedback system for cardiac rhythm management can comprise: (a) a wearable photoplethysmography (PPG) device with at least one light emitter and at least one light receiver, wherein variation in the amount (and/or spectrum) of light from the light emitter which is received by the light receiver caused by reflection of the light from (or transmission of the light through) body tissue is analyzed in order to measure one or more biometric parameters selected from the group consisting of oxygen saturation, VO2, and VO2max; and (b) an implanted cardiac pacemaker, wherein the operation of the implanted cardiac pacemaker is automatically adjusted based on the one or more biometric parameters, and wherein the operation of the implanted cardiac pacemaker is automatically adjusted by adjusting one or more of operating parameters selected from the group consisting of: Amplitude (e.g. Atrial Pulse, Ventricular Pulse, Current, Voltage); AV Delay (e.g. Post Pacing, Post Sensing, Minimum); Blanking Period (e.g. Ventricular); Coordination/Timing (e.g. Between Different Chambers); Electrode (e.g. Locations, Combination, Polarity); Frequency (e.g. Pulse, Heart Stimulations); Initiation or Cessation (e.g. Pacing, Stimulation); Mode (e.g. Pacing); Pacing Interval (e.g. AV, IV, VV); Polarity (e.g. Pacing); Pulse Width (e.g. Atrial, Ventricular); Rate (e.g. Basic, Upper Tracking, Hysteresis); Refractory Extension (e.g. Atrial); Refractory Period (e.g. Atrial, Ventricular, Post-Ventricular); Sensing (e.g. Atrial, Polarity, Ventricular, Polarity); and Sensitivity (e.g. Atrial).

In an example, a feedback system for cardiac rhythm management can comprise: (a) a finger ringer which is worn by a person, wherein the finger ring has at least one light emitter and at least one light receiver, wherein the finger ring functions as a wearable photoplethysmography (PPG) device, wherein variation in the amount (and/or spectrum) of light from the light emitter which is received by the light receiver caused by reflection of the light from (or transmission of the light through) body tissue is analyzed in order to measure one or more biometric parameters selected from the group consisting of Heart Rate (HR), Heart Rate Variability (HRV), Blood Volume Pulse (BVP), Inter-Beat Interval (IBI), Peak-to-Peak Interval (PPI), Blood Pulse Rate (BPR), Blood Volume Pulse (BVP), Blood Volume Amplitude (BVP), Peak Amplitude (PA), Pulse Area, Pulse Transit Time (PTT), Standard Deviation of Average Normal to Normal Beat (SDANN), Systolic Amplitude, Systolic Peak Amplitude, Blood Pressure, Oxygen Saturation, VO2, VO2max, Hydration Level, and Respiration and/or Breathing Rate; and (b) an implanted cardiac pacemaker, wherein the operation of the implanted cardiac pacemaker is automatically adjusted based on the one or more biometric parameters, and wherein the operation of the implanted cardiac pacemaker is automatically adjusted by adjusting one or more of operating parameters selected from the group consisting of: Amplitude (e.g. Atrial Pulse, Ventricular Pulse, Current, Voltage); AV Delay (e.g. Post Pacing, Post Sensing, Minimum); Blanking Period (e.g. Ventricular); Coordination/Timing (e.g. Between Different Chambers); Electrode (e.g. Locations, Combination, Polarity); Frequency (e.g. Pulse, Heart Stimulations); Initiation or Cessation (e.g. Pacing, Stimulation); Mode (e.g. Pacing); Pacing Interval (e.g. AV, IV, VV); Polarity (e.g. Pacing); Pulse Width (e.g. Atrial, Ventricular); Rate (e.g. Basic, Upper Tracking, Hysteresis); Refractory Extension (e.g. Atrial); Refractory Period (e.g. Atrial, Ventricular, Post-Ventricular); Sensing (e.g. Atrial, Polarity, Ventricular, Polarity); and Sensitivity (e.g. Atrial).

In an example, a system for treating congestive heart failure can comprise: (a) a wearable photoplethysmography (PPG) device with at least one light emitter and at least one light receiver, wherein variation in the amount (and/or spectrum) of light from the light emitter which is received by the light receiver caused by reflection of the light from (or transmission of the light through) body tissue is analyzed in order to measure hydration level; and (b) an implanted cardiac pacemaker, wherein the operation of the implanted cardiac pacemaker is automatically adjusted based on the one or more biometric parameters, and wherein the operation of the implanted cardiac pacemaker is automatically adjusted by adjusting one or more of operating parameters selected from the group consisting of: Amplitude (e.g. Atrial Pulse, Ventricular Pulse, Current, Voltage); AV Delay (e.g. Post Pacing, Post Sensing, Minimum); Blanking Period (e.g. Ventricular); Coordination/Timing (e.g. Between Different Chambers); Electrode (e.g. Locations, Combination, Polarity); Frequency (e.g. Pulse, Heart Stimulations); Initiation or Cessation (e.g. Pacing, Stimulation); Mode (e.g. Pacing); Pacing Interval (e.g. AV, IV, VV); Polarity (e.g. Pacing); Pulse Width (e.g. Atrial, Ventricular); Rate (e.g. Basic, Upper Tracking, Hysteresis); Refractory Extension (e.g. Atrial); Refractory Period (e.g. Atrial, Ventricular, Post-Ventricular); Sensing (e.g. Atrial, Polarity, Ventricular, Polarity); and Sensitivity (e.g. Atrial).

In one embodiment, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure systolic amplitude or peak amplitude; and (b) an implanted cardiac pacemaker, wherein the pacing interval of the pacemaker is decreased in response to high systolic amplitude or peak amplitude as measured by the PPG device. Alternatively, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure hydration level; and (b) an implanted cardiac pacemaker, wherein the pacing rate is automatically decreased in response to a high hydration level measured by the PPG device.

In an example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure systolic amplitude or peak amplitude; and (b) an implanted cardiac pacemaker, wherein the pacing voltage or current is increased in response to high systolic amplitude or peak amplitude as measured by the PPG device. In another example, a feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure blood pressure; and (b) an implanted cardiac pacemaker, wherein the pattern of electromagnetic energy stimulations by the implanted cardiac pacemaker is automatically adjusted based on measured blood pressure.

In one embodiment, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters selected from the group consisting of Heart Rate (HR), Heart Rate Variability (HRV), Blood Volume Pulse (BVP), Inter-Beat Interval (IBI), Peak-to-Peak Interval (PPI), Blood Pulse Rate (BPR), Blood Volume Pulse (BVP), Blood Volume Amplitude (BVP), Peak Amplitude (PA), Pulse Area, Pulse Transit Time (PTT), Standard Deviation of Average Normal to Normal Beat (SDANN), Systolic Amplitude, Systolic Peak Amplitude, Blood Pressure, Oxygen Saturation, VO2, VO2max, Hydration Level, and Respiration and/or Breathing Rate; and (b) an implanted cardiac pacemaker, wherein the pattern of heart contractions stimulated by the implanted cardiac pacemaker is automatically changed based on the one or more biometric parameters.

In an example, a peripheral feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure Heart Rate (HR); and (b) an implanted cardiac pacemaker, wherein the rate of heart contractions stimulated by the implanted cardiac pacemaker is automatically increased in response to a high Heart Rate (HR) as measured by the photoplethysmography (PPG) device. Alternatively, a feedback system for cardiac rhythm management can comprise: (a) a wearable photoplethysmography (PPG) device with at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein there is wireless communication between the wearable PPG device and the cardiac pacemaker (either directly or via an intermediary device), and wherein the operation of the implanted cardiac pacemaker is automatically changed based on the values of the one or more biometric parameters measured by the PPG device.

In an example, a peripheral feedback system for cardiac rhythm management can comprise: (a) a wearable photoplethysmography (PPG) device; wherein the PPG device further comprises at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and wherein the wearable PPG device further comprises an elastic member whose tension and/or length is adjusted to hold a light emitter, a light receiver, and/or a light guide snugly against a person's body; and (b) an implanted cardiac pacemaker, wherein the operation of the implanted cardiac pacemaker is automatically adjusted based on the one or more measured biometric parameters. In another example, a peripheral feedback system for cardiac rhythm management can comprise: (a) a wearable photoplethysmography (PPG) device; wherein the PPG device further comprises at least one light emitter and at least one light receiver, wherein changes in the amount (and/or spectrum) of light from the light emitter which is received by the light receiver caused by reflection of the light from (or transmission of the light through) body tissue are analyzed in order to measure one or more biometric parameters; and wherein the wearable PPG device further comprises one or more light barriers between one or more light emitters and light receivers to block transmission of light from the light emitters to the light receivers except through body tissue; and (b) an implanted cardiac pacemaker, wherein the operation of the implanted cardiac pacemaker is automatically adjusted based on the one or more measured biometric parameters.

In an example, a peripheral feedback system for cardiac rhythm management can comprise: (a) a wearable photoplethysmography (PPG) device, wherein the PPG device further comprises at least one light emitter which emits infrared, near-infrared, or ultraviolet light; wherein the PPG device further comprises at least one light receiver; and wherein changes in the amount (and/or spectrum) of light from the light emitter which is received by the light receiver caused by reflection of the light from (or transmission of the light through) body tissue are analyzed in order to measure one or more biometric parameters; and (b) an implanted cardiac pacemaker, wherein the operation of the implanted cardiac pacemaker is automatically adjusted based on the one or more biometric parameters.

I claim:

1. A system for cardiac function assistance comprising:
an implanted cardiac pacemaker or other implanted cardiac rhythm management device, wherein the implanted device has a plurality of operating parameters including pacing rate and is configured to be implanted in a person;
a wearable device configured to be worn by the person, wherein the wearable device comprises an arcuate array of biometric sensors, the arcuate array of biometric sensors comprises a plurality of light emitters and light receivers;

a plurality of actuators, wherein a subset of actuators in the plurality of actuators tilts, rotates, raises, or lowers light receivers in the plurality of light receivers in order to maintain a selected distance and/or selected angle between the light receivers and the surface of the person's body, wherein the implanted device and the wearable device are in wireless communication with each other, either directly or through an intermediary device, and wherein one or more of the operating parameters of the implanted cardiac pacemaker or other implanted cardiac rhythm management device are automatically adjusted based on analysis of data from the biometric sensors.

2. The system in claim 1 wherein the wearable device is selected from the group consisting of a smart watch or watch band, a wrist or arm band, a finger ring, a sleeve, an ear bud or other ear insert, a chest strap, a smart sock, an adhesive patch, and smart glasses.

3. The system in claim 1 wherein a subset of actuators in the plurality of actuators tilts, rotates, raises, or lowers light emitters in the plurality of light emitters in order to maintain a selected distance and/or selected angle between the light emitters and the surface of the person's body.

4. The system in claim 1 wherein the biometric sensors are oxygenation sensors.

5. The system in claim 4 wherein the system increases the frequency of heart contraction stimulations via the implanted cardiac pacemaker or other implanted cardiac rhythm management device when a low oxygenation level is detected by analysis of data from the oxygenation sensors.

6. The system in claim 4 wherein the system increases the magnitude of heart contraction stimulations via the implanted cardiac pacemaker or other implanted cardiac rhythm management device when a low oxygenation level is detected by analysis of data from the oxygenation sensors.

7. The system in claim 4 wherein the system increases the regularity of heart contraction stimulations via the implanted cardiac pacemaker or other implanted cardiac rhythm management device when a low oxygenation level is detected by analysis of data from the oxygenation sensors.

8. The system in claim 4 wherein the system changes the locations on the heart to which electromagnetic energy is delivered via the implanted cardiac pacemaker or other implanted cardiac rhythm management device when a low oxygenation level is detected by analysis of data from the oxygenation sensors.

9. The system in claim 4 wherein the system changes the degree of coordination and/or timing between stimulations to different heart chambers via the implanted cardiac pacemaker or other implanted cardiac rhythm management device when a low oxygenation level is detected by analysis of data from the oxygenation sensors.

10. A system for cardiac function assistance comprising:
an implanted Ventricular Assist Device (VAD) or other implanted blood-pumping device, wherein the implanted device has a plurality of operating parameters including rotational and/or flow speed and is configured to be implanted in a person;

a wearable device configured to be worn by the person, wherein the wearable device comprises an arcuate array of biometric sensors, the arcuate array of biometric sensors comprises a plurality of light emitters and light receivers;

a plurality of actuators, wherein a subset of actuators in the plurality of actuators tilts, rotates, raises, or lowers light receivers in the plurality of light receivers in order to maintain a selected distance and/or selected angle between the light receivers and the surface of the person's body, wherein the implanted device and the wearable device are in wireless communication with each other, either directly or through an intermediary device, and wherein one or more of the operating parameters of the Ventricular Assist Device (VAD) or other implanted blood-pumping device are automatically adjusted based on analysis of data from the biometric sensors.

11. The system in claim 10 wherein the wearable device is selected from the group consisting of a smart watch or watch band, a wrist or arm band, a finger ring, a sleeve, an ear bud or other ear insert, a chest strap, a smart sock, an adhesive patch, and smart glasses.

12. The system in claim 10 wherein a subset of actuators in the plurality of actuators tilts, rotates, raises, or lowers light emitters in the plurality of light emitters in order to maintain a selected distance and/or selected angle between the light emitters and the surface of the person's body.

13. The system in claim 10 wherein the biometric sensors are oxygenation sensors.

14. The system in claim 13 wherein the system activates the implanted Ventricular Assist Device (VAD) or other implanted blood-pumping device when a low oxygenation level is detected by analysis of data from the oxygenation sensors.

15. The system in claim 13 wherein the system increases the duration of operation of the implanted Ventricular Assist Device (VAD) or other implanted blood-pumping device when a low oxygenation level is detected by analysis of data from the oxygenation sensors.

16. The system in claim 13 wherein the system increases the rotational speed of the implanted Ventricular Assist Device (VAD) or other implanted blood-pumping device when a low oxygenation level is detected by analysis of data from the oxygenation sensors.

17. The system in claim 13 wherein the system increases the speed of undulation, compression, or contraction of the implanted Ventricular Assist Device (VAD) or other implanted blood-pumping device when a low oxygenation level is detected by analysis of data from the oxygenation sensors.

18. The system in claim 13 wherein the system increases the magnitude of undulation, compression, or contraction of the implanted Ventricular Assist Device (VAD) or other implanted blood-pumping device when a low oxygenation level is detected by analysis of data from the oxygenation sensors.

* * * * *